United States Patent
Carter et al.

(10) Patent No.: US 12,053,525 B2
(45) Date of Patent: Aug. 6, 2024

(54) MULTISPECIFIC ANTIGEN-BINDING PROTEINS

(71) Applicant: Genentech, Inc., South San Francisco, CA (US)

(72) Inventors: Paul Carter, Hillsborough, CA (US); Christoph Spiess, Mountain View, CA (US); Yiyuan Yin, Fremont, CA (US); Jianhui Zhou, Redwood City, CA (US); Wendy Sandoval, San Bruno, CA (US); Jacob Corn, Berkeley, CA (US); Michael Dillon, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 453 days.

(21) Appl. No.: 17/395,400

(22) Filed: Aug. 5, 2021

(65) Prior Publication Data

US 2022/0409725 A1    Dec. 29, 2022

Related U.S. Application Data

(60) Division of application No. 15/789,670, filed on Oct. 20, 2017, now Pat. No. 11,116,840, which is a continuation of application No. PCT/US2016/028850, filed on Apr. 22, 2016.

(60) Provisional application No. 62/310,555, filed on Mar. 18, 2016, provisional application No. 62/264,291, filed on Dec. 7, 2015, provisional application No. 62/152,735, filed on Apr. 24, 2015.

(51) Int. Cl.

| | | |
|---|---|---|
| *C07H 21/04* | (2006.01) | |
| *A61K 39/395* | (2006.01) | |
| *A61K 39/44* | (2006.01) | |
| *C07K 16/46* | (2006.01) | |
| *G16B 20/30* | (2019.01) | |
| *G16B 20/50* | (2019.01) | |
| *A61K 39/00* | (2006.01) | |
| *G01N 33/68* | (2006.01) | |
| *G16B 5/00* | (2019.01) | |
| *G16B 20/00* | (2019.01) | |

(52) U.S. Cl.
CPC ........ *A61K 39/44* (2013.01); *A61K 39/39558* (2013.01); *C07K 16/468* (2013.01); *G16B 20/30* (2019.02); *G16B 20/50* (2019.02); *A61K 39/3955* (2013.01); *A61K 39/39566* (2013.01); *A61K 2039/507* (2013.01); *C07K 2317/31* (2013.01); *C07K 2317/522* (2013.01); *C07K 2317/56* (2013.01); *G01N 33/6848* (2013.01); *G16B 5/00* (2019.02); *G16B 20/00* (2019.02)

(58) Field of Classification Search
None
See application file for complete search history.

(56) References Cited

U.S. PATENT DOCUMENTS

| | | |
|---|---|---|
| 3,773,919 A | 11/1973 | Boswell |
| 3,896,111 A | 7/1975 | Kupchan |
| 4,137,230 A | 1/1979 | Hashimoto |
| 4,151,042 A | 4/1979 | Asai |
| 4,248,870 A | 2/1981 | Miyashita |
| 4,256,746 A | 3/1981 | Miyashita |
| 4,260,608 A | 4/1981 | Miyashita |
| 4,265,814 A | 5/1981 | Hashimoto |
| 4,294,757 A | 10/1981 | Asai |
| 4,307,016 A | 12/1981 | Asal |
| 4,308,268 A | 12/1981 | Miyashita |
| 4,308,269 A | 12/1981 | Miyashita |
| 4,309,428 A | 1/1982 | Miyashita |
| 4,313,946 A | 2/1982 | Powell |
| 4,315,929 A | 2/1982 | Freedman |
| 4,317,821 A | 3/1982 | Miyashita |
| 4,322,348 A | 3/1982 | Asai |
| 4,331,598 A | 5/1982 | Hasegawa |
| RE30,985 E | 6/1982 | Cartaya |
| 4,361,650 A | 11/1982 | Asai |
| 4,362,663 A | 12/1982 | Kida |
| 4,364,866 A | 12/1982 | Asai |
| 4,371,533 A | 2/1983 | Akimoto |
| 4,424,219 A | 1/1984 | Hashimoto |
| 4,450,254 A | 5/1984 | Isley |
| 4,560,655 A | 12/1985 | Baker |

(Continued)

FOREIGN PATENT DOCUMENTS

| | | |
|---|---|---|
| EP | 0367566 B1 | 5/1990 |
| EP | 0425235 B1 | 9/1996 |

(Continued)

OTHER PUBLICATIONS

Abou-Nadler, M. et al. (2010, e-pub. Sep. 1, 2010). "Rapid Generation of Random Mutant Libraries," Bioengineered Bugs 1(5):337-340.

(Continued)

*Primary Examiner* — Meera Natarajan
(74) *Attorney, Agent, or Firm* — Morrison & Foerster LLP

(57) ABSTRACT

Provided are, inter alia, multispecific antigen binding proteins, or antigen-binding fragments thereof, comprising one or more mutations in the VH/VL domains and/or CH1/CL domains, pharmaceutical compositions comprising same, isolated nucleic acids, vectors, and host cells encoding/expressing same, method of making the multispecific antigen binding proteins, computer readable media for evaluating multispecific antigen binding proteins, and libraries.

21 Claims, 29 Drawing Sheets

Specification includes a Sequence Listing.

(56) References Cited

U.S. PATENT DOCUMENTS

| | | |
|---|---|---|
| 4,657,866 A | 4/1987 | Kumar |
| 4,767,704 A | 8/1988 | Cleveland |
| 4,816,567 A | 3/1989 | Cabilly |
| 4,927,762 A | 5/1990 | Darfler |
| 4,933,294 A | 6/1990 | Waterfield |
| 4,965,195 A | 10/1990 | Namen et al. |
| 4,968,607 A | 11/1990 | Dower et al. |
| 4,975,278 A | 12/1990 | Senter |
| 4,994,560 A | 2/1991 | Kruper, Jr. |
| 5,053,394 A | 10/1991 | Ellestad et al. |
| 5,122,469 A | 6/1992 | Mather |
| 5,208,020 A | 5/1993 | Chari |
| 5,223,409 A | 6/1993 | Ladner et al. |
| 5,274,119 A | 12/1993 | Frazier |
| 5,322,798 A | 6/1994 | Sadowski |
| 5,341,215 A | 8/1994 | Seher |
| 5,342,604 A | 8/1994 | Wilson |
| 5,362,852 A | 11/1994 | Geoghegan |
| 5,401,638 A | 3/1995 | Carney |
| 5,403,484 A | 4/1995 | Ladner |
| 5,416,064 A | 5/1995 | Chari |
| 5,427,908 A | 6/1995 | Dower |
| 5,428,139 A | 6/1995 | Kiefer |
| 5,432,018 A | 7/1995 | Dower et al. |
| 5,435,990 A | 7/1995 | Cheng |
| 5,489,425 A | 2/1996 | Kruper, Jr. |
| 5,498,530 A | 3/1996 | Schatz et al. |
| 5,498,538 A | 3/1996 | Fowlkes et al. |
| 5,500,362 A | 3/1996 | Robinson |
| 5,505,931 A | 4/1996 | Pribish |
| 5,571,689 A | 11/1996 | Heuckeroth |
| 5,580,717 A | 12/1996 | Dower |
| 5,627,024 A | 5/1997 | Maruyama et al. |
| 5,635,483 A | 6/1997 | Pettit |
| 5,641,870 A | 6/1997 | Rinderknecht |
| 5,643,768 A | 7/1997 | Kawasaki |
| 5,652,361 A | 7/1997 | Simon |
| 5,658,754 A | 8/1997 | Kawasaki |
| 5,663,143 A | 9/1997 | Ley |
| 5,663,149 A | 9/1997 | Pettit |
| 5,696,239 A | 12/1997 | Wilson |
| 5,698,426 A | 12/1997 | Huse |
| 5,712,374 A | 1/1998 | Kuntsmann |
| 5,714,586 A | 2/1998 | Kunstmann |
| 5,714,631 A | 2/1998 | Wilson |
| 5,723,286 A | 3/1998 | Dower et al. |
| 5,723,323 A | 3/1998 | Kauffman et al. |
| 5,731,168 A | 3/1998 | Carter |
| 5,734,018 A | 3/1998 | Rutter et al. |
| 5,739,116 A | 4/1998 | Hamann |
| 5,756,065 A | 5/1998 | Wilson |
| 5,763,192 A | 6/1998 | Kauffman et al. |
| 5,766,905 A | 6/1998 | Studier et al. |
| 5,767,285 A | 6/1998 | Hamann |
| 5,770,434 A | 6/1998 | Huse |
| 5,770,701 A | 6/1998 | Mcgahren |
| 5,770,710 A | 6/1998 | Mcgahren |
| 5,773,001 A | 6/1998 | Hamann |
| 5,780,588 A | 7/1998 | Pettit |
| 5,807,706 A | 9/1998 | Carter |
| 5,808,003 A | 9/1998 | Subramanian |
| 5,821,337 A | 10/1998 | Carter |
| 5,877,296 A | 3/1999 | Hamann |
| 6,037,525 A | 3/2000 | Thompson |
| 6,177,612 B1 | 1/2001 | Jordan |
| 6,239,328 B1 | 5/2001 | Thompson |
| 6,245,974 B1 | 6/2001 | Michalowski |
| 6,258,558 B1 | 7/2001 | Szostak et al. |
| 6,261,804 B1 | 7/2001 | Szostak et al. |
| 6,268,125 B1 | 7/2001 | Perkins |
| 6,289,286 B1 | 9/2001 | Andersson et al. |
| 6,373,577 B1 | 4/2002 | Braeuer et al. |
| 6,388,066 B1 | 5/2002 | Bruce |
| 6,416,950 B1 | 7/2002 | Lohse et al. |
| 7,129,062 B2 | 10/2006 | Mermod |
| 7,183,076 B2 | 2/2007 | Arathoon et al. |
| 7,259,010 B2 | 8/2007 | Kim |
| 7,326,567 B2 | 2/2008 | Saha |
| 7,422,874 B2 | 9/2008 | Kim |
| 8,714,907 B2 | 5/2014 | Alfes |
| 11,116,840 B2 | 9/2021 | Carter et al. |
| 2005/0169933 A1 | 8/2005 | Steeves |
| 2005/0186208 A1 | 8/2005 | Fyfe |
| 2005/0238649 A1 | 10/2005 | Doronina |
| 2009/0182127 A1 | 7/2009 | Kjaergaard |
| 2009/0232811 A1 | 9/2009 | Klein |
| 2010/0286374 A1 | 11/2010 | Kannan |
| 2014/0154254 A1 | 6/2014 | Kannan |
| 2014/0200331 A1 | 7/2014 | Corper et al. |
| 2018/0177873 A1 | 6/2018 | Carter et al. |

FOREIGN PATENT DOCUMENTS

| | | |
|---|---|---|
| EP | 1391213 A1 | 2/2004 |
| EP | 2543680 A1 | 1/2013 |
| EP | 2787078 A1 | 10/2014 |
| WO | 198700195 A1 | 1/1987 |
| WO | 199003430 A1 | 4/1990 |
| WO | 199105264 A1 | 4/1991 |
| WO | 199321232 A1 | 10/1993 |
| WO | 199411026 A3 | 8/1994 |
| WO | 199534683 A1 | 12/1995 |
| WO | 199627011 A1 | 9/1996 |
| WO | 199704801 A1 | 2/1997 |
| WO | 199735196 A1 | 9/1997 |
| WO | 199746251 A1 | 12/1997 |
| WO | 199747314 A1 | 12/1997 |
| WO | 199814277 A1 | 4/1998 |
| WO | 199815833 A1 | 4/1998 |
| WO | 199820036 A1 | 5/1998 |
| WO | 199820159 A1 | 5/1998 |
| WO | 199820169 A1 | 5/1998 |
| WO | 199856418 A1 | 12/1998 |
| WO | 2002088172 A2 | 11/2002 |
| WO | 2002088172 A3 | 2/2003 |
| WO | 2005062967 A2 | 7/2005 |
| WO | 2005062967 A3 | 12/2006 |
| WO | 2007147901 A1 | 12/2007 |
| WO | 2008068637 A2 | 6/2008 |
| WO | 2008068637 A3 | 10/2008 |
| WO | 2009080251 A1 | 7/2009 |
| WO | 2009080252 A1 | 7/2009 |
| WO | 2009080253 A1 | 7/2009 |
| WO | 2009080254 A1 | 7/2009 |
| WO | 2009089004 A1 | 7/2009 |
| WO | 2010034605 A1 | 4/2010 |
| WO | 2011131746 A2 | 10/2011 |
| WO | 2011131746 A3 | 12/2011 |
| WO | 2012131555 A2 | 10/2012 |
| WO | 2012131555 A3 | 12/2012 |
| WO | 2014055784 A1 | 4/2014 |
| WO | 2014081955 A1 | 5/2014 |
| WO | WO2014/081955 * | 5/2014 |
| WO | 2014082179 A1 | 6/2014 |
| WO | 2014150973 A1 | 9/2014 |
| WO | 2014165771 A2 | 10/2014 |
| WO | 2014165771 A3 | 11/2014 |
| WO | 2015173756 A2 | 11/2015 |
| WO | 2015181805 A1 | 12/2015 |
| WO | 2015173756 A3 | 1/2016 |

OTHER PUBLICATIONS

Adames, J.M. et al. (Dec. 12, 1985). "The c-myc Oncogene Driven by Immunoglobulin Enhancers Induces Lymphoid Malignancy in Transgenic Mice," Nature 318:533-538.

Aldrich, T.L. et al. (2003, e-pub. Jul. 19, 2003). "Ease Vectors for Rapid Stable Expression of Recombinant Antibodies," Biotechnol. Prog. 19(5):1433-1438.

Alexander, W.S. et al. (Apr. 1987). "Expression of the C-myc Oncogene Under Control of an Immunoglobulin Enhancer In Eµ-myc Transgenic Mice," Mol. Cell. Biol. 7(4):1436-1444.

(56) References Cited

OTHER PUBLICATIONS

Ausubel, F. et al. (1987). Current Protocols in Molecular Biology, Greene Publishing and Wiley Interscience, New York, TOC, 7 pages.
Ausubel, F.M. et al. (1995). Short Protocols in Molecular Biology, Greene Publishing and Wiley Interscience, New York, New York, (Table of Contents), 22 pages.
Baldwin, R.W. et al. (Mar. 15, 1986). "Monoclonal Antibodies in Cancer Treatment," Lancet 1(8481)603-605.
Barnes, D. et al. (Mar. 1, 1980). "Methods for Growth of Cultured Cells In Serum-Free Medium," Anal. Biochem. 102(2):255-270.
Benoist, C. et al. (Mar. 26, 1981). "In Vivo Sequence Requirements of the SV40 Early Promotor Region," Nature 290:304-310.
Boder, E.T. et al. (Jun. 1997). "Yeast Surface Display for Screening Combinatorial Polypeptide Libraries," Nat. Biotechnol. 15:553-557.
Bos, A.B. et al. (2014, e-pub. Apr. 1, 2014). "Development Of A Semi-Automated High Throughput Transient Transfection System," Journal of Biotechnology 180:10-16.
Bostrom, J. et al. (Mar. 2009). "Variants of the Antibody Herceptin That Interact with HER2 and VEGF at the Antigen Binding Site," Science 323:1610-1614.
Brinster, R.L. et al. (Mar. 4, 1982). "Regulation of Metallothionein-Thymidine Kinase Fusion Plasmids Injected Into Mouse Eggs," Nature 296:39-42.
Brisette, R. et al. (2007). "Chapter 13: The Use Of Phage Display Peptide Libraries For Basic And Translational Research," Methods Mol. Biol. 383:203-213.
Burton, D.R. (1985), "Immunoglobulin G: Functional Sites," Molec. Immunol. 22(3):161-206.
Capel, P.J. et al. (Feb. 1994). "Heterogeneity of Human IgG Fc Receptors," Immunomethods 4(1):25-34.
Carlsson, J. et al. (Sep. 1, 1978). "Protein Thiolation and Reversible Protein-Protein Conjugation. N-Succinimidyl 3-(2-pyridyldithio)Propionate, a New Heterobifunctional Reagent," Biochem. J. 173:723-737.
Carter, P. et al. (May 1992). "Humanization of an Anti-p185HER2 Antibody for Human Cancer Therapy," Proc. Natl. Acad. Sci. USA 89:4285-4289.
Chari, R.V.J. et al. (Jan. 1, 1992). "Immunoconjugates Containing Noveal maytansinoids: Promising Anticancer Drugs," Cancer Res. 52:127-131.
Chau, P.L. et al. (Oct. 1994). "Electrostatic Complementarity Between Proteins and Ligands. 1. Charge Disposition, Dielectric and Interface Effects," J. Comp. Mol. Des. 8:513-525.
Chen, B. et al. (Dec. 2003). "Influence Of Histidine On The Stability and Physical Properties Of A Fully Human Antibody In Aqueous and Solid Forms," Pharm Res 20(12):1952-1960.
Chen, Y. et al. (1999). "Selection and Analysis of an Optimized Anti-VEGF Antibody: Crystal Structure of an Affinity-Matured Fab In Complex With Antigen," J. Mol. Biol 293:865-881.
Chothia, C. et al. (1989). "Conformations of Immunoglobulin Hypervariable Regions," Nature 342(6252): 877-883.
Chothia, C. et al. (Aug. 20, 1987). "Canonical Structures for the Hypervariable Regions of Immunoglobulins," J. Mol. Biol. 196(4):901-917.
Cirino, P.C. et al. (2003). "Generating Mutant Libraries Using Error-Prone PCR," Methods Mol. Biol. 231:3-9.
Clackson, T. et al. (Aug. 15, 1991). "Making Antibody Fragments Using Phage Display Libraries," Nature 352:624-628.
Clynes, R. et al. (Jan. 1998). "Fc Receptors are Required in Passive and Active Immunity to Melanoma," Proc. Natl. Acad. Sci. U.S.A. 95:652-656.
Coligan, J.E. et al. (1991). Current Protocols in Immunology 3.12-3.12.14.
Corrêa, D.H.A. et al. (May 2009). "The Use Of Circular Dichroism Spectroscopy To Study Protein Folding, Form and Function," African J. Blochem. Res. 3(5):164-173.
Cosman, D. et al. (Dec. 20/27, 1984). "Cloning, Sequence and Expression of Human Interleukin-2 Receptor," Nature 312:768-771.
Cwirla, S.E. et al. (Aug. 1990). "Peptides On Phage: A Vast Library of Peptides for Identifying Ligands," PNAS USA 87:6378-6382.
Daëron, M. (1997). "Fc Receptor Biology," Ann. Rev. Immunol. 15:203-234.
De Haas, M. et al. (Oct. 1995). "Fc Gamma receptors of Phagocytes," J. Lab. Clin. Med. 126:330-341.
Deboer, H.A. et al. (Jan. 1983). "The Tac Promoter: a Functional Hybrid Derived From the trp and lac Promoters," Proc. Natl. Acad. Sci. U.S.A. 80(1):21-25.
Dong, S. et al. (Feb. 2002). "Some New Aspects In Biosensors," Review in Mol. Biotech. 82(4):303-323.
Doronina, S.O. et al. (Jul. 2003). "Development of Potent Monoclonal Antibody Auristatin Conjugates for Cancer Therapy," Nat. Biotechnol. 21(7):778-784.
Efimov, V.P. et al. (Jun. 1995). "Bacteriophage T4 as a Surface Display Vector," Virus Genes 10(2):173-177.
Final Office Action, mailed Jan. 15, 2021, for U.S. Appl. No. 15/789,670, filed Oct. 20, 2017. 7 pages.
Firth, A.E. et al. (2005). "Statistics Of Protein Library Construction," Bioinformatics 21(15):3314-3315.
Fivash, M. et al. (Feb. 1998), "BIAcore For Macromolecular Interaction," Current Opinion in Biotechnology 9(1):97-101.
Fraker, P.J. et al. (Feb. 28, 1978). "Protein and Cell Membrane Iodinations With a Sparingly Soluble Chloroamide, 1,3,4,6-Tetrachloro-3a,6a-Diphenylglycoluril," Biochem. Biophys. Res. Commun. 80(4):849-857.
Freshney, R. I. Animal Cell Culture, Alan R. Liss, Inc. New York (1985), 3 pages.
Freudl, R. et al. (Apr. 5, 1986). "Cell Surface Exposure Of The Outer Membrane Protein OmpA of *Escherichia coli* K-12," J. Mol. Biol. 188(3):491-494.
Gazzano-Santoro, H. et al. (Mar. 28, 1997). "A Non-Radioactive Complement-Dependent Cytotoxicity Assay for Anti-CD20 Monoclonal Antibody," J. Immunol. Methods 202:163-171.
Geoghegan, K. F. et al. (1992). "Site-Directed Conjugation of Nonpeptide Groups to Peptides and Proteins via Periodate Oxidation of a 2-Amino Alcohol. Application to Modification at N-Terminal Serine," Bioconjugate Chem. 3(2):138-146.
Georgiou, G. et al. (Jan. 1997). "Display of Heterologous Proteins on the Surface of Microorganisms: From the Screening of Combinatorial Libraries to Live Recombinant Vaccines," Natl Biotechnol 15:29-34.
Getz, J.A. et al. (2012). "Chapter four—Peptide Discovery Using Bacterial Display and Flow Cytometry," Methods Enzymol 503:75-97.
Ghirlando, R. et al. (May 3, 1999) "Glycosylation Of Human IgG-Fc: Influences On Structure Revealed By Differential Scanning Micro-Calorimetry," Immunol. Lett. 68(1):47-52.
Gluzman, Y. et al. (Jan. 1981). "SV40-Transformed Simian Cells Support the Replication of Early SV40 Mutants," Cell 23(1):175-182.
Gogineni, A. et al. (Jul. 16, 2013). "Inhibition of VEGF-C Modulates Distal Lymphatic Remodeling and Secondary Metastasis," PloS One 8(7):e68755, 15 pages.
Greenfield, N.J. et al. (2006). "Using circular dichroism collected as a function of temperature to determine the thermodynamics of protein unfolding and binding interactions," Nat. Protoc. 1:2876-2890.
Grosschedl, R. et al. (Oct. 1984). "Introduction of a p Immunoglobulin Gene Into the Mouse Germ Line: Specific Expression in Lymphoid Cells and Synthesis of Functional Antibody." Cell 38(3):647-658.
Guss, B. et al. (Jul. 1986). "Structure of the IgG-Binding Regions of Streptococcal Protein G," EMBO J. 5(7):1567-1575.
Guyer, R.L. et al. (Aug. 1976). "Immunoglobulin Binding By Mouse Intestinal Epithelial Cell Receptors," J. Immunol. 117(2):587-593.
Ham, R.J. et al. (1979). "Media and Growth Requirements," Meth. Enz. 58:44-93.
Hammer, R.E. et al. (Jan. 2, 1987). "Diversity of Alpha-Fetoprotein Gene Expression in Mice is Generated by a Combination of Separate Enhancer Elements," Science 235:53-58.

(56) References Cited

OTHER PUBLICATIONS

Hanahan, D. (May 9, 1985). "Heritable Formation of Pancreatic B-Cell Tumours in Transgenic Mice Expressing Recombinant Insulin/Simian Virus 40 Oncogenes," Nature 315:115-122.

Hanes, J. et al. (May 1997). "In vitro Selection and Evolution of Functional Proteins by Using Ribosome Display," PNAS USA 94:4937-4942.

Harlow, E. et al. (1988). Antibodies A Laboratory Manual, Table of Contents only, 9 pages.

Hartmann, F. et al. (Jul. 2001). "Anti-CD16/CD30 Bispecific Antibody Treatment For Hodgkin's Disease," Clin. Cancer Res. 7:1873-1881.

Hendsch, Z.S. et al. (Feb. 14, 2001). "Preferential Heterodimer Formation Via Undercompensated Electrostatic Interactions," Journal of the American Chemical Society 123(6):1264-1265.

Hinman, L.M. et al. (Jul. 15, 1993). "Preparation and Characterization of Monoclonal Antibody Conjugates of the Calicheamicins: A Novel and Potent Family of Antitumor Antibiotics," Cancer Research 53:3336-3342.

Honegger, A. et al. (2001). "Yet Another Numbering Scheme for Immunoglobulin Variable Domains: An Automatic Modeling and Analysis Tool," J Mol Biol. 309(3):657-670.

Hope, I.A. et al. (1987). "GCN4, A Eukaryotic Transcriptional Activator Protein, Binds as a Dimer to Target DNA," The EMBO Journal 6(9):2781-2784.

Hope, I.A. et al. (Jun. 16, 1988). "Structural and Functional Characterization of the Short Acidic Transcriptional Activation Region of Yeast GCN4 Protein," Nature 333:635-640.

Hope, I.A. et al. (Nov. 1985). "GCN4 Protein, Synthesized in Vitro, Binds HIS3 Regulatory Sequences: Implications for General Control of Amino Acid Biosynthetic Genes in Yeast," Cell 43(1):177-188.

Hope, I.A. et al. (Sep. 12, 1986). "Functional Dissection of a Eukaryotic Transcriptional Activator Protein, GCN3 of Yeast," Cell 46:885-894.

Humphreys, D.P. et al. (1998). "F(ab') 2 Molecules Made From *Escherichia coli* Produced Fab' With Hinge Sequences Conferring Increased Serum Survival in an Animal Model," J Immunol Methods 217:1-10.

Igawa, T. (2010, e-pub. Jun. 24, 2010). "VH/VL Interface Engineering To Promote Selective Expression and Inhibit Conformational Isomerization Of Thrombopoietin Receptor Agonist Single-Chain Diabody," Protein Engineering, Design & Selection 23(8):667-677.

Inactive Ingredient Guide prepared by the U.S. Food and Drug Administration, retrieved from https://www.fda.gov/drugs/informationondrugs/ucm113978.htm, last visited Jul. 13, 2018, 1 page.

International Preliminary Report On Patentability for PCT Application No. PCT/US2016/028850, issued Oct. 24, 2017, filed Apr. 22, 2016, 32 pages.

International Search Report for PCT Application No. PCT/US2016/028850, mailed Nov. 14, 2016, filed Apr. 22, 2016, 23 pages.

Ionescu, R.M. et al. (Apr. 2008). "Contribution Of Variable Domains To The Stability Of Humanized IgG1 Monoclonal Antibodies," J. Pharm. Sci. 97(4):1414-1426.

Jackman, J. et al. (Jul. 2, 2010). "Development of a Two-part Strategy to Identify a Therapeutic Human Bispedfic Antibody That Inhibits IgE Receptor Signaling," The Journal of Biological Chemistry 285(27):20850-20859.

Jalkanen, M. et al. (Dec. 1987). "Cell Surface Proteoglycan Of Mouse Mammary Epithelial Cells Is Shed By Cleavage Of Its Matrix-Binding Ectodomain From Its Membrane-Associated Domain," J. Cell. Biol. 105(6):3087-3096.

Jalkanen, M. et al. (Sep. 1985). "Heparan Sulfate Proteoglycans From Mouse Mammary Epithelial Cells: Localization On The Cell Surface With A Monoclonal Antibody," J. Cell. Biol. 101:976-985.

Jefferis, R. et al. (Jul./Aug. 2009). "Human Immunoglobulin Allotypes," Mabs 1(4):332-338.

Jiang, J. et al. (Nov. 1997). "Display of a PorA Peptide from Neisseria Meningitidis on the Bacteriophage T4 Capsid Surface," Infection & Immunity 65(11):4770-4777.

Jones, P. et al. (May 29, 1986). "Replacing The Complementarity-Determining Regions In A Human Antibody With Those From A Mouse," Nature 321:522-525.

Kabat, E.A. et al. (1991). Sequences of Proteins of Immunological Interest, 5th ed. NIH, Bethesda, MD, vol. 1, pp. 688-696.

Kabat, E.A. et al. (1991). Sequences of Proteins of Immunological Interest, Fifth Edition, National Institute of Health, Bethesda, Md., 10 pages.

Kang, A.S. et al. (May 1991). "Linkage of Recognition and Replication Functions by Assembling Combinatorial Antibody Fab Libraries Along Phage Surfaces," Proc. Natl. Acad. Sci. USA, 88:4363-4366.

Kelly, S.M. et al. (2000). "The Use of Circular Dichroism in the Investigation of Protein Structure and Function," Curr. Prot. And Peptide Sci. 1(4):349-384.

Kelsey, G.D. et al. (Apr. 1987). "Species- and Tissue-Specific Expression of Human alpha 1-Antitrypsin in Transgenic Mice," Genes and Devel. 1(2):161-171.

Kenrick, S.A. et al. (2010, e-pub. Nov. 10, 2009). "Bacterial Display Enables Efficient And Quantitative Peptide Affinity Maturation," Protein Eng .Des. Sel. 23(1):9-17.

Kim, J-K. et al. (1994). "Localization of the Site of the Murine IgGl Molecule That is Involved in Binding to the Murine Intestinal Fc Receptor," Eur. J. Immunol. 24:2429-2434.

Klein, C. et al. (2012). "Progress in Overcoming the Chain Association Issue in Bispecific Heterodimeric IgG Antibodies," mAbs 4(6):653-663.

Kollias, G. et al. (Jul. 4, 1986). "Regulated Expression of Human A γ-, β-, and Hybrid γβ-Globin Genes in Transgenic Mice: Manipulation of the Developmental Expression Patterns," Cell 46(1):89-94.

Krumlauf, R. et al. (Jul. 1985). "Developmental Regulation of Alpha-Fetoprotein Genes in Transgenic Mice," Mol. Cell. Biol. 5(7):1639-1648.

Lawrence, M.C. et al. (Dec. 20, 1993). "Shape Complementarity at Protein/Protein Interfaces," J. Mol. Biol. 234(4):946-950.

Leaver-Fay, A. et al. (2011). "ROSETTA3: An Object-Oriented Software Suite For The Simulation And Design Of Macromolecules," Methods Enzymol, 487:545-574, 27 pages.

Leder, A. et al. (May 23, 1986). "Consequences of Widespread Deregulation of the c-myc Gene in Transgenic Mice: Multiple Neoplasms and Normal Development," Cell 45:485-495.

Lee, L.-P. et al. (2001). "Optimization Of Binding Electrostatics: Charge Complementarity In The Barnase-Barstar Protein Complex," Protein Sci. 10:362-377.

Lefranc, M.P. et al. (Jan. 2003). "IMGT Unique Numbering For Immunoglobulin And T Cell Receptor Variable Domains And Ig Superfamily V-Like Domains," Dev. Comp. Immunol. 27(1):55-77.

Lewis, S.M. et al. (Feb. 2014, e-pub, Jan. 26, 2014, "Generation Of Bispecific IgG Antibodies By Structure-Based Design Of An Orthogonal Fab Interface," Nature Biotechnology 32(2):191-198, 12 pages.

Li, X.-W. et al. (2014). "Structure Design of Bispecific Antibodies and Progress in the Assembly Process," Chinese Journal of New Drugs 23(20):2430-2436. English Abstract Only.

Li, Y. et al. (Jun. 1998). "Filamentous Bacteriophage Display of a Bifunctional Protein A::Scfv Fusion," Molecular Biotechnology 9:187-193.

Liang, W.-C. et al. (Nov. 7, 2005). "Cross-Species Vascular Endothelial Growth Factor (VEGF)-Blocking Antibodies Completely Inhibit The Growth Of Human Tumor Xenografts and Measure The Contribution Of Stromal VEGF," J. Biol. Chem. 281:951-961.

Lindmark, R. et al. (1983). "Binding of Immunoglobulins to Protein A and Immunoglobulin Levels in Mammalian Sera," J. Immunol. Meth. 62:1-13.

Lipovsek, D et al. (2004, e-pub. May 31, 2004). "In-Vitro Protein Evolution By Ribosome Display and mRNA Display," J. Imm. Methods 290:51-67.

Liu, C. et al. (Aug. 1996). "Eradication of Large Colon Tumor Xenografts by Targeted Delivery of Maytansinoids," Proc. Natl, Acad. Sci. USA 93:8618-8623.

(56) References Cited

OTHER PUBLICATIONS

Liu, Z. et al. (Mar. 20, 2015, e-pub. Jan. 12, 2015). "A Novel Antibody Engineering Strategy for Making Monovalent Bispecific Heterodimeric IgG Antibodies by Electrostatic Steering Mechanism," J. Biol Chem. 290(12):7535-7562.
Lode, H.N. et al. (Jul. 15, 1998). "Targeted Therapy with a Novel Enediyene Antibiotic Calicheamicin 011 Effectively Suppresses Growth and Dissemination of Liver Metastases in a Syngeneic Model of Murine Neuroblastoma," Cancer Res. 58:2925-2928.
Lowman, H.B. et al. (1991). "Selecting High-Affinity Binding Proteins By Monovalent Phage Display," Biochemistry 30(45):10832-10838.
Lowman, H.B. et al. (Dec. 1991), "Monovalent Phage Display: A Method for Selecting Varinant Proteins From Random Libraries," Methods: A Companion to Methods in Enzymology 3(3):205-216.
Luckow, V.A. et al. (Jan. 1988). "Trends in the Development of Baculovirus Expression Vectors," Biotechnology 6:47-55.
Macdonald, R.J. (Jan.-Feb. 1987). "Expression of the Pancreatic Elastase I Gene in Transgenic Mice," Hepatology 7(1):42S-51S.
Mack, M. et al. (Jul. 1995). "A Small Bispecific Antibody Construct Expressed as a Functional Single-Chain Molecule With High Tumor Cell Cytotoxicity," Proc. Natl. Acad. Sci. USA 92:7021-7025.
Magram, J. et al. (May 23, 1985). "Developmental Regulation of a Cloned Adult β-Globin Gene in Transgenic Mice," Nature 315(6017):338-340.
Mandler, R. et al. (2000). "Synthesis and Evaluation of Antiproliferative Activity of a Geldanamycin-Herceptin TM Immunoconjugate," Bioorganic & Med. Chem. Letters 10:1025-1028.
Mandler, R. et al. (2002, e-pub. Jun. 19, 2002). "Modifications in Synthesis Strategy Improve the Yield and Efficacy of Geldanamycin-Herceptin Immunoconjugates," Bioconjugate Chem. 13:786-791.
Mandler, R. et al. (Oct. 2000). "Immunoconjugates of Geldananlycin and Anti-HER2 Monoclonal Antibodies: Antiproliferative Activity on Human Breast Carcinoma Cell Lines," J. Nat. Cancer Inst. 92(19):1573-1581.
Marks, J.D. et al. (1991). "By-Passing Immunization Human Antibodies from V-gene Libraries Displayed on Phage," J. Mol. Biol. 222:581-597.
Marvin, J.S. et al. (Jun. 2005). "Recombinant Approaches to IgG-Like Bispecific Antibodies," Acta Pharmacol. Sin. 26(6):649-658.
Mason, A.J. et al. (Dec. 12, 1986). "The Hypogonadal Mouse: Reproductive Functions Restored by Gene Therapy," Science 234:1372-1378.
Mazor, Y. et al. (Mar./Apr. 2015, e-pub. Jan. 26, 2015). "Improving Target Cell Specificity Using A Novel Monovalent Bispecific Igg Design," Mabs. 7(2):377-389.
Mccoy, A.J. et al. (1997). "Electrostatic Complementarity at Protein/Protein Interfaces," J. Mol. Biol. 268:570-584.
Mcmahan, C.J. et al. (Oct. 1991). "A Novel IL-1 Receptor, Cloned From B cells by Mammalian Expression, is Expressed in Many Cell Types," EMBO J. 10(10):2821-2832.
Mcphee, F. (Oct. 1996). "Engineering Human Immunodeficiency Virus 1 Protease Heterodimers As Macromolecular Inhibitors Of Viral Maturation," Proc. Natl. Acad. Sel. USA 93:11477-11481.
Melton, D.A. et al. (1984). "Efficient In Vitro Synthesis of Biologically Active RNA and RNA Hybridization Probes From Plasmids Containing a Bacteriophage SP6 Promoter," Nucl. Acids Res. 12(18):7057-7070.
Merchant, A. M. et al. (Jul. 1998). "An Efficient Route To Human Bispecific IgG," Nature Biotechnology 16:677-681.
Merchant, A. M. et al. (Jul. 23, 2013) "Monovalent antibody design and mechanism of action of onartuzumab, a MET antagonist with anti-tumor activity as a therapeutic agent," PNAS, E2987-E2996.
Miller, O.J. et al. (Jul. 2006). "Directed Evolution By in vitro Compartmentalization," Nat Methods 3(7):561-570.
Molek, P. et al. (Jan. 21, 2011). "Peptide Phage Display As A Tool For Drug Discovery: Targeting Membrane Receptors," Molecules 16:857-887.

Morrison, S.C. et al. (Nov. 1984). "Chimeric Human Antibody Molecules: Mouse Antigen-Binding Domains With Human Constant Region Domains," Proc. Natl. Acad. Sci. USA 81:6851-6855.
Mullet, W.M. et al. (Sep. 2000). "Surface Plasmon Resonance-Based Immunoassays," Methods 22(1):77-91.
Murray, A. et al. (Jul. 2002). "Epitope Affinity Chromatography and Biophysical Studies Of Monocional Antibodies and Recombinant Antibody Fragments," J. Chromatogr Sci. 40:343-349.
Niculesu-Duvaz, I. et al. (1997). "Antibody-Directed Enzyme Prodrug Therapy (Adept): A Review," Adv. Drug Del. Rev. 26:151-172.
Niesen, F.H. et al. (2007). "The use of differential scanning fluorimetry to detect ligand interactions that promote protein stability," Nat. Protoc. 2(9):2212-2221.
Non-Final Office Action, mailed Jun. 22, 2020, for U.S. Appl. No. 15/789,670, filed Oct. 20, 2017, 6 pages.
Odegrip, R. et al. (Mar. 2, 2004). "CIS Display: In vitro Selection Of Peptides From Libraries Of Protein-DNA Complexes," Proc. Natl. Acad. Sci. USA 101(9):2806-2810.
Ornitz, D.M. et al. (1985). "Elastase I Promoter Directs Expression of Human Growth Hormone and SV 40 T Antigen Genes to Pancreatic Acinar Cells in Transgenic Mice," Cold Spring Harbor Symp. Quant. Biol. 50:399-409.
Pack, P et al. (Nov. 1993). "Improved Bivalent Miniantibodies, With Identical Avidity as Whole Antibodies, Produced by High Cell Density Fermentation of *Escherichia coli*," Bio/Technology 11:1271-1277.
Pack, P. et al. (Feb. 18, 1992). "Miniantibodies: Use of Amphipathic Helices to Produce Functional, Flexibly Linked Dimeric FV Fragments with High Avidity in *Escherichia coli*," Biochem. 31(6):1579-1584.
Padlan, E.A. et al. (Sep. 1986). "Antibody Fab Assembly: The Interface Residues Between CH1 and CL," Mol. Immunol. 23(9):951-960.
Pettit, G.R. (1997). "The Dolastatins," Progress in the Chemistry of Organic Natural Products, Springer-Verlag, New York, 70:1-79.
Pettit, G.R. et al. (1998). "Antineoplastic Agents 360. Synthesis and Cancer Cell Growth Inhibitory Studies of Dolastatin 15 Structural Modifications," Anti-Cancer Drug Design 13:47-66.
Pettit, G.R. et al. (Jul.-Aug. 1981). "Marine Animal Biosynthetic Constituents for Cancer Chemotherapy," J. Nat. Prod. 44:482-485.
Pettit, R.K. et al. (Nov. 1998). "Specific Activities of Dolastatin 10 and Peptide Derivatives Against Cryptococcus neoformans," Antimicrobial Agents and Chemotherapy 42(11):2961-2965.
Pinkert, C.A. et al. (1987). "An Albumin Enhancer Located 10 kb Upstream Functions Along With its Promoter to Direct Efficient, Liver-Specific Expression in Transgenic Mice," Genes and Devel. 1:268-276.
Pirakitikulr. N. (Dec. 2010). "PCRless Library Mutagenesis Via Oligonucleotide Recombination in Yeast," Protein Sci. 19(12):2336-2346.
Poncet, J. (1999). "The Dolastatins, A Family of Promising Antineoplastic Agents," Curr. Pharm. Des. 5:139-162.
Portolano, S. et al. (Feb. 1, 1993). "Lack of Promiscuity in Autoantigen-Specific H and L Chain Combinations as Revealed by Human H And L Chain 'Roulette'," The Journal of Immunology 150(3):880-887.
Presta, L.G. (1992). "Antibody Engineering," Current Opinion in Structural Biology 2:593-596.
Presta, L.G. et al. (Oct. 15, 1997). "Humanization of an Anti-Vascular Endothellal Growth Factor Monoclonal Antibody for the Therapy of Solid Tumors and Other Disorders," Cancer Res. 57:4593-4599.
Rasmussen, B. et al. (1998). "Isolation, Characterization and Recombinant Protein Expression in Veggie-CHO: A Serum-free CHO Host Cell Line," Cytotechnology 28(1-3):31-42.
Ravetch, J.V. et al. (1991). "Fc Receptors," Annu, Rev. Immunol. 9:457-492.
Readhead, C. et al. (Feb. 27, 1987). "Expression of A Myelin Basic Protein Gene in Transgenic Shiverer Mice: Correction of the Dysmyelinating Phenotype," Cell 48:703-713.
Remington's Pharmaceutical Sciences. (1980). 16th edition, Osol, A. Ed, pp. 1-2, (Table of Contents Only).

(56) References Cited

OTHER PUBLICATIONS

Ren, Z.J. et al. (1997). "Cloning of Linear Dnas in Vivo by Overexpressed T4 DNA Ligase: Construction of a T4 Phage Hoc Gene Display Vector," Gene 195:303-311.

Ren, Z.J. et al. (1998). "Phage T4 SOC and HOC Display of Biologically Active, Full-Length Proteins on the Viral Capsid," Gene 215:439-444.

Ren, Z.J. et al. (Sep. 1996). "Phage Display of Intact Domains at High Copy Number: A System Based On SOC, the Small Outer Capsid Protein of Bacteriophage T4," Protein Sci. 5(9):1833-1843.

Rich, R.L. et al. (Feb. 2000). "Advances In Surface Plasmon Resonance Biosensor Analysis," Current Opinion In Biotechnology 11(1):54-61.

Ridgway, J.B.B. et al. (1996). "'Knobs-Into-Holes' Engineering of Antibody CH3 Domains for Heavy Chain Heterodimerization," Protein Engineering 9(7):617-621.

Riechmann, L. et al. (Mar. 24, 1988). "Reshaping Human Antibodies for Therapy," Nature 33(6162):323-327.

Rowland, G.F. et al. (1986). "Drug Localisation And Growth Inhibition Studies of Vindesine-Monoclonal Anti-CEA Conjugates in a Human Tumour Xenograft," Cancer Immunol. Immunother. 21:183-187.

Sambrook, J. et al. (1989). Molecular Cloning—A Laboratory Manual, 2nd Edition, Maniatis, T.(ed.) et al., Cold Spring Harbor Laboratory Press, New York, NY pp. v-xxxii, 28 pages, (Table of Contents only).

Schaefer, G. et al. (Oct. 18, 2011). "A Two-in-One Antibody against HER3 and EGFR Has Superior Inhibitory Activity Compared with Monospecific Antibodies," Cancer Cell 20:472-486.

Schaefer, W. et al. (Jul. 5, 2011, e-pub. Jun. 20, 2011). "Immunoglobulin Domain Crossover as a Generic Approach for the Production of Bispecific IgG Antibodies," Proc. Natl. Acad. Sci. U.S.A. 108(27):11187-11192.

Schröder, E. et al. (1965). "Formation of Peptide Bond," in The Peptides: Methods of Peptide Synthesis, Academic Press Inc., 111 Fifth Avenue, New York, New York 10003, 1:76-136.

Schueler-Furman, O. et al. (2005). Progress In Protein-Protein Docking: Atomic Resolution Predictions In The CAPRI Experiment Using RosettaDock With An Improved Treatment Of Side-Chain Flexibility Proteins 60:187-194.

Scott, J.K. et al. (Jul. 1990). "Searching for Peptide Ligands with an Epitope Library," Science 249(4967):386-390.

Sergeeva, A. et al. (Dec. 30, 2006). "Display Technologies: Application for the Discovery of Drug and Gene Delivery Agents," Adv. Drug Dellv. Rev. 58(15):1622-1654.

Shani, M. (Mar. 21, 1985). "Tissue-Specific Expression Of Rat Myosin Light-Chain 2 Gene In Transgenic Mice," Nature 314(6008):283-286.

Shatz, W. et al. (Nov./Dec. 2013, e-pub. Aug. 29, 2013). Knobs-Into-Holes Antibody Production in Mammalian Cell Lines Reveals That Asymmetric Afucosylation is Sufficient For Full Antibody-Dependent Cellular Cytotoxicity, mAbs 5(6):872-881.

Sias, P.E. et al. (1990). "ELISA for Quantitation of the Extracellular Domain of p185HER2 in Biological Fluids," J. Immunol. Methods 132:73-80.

Simmons, L.C. et al. (May 1, 2002). "Expression of Full-Length Immunoglobulins in *Escherichia coli*: Rapid and Efficient Production of Aglycosylaled Antibodies," J. Immunol. Meth. 263(1-2):133-147.

Singleton, P. et al. (1994). Dictionary of Microbiology and Molecular Biology 2nd ed., J. Wiley & Sons (New York, N.Y.), 8 pages.

Smith, E.S. et al. (2014). "Antibody Library Display on A Mammalian Virus Vector: Combining The Advantages Of Both Phage and Yeast Display Into One Technology," Curr. Drug Discov. Technol. 11:48-55.

Smith, G. P. et al. (Oct. 1991). "Surface Presentation of Protein Epitopes Using Bacteriophage Expression Systems," Curr Opin Biotechnol. 2(5):668-673.

Smith, G.P. et al. (1985). "Filamentous Fusion Phage: Novel Expression Factors that Display Cloned Antigens on the Virion Surface," Science 228:1315-1317.

Smith, G.P. et al. (1993). "Libraries of Peptides and Proteins Displayed on Filamentous Phage," Methods in Enzymology 217:228-257.

Spiess, C. et al. (2015, e-pub. Jan. 27, 2015). "Alternative Molecular Formats and Therapeutic Applications For Bispecific Antibodies," Mol. Immunol. 67:95-106.

Steffens, D.L. et al. (Jul. 2007). "Efficient Site-Directed Saturation Mutagenesis Using Degenerate Oligonucleotides," J. Biomol. Tech 18(3):147-149.

Stella, V.J. et al. (1985). "Prodrugs: A Chemical Approach to Targeted Drug Delivery," in Directed Drug Delivery, pp. 247-267.

Strop, P. et al. (2012). "Generating Bispecific Human IgG1 and IgG2 Antibodies from Any Antibody Pair," Journal of Molecular Biology 420(3):204-219.

Summers, M.D. et al. (May 1987). "A Manual of Methods for Baculovirus Vectors and Insect Cell Culture Procedures," Texas Agricultural Experiment Station Bulletin No. 1555, 60 pages.

Swift, G.H. et al. (Oct. 1984). "Tissue-Specific Expression of the Rat Pancreatic Elastase I Gene in Transgenic Mice," Cell 38:639-646.

Syrigos, K. et al. (1999). "Antibody Directed Enzyme Prodrug Therapy (ADEPT): A Review of the Experimental and Clinical Considerations," Anticancer Research 19:605-614.

Thomsen, D.L. et al. (Feb. 1984). "Promoter-Regulatory Region of the Major Immediate Early Gene of Human Cytomegalovirus," Proc. Natl. Acad. Sci. U.S.A. 81:659-663.

Thorpe, P.E. (1985). "Antibody Carriers of Cytotoxic Agents in Cancer Therapy: A Review," in Monoclonal Antibodies '84: Biological and Clinical Applications, A. Pinchera et al. eds., Editrice Kurtis s.r.l., pp. 475-506.

Ullman, C.G. et al. (2011). "In vitro Methods For Peptide Display And Their Applications," Brief. Funct. Genomics, 10(3):125-134.

Ultsch M, et al. (Apr. 2013), "Structural Basis Of Signaling Blockade By Anti-IL-13 Antibody Lebrikizumab," J. Mol. Biol. 425(8):1330-1339.

Villa-Kamaroff, L. et al. (Aug. 1978). "A Bacterial Clone Synthesizing Proinsulin," Proc. Natl. Acad. Sci. USA 75(8):3727-3731.

Vitetta, E.S. et al. (Nov. 20, 1987). "Redesigning Nature's Poisons to Create Anti-Tumor Reagents," Science 238:1098-1104.

Wagner, M.J. et al. (Mar. 1981). "Nucleotide sequence of the thymidine kinase gene of herpes simplex virus type 1," Proc. Natl. Acad. Sci. U.S.A. 78(3):1444-1445.

Walls, P.H. et al. (Nov. 5, 1992). "New Algorithm To Model Protein-Protein Recognition Based On Surface Complementarity: Applications To Antibody-Antigen Docking," J. Mol. Biol. 228(1):277-297.

Wells, J.A. et al. (1992). "Rapid Evolution of Peptide and Protein Binding Properties in Vitro," Curr. Opin. Struct. Biol. 3:355-362.

Welsch, M.E. et al. (2010). "Privileged Scaffolds for Library Design and Drug Discovery," Curr. Opin. Chem. Biol. 14:1-15.

Wilman, D.E. (1986). "Prodrugs in Cancer Chemotherapy" Biochemical Society Transactions, 615th Meeting Belfast, 14:376-382.

Wilson et al. "The Use of mRNA Display to Select High-Affinity Protein-Binding Peptides," Proc Natl Acad Sci USA (2001) 98(7):3750-3755.

Wolf, E. et al. (Sep. 2005). "BITEs: Bispecific Antibody Constructs With Unique Anti-Tumor Activity," Drug Discovery Today 10(18):1237-1244.

Woyke, T. et al. (Dec. 2001). "In Vitro Activities and Postantifungal Effects of the Potent Dolastatin 10 Derivative Auristatin PHE," Antimicrob. Agents and Chemother. 45(12):3580-3584.

Written Opinion Of The International Searching Authority for PCT Application No. PCT/US2016/028850, mailed Nov. 14, 2016, filed Apr. 22, 2016, 31 pages.

Wu, C. et al. (Nov. 2007; e-pub. Oct. 14, 2007). "Simultaneous Targeting of Multiple Disease Mediators by a Dual-Variable-Domain Immunoglobulin," Nat. Biotechnol. 25(11):1290-1297.

Wu, H. et al. (May 1998). "Stepwise in Vitro Affinity Maturation of Vitaxin, an αvβ3-Specific Humanized mAb," Proc Natl Acad Sci USA. 95:6037-6042.

(56) References Cited

OTHER PUBLICATIONS

Yamamoto, T. et al. (Dec. 1980). "Identification of a functional promoter in the long terminal repeat of Rous sarcoma virus," Cell 22:787-797.
Yin, L. et al. (Jun. 2015, e-pub. Mar. 14, 2015). "Therapeutic Outcomes, Assessments, Risk Factors and Mitigation Efforts Of Immunogenicity Of Therapeutic Protein Products," Cell Immunol. 295(2):118-126.
Zapata, G. et al. (1995). "Engineering Linear F(ab')2 Fragments for Efficient Production in *Escherichia coli* and Enhanced Antiproliferative Activity," Protein Eng. 8(10):1057-1062.
Zhu, Z. et al. (1994). "Tumor Localization and therapeutic Potential Of An Antitumor-Anti-CD3 Heteroconjugate Antibody In Human Renal Cell Carcinoma Xenograft Models," Cancer Lett. 86:127-134.
Zhu, Z. et al. (1997). "Remodeling Domain Interfaces to Enhance Heterodimer Formation," Protein Science 6:781-788.
Zhu, Z. et al. (Aug. 1, 1998). "Inhibition of Vascular Endothellal Growth Factor-induced Receptor Activation with Anti-Kinase Insert Domain-containing Receptor Single-Chain Antibodies from a Phage Display Library," Cancer Res 58:3209-3214.
Zhu, Z. et al. (Aug. 15, 1995). "Identification Of Heavy Chain Residues In A Humanized Anti-CD3 Antibody Important For Efficient Antigen Binding and T Cell Activation," J. Immunol. 155(4):1903-1910.

\* cited by examiner

FIG. 1B

Yield (mg)/30ml 293T

Heavy Chain

| Light Chain | | WT | S183A | S183T | S183V | S183Y | S183F | S183H | S183N | S183D | S183E | S183R | S183K |
|---|---|---|---|---|---|---|---|---|---|---|---|---|---|
| | WT | 2.8 | 2.7 | 2.9 | 2.8 | 3.2 | 3.2 | 1.8 | 1.6 | 0.3 | 2.0 | 0.2 | 0.7 |
| | V133E | 1.7 | 2.3 | 3.6 | 4.5 | 2.9 | 4.4 | 0.1 | 0.0 | 0.0 | 0.0 | 0.2 | 0.2 |
| | V133S | 1.4 | 1.9 | 3.0 | 3.0 | 3.4 | 3.8 | 1.1 | 0.4 | 0.0 | 0.3 | 0.2 | 0.2 |
| | V133L | 1.8 | 2.6 | 2.3 | 2.9 | 3.2 | 3.0 | 1.8 | 1.1 | 0.2 | 1.0 | 0.1 | 0.2 |
| | V133W | 1.1 | 2.2 | 2.6 | 2.8 | 3.4 | 3.4 | 0.8 | 0.2 | 0.0 | 0.0 | 0.1 | 0.1 |
| | V133K | 0.4 | 1.4 | 2.6 | 2.2 | 2.4 | 3.6 | 0.0 | 0.0 | 0.4 | 0.2 | 0.1 | 0.1 |
| | V133R | 0.2 | 1.0 | 1.8 | 2.2 | 2.1 | 3.1 | 0.0 | 0.0 | 0.0 | 0.0 | 0.1 | 0.1 |
| | V133D | 0.3 | 1.1 | 2.0 | 2.0 | 1.7 | 3.2 | 0.1 | 0.0 | 0.0 | 0.0 | 0.2 | 0.2 |

*FIG. 4*

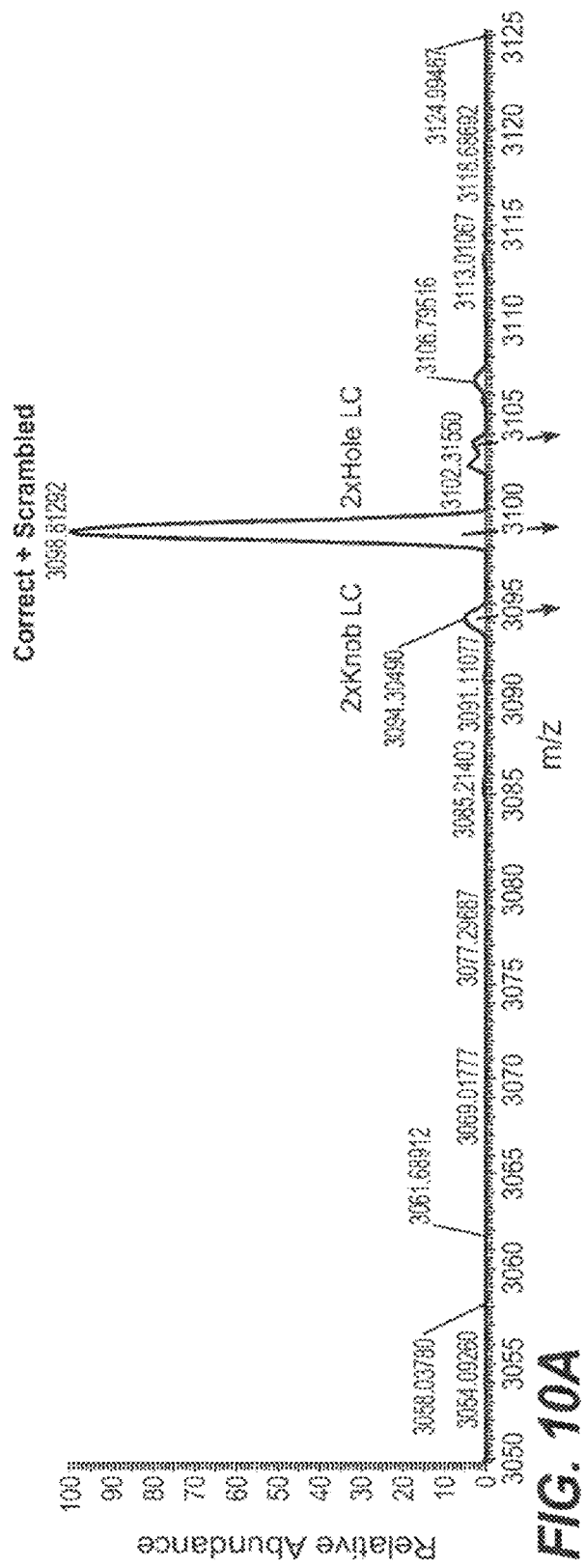
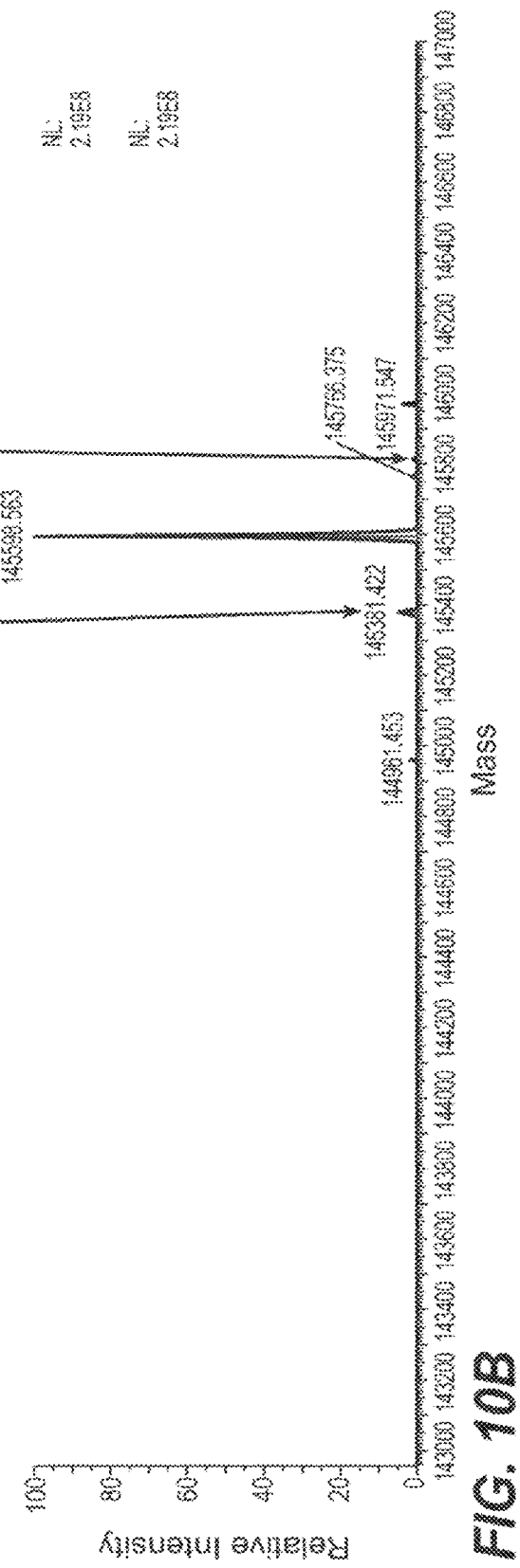
FIG. 10A
FIG. 10B

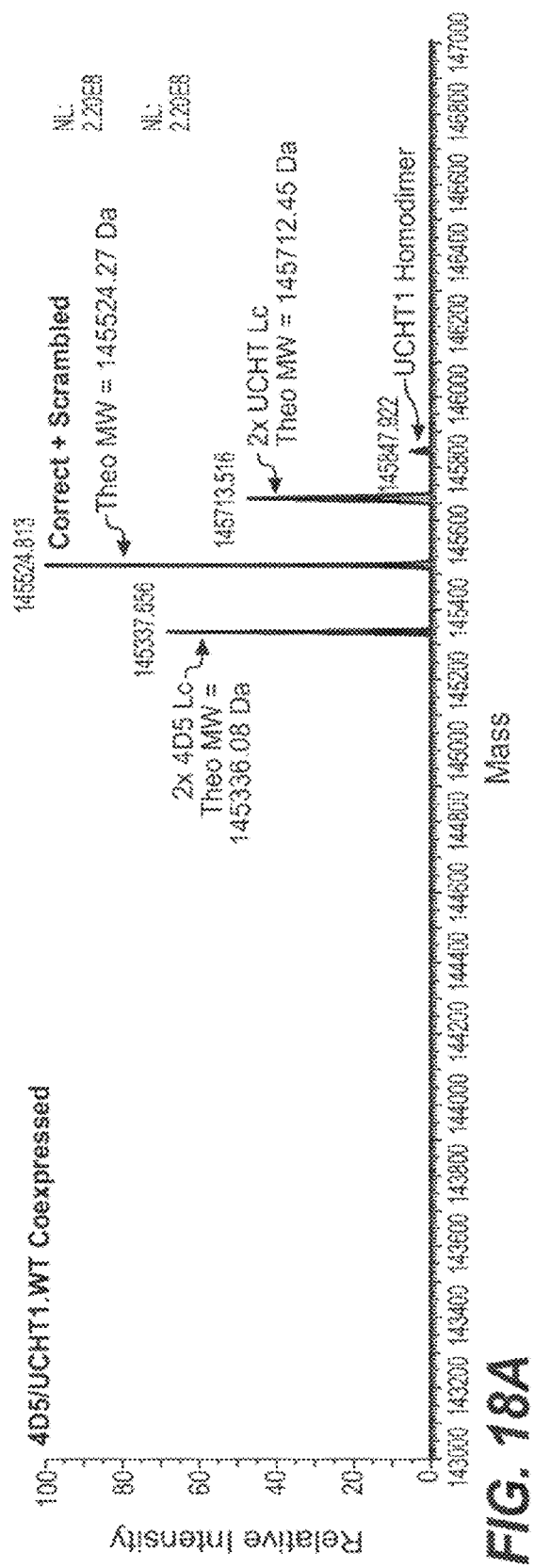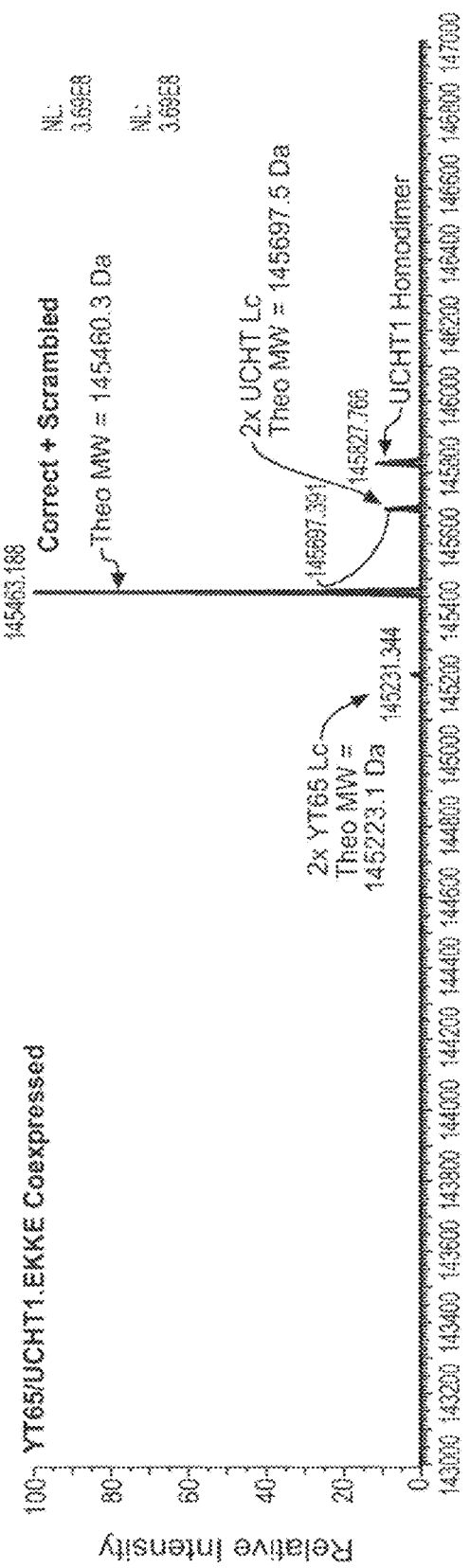
FIG. 18A
FIG. 18B

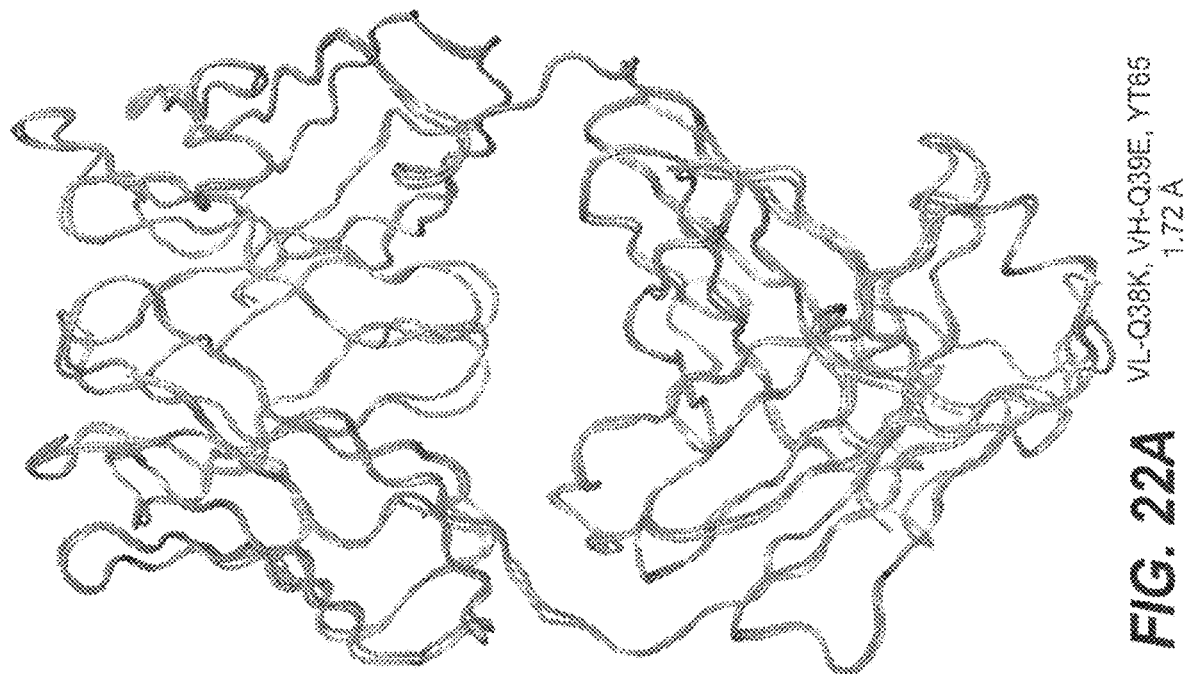
FIG. 22A  VL-Q38K, VH-Q39E, YT65
1.72 Å
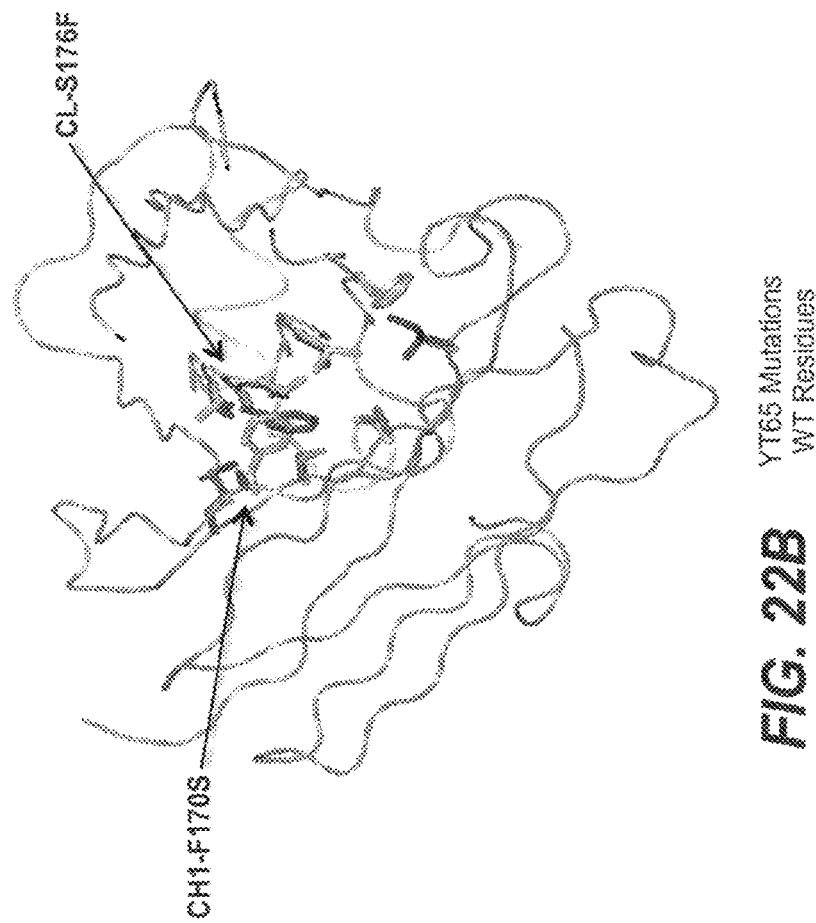
FIG. 22B  YT65 Mutations
WT Residues

MULTISPECIFIC ANTIGEN-BINDING PROTEINS

CROSS REFERENCE TO RELATED APPLICATIONS

This application is a divisional application of U.S. patent application Ser. No. 15/789,670, filed Oct. 20, 2017, now U.S. Pat. No. 11,116,840, issued Sep. 14, 2021, which is a continuation of PCT Application No. PCT/US2016/028850, filed Apr. 22, 2016, which claims the benefit of priority to U.S. Provisional Application No. 62/152,735 filed Apr. 24, 2015, U.S. Provisional Application No. 62/264,291 filed Dec. 7, 2015, and U.S. Provisional Application No. 62/310,555 filed Mar. 18, 2016, the contents of each of which are herein incorporated by reference in their entireties.

SEQUENCE LISTING

The content of the following submission on ASCII text file is incorporated herein by reference in its entirety: a computer readable form (CRF) of the Sequence Listing (file name: 146392027310SEQLIST.TXT, date recorded: Aug. 3, 2021, size: 131,266 bytes).

BACKGROUND OF THE INVENTION

The development of bispecific antibodies as therapeutic agents for human diseases has great clinical potential. However, production of bispecific antibodies in IgG format has been challenging, as antibody heavy chains have evolved to bind antibody light chains in a relatively promiscuous manner. As a result of this promiscuous pairing, concomitant expression of, e.g., two antibody heavy chains and two antibody light chains naturally leads to heavy chain homodimerization and scrambling of heavy chain/light chain pairings.

One approach to circumvent the problem of heavy chain homodimerization, known as 'knobs-into-holes', aims at forcing the pairing of two different antibody heavy chains by introducing mutations into the CH3 domains to modify the contact interface. On one heavy chain original amino acids were replaced by amino acids with short side chains to create a 'hole'. Conversely, amino acids with large side chains were introduced into the other CH3 domain, to create a 'knob'. By coexpressing these two heavy chains (and two identical light chains, which have to be appropriate for both heavy chains), high yields of heterodimer formation ('knob-hole') versus homodimer formation ('hole-hole' or 'knob-knob') was observed (Ridgway. J. B., Protein Eng. 9 (1996) 617-621; and WO 96/027011).

Minimizing the scrambling of heavy chain/light chain has been more difficult due to the complex multidomain heterodimeric interactions within antibody Fabs. Bispecific antibodies formats aimed at addressing heavy chain/light scrambling include: DVD-Ig (Dual Variable Domain Ig) (Nature Biotechnology 25, 1290-1297 (2007)); Cross-over Ig (Schaefer W et al (2011) PNAS 108(27): 11187-11192); Two-in-One Ig (Science 2009, 323, 1610); BiTE® antibodies (PNAS 92(15):7021-7025; 1995) and strategies described in Lewis et al. (2014) "Generation of bispecific IgG antibodies by structure-based design of an orthogonal Fab interface." *Nat Biotechnol* 32, 191-8; Liu et al. (2015) "A Novel Antibody Engineering Strategy for Making Monovalent Bispecific Heterodimeric IgG Antibodies by Electrostatic Steering Mechanism" *J Biol Chem*. Published online Jan. 12, 2015, doi:10.1074/jbc.M114.620260; Mazor et al. 2015. "Improving target cell specificity using a novel monovalent bispecific IgG design." *Mabs*. Published online Jan. 26, 2015, doi: 10.1080/19420862.2015.1007816; WO 2014/081955, WO 2014/082179, and WO 2014/150973.

There continues to be a need to reduce mispaired heavy chain/light chain by-products and increase bispecific antibody yield.

BRIEF SUMMARY OF THE INVENTION

As described in more detail below, multispecific antigen-binding proteins (such as bispecific antibodies) that have been modified to include such asymmetrical mutations are produced in a single cell with, inter alia, improved correct heavy chain/light chain pairing and/or improved yields of multispecific antigen-binding proteins as compared with multispecific antigen-binding proteins with sequences without modifications. In certain embodiments, the multispecific antigen-binding proteins comprise modification(s) in the VH/VL and/or CH1/CL regions to facilitate correct heavy/light chain pairing. In certain other embodiments, the multispecific antigen-binding proteins further comprise modification(s) in the Fc region to facilitate heterodimerization of the two arms of the multispecific antigen-binding protein.

Provided herein is a multispecific antigen binding protein, or an antigen-binding fragment thereof, comprising: a) a first heavy chain/light chain pair binding to a first antigen which comprises a first heavy chain polypeptide (H1) and a first light chain polypeptide (L1), and b) a second heavy chain/light chain pair binding to a second antigen which comprises a second heavy chain polypeptide (H2) and a second light chain polypeptide (L2), wherein each H1 and H2 comprises a heavy chain variable domain (VH) and a heavy chain constant domain (CH1), and each L1 and L2 comprises a light chain variable domain (VL) and a light chain constant domain (CL); wherein the CH1 domain of H1 comprises an amino acid substitution at S183 (EU numbering), and wherein the CL domain of L1 comprises an amino acid substitution at V133 (EU numbering). In certain embodiments according to (or as applied to) any of the embodiments above, L1 is a kappa chain. In certain embodiments according to (or as applied to) any of the embodiments above, L2 is a kappa chain. In certain embodiments according to (or as applied to) any of the embodiments above, L1 and L2 are each a kappa chain.

In some embodiments according to (or as applied to) any of the embodiments above, the S183 substitution is selected from the group consisting of S183A, S183T, S183V, S183Y, S183F, S183H, S183N, S183D, S183E, S183R, and S183K, and the V133 substitution is selected from the group consisting of V133E, V133S, V133L, V133W, V133K, V133R, and V133D. In some embodiments according to (or as applied to) any of the embodiments above the amino acid at EU position S183 on the CH1 domain of H1 is replaced with a positively charged residue, and the amino acid at V133 on the CL domain of L1 is replaced with a negatively charged residue. In some embodiments according to (or as applied to) any of the embodiments above the amino acid at EU position S183 on the CH1 domain of H1 is replaced with a negatively charged residue, and the amino acid at V133 on the CL domain of L1 is replaced with a positively charged residue. In some embodiments according to (or as applied to) any of the embodiments above the positively charged residue is selected from the group consisting of R and K. In some embodiments according to (or as applied to) any of the embodiments above the negatively charged residue is selected from the group consisting of D and E.

In certain embodiments according to (or as applied to) any of the embodiments above, the CH1 domain of H1 consists of an amino acid substitution at S183 (EU numbering), and the CL domain of L1 consists of an amino acid substitution at V133 (EU numbering).

In some embodiments according to (or as applied to) any of the embodiments above, the CH1 domain of H1 comprises the S183D mutation, and the CL domain of L1 comprises the V133K mutation; the CH1 domain of H1 comprises the S183E mutation, and the CL domain of L1 comprises the V133K mutation; the CH1 domain of H1 comprises the S183A mutation, and the CL domain of L1 comprises the V133E mutation: the CH1 domain of H1 comprises the S183A mutation, and the CL domain of L1 comprises the V133S mutation: the CH1 domain of H1 comprises the S183A mutation, and the CL domain of L1 comprises the V133L mutation; the CH1 domain of H1 comprises the S183A mutation, and the CL domain of L1 comprises the V133W mutation; the CH1 domain of H1 comprises the S183A mutation, and the CL domain of L1 comprises the V133K mutation; the CH1 domain of H1 comprises the S183A mutation, and the CL domain of L1 comprises the V133R mutation; the CH1 domain of H1 comprises the S183A mutation, and the CL domain of L1 comprises the V133D mutation; the CH1 domain of H1 comprises the S183T mutation, and the CL domain of L1 comprises the V133E mutation; the CH1 domain of H1 comprises the S183T mutation, and the CL domain of L1 comprises the V133S mutation; the CH1 domain of H1 comprises the S183T mutation, and the CL domain of L1 comprises the V133L mutation; the CH1 domain of H1 comprises the S183T mutation, and the CL domain of L1 comprises the V133W mutation; the CH1 domain of H1 comprises the S183T mutation, and the CL domain of L1 comprises the V133K mutation; the CH1 domain of H1 comprises the S183T mutation, and the CL domain of L1 comprises the V133R mutation; the CH1 domain of H1 comprises the S183T mutation, and the CL domain of L1 comprises the V133D mutation; the CH1 domain of H1 comprises the S183V mutation, and the CL domain of L1 comprises the V133E mutation; the CH1 domain of H1 comprises the S183V mutation, and the CL domain of L1 comprises the V133S mutation; the CH1 domain of H1 comprises the S183V mutation, and the CL domain of L1 comprises the V133L mutation; the CH1 domain of H1 comprises the S183V mutation, and the CL domain of L1 comprises the V133W mutation; the CH1 domain of H1 comprises the S183V mutation, and the CL domain of L1 comprises the V133K mutation; the CH1 domain of H1 comprises the S183V mutation, and the CL domain of L1 comprises the V133R mutation; the CH1 domain of H1 comprises the S183V mutation, and the CL domain of L1 comprises the V133D mutation; the CH1 domain of H1 comprises the S183Y mutation, and the CL domain of L1 comprises the V133E mutation; the CH1 domain of H1 comprises the S183Y mutation, and the CL domain of L comprises the V133S mutation; the CH1 domain of H1 comprises the S183Y mutation, and the CL domain of L1 comprises the V133L mutation; the CH1 domain of H1 comprises the S183Y mutation, and the CL of L1 domain comprises the V133W mutation; the CH1 domain of H1 comprises the S183Y mutation, and the CL of L1 domain comprises the V133K mutation; the CH1 domain of H1 comprises the S183Y mutation, and the CL domain of L1 comprises the V133R mutation; the CH1 domain of H1 comprises the S183Y mutation, and the CL domain of L1 comprises the V133D mutation; the CH1 domain of H1 comprises the S183F mutation, and the CL domain of L1 comprises the V133E mutation; the CH1 domain of H1 comprises the S183F mutation, and the CL domain of L1 comprises the V133S mutation; the CH1 domain of H1 comprises the S183F mutation, and the CL domain of L1 comprises the V133L mutation; the CH1 domain of H1 comprises the S183F mutation, and the CL domain of L1 comprises the V133W mutation; the CH1 domain of H1 comprises the S183F mutation, and the CL domain of L1 comprises the V133K mutation; the CH1 domain of H1 comprises the S183F mutation, and the CL domain of L1 comprises the V133R mutation; the CH1 domain of H1 comprises the S183F mutation, and the CL of L1 domain comprises the V133D mutation; the CH1 domain of H1 comprises the S183H mutation, and the CL domain of L1 comprises the V133S mutation; the CH1 domain of H1 comprises the S183H mutation, and the CL domain of L1 comprises the V133L mutation; the CH1 domain of H1 comprises the S183H mutation, and the CL domain of L1 comprises the V133W mutation; the CH1 domain of H1 comprises the S183N mutation, and the CL domain of L1 comprises the V133L mutation; or the CH1 domain of H1 comprises the S183E mutation, and the CL domain of L1 comprises the V133L mutation.

In some embodiments according to (or as applied to) any of the embodiments above, the CH1 domain of H1 comprises the S183D mutation, and the CL domain of L1 comprises the V133K mutation; the CH1 domain of H1 comprises the S183E mutation, and the CL domain of L1 comprises the V133K mutation; the CH1 domain of H1 comprises the S183T mutation, and the CL domain of L1 comprises the V133K mutation; or the CH1 domain of H1 comprises the S183V mutation, and the CL domain of L1 comprises the V133E mutation.

In certain embodiments, the CH1 domain of H1 comprises the S183K mutation, and the CL domain of L1 comprises the V133E mutation.

In some embodiments according to (or as applied to) any of the embodiments above, the CH1 domain of H1 consists of the S183D mutation, and the CL domain of L1 consists of the V133K mutation; the CH1 domain of H1 consists of the S183E mutation, and the CL domain of L1 consists of the V133K mutation: the CH1 domain of H1 consists of the S183T mutation, and the CL domain of L1 consists of the V133K mutation; or the CH1 domain of H1 consists of the S183V mutation, and the CL domain of L1 consists of the V133E mutation. In certain embodiments, the CH1 domain of H1 consists of the S183K mutation, and the CL domain of L1 consists of the V133E mutation.

In some embodiments according to (or as applied to) any of the embodiments above the CH1 domain of H2 and/or the CL domain of L2 does not comprise an amino acid substitution. In some embodiments according to (or as applied to) any of the embodiments above the CH1 domain of H2 does not comprise a substitution at S183 and the CL domain of L2 do not comprise substitution at V133.

In some embodiments according to (or as applied to) any of the embodiments above the VH domain of H1 and/or H2 comprises an amino acid substitution at position Q39 (Kabat numbering), and the VL domain of L1 and/or L2 comprises an amino acid substitution at position Q38 (Kabat numbering). In some embodiments according to (or as applied to) any of the embodiments above the amino acid at Q39 in the VH domain is replaced with a positively charged residue, and the amino acid at Q38 in the VL domain is replaced with a negatively charged residue. In some embodiments according to (or as applied to) any of the embodiments above the amino acid at Q39 in the VH domain is replaced with a negatively charged residue, and the amino acid at Q38 in the VL domain is replaced with a positively charged residue. In some embodiments according to (or as applied to) any of the embodiments above the positively charged residue is selected from the group consisting of R and K. In some embodiments according to (or as applied to) any of the embodiments above the negatively charged residue is selected from the group consisting of D and E.

In some embodiments according to (or as applied to) any of the embodiments above the amino acid at EU position S183 on the CH1 domain of H1 is replaced with a negatively charged residue, the amino acid at Q39 in the VH domain is replaced with a positively charged residue, the amino acid at V133 on the CL domain of L1 is replaced with a positively charged residue, and the amino acid at Q38 in the VL domain is replaced with a negatively charged residue (Kabat numbering).

In some embodiments according to (or as applied to) any of the embodiments above the amino acid at EU position S183 on the CH1 domain of H1 is replaced with a positively charged residue, the amino acid at Q39 in the VH domain is replaced with a negatively charged residue, the amino acid at V133 on the CL domain of L1 is replaced with a negatively charged residue, and the amino acid at Q38 in the VL domain is replaced with a positively charged residue (Kabat numbering). In some embodiments according to (or as applied to) any of the embodiments above the amino acid at EU position S183 on the CH1 domain of H1 is replaced with a positively charged residue, the amino acid at Q39 in the VH domain is replaced with a negatively charged residue, the amino acid at V133 on the CL domain of L is replaced with a negatively charged residue, and the amino acid at Q38 in the VL domain of L is replaced with a positively charged residue (Kabat numbering). In further embodiments, the amino acid at EU position S183 on the CH1 domain of H2 is replaced with a negative charged residue, the amino acid at Q39 in the VH domain of H2 is replaced with a positively charged residue, the amino acid at V133 on the CL domain of L2 is replaced with a positively charged residue, and the amino acid at Q38 in the VL domain is replaced with a negatively charged residue (Kabat numbering).

In some embodiments according to (or as applied to) any of the embodiments above, the VH domain of H1 comprises a Q39E substitution mutation (Kabat numbering), and the VL domain of L1 comprises a Q38K substitution mutation (Kabat numbering). In some embodiments according to (or as applied to) any of the embodiments above the VH domain of H1 comprises a Q39E substitution mutation, the VL domain of L1 comprises a Q38K substitution mutation, and the VH domain of H2 comprises a Q39K substitution mutation. In some embodiments according to (or as applied to) any of the embodiments above, the VH domain of H1 comprises the Q39E substitution mutation, the VL domain of L1 comprises the Q38K substitution mutation, the VH domain of H2 comprises a Q39K substitution mutation, and the VL domain of L2 comprises a Q38E substitution mutation.

In some embodiments according to (or as applied to) any of the embodiments above, the VH domain of H1 comprises a Q39K substitution mutation (Kabat numbering), and the VL domain of L1 comprises a Q38E substitution mutation (Kabat numbering). In some embodiments according to (or as applied to) any of the embodiments above, the VH domain of H1 comprises a Q39K substitution mutation, the VL domain of L1 comprises a Q38E substitution mutation, and the VH domain of H2 comprises a Q39E substitution mutation (all Kabat numbering). In some embodiments according to (or as applied to) any of the embodiments above, the VH domain of H1 comprises a Q39K substitution mutation, the VH domain of H2 comprises a Q39E substitution mutation, and the VL domain of L2 comprises a Q38K substitution mutation (all Kabat numbering). In some embodiments according to (or as applied to) any of the embodiments above, the VH domain of H1 comprises the Q39K substitution mutation, the VL domain of L1 comprises the Q38E substitution mutation, the VH domain of H2 comprises a Q39E substitution mutation, and the VL domain of L2 comprises a Q38K substitution mutation (all Kabat numbering).

In some embodiments according to (or as applied to) any of the embodiments above, the interaction between the two substituted amino acids is via hydrogen bonds. In some embodiments according to (or as applied to) any of the embodiments above, the interaction between the two substituted amino acids is via electrostatic interaction.

In some embodiments according to (or as applied to) any of the embodiments above, the VH domain of H1 comprises a Q39K substitution mutation and the CH1 domain of H1 comprises the S183E substitution mutation, the VL domain of L1 comprises a Q38E substitution mutation and the CL domain of L1 comprises the V133K mutation, the VH domain of H2 comprises the Q39E substitution mutation, and the VL domain of L2 comprises the Q38K substitution mutation.

In some embodiments according to (or as applied to) any of the embodiments above, the VH domain of H1 comprises a Q39K substitution mutation and the CH1 domain of H1 comprises the S183T substitution mutation, the VL domain of L1 comprises a Q38E substitution mutation and the CL domain of L1 comprises the V133K mutation, the VH domain of H2 comprises the Q39E substitution mutation, and the VL domain of L2 comprises the Q38K substitution mutation.

In some embodiments according to (or as applied to) any of the embodiments above, the VH domain of H1 comprises a Q39K substitution mutation and the CH1 domain of H1 comprises the S183Y substitution mutation, the VL domain of L1 comprises a Q38E substitution mutation and the CL domain of L comprises the V133K mutation, the VH domain of H2 comprises the Q39E substitution mutation, and the VL domain of L2 comprises the Q38K substitution mutation.

In some embodiments according to (or as applied to) any of the embodiments above, the VH domain of H1 comprises a Q39K substitution mutation and the CH1 domain of H1 comprises the S183F substitution mutation, the VL domain of L1 comprises a Q38E substitution mutation and the CL domain of L1 comprises the V133K mutation, the VH domain of H2 comprises the Q39E substitution mutation, and the VL domain of L2 comprises the Q38K substitution mutation.

In some embodiments according to (or as applied to) any of the embodiments above, the VH domain of H1 comprises a Q39E substitution mutation and the CH1 domain of H1 comprises the S183E substitution mutation, the VL domain of L1 comprises a Q38K substitution mutation and the CL domain of L1 comprises the V133K mutation, the VH domain of H2 comprises the Q39K substitution mutation, and the VL domain of L2 comprises the Q38E substitution mutation.

In some embodiments according to (or as applied to) any of the embodiments above, the VH domain of H1 comprises a Q39K substitution mutation, the VL domain of L1 comprises a Q38E substitution mutation, the VH domain of H2 comprises the Q39E substitution mutation and the CH1 domain of H2 comprises the S183E substitution mutation, and the VL domain of L2 comprises the Q38K substitution mutation and the CL domain of L1 comprises the V133K mutation.

In some embodiments according to (or as applied to) any of the embodiments above, the VH domain of H1 comprises the Q39E substitution mutation and the CH1 domain of H1 comprises the S183K substitution mutation, the VL domain of L1 comprises the Q38K substitution mutation and the CL domain of L1 comprises the V133E substitution mutation, the VH domain of H2 comprises a Q39K substitution mutation and the CH1 domain of H2 comprises the S183E substitution mutation, and the VL domain of L2 comprises a Q38E substitution mutation and the CL domain of L2 comprises the V133K mutation.

In some embodiments according to (or as applied to) any of the embodiments above, the VH domain of H1 comprises the Q39E substitution mutation and the CH1 domain of H1 comprises the S183E substitution mutation, the VL domain of L comprises the Q38K substitution mutation and the CL domain of L1 comprises the V133K substitution mutation, the VH domain of H2 comprises a Q39K substitution mutation and the CH1 domain of H2 comprises the S183K substitution mutation, and the VL domain of L2 comprises a Q38E substitution mutation and the CL domain of L2 comprises the V133E mutation.

In some embodiments according to (or as applied to) any of the embodiments above, the VH domain of H1 comprises the Q39E substitution mutation and the CH1 domain of H1 comprises the S183E substitution mutation, the VL domain of L comprises the Q38K substitution mutation and the CL domain of L1 comprises the V133K substitution mutation, the VH domain of H2 comprises a Q39K substitution mutation and the CH1 domain of H2 comprises the S183K substitution mutation, and the VL domain of L2 comprises a Q38E substitution mutation and the CL domain of L2 comprises the V133E mutation.

In some embodiments according to (or as applied to) any of the embodiments above, the VH domain of H1 comprises the Q39K substitution mutation and the CH1 domain of H1 comprises the S183E substitution mutation, the VL domain of L1 comprises the Q38K substitution mutation and the CL domain of L comprises the V133E substitution mutation, the VH domain of H2 comprises a Q39E substitution mutation and the CH1 domain of H2 comprises the S183E substitution mutation, and the VL domain of L2 comprises a Q38K substitution mutation and the CL domain of L2 comprises the V133K mutation.

In some embodiments according to (or as applied to) any of the embodiments above, the VH domain of H1 comprises the Q39K substitution mutation and the CH1 domain of H1 comprises the S183E substitution mutation, the VL domain of L1 comprises the Q38E substitution mutation and the CL domain of L1 comprises the V133K substitution mutation, the VH domain of H2 comprises a Q39E substitution mutation and the CH1 domain of H2 comprises the S183K substitution mutation, and the VL domain of L2 comprises a Q38K substitution mutation and the CL domain of L2 comprises the V133E mutation.

In some embodiments according to (or as applied to) any of the embodiments above, the VH domain of H1 comprises the Q39K substitution mutation, the CH1 domain of H1 comprises the S183K substitution mutation, the VL domain of L1 comprises the Q38E substitution mutation, the CL domain of L1 comprises the V133E substitution mutation, the VH domain of H2 comprises a Q39E substitution mutation, the CH1 domain of H2 comprises the S183E substitution mutation, the VL domain of L2 comprises a Q38K substitution mutation, and the CL domain of L2 comprises the V133K mutation.

In some embodiments according to (or as applied to) any of the embodiments above, each of H1 and/or H2 comprises an Fc region comprising a CH2 and a CH3 domain. In some embodiments according to (or as applied to) any of the embodiments above, the Fc region of H1 and/or H2 is human IgG1, human IgG2 or human IgG4 Fc. In some embodiments according to (or as applied to) any of the embodiments above, the Fc region of H1 and/or H2 is mouse IgG1, mouse IgG2 or mouse IgG4 Fc. In some embodiments according to (or as applied to) any of the embodiments above, the CH3 domains of H1 and H2 each meet at an interface, and each of the CH3 domains comprises an amino acid substitution such that the Fc region of H1 preferentially pairs with that of H2 as compared to H1. In some embodiments according to (or as applied to) any of the embodiments above, the amino acid substitutions in the CH3 domains result in greater electrostatic complementarity. In some embodiments according to (or as applied to) any of the embodiments above, the amino acid substitutions in the CH3 domains result in greater steric complementarity. In some embodiments according to (or as applied to) any of the embodiments above, the CH3 domain of H1 is altered, so that within the CH3/CH3 interface, one or more amino acid residues are replaced with one or more amino acid residues having a larger side chain volume, thereby generating a protuberance on the surface of the CH3 domain of H1 that interacts with the CH3 domain of H2 and the CH3 domain of H2 is altered so that within the CH3/CH3 interface one or more amino acid residues are replaced with amino acid residues having a smaller side chain volume, thereby generating a cavity on the surface of the CH3 domain of H2 that interacts with the CH3 domain of H1. In some embodiments according to (or as applied to) any of the embodiments above, the CH3 domain of H2 is altered, so that within the CH3/CH3 interface, one or more amino acid residues are replaced with one or more amino acid residues having a larger side chain volume, thereby generating a protuberance on the surface of the CH3 domain of H2 that interacts with the CH3 domain of H1 and the CH3 domain of H1 is altered so that within the CH3/CH3 interface, one or more amino acid residues are replaced amino acid residues having a smaller side chain volume, thereby generating a cavity on the surface of the CH3 domain of H1 that interacts with the CH3 domain of H2. In some embodiments according to (or as applied to) any of the embodiments above, the protuberance is a knob mutation. In some embodiments according to (or as applied to) any of the embodiments above, the alteration to generate the knob is T366W (EU numbering). In some embodiments according to (or as applied to) any of the embodiments above, the cavity is a hole mutation (EU numbering). In some embodiments according to (or as applied to) any of the embodiments above, the alterations to generate the hole are at least one of T366S, L368A, and Y407V.

In some embodiments according to (or as applied to) any of the embodiments above, the knob comprises T366W (EU numbering). In some embodiments according to (or as applied to) any of the embodiments above, the hole mutation comprises at least one, at least two, or all three of T366S, L368A, and Y407V.

In some embodiments according to (or as applied to) any of the embodiments above, the CH1 domain of H1 is further altered so that within the CH1/CL interface, two or more amino acid residues are replaced with an equivalent number of amino acid residues having a larger side chain volume, thereby generating a protuberance on the surface of the CH1 domain of H1 that interacts with the CL domain of L1, and the CL domain of L1 is further altered so that within the CH1/CL interface, two or more amino acid residues are replaced with an equivalent number of amino acid residues having a smaller side chain volume, thereby generating a cavity on the surface of the CL domain of L1 that interacts with the CH1 domain of H1.

In some embodiments according to (or as applied to) any of the embodiments above, the CL domain is further altered so that within the CH1/CL interface, two or more amino acid residues are replaced with an equivalent number of amino acid residues having a larger side chain volume, thereby generating a protuberance on the surface of the CL domain that interacts with the CH1 domain of H1, and the CH1 domain of H1 is further altered so that within the CH1/CL interface, two or more amino acid residues are replaced with an equivalent number of amino acid residues having a smaller side chain volume, thereby generating a cavity on the surface of the CH1 domain of H1 that interacts with the CL domain.

Also provided herein is a multispecific antigen binding protein, or an antigen-binding fragment thereof, comprising: a) a first heavy chain/light chain pair comprising a first heavy chain polypeptide (H1) and a first light chain polypeptide (L1), and b) a second heavy chain/light chain pair comprising a second heavy chain polypeptide (H2) and a second light chain polypeptide (L2), each H1 and H2 comprises a heavy chain variable domain (VH) and a heavy chain constant domain (CH1), and each L1 and L2 comprises a light chain variable domain (VL) and a light chain constant domain (CL); the CH1 domain of H1 comprises an amino acid substitution at F170 (EU numbering), and the CL domain of L1 comprises an amino acid substitution at S176 (EU numbering). In certain embodiments according to (or as applied to) any of the embodiments above, L1 is a kappa chain. In certain embodiments according to (or as applied to) any of the embodiments above, L2 is a kappa chain. In certain embodiments according to (or as applied to) any of the embodiments above, L1 and L2 are each a kappa chain.

In some embodiments according to (or as applied to) any of the embodiments above, the CH1 domain of H1 further comprises one or more amino acid substitutions at a position selected from the group consisting of: A141, S181, S183, and V185 (EU numbering). In some embodiments according to (or as applied to) any of the embodiments above, the CL domain of L1 further comprises one or more amino acid substitutions at a position selected from the group consisting of F116, S131, V133, L135, S162, S174, and T178 (EU numbering). In some embodiments according to (or as applied to) any of the embodiments above, the amino acid substitutions result in steric complementarity.

In some embodiments according to (or as applied to) any of the embodiments above, the one or more amino acid substitutions at a position selected from the group consisting of A141, F170, S181, S183, and V185 (EU numbering) of CH1 and/or the one or more amino acid substitutions at a position selected from the group consisting of F116, S131, V133, L135, S162, S174, S176, and T178 (EU numbering) of CL are not substituted with charged amino acid residues.

In some embodiments according to (or as applied to) any of the embodiments above, the CH1 domain of H1 comprises an amino acid substitution selected from the group consisting of F170S and F170A, and the CL domain of L1 comprises an amino acid substitution of S176F. In some embodiments according to (or as applied to) any of the embodiments above, the CH1 domain of H1 comprises the F170S mutation, and the CL domain of L1 comprises the S176F mutation; or the CH1 domain of H1 comprises the F170A mutation, and the CL domain of L1 comprises the S176F mutation. In some embodiments according to (or as applied to) any of the embodiments above, the CH1 domain of H1 comprises the F170S mutation, and the CL domain of L1 comprises the S176F mutation.

In some embodiments according to (or as applied to) any of the embodiments above, the CH1 domain of H1 comprises the A141I, F170S, S181M, S183V, and V185A mutations, and the CL domain of L1 comprises the F116A, V133I, L135V, S162M, S174A, S176F, and T178V mutations; the CH1 domain of H1 comprises the A141I, F170S, S181M, S183A, and V185A mutations and the CL domain of L1 comprises the F116A, S131D, L135V, S162A, S174A, S176F, and T178I mutations; the CH1 domain of H1 comprises the A141I, F170S, S181M, S183A, and V185A mutations and the CL domain of L1 comprises the F116A, L135V, S174A, S176F, and T178V mutations; or the CH1 domain of H1 comprises the A141I, F170A, S181M, S183V, and V185A mutations and the CL domain of L1 comprises the F116A, L135V, S162M, S174A, S176F, and T178V mutations. In some embodiments according to (or as applied to) any of the embodiments above, the CH1 domain of H1 comprises A141I, F170S, S181M, S183A, and V185A mutations and the CL domain of L1 comprises F116A, L135V, S174A, S176F, and T178V mutations.

In some embodiments according to (or as applied to) any of the embodiments above, the CH1 domain of H1 comprises A141I, F170S, S181M, S183A, and V185A mutations and the CL domain of L1 comprises F116A, L135V, S174A, S176F, and T178V mutations. In some embodiments according to (or as applied to) any of the embodiments above, the CH1 domain of H1 comprises A141I, F170S, S181M, S183A, and V185A mutations, the CL domain of L1 comprises F116A, L135V, S174A, S176F, and T178V mutations, the CH1 domain of H2 comprises an amino acid substitution mutation at S183 (EU numbering) and the CL domain of L2 comprises an amino acid substitution mutation V133K (EU numbering). In some embodiments according to (or as applied to) any of the embodiments above, the CH1 domain of H1 comprises A141I, F170S, S181M, S183A, and V185A mutations, the CL domain of L1 comprises F116A, L135V, S174A, S176F, and T178V mutations, the CH1 domain of H2 comprises an amino acid substitution mutation at S183 (EU numbering) and the CL domain of L2 comprises an amino acid substitution mutation V133 (EU numbering). In certain embodiments according to (or as applied to) any of the embodiments above, the amino acid at position S183 in the CH1 domain of H2 is replaced with a positively charged amino acid, and the amino acid at position V133 in the CL domain of L2 is replaced with a negatively charged amino acid. In certain embodiments according to (or as applied to) any of the embodiments above, the amino acid at position S183 in the CH1 domain of H2 is replaced with a negatively charged amino acid, and wherein the amino acid at position V133 in the CL domain of L2 is replaced with a positively charged amino acid.

In some embodiments according to (or as applied to) any of the embodiments above, the CH1 domain of H1 comprises A141I, F170S, S181M, S183A, and V185A mutations (EU numbering), the VH domain of H1 comprises a Q39E mutation (Kabat numbering) and the CL domain of L1 comprises F116A, L135V, S174A, S176F, and T178V mutations (EU numbering), the VL domain of L comprises a Q38K mutation (Kabat numbering), the VH domain of H2 comprises a Q39K mutation (Kabat numbering), and the VL domain of L2 comprises a Q38E mutation (Kabat numbering).

In some embodiments according to (or as applied to) any of the embodiments above, the CH1 domain of H1 comprises A141I, F170S, S181M, S183A, and V185A mutations (EU numbering) and the CL domain of L1 comprises F116A, L135V, S174A, S176F, and T178V mutations (EU numbering), the CH1 domain of H2 comprises an S183E mutation (EU numbering) and the CL domain of L2 comprises a V133K mutation (EU numbering).

In some embodiments according to (or as applied to) any of the embodiments above, the CH1 domain of H1 comprises A141I, F170S, S181M, S183A, and V185A mutations (EU numbering), the VH domain of H1 comprises a Q39E mutation (Kabat numbering) and the CL domain of L1 comprises F116A, L135V, S174A, S176F, and T178V mutations (EU numbering), the VL domain of L1 comprises a Q38K mutation (Kabat numbering), the CH1 domain of H2 comprises an S183E mutation (EU numbering), the VH domain of H2 comprises a Q39K mutation (Kabat numbering), the CL domain of L2 comprises a V133K mutation (EU numbering), and the VL domain of L2 comprises a Q38E mutation (Kabat numbering).

In some embodiments according to (or as applied to) any of the embodiments above, the CH1 domain of H1 comprises A141I, F170S, S181M, S183A, and V185A mutations (EU numbering), the VH domain of H1 comprises a Q39K mutation (Kabat numbering), the CL domain of L1 comprises F116A, L135V, S174A, S176F, and T178V mutations, the VL domain of L1 comprises a Q38E mutation (Kabat numbering), the VH domain of H2 comprises a Q39E mutation (Kabat numbering), and the VL domain of L2 comprises a Q38K mutation (Kabat numbering).

In some embodiments according to (or as applied to) any of the embodiments above, the CH1 domain of H1 comprises A141I, F170S, S181M, S183A, and V185A mutations, the CL domain of L1 comprises F116A, L135V, S174A, S176F, and T178V mutations, the CH1 domain of H2 comprises an S183K mutation (EU numbering), and the CL domain of L2 comprises a V133K mutation (EU numbering).

In some embodiments according to (or as applied to) any of the embodiments above, the CH1 domain of H1 comprises A141I, F170S, S181M, S183A, and V185A mutations (EU numbering), the VH domain of H1 comprises a Q39K mutation (Kabat numbering), the CL domain of L1 comprises F116A, L135V, S174A, S176F, and T178V mutations, the VL domain of L1 comprises a Q38E mutation (Kabat numbering), the CH1 domain of H2 comprises an S183K mutation (EU numbering), the VH domain of H2 comprises a Q39E mutation (Kabat numbering), the CL domain of L2 comprises a V133K mutation (EU numbering), and the VL domain of L2 comprises a Q38K mutation (Kabat numbering).

In some embodiments according to (or as applied to) any of the embodiments above, the CH1 domain of H1 comprises F170S, S181M, S183A, and V185A mutations and the CL domain of L1 comprises L135V, S174A, S176F, and T178V mutations; the CH1 domain of H1 comprises A141I, F170S, S183A, and V185A mutations and the CL domain of L1 comprises F116A, S174A, S176F, and T178V mutations; the CH1 domain of H1 comprises A141I, F170S, S181M, and V185A mutations and the CL domain of L1 comprises F116A, L135V, S176F, and T178V mutations: the CH1 domain of H1 comprises A141I, F170S, S181M, and S183A mutations and the CL domain of L comprises F116A, L135V, S174A, S176F, and T178V mutations: the CH1 domain of H1 comprises F170S, S183A, and V185A mutations and the CL domain of L1 comprises F116A, S176F, and T178V mutations; the CH1 domain of H1 comprises F170S, S181M, and V185A mutations and the CL domain of L1 comprises F116A, L135V, and S176F mutations; the CH1 domain of H1 comprises F170S, S181M, and S183A mutations and the CL domain of L1 comprises F116A, L135V, and S176F mutations; the CH1 domain of H1 comprises A141I, F170S, and V185A mutations and the CL domain of L1 comprises F116A and S176F mutations: the CH1 domain of H1 comprises A141I, F170S, and S183A mutations and the CL domain of L1 comprises F116A and S176F mutations; the CH1 domain of H1 comprises A141I, F170S, and S181M mutations and the CL domain of L1 comprises F116A, L135V, S174A, S176F, and T178V mutations; the CH1 domain of H1 comprises F170S and V185A mutations and the CL domain of L1 comprises F116A and S176F mutations; the CH1 domain of H1 comprises A141I and F170S mutations and the CL domain of L1 comprises F116A, L135V, S174A, S176F, and T178V mutations; the CH1 domain of H1 comprises A141I and F170S mutations and the CL domain of L comprises F116A, L135V, S176F, and T178V mutations; the CH1 domain of H1 comprises A141I and F170S mutations and the CL domain of L1 comprises F116A, L135V, S174A, S176F, and T178V mutations; the CH1 domain of H1 comprises A141I and F170S mutations and the CL domain of L1 comprises F116A, L135V, and S176F mutations: the CH1 domain of H1 comprises A141I and F170S mutations and the CL domain of L1 comprises F116A, L135V, and S176F mutations: the CH1 domain of H1 comprises the F170S mutation and the CL domain of L1 comprises F116A, L135V, S174A, S176F, and T178V mutations; the CH1 domain of H1 comprises the F170S mutation and the CL domain of L comprises F116A, L135V, S176F, and T178V mutations; the CH1 domain of H1 comprises the F170S mutation and the CL domain of L1 comprises F116A, L135V, S174A, S176F, and T178V mutations; the CH1 domain of H1 comprises the F170S mutation and the CL domain of L1 comprises F116A, L135V, and S176F mutations; or the CH1 domain of H1 comprises the F170S mutation and the CL domain of L1 comprises F116A, L135V, and S176F mutations.

In some embodiments according to (or as applied to) any of the embodiments above, the CH1 domain of H1 comprises the CH1 domain of H1 comprises A141I, F170S, S181M, and S183A mutations and the CL domain of L1 comprises F116A, L135V, S174A, and S176F mutations: the CH1 domain of H1 comprises F170S, S181M, and S183A mutations and the CL domain of L1 comprises F116A, and S176F mutations; the CH1 domain of H1 comprises A141I and F170S mutations and the CL domain of L1 comprises F116A, L135V, S174A, and S176F mutations; the CH1 domain of H1 comprises A141I and F170S mutations and the CL domain of L1 comprises F116A, and S176F mutations; the CH1 domain of H1 comprises the F170S mutation and the CL domain of L1 comprises F116A, L135V, S174A, and S176F mutations; or the CH1 domain of H1 comprises the F170S mutation and the CL domain of L1 comprises F116A, and S176F mutations.

In some embodiments according to (or as applied to) any of the embodiments above, the CH1 domain of H1 comprises A141I, F170S, and S181M mutations and the CL domain of L1 comprises F116A, L135V, S174A, S176F, and T178V mutations. In some embodiments according to (or as applied to) any of the embodiments above, the CH1 domain of H1 comprises A141I and F170S mutations and the CL domain of L comprises F116A, L135V, S174A, S176F, and T178V mutations. In some embodiments according to (or as applied to) any of the embodiments above, the CH1 domain of H1 comprises the F170S mutation and the CL domain of L comprises F116A, L135V, S174A, S176F, and T178V mutations.

In some embodiments according to (or as applied to) any of the embodiments above, the CH1 domain of H1 comprises A141I and F170S mutations and the CL domain of L1 comprises F116A, L135V, S174A, and S176F mutations.

Provided herein is an antigen binding protein, or an antigen-binding fragment thereof, comprising: a) a first heavy chain/light chain pair comprising a first heavy chain sequence (H1) and a first light chain sequence (L1), and b) a second heavy chain/light chain pair comprising a second heavy chain sequence (H2) and a second light chain sequence (L2), each H1 and H2 comprises a heavy chain variable domain (VH) and a heavy chain constant domain (CH1), and each L1 and L2 comprises a light chain variable domain (VL) and a light chain constant domain (CL); the CH1 domain of H1 comprises amino acid substitutions at L128 and V185, (EU numbering) and the CL domain of C1 comprises a amino acid substitutions at F118 and L135 (EU numbering). In certain embodiments according to (or as applied to) any of the embodiments above, L1 is a kappa chain. In certain embodiments according to (or as applied to) any of the embodiments above, L2 is a kappa chain. In certain embodiments according to (or as applied to) any of the embodiments above, L1 and L2 are each a kappa chain.

Also provided herein is an antigen binding protein, or an antigen-binding fragment thereof, comprising: a) a first heavy chain/light chain pair comprising a first heavy chain sequence (H1) and a first light chain sequence (L1), and b) a second heavy chain/light chain pair comprising a second heavy chain sequence (H2) and a second light chain sequence (L2), each H1 and H2 comprises a heavy chain variable domain (VH) and a heavy chain constant domain (CH1), and each L1 and L2 comprises a light chain variable domain (VL) and a light chain constant domain (CL); the CH1 domain of H1 comprises an amino acid substitutions at L128, (EU numbering) and the CL domain of C1 comprises a amino acid substitutions at F118 and L135 (EU numbering). In certain embodiments according to (or as applied to) any of the embodiments above, L1 is a kappa chain. In certain embodiments according to (or as applied to) any of the embodiments above, L2 is a kappa chain. In certain embodiments according to (or as applied to) any of the embodiments above, L1 and L2 are each a kappa chain. In some embodiments according to (or as applied to) any of the embodiments above, the CH1 domain of H1 further comprises an amino acid substitution at V185 (EU numbering).

In some embodiments according to (or as applied to) any of the embodiments above, the CH1 domain of H1 further comprises one or more amino acid substitutions at a position selected from the group consisting of: A141, F170, S181, and S183 (EU numbering). In some embodiments according to (or as applied to) any of the embodiments above, the CL domain of L1 further comprises one or more amino acid substitutions at a position selected from the group consisting of S131, V133, S162, T164, S176 and T178 (EU numbering). In some embodiments according to (or as applied to) any of the embodiments above, the amino acid substitutions result in greater steric complementarity.

In some embodiments according to (or as applied to) any of the embodiments above, the CH1 domain of H1 comprises an amino acid substitution at a position selected from the group consisting of A141, F170, S181, and S183, and the CL domain comprises an amino acid substitution at a position selected from the group consisting of S131, V133, S162, T164, S176 and T178.

In some embodiments according to (or as applied to) any of the embodiments above, the one or more amino acid substitutions at a position selected from the group consisting of L128 A141, F170, S181, S183, V185 (EU numbering) of CH1 and/or the one or more amino acid substitutions at a position selected from the group consisting of F118, S131, V133, and L135 S162, T164, S176 and T178 (EU numbering) of CL are not substituted with charged amino acid residues.

In some embodiments according to (or as applied to) any of the embodiments above, the CH1 domain of H1 comprises L128F, A141M, F170M, S181I and S183A mutations and the CL domain comprises F118V, S131T, V133A, L135Y, S162A, T164S, S176M, and T178L mutations: the CH1 domain of H1 comprises L128F, A141M, F170Y, S181I, S183A, and V185A mutations and the CL domain comprises F118V, S131T, V133A, L135F, S162A, S176A, and T178L mutations: the CH1 domain of H1 comprises L128F, A141T, F170M, S181T, S183A, and V185L mutations and the CL domain comprises F118V, S131T, V133A, L135F, S162A, T164S, S176T, and T178L mutations; or the CH1 domain of H1 comprises L128F, A141M, F170M, S181T, and S183A, mutations and the CL domain comprises F118V, S131T, V133A, L135F, S162M, T164S, S176M, and T178L mutations. In some embodiments according to (or as applied to) any of the embodiments above, the CH1 domain of H1 comprises the L128F, A141M, F170Y, S181I, S183A, and V185A mutations, and the CL domain comprises the F118V, S131T, V133A, L135F, S162A, S176A, and T178L mutations.

In some embodiments according to (or as applied to) any of the embodiments above, the CH1 domain of H2 comprises S183E mutation, and the CL domain of L2 comprises V133K mutation. In some embodiments according to (or as applied to) any of the embodiments above, the VH domain of H1 comprises a Q39E mutation, the VL domain of L1 comprises a Q38K mutation, the VH domain of H2 comprises a Q39K mutation and the VL domain of L2 comprises a Q38E mutation.

In some embodiments according to (or as applied to) any of the embodiments above, the CH1 domain of H2 comprises S183K mutation, and the CL domain of L2 comprises V133E mutation. In some embodiments according to (or as applied to) any of the embodiments above, the VH domain of H1 comprises a Q39K mutation, the VL domain of L1 comprises a Q38E mutation, the VH domain of H2 comprises a Q39E mutation and the VL domain of L2 comprises a Q38K mutation.

In some embodiments according to (or as applied to) any of the embodiments above, the CH1 domain of H2 comprises an amino acid substitution at EU position S183, and the CL domain of L2 comprises an amino acid substitution at EU position V133. In some embodiments according to (or as applied to) any of the embodiments above, the interaction between the amino acid substitution at EU position S183 on the CH1 domain of H2 and the amino acid substitution at EU position V133 on the CL domain of L2 is via electrostatic interaction. In some embodiments according to (or as applied to) any of the embodiments above, the amino acid at EU position S183 on the CH1 domain of H2 is replaced with a positively charged residue, and the amino acid at EU position V133 on the CL domain of L2 is replaced with a negatively charged residue. In some embodiments according to (or as applied to) any of the embodiments above, the amino acid at EU position S183 on the CH1 domain of H2 is replaced with a negatively charged residue, and the amino acid at EU position V133 on the CL domain of L2 is replaced with a positively charged residue. In some embodiments according to (or as applied to) any of the embodiments above, the CH1 domain of H2 comprises an amino acid substitution at a position selected from the group consisting of EU position S183A, S183T, S183V, S183Y, S183F, S183H, S183N, S183D, S183E, S183R, and S183K, and the CL domain of L2 comprises an amino acid substitution at a position selected from the group consisting of EU position V133E, V133S, V133L, V133W, V133K, V133R, and V133D.

In some embodiments according to (or as applied to) any of the embodiments above, the CH1 domain of H2 comprises the EU position S183D mutation, and the CL domain of L2 comprises the EU position V133K mutation; the CH1 domain of H2 comprises the EU position S183E mutation, and the CL domain of L2 comprises the EU position V133K mutation: the CH1 domain of H2 comprises the EU position S183A mutation, and the CL domain of L2 comprises the EU position V133E mutation: the CH1 domain of H2 comprises the EU position S183A mutation, and the CL domain of L2 comprises the EU position V133S mutation; the CH1 domain of H2 comprises the EU position S183A mutation, and the CL domain of L2 comprises the EU position V133L mutation; the CH1 domain of H2 comprises the EU position S183A mutation, and the CL domain of L2 comprises the EU position V133W mutation: the CH1 domain of H2 comprises the EU position S183A mutation, and the CL domain of L2 comprises the EU position V133K mutation; the CH1 domain of H2 comprises the EU position S183A mutation, and the CL domain of L2 comprises the EU position V133R mutation; the CH1 domain of H2 comprises the EU position S183A mutation, and the CL domain of L2 comprises the EU position V133D mutation: the CH1 domain of H2 comprises the EU position S183T mutation, and the CL domain of L2 comprises the EU position V133E mutation; the CH1 domain of H2 comprises the EU position S183T mutation, and the CL domain of L2 comprises the EU position V133S mutation; the CH1 domain of H2 comprises the EU position S183T mutation, and the CL domain of L2 comprises the EU position V133L mutation: the CH1 domain of H2 comprises the EU position S183T mutation, and the CL domain of L2 comprises the EU position V133W mutation; the CH1 domain of H2 comprises the EU position S183T mutation, and the CL domain of L2 comprises the EU position V133K mutation; the CH1 domain of H2 comprises the EU position S183T mutation, and the CL domain of L2 comprises the EU position V133R mutation; the CH1 domain of H2 comprises the EU position S183T mutation, and the CL domain of L2 comprises the EU position V133D mutation; the CH1 domain of H2 comprises the EU position S183V mutation, and the CL domain of L2 comprises the EU position V133E mutation: the CH1 domain of H2 comprises the EU position S183V mutation, and the CL domain of L2 comprises the EU position V133S mutation; the CH1 domain of H2 comprises the EU position S183V mutation, and the CL domain of L2 comprises the EU position V133L mutation; the CH1 domain of H2 comprises the EU position S183V mutation, and the CL domain of L2 comprises the EU position V133W mutation: the CH1 domain of H2 comprises the EU position S183V mutation, and the CL domain of L2 comprises the EU position V133K mutation; the CH1 domain of H2 comprises the EU position S183V mutation, and the CL domain of L2 comprises the EU position V133R mutation; the CH1 domain of H2 comprises the EU position S183V mutation, and the CL domain of L2 comprises the EU position V133D mutation; the CH1 domain of H2 comprises the EU position S183Y mutation, and the CL domain of L2 comprises the EU position V133E mutation; the CH1 domain of H2 comprises the EU position S183Y mutation, and the CL domain of L2 comprises the EU position V133S mutation; the CH1 domain of H2 comprises the EU position S183Y mutation, and the CL domain of L2 comprises the EU position V133L mutation; the CH1 domain of H2 comprises the EU position S183Y mutation, and the CL of L2 domain comprises the EU position V133W mutation; the CH1 domain of H2 comprises the EU position S183Y mutation, and the CL of L2 domain comprises the EU position V133K mutation; the CH1 domain of H2 comprises the EU position S183Y mutation, and the CL domain of L2 comprises the EU position V133R mutation; the CH1 domain of H2 comprises the EU position S183Y mutation, and the CL domain of L2 comprises the EU position V133D mutation; the CH1 domain of H2 comprises the EU position S183F mutation, and the CL domain of L2 comprises the EU position V133E mutation; the CH1 domain of H2 comprises the EU position S183F mutation, and the CL domain of L2 comprises the EU position V133S mutation; the CH1 domain of H2 comprises the EU position S183F mutation, and the CL domain of L2 comprises the EU position V133L mutation: the CH1 domain of H2 comprises the EU position S183F mutation, and the CL domain of L2 comprises the EU position V133W mutation; the CH1 domain of H2 comprises the EU position S183F mutation, and the CL domain of L2 comprises the EU position V133K mutation; the CH1 domain of H2 comprises the EU position S183F mutation, and the CL domain of L2 comprises the EU position V133R mutation: the CH1 domain of H2 comprises the EU position S183F mutation, and the CL of L2 domain comprises the EU position V133D mutation; the CH1 domain of H2 comprises the EU position S183H mutation, and the CL domain of L2 comprises the EU position V133S mutation; the CH1 domain of H2 comprises the EU position S183H mutation, and the CL domain of L2 comprises the EU position V133L mutation; the CH1 domain of H2 comprises the EU position S183H mutation, and the CL domain of L2 comprises the EU position V133W mutation; the CH1 domain of H2 comprises the EU position S183N mutation, and the CL domain of L2 comprises the EU position V133L mutation; or the CH1 domain of H2 comprises the EU position S183E mutation, and the CL domain of L2 comprises the EU position V133L mutation. In some embodiments according to (or as applied to) any of the embodiments above, the CH1 domain of H2 comprises the EU position S183D substitution, and the CL domain of L2 comprises EU position V133K substitution. In some embodiments according to (or as applied to) any of the embodiments above, the CH1 domain of H2 and the VL domain of L2 do not comprise an amino acid substitution.

In some embodiments according to (or as applied to) any of the embodiments above, the VH domain of H1 comprises an amino acid substitution at Kabat position Q39, and the VL domain of V1 comprises an amino acid substitution at Kabat position Q38. In some embodiments according to (or as applied to) any of the embodiments above, the amino acid at Kabat position Q39 on the VH domain of H1 is replaced with a positively charged residue, and the amino acid at Kabat position Q38 on the VL domain of L1 is replaced with a negatively charged residue. In some embodiments according to (or as applied to) any of the embodiments above, the amino acid at Kabat position Q39 on the VH domain of H1 is replaced with a negatively charged residue, and the amino acid at Kabat position Q38 on the VL domain of L1 is replaced with a positively charged residue. In some embodiments according to (or as applied to) any of the embodiments above, the positively charged residue is selected from the group consisting of R and K. In some embodiments according to (or as applied to) any of the embodiments above, the negatively charged residue is selected from the group consisting of D and E. In some embodiments according to (or as applied to) any of the embodiments above, the VH domain of H1 comprises a Kabat position Q39E substitution mutation, the VL domain of L1 comprises a Kabat position Q38K substitution, the VH domain of H2 comprises a Kabat position Q39K substitution mutation, and the VL domain of L2 comprises a Kabat position Q38E substitution mutation.

In some embodiments according to (or as applied to) any of the embodiments above, the VH domain of H1 comprises a Kabat position Q39E substitution mutation, the VL domain of L1 comprises a Kabat position Q38K substitution. In some embodiments according to (or as applied to) any of the embodiments above, the VH domain of H1 comprises a Kabat position Q39E substitution mutation, the VL domain of L1 comprises a Kabat position Q38K substitution, and the VH domain of H2 comprises a Kabat position Q39K substitution mutation. In some embodiments according to (or as applied to) any of the embodiments above, the VH domain of H1 comprises a Kabat position Q39E substitution mutation, the VL domain of L1 comprises a Kabat position Q38K substitution, the VH domain of H2 comprises a Kabat position Q39K substitution mutation, and the VL domain of L2 comprises a Kabat position Q38E substitution mutation.

In some embodiments according to (or as applied to) any of the embodiments above, the VH domain of H1 comprises a Kabat position Q39K substitution mutation, the VL domain of L1 comprises a Kabat position Q38E substitution. In some embodiments according to (or as applied to) any of the embodiments above, the VH domain of H1 comprises a Kabat position Q39K substitution mutation, the VL domain of L1 comprises a Kabat position Q38E substitution, and the VH domain of H2 comprises a Kabat position Q39E substitution mutation in some embodiments according to (or as applied to) any of the embodiments above, the VH domain of H1 comprises a Kabat position Q39K substitution mutation, the VL domain of L1 comprises a Kabat position Q38E substitution, the VH domain of H2 comprises a Kabat position Q39E substitution mutation, and the VL domain of L2 comprises a Kabat position Q38K substitution mutation.

In some embodiments according to (or as applied to) any of the embodiments above, H1 preferentially pairs with L1 as compared to L2, and H2 preferentially pairs with L2 as compared to L1.

In some embodiments according to (or as applied to) any of the embodiments above, H1 comprises an Fc region comprising a CH2 and a CH3 domain. In some embodiments according to (or as applied to) any of the embodiments above, the Fc region of H1 and/or H2 is IgG1, IgG2 or IgG4 Fc.

In some embodiments according to (or as applied to) any of the embodiments above, the Fc region of H1 and/or H2 is mouse IgG1, mouse IgG2 or mouse IgG4 Fc.

In some embodiments according to (or as applied to) any of the embodiments above, the CH3 domains of H1 and H2 each meet at an interface, and each of the CH3 domains comprises an amino acid substitution such that the Fc region of H1 preferentially pairs with that of H2 as compared to H1.

In some embodiments according to (or as applied to) any of the embodiments above, the amino acid substitutions in the CH3 domains result in greater electrostatic complementarity. In some embodiments according to (or as applied to) any of the embodiments above, the amino acid substitutions in the CH3 domains result in greater steric complementarity.

In some embodiments according to (or as applied to) any of the embodiments above, the CH3 domain of H1 is altered, so that within the CH3/CH3 interface, one or more amino acid residues are replaced with one or more amino acid residues having a larger side chain volume, thereby generating a protuberance on the surface of the CH3 domain of H1 that interacts with the CH3 domain of H2; and the CH3 domain of H2 is altered so that within the CH3/CH3 interface one or more amino acid residues are replaced with amino acid residues having a smaller side chain volume, thereby generating a cavity within on the surface of the CH3 domain of H2 that interacts with the CH3 domain of H1.

In some embodiments according to (or as applied to) any of the embodiments above, the CH3 domain of H2 is altered, so that within the CH3/CH3 interface, one or more amino acid residues are replaced with one or more amino acid residues having a larger side chain volume, thereby generating a protuberance on the surface of the CH3 domain of H2 that interacts with the CH3 domain of H1; and the CH3 domain of H1 is altered so that within the CH3/CH3 interface, one or more amino acid residues are replaced amino acid residues having a smaller side chain volume, thereby generating a cavity on the surface of the CH3 domain of H1 that interacts with the CH3 domain of H2.

In some embodiments according to (or as applied to) any of the embodiments above, the protuberance is a knob. In some embodiments according to (or as applied to) any of the embodiments above, the alteration to generate the knob is T366W. In some embodiments according to (or as applied to) any of the embodiments above, the cavity is a hole. In some embodiments according to (or as applied to) any of the embodiments above, the alterations to generate the hole are at least one of T366S, L368A, and Y407V.

In some embodiments according to (or as applied to) any of the embodiments above, the knob comprises T366W (EU numbering). In some embodiments according to (or as applied to) any of the embodiments above, the hole mutation comprises at least one, at least two, or all three of T366S, L368A, and Y407V.

In some embodiments according to (or as applied to) any of the embodiments above, H1 preferentially pairs with L1 as compared to L2, and wherein H2 preferentially pairs with L2 as compared to L1.

In some embodiments according to (or as applied to) any of the embodiments above, the first antigen and the second antigen are the same. In some embodiments according to (or as applied to) any of the embodiments above, the first heavy chain/light chain pair and the second heavy chain/light chain pair each bind to a different epitope on the same antigen. In some embodiments according to (or as applied to) any of the embodiments above, the first antigen and the second antigen are different.

Also provided herein is a pharmaceutical composition comprising the multispecific antigen binding protein of any of the embodiments above, and a pharmaceutically acceptable carrier. Further provided herein is a method of treating a disease in an individual, comprising administering to the individual an effective amount of the pharmaceutical composition according to (or as applied to) any of the embodiments above.

Isolated nucleic acids(s) encoding at least one polypeptide sequence of the multispecific antigen binding protein of any one of the embodiments above are provided. Also provided is a vector comprising the nucleic acid(s) according to (or as applied to) any of the embodiments above. Also provided is an isolated host cell comprising the nucleic acid(s) according to (or as applied to) any of the embodiments above, or the vector according to (or as applied to) any of the embodiments above.

In some embodiments according to (or as applied to) any of the embodiments above, the host cell is a prokaryotic host cell, and E. coli cell, a eukaryotic host cell, a yeast cell, a mammalian cell, or a CHO cell.

Provided herein is a method of producing the multispecific antigen binding protein according to (or as applied to) any of the embodiments above, comprising: (a) obtaining the H1, H2, L1, and L2 polypeptides; (b) allowing H1 to pair preferentially with L1 as compared to L2, and H2 to pair preferentially with L2 as compared to L1 so as to form the multispecific antigen binding protein.

Also provided is a method of producing the multispecific antigen binding protein according to (or as applied to) any of the embodiments above, comprising. (a) introducing a set of polynucleotides encoding H1, L1, H2, and L2 into a host cell; and (b) culturing the host cell to produce the multispecific antigen binding protein. In some embodiments according to (or as applied to) any of the embodiments above, the set of polynucleotides encoding H1, L1, H2, and L2 is introduced into the same host cell. In some embodiments according to (or as applied to) any of the embodiments above, the set of polynucleotides encoding H1, L1, H2, and L2 is introduced into a cell line. In some embodiments according to (or as applied to) any of the embodiments above, the cell line is a stable cell line stably coexpressing H1, L1, H2, and L2. In some embodiments according to (or as applied to) any of the embodiments above, the cell line is a stable cell line stably expressing the multispecific antigen binding protein. In some embodiments according to (or as applied to) any of the embodiments above, the set of polynucleotides encoding H1, L1, H2, and L2 are introduced into the host cell at a predetermined ratio. In some embodiments according to (or as applied to) any of the embodiments above, the method further comprises determining an optimal ratio of the polynucleotides for introduction into the host cell. In some embodiments according to (or as applied to) any of the embodiments above, the multispecific antigen binding protein is produced with a relative yield of 60% or higher. In certain embodiments according to (or as applied to) any of the embodiments above, the multispecific antigen binding protein is produced with a relative yield of at least about 70%, at least about 71%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 99%, or more than about 99%. In certain embodiments according to (or as applied to) any of the embodiments above, the multispecific antigen binding protein is produced with a relative yield of at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 99%, or more than about 99%. In certain embodiments according to (or as applied to) any of the embodiments above, the multispecific antigen binding protein is produced with a relative yield of at least about 90%, at least about 91%, at least about 92%, at least about 93%, at least about 94%, at least about 95%, at least about 96%, at least about 97%, at least about 99%, or more than about 99%. In certain embodiments according to (or as applied to) any of the embodiments above, the multispecific antigen binding protein is produced with a relative yield of at least about 95%, at least about 96%, at least about 97%, at least about 99%, or more than about 99%.

Also provided is a method of producing a multispecific antigen binding protein comprising culturing the host cell according to (or as applied to) any of the embodiments above, and producing the multispecific antigen binding protein. In some embodiments according to (or as applied to) any of the embodiments above, the method further comprises recovering the multispecific antigen binding protein. Also provided is a multispecific antigen binding protein produced by the methods according to (or as applied to) any of the embodiments above.

Provided herein is a library comprising a plurality of polynucleotides encoding a plurality of multispecific antigen binding proteins according to (or as applied to) any of the embodiments above. Also provided is a method of screening for a multispecific antigen binding protein that binds to a first antigen and a second antigen, comprising: (a) obtaining a plurality of multispecific antigen binding proteins from the library according to (or as applied to) any of the embodiments above; (b) assaying for binding of the plurality of multispecific antigen binding proteins to the first and second antigen; and (c) identifying the multispecific antigen binding protein that binds to the first and second antigen.

Also provided is a computer readable medium for evaluating a multispecific antigen binding protein comprising 1) a first heavy chain/light chain pair binding to a first antigen which comprises a first heavy chain sequence (H1) and a first light chain sequence (L1), and 2) a second heavy chain/light chain pair binding to a second antigen which comprises a second heavy chain sequence (H2) and a second light chain sequence (L2), wherein each H1 and H2 comprises a heavy chain variable domain (VH) and a heavy chain constant domain (CH1), and each L1 and L2 comprises a light chain variable domain (VL) and a light chain constant domain (CL); comprising: a) a dataset comprising data representing amino acid substitutions in H1, L1, H2, and L2, wherein at least one of the amino acid substitutions in the CH1 domain of H1 comprises an amino acid substitution at EU position F170 or L128 and V185, and wherein the CL domain comprises an amino acid substitution at EU position S176 or F118 and L135; and/or a dataset comprising data representing amino acid substitutions in H1, L1, H2, and L2, wherein at least one of the amino acid substitutions in the CH1 domain of H1 comprises an amino acid substitution at EU position S183, and wherein the of C1 comprises an amino acid substitution at EU position V133; and (b) computer executable code for determining the likelihood that H1 will preferentially pair with L1 as compared to L2 and/or H2 will preferentially pair with L2 as compared to L1.

Also provided is a computer readable medium for evaluating a multispecific antigen binding protein comprising 1) a first heavy chain/light chain pair binding to a first antigen which comprises a first heavy chain sequence (H1) and a first light chain sequence (L1), and 2) a second heavy chain/light chain pair binding to a second antigen which comprises a second heavy chain sequence (H2) and a second light chain sequence (L2), wherein each H1 and H2 comprises a heavy chain variable domain (VH) and a heavy chain constant domain (CH1), and each L1 and L2 comprises a light chain variable domain (VL) and a light chain constant domain (CL); comprising: a) a dataset comprising data representing amino acid substitutions in H1, L1, H2, and L2, wherein at least one of the amino acid substitutions in the CH1 domain of H1 comprises an amino acid substitution at EU position F170 or L128, and wherein the CL domain comprises an amino acid substitution at EU position S176 or F118 and L135; and/or a dataset comprising data representing amino acid substitutions in H1, L1, H2, and L2, wherein at least one of the amino acid substitutions in the CH1 domain of H1 comprises an amino acid substitution at EU position S183, and wherein the of C1 comprises an amino acid substitution at EU position V133; and (b) computer executable code for determining the likelihood that H1 will preferentially pair with L1 as compared to L2 and/or H2 will preferentially pair with L2 as compared to L1. In certain embodiments, in the dataset comprising data representing amino acid substitutions in H1, L1, H2, and L2, the at least one of the amino acid substitutions in the CH1 domain of H1 comprises an amino acid substitution at EU position F170 or L128 and V185.

BRIEF DESCRIPTION OF THE DRAWINGS

FIG. 4 provides the results of mammalian culture expression assays that were performed to analyze antibody expression in cultures expressing a light chains/heavy chain pair having V133X/S183X substitution mutations.

FIG. 10A shows an enlargement of FIG. 10B. FIG. 10B shows the results of high resolution mass spectrometry performed to assess heavy chain/light chain paring in a bispecific 4D5/UCHT1 antibody in which the UCHT1 arm was modified to contain VL-Q38E. CL-V133K, VH-Q39K, and CH-1-S183E mutations, and in which the 4D5 arm of the 4D5/UCHT1 antibody was modified to contain VL-Q38K and VH-Q39E mutations.

Figures 16A, 16B:
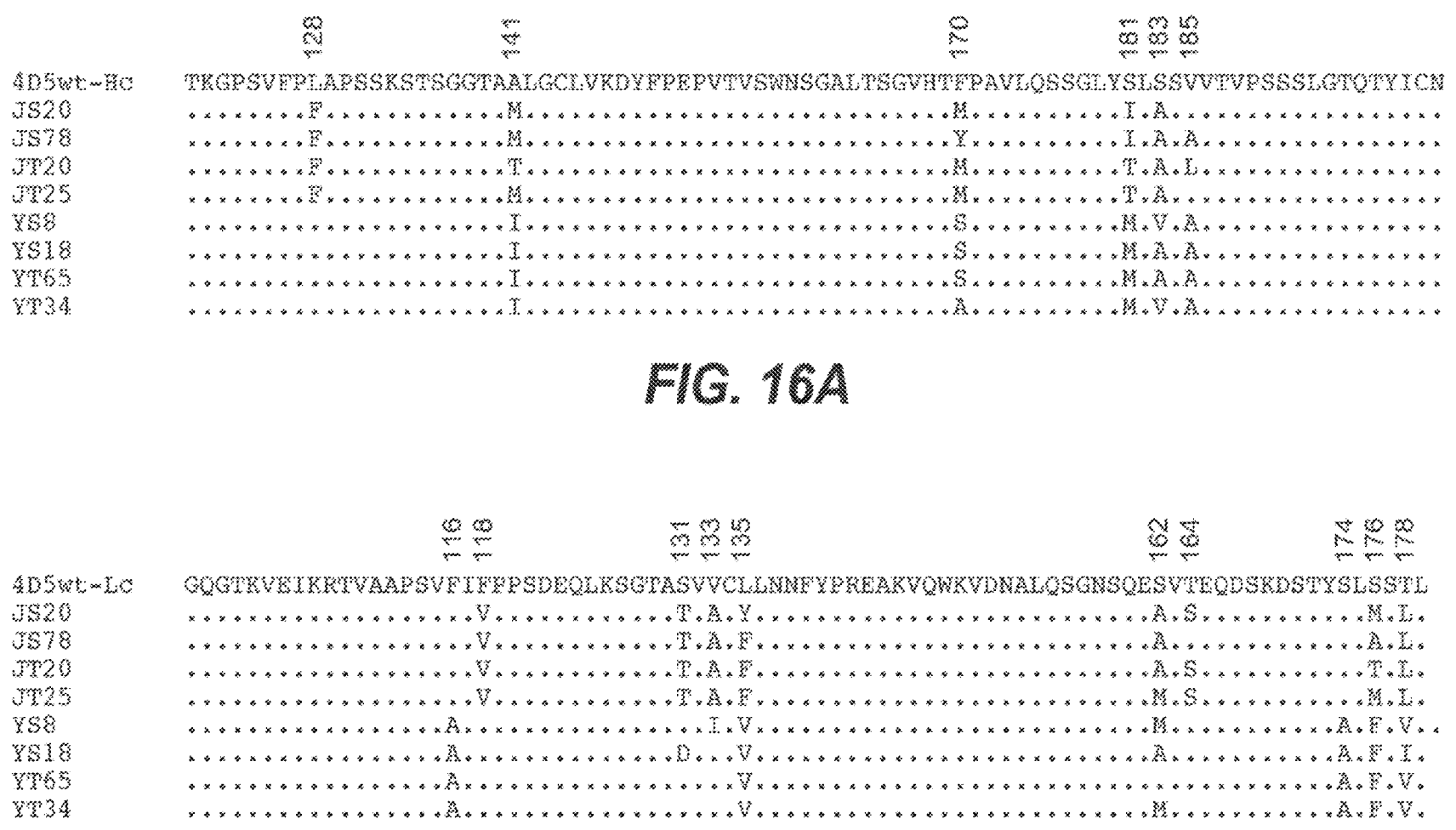

FIG. 16A provides the amino acid sequences of portion of the heavy chains of JS20 (SEQ ID NO: 49), JS78 (SEQ ID NO: 50), JT20 (SEQ ID NO: 51), JT25 (SEQ ID NO: 52), YS08 (SEQ ID NO: 28), YS18 (SEQ ID NO: 29), YT65 (SEQ ID NO: 29), and YT34 variants (SEQ ID NO: 44). FIG. 16A also provides the amino acid sequence of portion of the 4D5 wild type heavy chain "4D5 wt-Hc" (SEQ ID NO: 67). FIG. 16B provides the amino acid sequences of portion of the light chains of JS20 (SEQ ID NO: 69), JS78 (SEQ ID NO: 70), JT20 (SEQ ID NO: 71), JT25 (SEQ ID NO: 72), YS08 (SEQ ID NO: 73). YS18 (SEQ ID NO: 74), YT65 (SEQ ID NO: 75), and YT34 variants (SEQ ID NO: 76). FIG. 16B also provides the amino acid sequence of portion of the 4D5 WT light chain "4D5 wt-Lc" (SEQ ID NO: 68.

FIG. 18A shows the results of mass spectrometry performed on a wild-type 4D5/UCHT1 bispecific antibody. FIG. 18B shows the results of mass spectrometry performed on a 4D5/UCHT1 antibody comprising YT65 CH1/CL mutations and VH-Q39E and VL-Q38K mutations on the 4D5 arm, and VL-Q38E and VH-Q39K mutations on the UCHT1 arm.

Figures 19A, 19B:
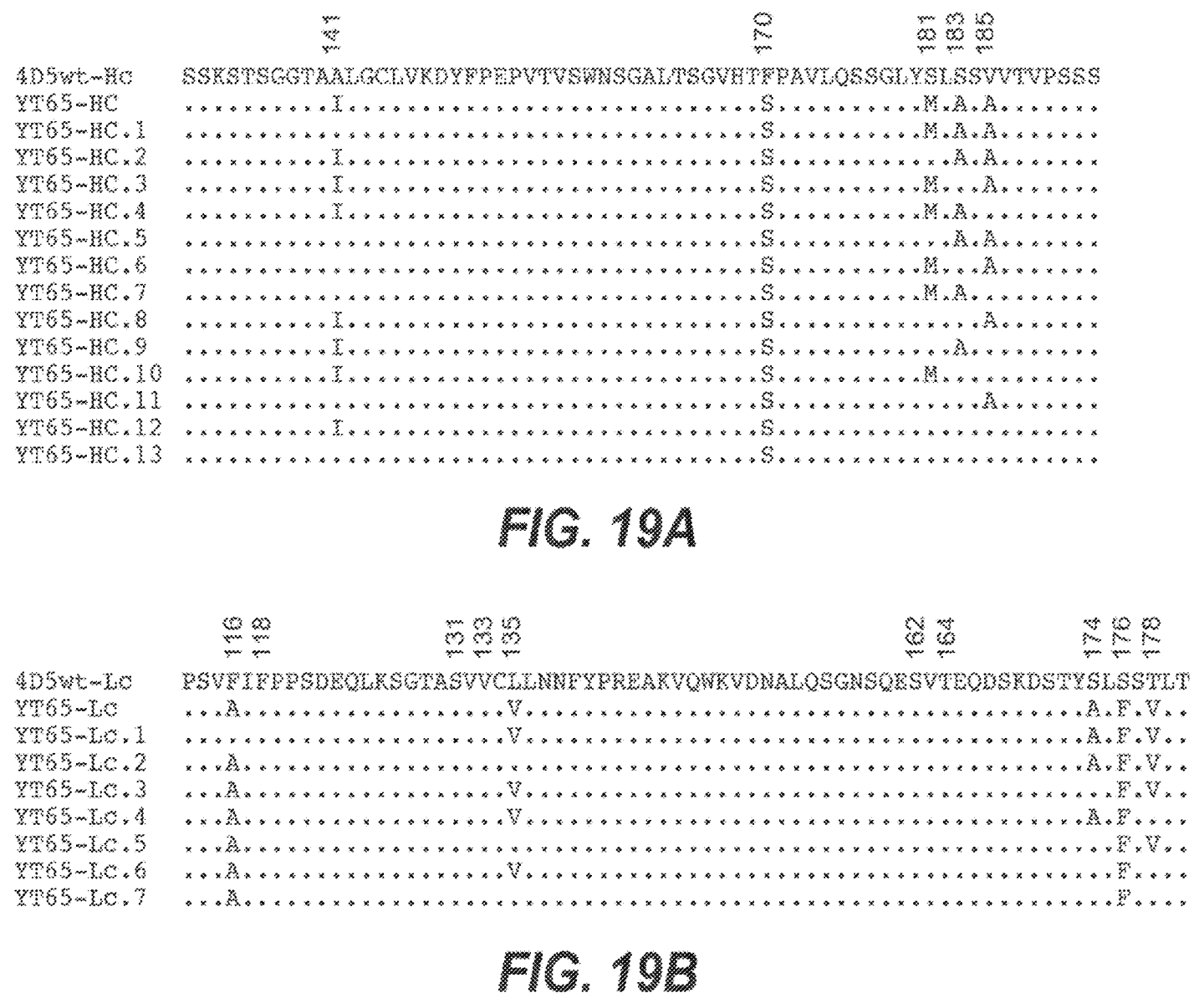

FIG. 19A provides the amino acid sequences of portion of the heavy chains of the YT65 (SEQ ID NO: 78), YT65.1 (SEQ ID NO: 79), YT65.2 (SEQ ID NO: 80), YT65.3 (SEQ ID NO: 81), YT65.4 (SEQ ID NO: 82), YT65.5 (SEQ ID NO: 83), YT65.6 (SEQ ID NO: 84), YT65.7 (SEQ ID NO: 85), YT65.8 (SEQ ID NO: 86), YT65.9 (SEQ ID NO: 87), YT65.10 (SEQ ID NO: 88), YT65.11 (SEQ ID NO: 89), YT65.12 (SEQ ID NO: 90), and YT65.13 variants (SEQ ID NO: 91). FIG. 19B discloses portion of the 4D5 wt heavy chain sequence "4D5 wt-Hc" as SEQ ID NO: 77. FIG. 19B provides the amino acid sequences of portion of the light chains of the YT65 (SEQ ID NO: 93), YT65.1 (SEQ ID NO: 94), YT65.2 (SEQ ID NO: 95), YT65.3 (SEQ ID NO: 96), YT65.4 (SEQ ID NO: 97), YT65.5 (SEQ ID NO: 98), YT65.6 (SEQ ID NO: 99), and YT65.7 variants (SEQ ID NO: 100). FIG. 19B discloses portion of the 4D5 wt light chain sequence "4D5 wt-Lc" as SEQ ID NO: 92.

FIG. 22A shows the crystal structure of the 4D5 Fab modified to have VL-Q38K, VH-Q39E, and the YT65 mutations. FIG. 22B shows overlapping crystal structures of a CH1 domain of the wild type 4D5 Fab and the CH1 domain of the 4D5 Fab modified to have the YT65 mutations.

DETAILED DESCRIPTION OF THE INVENTION

Figure 1A:
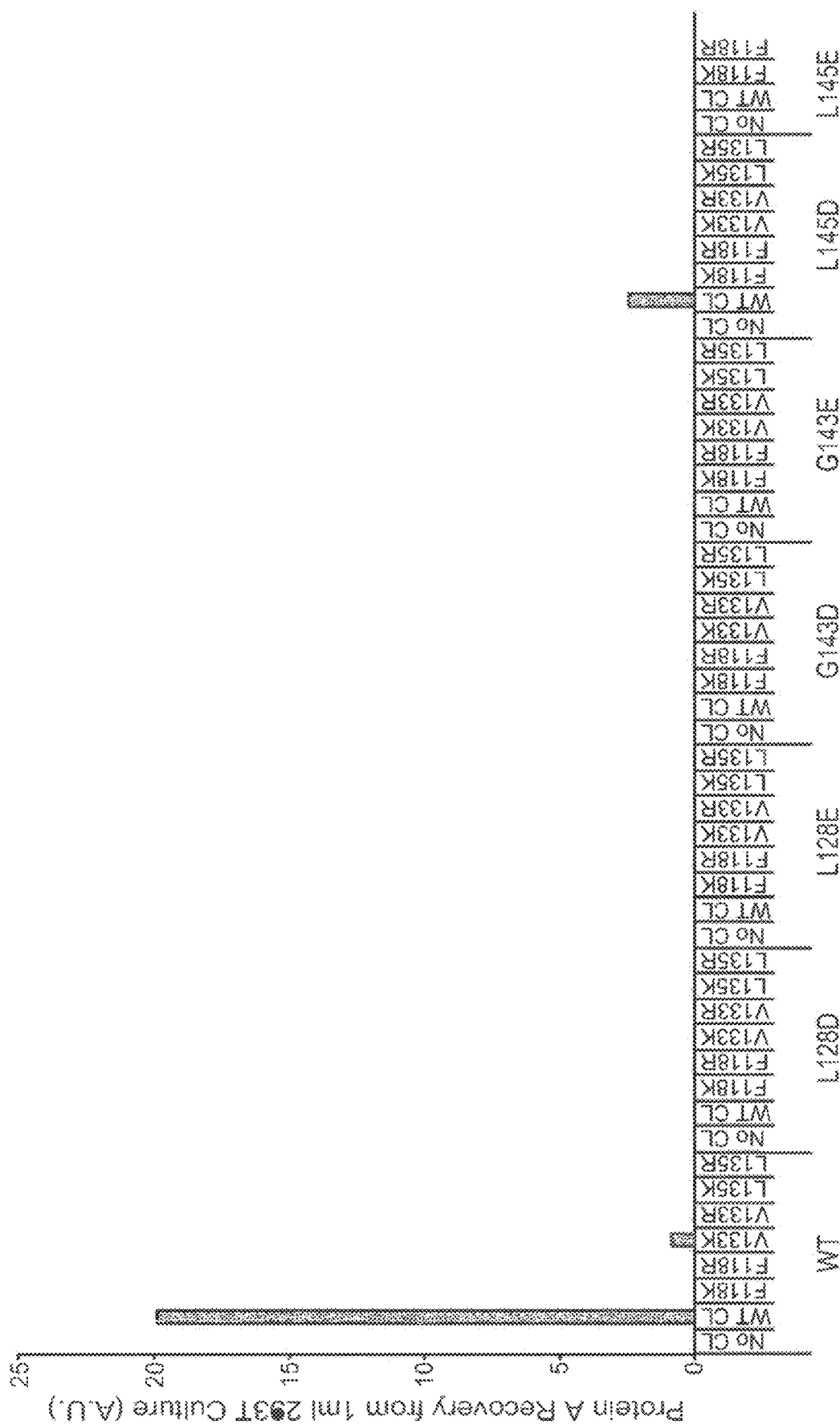
FIG. 1 (FIG. 1A and FIG. 1B) shows protein A recovery from 1 ml 293T cultures of antibodies containing a heavy chain bearing a substitution mutation at position L128, G143, L145, S183, or V185 and a light chain bearing a substitution at F118, V133, or L135.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D Ed., John Wiley and Sons, New York (1994), and Hale & Margham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

Numeric ranges are inclusive of the numbers defining the range.

Unless otherwise indicated, nucleic acids are written left to right in 5' to 3' orientation; amino acid sequences are written left to right in amino to carboxy orientation, respectively.

The headings provided herein are not limitations of the various aspects or embodiments which can be had by reference to the specification as a whole. Accordingly, the terms defined immediately below are more fully defined by reference to the specification as a whole.

Definitions

The term "multispecific antigen-binding protein" herein is used in the broadest sense refers to a binding protein capable of binding two or more antigens. In certain aspects the multispecific binding protein refers to a bispecific antibody, e.g., a human bispecific antibody, a humanized bispecific antibody, a chimeric bispecific antibody, or a mouse bispecific antibody. In certain embodiments, a multispecific antigen-binding protein provided herein, such as a bispecific antibody, binds to two different antigens. In certain embodiments, the multispecific antigen-binding protein, such as a bispecific antibody, binds to different epitopes on one antigen.

The term "antibody" herein is used in the broadest sense and refers to any immunoglobulin (Ig) molecule comprising two heavy chains and two light chains, and any fragment, mutant, variant or derivation thereof so long as they exhibit the desired biological activity (e.g., epitope binding activity). Examples of antibodies include monoclonal antibodies, polyclonal antibodies, multispecific antibodies (e.g., bispecific antibodies) and antibody fragments as described herein. An antibody can be mouse, chimeric, human, humanized and/or affinity matured.

As a frame of reference, as used herein an antibody will refer to the structure of an immunoglobulin G (IgG). However, one skilled in the art would understand/recognize that an antibody of any immunoglobulin class may be utilized in the inventive method described herein. For clarity, an IgG molecule contains a pair of heavy chains (HCs) and a pair of light chains (LCs). Each LC has one variable domain (VL) and one constant domain (CL), while each HC has one variable (VH) and three constant domains (CH1, CH2, and CH3). The CH1 and CH2 domains are connected by a hinge region. This structure is well known in the art.

Briefly, the basic 4-chain antibody unit is a heterotetrameric glycoprotein composed of two light (L) chains and two heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, CT, 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, γ, ε, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "VL" domain comprises the amino terminal variable domain of an immunoglobulin light chai.

The term "VH domain" comprises the amino terminal variable domain of an immunoglobulin heavy chain.

The term "CL domain" comprises the constant region domain of an immunoglobulin light chain that extends, e.g. from about Kabat position 107A-216 (EU positions 108-214 (kappa)). The Eu/Kabat conversion table for the Kappa C domain is provided below. The CL domain is adjacent to the VL domain and includes the carboxy terminal of an immunoglobulin light chain. An exemplary amino acid sequence for CL domain of human kappa light chain is shown below in SEQ ID NO: 30, including the R residue at the N-terminus that is present in the mature CL domain as the result of gene splicing.

TABLE A

| Human IG Kappa Chain amino acid translation (SEQ ID NO: 30) | EU numbering | Kabat numbering |
|---|---|---|
| (R) | 108 | 108 |
| T | 109 | 109 |
| V | 110 | 110 |
| A | 111 | 111 |
| A | 112 | 112 |
| P | 113 | 113 |
| S | 114 | 114 |
| V | 115 | 115 |
| F | 116 | 116 |
| I | 117 | 117 |
| F | 118 | 118 |
| P | 119 | 119 |
| P | 120 | 120 |
| S | 121 | 121 |
| D | 122 | 122 |
| E | 123 | 123 |

TABLE A-continued

| Human IG Kappa Chain amino acid translation (SEQ ID NO: 30) | EU numbering | Kabat numbering |
|---|---|---|
| Q | 124 | 124 |
| L | 125 | 125 |
| K | 126 | 126 |
| — | — | — |
| — | — | — |
| — | — | — |
| S | 127 | 127 |
| G | 128 | 128 |
| T | 129 | 129 |
| A | 130 | 130 |
| S | 131 | 131 |
| V | 132 | 132 |
| V | 133 | 133 |
| C | 134 | 134 |
| L | 135 | 135 |
| L | 136 | 136 |
| N | 137 | 137 |
| N | 138 | 138 |
| F | 139 | 139 |
| Y | 140 | 140 |
| P | 141 | 141 |
| — | — | — |
| R | 142 | 142 |
| E | 143 | 143 |
| A | 144 | 144 |
| K | 145 | 145 |
| V | 146 | 146 |
| Q | 147 | 147 |
| W | 148 | 148 |
| K | 149 | 149 |
| V | 150 | 150 |
| D | 151 | 151 |
| N | 152 | 152 |
| A | 153 | 153 |
| L | 154 | 154 |
| Q | 155 | 155 |
| S | 156 | 156 |
| G | 157 | 157 |
| — | — | — |
| N | 158 | 158 |
| S | 159 | 159 |
| Q | 160 | 160 |
| E | 161 | 161 |
| S | 162 | 162 |
| V | 163 | 163 |
| T | 164 | 164 |
| E | 165 | 165 |
| Q | 166 | 166 |
| D | 167 | 167 |
| S | 168 | 168 |
| K | 169 | 169 |
| D | 170 | 170 |
| — | — | — |
| — | — | — |
| — | — | — |
| S | 171 | 171 |
| T | 172 | 172 |
| Y | 173 | 173 |
| S | 174 | 174 |
| L | 175 | 175 |
| S | 176 | 176 |
| S | 177 | 177 |
| T | 178 | 178 |
| L | 179 | 179 |
| T | 180 | 180 |
| L | 181 | 181 |
| S | 182 | 182 |
| K | 183 | 183 |
| A | 184 | 184 |
| D | 185 | 185 |
| Y | 186 | 186 |
| — | — | — |
| — | — | — |

TABLE A-continued

| Human IG Kappa Chain amino acid translation (SEQ ID NO: 30) | EU numbering | Kabat numbering |
|---|---|---|
| E | 187 | 187 |
| K | 188 | 188 |
| H | 189 | 189 |
| K | 190 | 190 |
| V | 191 | 191 |
| Y | 192 | 192 |
| A | 193 | 193 |
| C | 194 | 194 |
| E | 195 | 195 |
| V | 196 | 196 |
| T | 197 | 197 |
| H | 198 | 198 |
| Q | 199 | 199 |
| G | 200 | 200 |
| — | — | — |
| — | — | — |
| L | 201 | 201 |
| S | 202 | 202 |
| S | 203 | 203 |
| P | 204 | 204 |
| V | 205 | 205 |
| T | 206 | 206 |
| K | 207 | 207 |
| S | 208 | 208 |
| F | 209 | 209 |
| N | 210 | 210 |
| R | 211 | 211 |
| G | 212 | 212 |
| E | 213 | 213 |
| C | 214 | 214 |
| — | — | 215 |
| — | — | 216 |

As used herein, the term "CH1 domain" of a human IgG comprises the first (most amino terminal) constant region domain of an immunoglobulin heavy chain that extends, e.g., from about positions 114-223 in the Kabat numbering system (EU positions 118-215). The CH1 domain is adjacent to the VH domain and amino terminal to the hinge region of an immunoglobulin heavy chain molecule, does not form a part of the Fc region of an immunoglobulin heavy chain, and is capable of dimerizing with an immunoglobulin light chain constant domain (i.e., "CL").

The EU/Kabat conversion tables for the IgG1 heavy chain (SEQ ID NO: 65) are provided below. The exemplary CH1 sequence is shown in SEQ ID NO:53, hinge sequence is shown in SEQ ID NO: 129, CH2 sequence is shown in SEQ ID NO: 130, and CH3 sequence is shown in SEQ ID NO: 131.

TABLE B

CH1 (SEQ ID NO: 53)

| | EU numbering | Kabat numbering |
|---|---|---|
| (A) | 118 | 114 |
| S | 119 | 115 |
| T | 120 | 116 |
| K | 121 | 117 |
| G | 122 | 118 |
| P | 123 | 119 |
| S | 124 | 120 |
| V | 125 | 121 |
| F | 126 | 122 |
| P | 127 | 123 |
| L | 128 | 124 |
| A | 129 | 125 |
| P | 130 | 126 |
| S | 131 | 127 |
| S | 132 | 128 |
| K | 133 | 129 |
| S | 134 | 130 |
| T | 135 | 133 |
| S | 136 | 134 |
| G | 137 | 135 |
| G | 138 | 136 |
| T | 139 | 137 |
| A | 140 | 138 |
| A | 141 | 139 |
| L | 142 | 140 |
| G | 143 | 141 |
| C | 144 | 142 |
| L | 145 | 143 |
| V | 146 | 144 |
| K | 147 | 145 |
| D | 148 | 146 |
| Y | 149 | 147 |
| F | 150 | 148 |
| P | 151 | 149 |
| E | 152 | 150 |
| P | 153 | 151 |
| V | 154 | 152 |
| T | 155 | 153 |
| V | 156 | 154 |
| S | 157 | 156 |
| W | 158 | 157 |
| N | 159 | 162 |
| S | 160 | 163 |
| G | 161 | 164 |
| A | 162 | 165 |
| L | 163 | 166 |
| T | 164 | 167 |
| S | 165 | 168 |
| G | 166 | 169 |
| V | 167 | 171 |
| H | 168 | 172 |
| T | 169 | 173 |
| F | 170 | 174 |
| P | 171 | 175 |
| A | 172 | 176 |
| V | 173 | 177 |
| L | 174 | 178 |
| Q | 175 | 179 |
| S | 176 | 180 |
| S | 177 | 182 |
| G | 178 | 183 |
| L | 179 | 184 |
| Y | 180 | 185 |
| S | 181 | 186 |
| L | 182 | 187 |
| S | 183 | 188 |
| S | 184 | 189 |
| V | 185 | 190 |
| V | 186 | 191 |
| T | 187 | 192 |
| V | 188 | 193 |
| P | 189 | 194 |
| S | 190 | 195 |
| S | 191 | 196 |
| S | 192 | 197 |
| L | 193 | 198 |
| G | 194 | 199 |
| T | 195 | 200 |
| Q | 196 | 203 |
| T | 197 | 205 |
| Y | 198 | 206 |
| I | 199 | 207 |
| C | 200 | 208 |
| N | 201 | 209 |
| V | 202 | 210 |
| N | 203 | 211 |
| H | 204 | 212 |
| K | 205 | 213 |
| P | 206 | 214 |

TABLE B-continued

CH1 (SEQ ID NO: 53)

| | EU numbering | Kabat numbering |
|---|---|---|
| S | 207 | 215 |
| N | 208 | 216 |
| T | 209 | 217 |
| K | 210 | 218 |
| V | 211 | 219 |
| D | 212 | 220 |
| K | 213 | 221 |
| K | 214 | 222 |
| V | 215 | 223 |
| — | — | — |

TABLE C

HINGE (SEQ ID NO: 129)

| | EU numbering | Kabat numbering |
|---|---|---|
| (E) | 216 | 226 |
| P | 217 | 227 |
| K | 218 | 228 |
| S | 219 | 232 |
| C | 220 | 233 |
| D | 221 | 234 |
| K | 222 | 235 |
| T | 223 | 236 |
| H | 224 | 237 |
| T | 225 | 238 |
| C | 226 | 239 |
| P | 227 | 240 |
| P | 228 | 241 |
| C | 229 | 242 |
| P | 230 | 243 |

TABLE D

CH2 (SEQ ID NO: 130)

| | EU numbering | Kabat numbering |
|---|---|---|
| (A) | 231 | 244 |
| P | 232 | 245 |
| E | 233 | 246 |
| L | 234 | 247 |
| L | 235 | 248 |
| G | 236 | 249 |
| G | 237 | 250 |
| P | 238 | 251 |
| S | 239 | 252 |
| V | 240 | 253 |
| F | 241 | 254 |
| L | 242 | 255 |
| F | 243 | 256 |
| P | 244 | 257 |
| P | 245 | 258 |
| K | 246 | 259 |
| P | 247 | 260 |
| K | 248 | 261 |
| D | 249 | 262 |
| T | 250 | 263 |
| L | 251 | 264 |
| M | 252 | 265 |
| I | 253 | 266 |
| S | 254 | 267 |
| R | 255 | 268 |
| T | 256 | 269 |
| P | 257 | 270 |
| E | 258 | 271 |
| V | 259 | 272 |
| T | 260 | 273 |
| C | 261 | 274 |
| V | 262 | 275 |
| V | 263 | 276 |
| V | 264 | 277 |
| D | 265 | 278 |
| V | 266 | 279 |
| S | 267 | 280 |
| H | 268 | 281 |
| E | 269 | 282 |
| D | 270 | 283 |
| P | 271 | 284 |
| E | 272 | 285 |
| V | 273 | 286 |
| K | 274 | 287 |
| F | 275 | 288 |
| N | 276 | 289 |
| W | 277 | 290 |
| Y | 278 | 291 |
| V | 279 | 292 |
| D | 280 | 295 |
| G | 281 | 296 |
| V | 282 | 299 |
| E | 283 | 300 |
| V | 284 | 301 |
| H | 285 | 302 |
| N | 286 | 303 |
| A | 287 | 304 |
| K | 288 | 305 |
| T | 289 | 306 |
| K | 290 | 307 |
| P | 291 | 308 |
| R | 292 | 309 |
| E | 293 | 310 |
| E | 294 | 311 |
| Q | 295 | 312 |
| Y | 296 | 313 |
| N | 297 | 314 |
| S | 298 | 317 |
| T | 299 | 318 |
| Y | 300 | 319 |
| R | 301 | 320 |
| V | 302 | 321 |
| V | 303 | 322 |
| S | 304 | 323 |
| V | 305 | 324 |
| L | 306 | 325 |
| T | 307 | 326 |
| V | 308 | 327 |
| L | 309 | 328 |
| H | 310 | 329 |
| Q | 311 | 330 |
| D | 312 | 331 |
| W | 313 | 332 |
| L | 314 | 333 |
| N | 315 | 334 |
| G | 316 | 335 |
| K | 317 | 336 |
| E | 318 | 337 |
| Y | 319 | 338 |
| K | 320 | 339 |
| C | 321 | 340 |
| K | 322 | 341 |
| V | 323 | 342 |
| S | 324 | 343 |
| N | 325 | 344 |
| K | 326 | 345 |
| A | 327 | 346 |
| L | 328 | 347 |
| P | 329 | 348 |
| A | 330 | 349 |
| P | 331 | 350 |
| I | 332 | 351 |
| E | 333 | 352 |
| K | 334 | 353 |

TABLE D-continued

CH2 (SEQ ID NO: 130)

| | EU numbering | Kabat numbering |
|---|---|---|
| T | 335 | 354 |
| I | 336 | 355 |
| S | 337 | 357 |
| K | 338 | 358 |
| A | 339 | 359 |
| K | 340 | 360 |
| — | — | — |
| — | — | — |

TABLE E

CH3 (SEQ ID NO: 131)

| | EU numbering | Kabat numbering |
|---|---|---|
| (G) | 341 | 361 |
| Q | 342 | 363 |
| P | 343 | 364 |
| R | 344 | 365 |
| E | 345 | 366 |
| P | 346 | 367 |
| Q | 347 | 368 |
| V | 348 | 369 |
| Y | 349 | 370 |
| T | 350 | 371 |
| L | 351 | 372 |
| P | 352 | 373 |
| P | 353 | 374 |
| S | 354 | 375 |
| R | 355 | 376 |
| D | 356 | 377 |
| E | 357 | 378 |
| L | 358 | 381 |
| T | 359 | 382 |
| K | 360 | 383 |
| N | 361 | 384 |
| Q | 362 | 385 |
| V | 363 | 386 |
| S | 364 | 387 |
| L | 365 | 388 |
| T | 366 | 389 |
| C | 367 | 390 |
| L | 368 | 391 |
| V | 369 | 392 |
| K | 370 | 393 |
| G | 371 | 394 |
| F | 372 | 395 |
| Y | 373 | 396 |
| P | 374 | 397 |
| S | 375 | 398 |
| D | 376 | 399 |
| I | 377 | 400 |
| A | 378 | 401 |
| V | 379 | 402 |
| E | 380 | 405 |
| W | 381 | 406 |
| E | 382 | 407 |
| S | 383 | 408 |
| N | 384 | 410 |
| G | 385 | 411 |
| Q | 386 | 414 |
| P | 387 | 415 |
| E | 388 | 416 |
| N | 389 | 417 |
| N | 390 | 418 |
| Y | 391 | 419 |
| K | 392 | 420 |
| T | 393 | 421 |
| T | 394 | 422 |
| P | 395 | 423 |
| P | 396 | 424 |

TABLE E-continued

CH3 (SEQ ID NO: 131)

| | EU numbering | Kabat numbering |
|---|---|---|
| V | 397 | 425 |
| L | 398 | 426 |
| D | 399 | 427 |
| S | 400 | 428 |
| D | 401 | 430 |
| G | 402 | 433 |
| S | 403 | 434 |
| F | 404 | 435 |
| F | 405 | 436 |
| L | 406 | 437 |
| Y | 407 | 438 |
| S | 408 | 439 |
| K | 409 | 440 |
| L | 410 | 441 |
| T | 411 | 442 |
| V | 412 | 443 |
| D | 413 | 444 |
| K | 414 | 445 |
| S | 415 | 446 |
| R | 416 | 447 |
| W | 417 | 448 |
| Q | 418 | 449 |
| Q | 419 | 450 |
| G | 420 | 451 |
| N | 421 | 452 |
| V | 422 | 453 |
| F | 423 | 454 |
| S | 424 | 455 |
| C | 425 | 456 |
| S | 426 | 457 |
| V | 427 | 458 |
| M | 428 | 459 |
| H | 429 | 460 |
| E | 430 | 461 |
| A | 431 | 462 |
| L | 432 | 463 |
| H | 433 | 464 |
| N | 434 | 465 |
| H | 435 | 466 |
| Y | 436 | 467 |
| T | 437 | 468 |
| Q | 438 | 469 |
| K | 439 | 470 |
| S | 440 | 471 |
| L | 441 | 472 |
| S | 442 | 473 |
| L | 443 | 474 |
| S | 444 | 475 |
| P | 445 | 476 |
| G | 446 | 477 |
| K | 447 | 478 |

As used herein, the term "complementarity" refers to the combination of interactions at the interface of, e.g., the CH1 of a heavy chain and the CL of a light chain of a multispecific antigen-binding protein described herein, that influence heavy chain/light chain pairing. "Steric complementarity" or "conformational complementarity" refers to the compatibility of the three dimensional structures at the interacting surfaces of, e.g., a CH1 domain of a heavy chain and a CL domain of a light chain. "Electrostatic complementarity" refers to the compatibility of the placement of negatively- and/or positively-charged atoms at the interacting surfaces of, e.g., a CH1 domain of a heavy chain and a CL domain of a light chain and/or a VH domain of a heavy chain and a VL domain of a light chain.

The term "CH2 domain" of a human IgG Fc region usually comprises about residues 231 to about 340 of the IgG according to the EU numbering system. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, Mol. Immunol. 22:161-206 (1985).

The term "CH3 domain" comprises residues C-terminal to a CH2 domain in an Fc region (i.e., from about amino acid residue 341 to about amino acid residue 447 of an IgG according to the EU numbering system).

The term "Fc region," as used herein, generally refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain might vary, the human IgG heavy chain Fc sequence comprises about position Cys226, or from about position Pro230, to the carboxyl terminus of the Fc sequence. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, MD, 1991. The Fc sequence of an immunoglobulin generally comprises two constant domains, a CH2 domain and a CH3 domain, and optionally comprises a CH4 domain. By "Fc polypeptide" herein is meant one of the polypeptides that make up an Fc region, e.g., a monomeric Fc. An Fc polypeptide may be obtained from any suitable immunoglobulin, such as human IgG1, IgG2, IgG3, or IgG4 subtypes, IgA, IgE, IgD or IgM. An Fc polypeptide may be obtained from mouse, e.g., a mouse IgG2a. The Fc region comprises the carboxy-terminal portions of both H chains held together by disulfides. The effector functions of antibodies are determined by sequences in the Fc region; this region is also the part recognized by Fc receptors (FcR) found on certain types of cells. In some embodiments, an Fc polypeptide comprises part or all of a wild type hinge sequence (generally at its N terminus). In some embodiments, an Fc polypeptide does not comprise a functional or wild type hinge sequence.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g., B cell receptor; BCR), etc. Such effector functions generally require the Fc region to be combined with a binding domain (e.g., an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence humanIgG1 Fc region (non-A and A allotypes); native sequence human IgG2 Fc region; native sequence human IgG3 Fc region; and native sequence human IgG4 Fc region as well as naturally occurring variants thereof. A native sequence Fc regions also include a native sequence mouse IgG2a.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent poly peptide, e.g., from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95%, at least about 96%, at least about 97%, at least about 98% or at least about 99% homology therewith.

"Fc component" as used herein refers to a hinge region, a CH2 domain or a CH3 domain of an Fc region.

In certain embodiments, the Fc region comprises an IgG Fc region, preferably derived from a wild-type human IgG Fc region. In certain embodiments, the Fc region is derived from a "wild type" mouse IgG, such as a mouse IgG2a. By "wild-type" human IgG Fc or "wild type" mouse IgG Fc it is meant a sequence of amino acids that occurs naturally within the human population or mouse population, respectively. Of course, just as the Fc sequence may vary slightly between individuals, one or more alterations may be made to a wild type sequence and still remain within the scope of the invention. For example, the Fc region may contain alterations such as a mutation in a glycosylation site or inclusion of an unnatural amino acid.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology,* 61st ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The phrase "antigen binding arm," "target molecule binding arm," "target binding arm" and variations thereof, as used herein, refers to a component part of a multispecific antigen-binding protein provided herein that has an ability to specifically bind a target of interest. Generally and preferably, the antigen binding arm is a complex of immunoglobulin polypeptide sequences, e.g., CDR and/or variable domain sequences of an immunoglobulin light and heavy chain.

A "target" or "target molecule" refers to a moiety recognized by a binding arm of the multispecific antigen-binding protein. For example, if the multispecific antigen-binding protein is an antibody, then the target may be epitopes on a single molecule or on different molecules, or a pathogen or a tumor cell, depending on the context. Similarly, if the multispecific antigen-binding protein is a receptor-Fc fusion protein the target would be the cognate binding partner for the receptor. One skilled in the art will appreciate that the target is determined by the binding specificity of the target binding arm and that different target binding arms may recognize different targets. A target preferably binds to a multispecific antigen-binding protein provided herein with affinity higher than 1 µM Kd (according to Scatchard analysis). Examples of target molecules include, but are not limited to, serum soluble proteins and/or their receptors, such as cytokines and/or cytokine receptors, adhesins, growth factors and/or their receptors, hormones, viral particles (e.g., RSV F protein, CMV, Staph A, influenza, hepatitis C virus), microorganisms (e.g., bacterial cell proteins, fungal cells), adhesins, CD proteins and their receptors.

The term "interface" as used herein refers to the association surface that results from interaction of one or more amino acids in a first antibody domain with one or more amino acids of a second antibody domain. Exemplary interfaces include, e.g., CH1/CL, VH/VL and CH3/CH3. In some embodiments, the interface includes, for example, hydrogen bonds, electrostatic interactions, or salt bridges between the amino acids forming an interface.

One example of an "intact" or "full-length" antibody is one that comprises an antigen-binding arm as well as a CL and at least heavy chain constant domains, CH1, CH2, and CH3. The constant domains can be native sequence constant domains (e.g., human native sequence constant domains) or amino acid sequence variants thereof.

The term "coupling" as used herein refers to the steps necessary to link the first and second heavy chain polypeptides (i.e., H1 and H2) to each other, e.g., formation of a covalent bond. Such steps comprise the reducing, annealing and/or oxidizing of cysteine residues in the first and second heavy chain polypeptides (i.e., H1 and H2) to form an inter-chain disulfide bond. The coupling may be achieved by chemical cross-linking or the use of a redox system. See, e.g., Humphreys et al., J. Immunol. Methods (1998) 217:1-10 and Zhu et al. Cancer Lett., (1994) 86: 127-134.

"Monospecific" antigen-binding protein refers to the ability of the antigen binding protein, such as an antibody, to bind only one epitope. "Bispecific" antigen-binding protein refers to the ability of the antigen binding protein to bind two different epitopes. "Multispecific" antigen binding protein refers to the ability of the antigen binding protein to bind more than one epitope. In certain embodiments, a multispecific antigen-binding protein, such as a multispecific antibody, encompasses a bispecific antigen-binding protein or a bispecific antibody. For bispecific and multispecific antigen-binding proteins provided herein, the epitopes can be on the same antigen, or each epitope can be on a different antigen. Therefore, in certain embodiments, a multispecific antigen-binding protein provided herein, such as a bispecific antibody, binds to two different antigens. In certain embodiments, the multispecific antigen-binding protein, such as a bispecific antibody, binds to different epitopes on one antigen. In certain embodiments, a multispecific antigen-binding protein provided herein binds to each epitope with a dissociation constant (Kd) of about ≤1 µM, about ≤100 nM, about ≤10 nM, about ≤1 nM, about ≤0.1 nM, about ≤0.01 nM, or about ≤0.001 nM (e.g., about $10^{-8}$ M or less, e.g., from about $10^{-8}$ M to about $10^{-13}$ M, e.g., from about $10^{-9}$ M to about $10^{-13}$ M).

"Antibody fragments" comprise a portion of an intact antibody, preferably the antigen binding or a variable region of the intact antibody. Examples of antibody fragments include Fab, Fab', F(ab')2, and Fv fragments; diabodies (Db); tandem diabodies (taDb), linear antibodies (e.g., U.S. Pat. No. 5,641,870; Zapata et al., Protein Eng. 8(10):1057-1062 (1995)); one-armed antibodies, single variable domain antibodies, minibodies, single-chain antibody molecules; and multispecific antibodies formed from antibody fragments (e.g., including but not limited to, Db-Fc, taDb-Fc, taDb-CH3 and (scFV)4-Fc).

Antibodies provided herein can be "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, provided that they exhibit the desired biological activity (U.S. Pat. No. 4,816,567; and Morrison et al., Proc. Natl. Acad. Sci. USA 81:6851-6855 (1984)). Chimeric antibodies of interest herein include primatized antibodies comprising variable domain antigen-binding sequences derived from a non-human primate (e.g., Old World Monkey, Ape, etc.) and human constant region sequences.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a nonhuman immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

"Complex" or "complexed" as used herein refers to the association of two or more molecules that interact with each other through bonds and/or forces (e.g., van der Waals, hydrophobic, hydrophilic forces) that are not peptide bonds. In one embodiment, the complex is heteromultimeric. It should be understood that the term "protein complex" or "polypeptide complex" as used herein includes complexes that have a non-protein entity conjugated to a protein in the protein complex (e.g., including, but not limited to, chemical molecules such as a toxin or a detection agent).

A multispecific antigen-binding protein provided herein "which binds an antigen of interest" is one that binds the antigen, e.g., a protein, with sufficient affinity such that the multispecific antigen-binding protein is useful as a diagnostic and/or therapeutic agent in targeting a protein or a cell or tissue expressing the protein, and does not significantly cross-react with other proteins. In such embodiments, the extent of binding of the antigen-binding protein to a "non-target" protein will be less than about 10% of the binding of the antibody to its particular target protein as determined by fluorescence activated cell sorting (FACS) analysis or radioimmunoprecipitation (RIA) or ELISA. With regard to the binding of a multispecific antigen-binding protein to a target molecule, the term "specific binding" or "specifically binds to" or is "specific for" a particular polypeptide or an epitope on a particular polypeptide target means binding that is measurably different from a nonspecific interaction (e.g., a non-specific interaction may be binding to bovine serum albumin or casein). Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about 200 nM, alternatively at least about 150 nM, alternatively at least about 100 nM, alternatively at least about 60 nM, alternatively at least about 50 nM, alternatively at least about 40 nM, alternatively at least about 30 nM, alternatively at least about 20 nM, alternatively at least about 10 nM, alternatively at least about 8 nM, alternatively at least about 6 nM, alternatively at least about 4 nM, alternatively at least about 2 nM, alternatively at least about 1 nM, or greater affinity. In one embodiment, the term "specific binding" refers to binding where a multispecific antigen-binding protein binds to a particular polypeptide or epitope on a particular polypeptide without substantially binding to any other polypeptide or polypeptide epitope.

"Binding affinity" generally refers to the strength of the sum total of noncovalent interactions between a single binding site of a molecule (e.g., an antibody or a multispecific antigen-binding protein) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). For example, the Kd can be about 200 nM or less, about 150 nM or less, about 100 nM or less, about 60 nM or less, about 50 nM or less, about 40 nM or less, about 30 nM or less, about 20 nM or less, about 10 nM or less, about 8 nM or less, about 6 nM or less, about 4 nM or less, about 2 nM or less, or about 1 nM or less. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

In one embodiment, the "Kd" or "Kd value" is measured by using surface plasmon resonance assays using a BIAcore™-2000 or a BIAcore™-3000 (BIAcore, Inc., Piscataway, NJ) at 25° C. with immobilized target (e.g., antigen) CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 µg/ml (~0.2 µM) before injection at a flow rate of 5 µl/minute to achieve approximately 10 response units (RU) of coupled protein. Following the injection of antigen, 1M ethanolamine is injected to block unreacted groups. For kinetics measurements, two-fold serial dilutions of Fab (e.g., 0.78 nM to 500 nM) are injected in PBS with 0.05% Tween 20 (PBST) at 25° C. at a flow rate of approximately 25 l/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen et al., J. Mol. Biol. 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

"Biologically active" and "biological activity" and "biological characteristics" with respect to a multispecific antigen-binding protein provided herein, such as an antibody (e.g., a bispecific antibody), fragment, or derivative thereof, means having the ability to bind to a biological molecule, except where specified otherwise.

"Isolated," when used to describe the various heteromultimer polypeptides means a heteromultimer which has been separated and/or recovered from a cell or cell culture from which it was expressed. Contaminant components of its natural environment are materials which would interfere with diagnostic or therapeutic uses for the heteromultimer, and may include enzymes, hormones, and other proteinaceous or nonproteinaceous solutes. In certain embodiments, the heteromultimer will be purified (1) to greater than 95% by weight of protein as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS PAGE under reducing or nonreducing conditions using Coomassie blue or, preferably, silver stain. Ordinarily, however, isolated polypeptide will be prepared by at least one purification step.

The multispecific antigen-binding proteins provided herein are generally purified to substantial homogeneity. The phrases "substantially homogeneous," "substantially homogeneous form," and "substantial homogeneity" are used to indicate that the product is substantially devoid of by-products originated from undesired polypeptide combinations (e.g., homomultimers).

Expressed in terms of purity, substantial homogeneity means that the amount of by-products does not exceed 10%, 9%, 8%, 7%, 6%, 4%, 3%, 2% or 1% by weight or is less than 1% by weight. In one embodiment, the by-product is below 5%.

"Biological molecule" refers to a nucleic acid, a protein, a carbohydrate, a lipid, and combinations thereof. In one embodiment, the biologic molecule exists in nature.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxic agents. The antibodies "arm" the cytotoxic cells and are absolutely required for such killing. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, Annu. Rev. Immunol. 9:457-92 (1991). To assess ADCC activity of a molecule of interest, an in vitro ADCC assay, such as that described in U.S. Pat. No. 5,500,362 or 5,821,337 can be performed. Useful effector cells for such assays include peripheral blood mononuclear cells (PBMC) and Natural Killer (NK) cells. Alternatively, or additionally. ADCC activity of the molecule of interest can be assessed in vivo. e.g., in an animal model such as that disclosed in Clynes et al., Proc. Natl. Acad. Sci. USA 95:652-656 (1998).

"Fc receptor" or "FcR" describes a receptor that binds to the Fc region of an antibody. The preferred FcR is a human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. Daeron, Annu. Rev. Immunol. 15:203-234 (1997)). FcRs are reviewed in Ravetch and Kinet, Annu. Rev. Immunol. 9:457-492 (1991); Capel et al., Immunomethods 4:25-34 (1994); and de Haas et al., J. Lab. Clin. Med. 126:33041 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes that express one or more FcRs and perform effector functions. Preferably, the cells express at least FcγRIII and perform ADCC effector function. Examples of human leukocytes that mediate ADCC include peripheral blood mononuclear cells (PBMC), natural killer (NK) cells, monocytes, cytotoxic T cells, and neutrophils; with PBMCs and NK cells being preferred. The effector cells can be isolated from a native source. e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) that are bound to their cognate antigen. To assess complement activation, a CDC assay, e.g., as described in Gazzano-Santoro et al., J. Immunol. Methods 202:163 (1996), can be performed.

The term "therapeutically effective amount" refers to an amount of an antibody (including a multispecific antibody), antigen-binding antibody fragment thereof, or derivative thereof to treat a disease or disorder in a subject. In the case of tumor (e.g., a cancerous tumor), the therapeutically effective amount of the antibody or antibody fragment (e.g., a multispecific antibody or antibody fragment may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the antibody or antibody fragment thereof, or derivative thereof may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

By "reduce or inhibit" is meant the ability to cause an overall decrease preferably of 20% or greater, more preferably of 50% or greater, and most preferably of 75%, 85%, 90%, 95%, or greater. Reduce or inhibit can refer to the symptoms of the disorder being treated, the presence or size of metastases, the size of the primary tumor, or the size or number of the blood vessels in angiogenic disorders.

The terms "cancer" and "cancerous" refer to or describe the physiological condition in mammals that is typically characterized by unregulated cell growth/proliferation. Included in this definition are benign and malignant cancers. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastric or stomach cancer including gastrointestinal cancer, pancreatic cancer, glioblastoma, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer (e.g., renal cell carcinoma), liver cancer, prostate cancer, vulval cancer, thyroid cancer, hepatic carcinoma, anal carcinoma, penile carcinoma, melanoma, and various types of head and neck cancer. By "early stage cancer" is meant a cancer that is not invasive or metastatic or is classified as a Stage 0, I, or II cancer. The term "precancerous" refers to a condition or a growth that typically precedes or develops into a cancer. By "non-metastatic" is meant a cancer that is benign or that remains at the primary site and has not penetrated into the lymphatic or blood vessel system or to tissues other than the primary site. Generally, a nonmetastatic cancer is any cancer that is a Stage 0, I, or II cancer, and occasionally a Stage III cancer.

An "autoimmune disease" herein is a disease or disorder arising from and directed against an individual's own tissues or a co-segregate or manifestation thereof or resulting condition therefrom. Examples of autoimmune diseases or disorders include, but are not limited to rheumatoid arthritis, autoimmune hemolytic anemia (e.g., immune pancytopenia, paroxysmal nocturnal hemoglobinuria), autoimmune thrombocytopenia (e.g., idiopathic thrombocytopenic purpura, immune-mediated thrombocytopenia), thyroiditis (e.g., Grave's disease, Hashimoto's thyroiditis, juvenile lymphocytic thyroiditis, atrophic thyroiditis), type I diabetes mellitus or insulin-dependent diabetes, demyelinating diseases of the central and peripheral nervous systems (e.g., multiple sclerosis, idiopathic demyelinating polyneuropathy or Guillain-Barré syndrome), chronic inflammatory demyelinating polyneuropathy, bullous skin diseases, erythema multiforme, contact dermatitis, and autoimmune chronic active hepatitis.

The term "cytotoxic agent" as used herein refers to a substance that inhibits or prevents the function of a cell and/or causes destruction of a cell. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $Ra^{223}$, $P^{32}$, and radioactive isotopes of Lu), chemotherapeutic agents, e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor, anticancer, and chemotherapeutic agents disclosed herein. Other cytotoxic agents are described herein. A tumoricidal agent causes destruction of tumor cells.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug Administration.

"Anti-cancer therapy" as used herein refers to a treatment that reduces or inhibits cancer in a subject. Examples of anti-cancer therapy include cytotoxic radiotherapy as well as the administration of a therapeutically effective amount of a cytotoxic agent, a chemotherapeutic agent, a growth inhibitory agent, a cancer vaccine, an angiogenesis inhibitor, a prodrug, a cytokine, a cytokine antagonist, a corticosteroid, an immunosuppressive agent, an anti-emetic, an antibody or antibody fragment, or an analgesic to the subject.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam containing prodrugs, optionally substituted phenoxyacetamide-containing prodrugs or optionally substituted phenylacetamide-containing prod rugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "subject" is a vertebrate, such as a mammal, e.g., a human. Mammals include, but are not limited to, farm animals (such as cows), sport animals, pets (such as cats, dogs and horses), primates, mice, and rats.

Except where indicated otherwise by context, the terms "first" polypeptide (such as a heavy chain (H1) or light chain (L1)) and "second" polypeptide (such as a heavy chain (H2) or light chain (L2)), and variations thereof, are merely generic identifiers, and are not to be taken as identifying a specific or a particular polypeptide or component of multispecific antigen-binding proteins provided herein.

Commercially available reagents referred to in the Examples were used according to manufacturer's instructions unless otherwise indicated. The source of those cells identified in the following Examples, and throughout the specification, by ATCC accession numbers is the American Type Culture Collection, Manassas, VA. Unless otherwise noted, the present invention uses standard procedures of recombinant DNA technology, such as those described hereinabove and in the following textbooks: Sambrook et al., supra; Ausubel et al., Current Protocols in Molecular Biology (Green Publishing Associates and Wiley Interscience, N Y, 1989); Innis et al., PCR Protocols: A Guide to Methods and Applications (Academic Press, Inc., NY, 1990); Harlow et al., Antibodies: A Laboratory Manual (Cold Spring Harbor Press, Cold Spring Harbor, 1988); Gait, Oligonucleotide Synthesis (IRL Press, Oxford, 1984); Freshney, Animal Cell Culture, 1987; Coligan et al., Current Protocols in Immunology, 1991.

Reference to "about" a value or parameter herein refers to the usual error range for the respective value readily known to the skilled person in this technical field. Reference to "about" a value or parameter herein includes (and describes) aspects that are directed to that value or parameter per se. For example, description referring to "about X" includes description of "X."

It is understood that aspects and embodiments of the invention described herein include "comprising," "consisting of," and "consisting essentially of" aspects and embodiments.

All references cited herein, including patent applications and publications, are hereby incorporated by reference in their entirety.

Multispecific Antigen-Binding Proteins Comprising Mutant or Modified Heavy/Light Chain Pairs The present application is based on the identification of novel mutations in the CH1/CL interface, and/or the VH/VL interface that improve heavy chain/light chain pairing selectivity.

The multispecific antigen-binding proteins provided herein comprise amino acid modifications at particular residues within the variable and/or constant domains of heavy chain and light chain polypeptides. As one of ordinary skill in the art will appreciate, various numbering conventions may be employed for designating particular amino acid residues within IgG variable region sequences. Commonly used numbering conventions include Kabat and EU index numbering (see, Kabat et al., *Sequences of Proteins of Immunological Interest*, 5th Ed, Public Health Service, National Institutes of Health, Bethesda, MD (1991)). Other conventions that include corrections or alternate numbering systems for variable domains include Chothia (Chothia C, Lesk A M (1987), *J Mal Biol* 196: 901-917; Chothia, et al. (1989), *Nature* 342: 877-883), IMGT (Lefranc, et al. (2003), *Dev Comp Immunol* 27: 55-77), and AHo (Honegger A, Plückthun A (2001) *J Mol Biol* 309: 657-670). These references provide amino acid sequence numbering schemes for immunoglobulin variable regions that define the location of variable region amino acid residues of antibody sequences.

Unless otherwise expressly stated herein, all references to immunoglobulin heavy chain variable region (i.e., VH) amino acid residues (i.e. numbers) appearing in the Examples and Claims are based on the Kabat numbering system, as are all references to VL residues. All references to immunoglobulin heavy chain constant region CH1 residues (i.e., numbers) appearing in the Examples and Claims are based on the EU system, as are all references to CL residues. With knowledge of the residue number according to Kabat or EU Index numbering, one of ordinary skill can identify amino acid sequence modifications described herein, according to any commonly used numbering convention.

While the Examples and Claims herein employ Kabat or EU Index to identify particular amino acid residues, it is understood that the SEQ IDs appearing in the Sequence Listing, incorporated herein in its entirety, provide sequential numbering of amino acids within a given polypeptide and, thus, do not conform to the corresponding amino acid numbers as provided by Kabat or EU index. For example, the serine residue number 66 of SEQ ID NO:53 corresponds to S183 of CH1 under the EU numbering system.

Although items, components, or elements provided herein (such as "multispecific antigen-binding protein") may be described or claimed in the singular, the plural is contemplated to be within the scope thereof unless limitation to the singular is explicitly stated.

As described in more detail below, provided herein are modified multispecific antigen-binding proteins that can be produced in a single cell with improved correct heavy chain/light chain pairing and/or improved yields as compared with multispecific antigen-binding proteins with sequences without modifications. In certain embodiments, the multispecific antigen-binding proteins comprise modification(s) in the VH/VL and/or CH1/CL regions to facilitate correct heavy/light chain pairing (i.e., the pairing of a first heavy chain H1 (or fragment thereof) with a first light chain L1 for form a first heavy/light chain pair (i.e., H1/L1) capable of binding a first epitope and the pairing of a second heavy chain H2 (or fragment thereof) with a second light chain L2 to form a second heavy/light chain pair (i.e., H2/L2) capable of binding a second (e.g., different) epitope). It will be apparent to those of ordinary skill in the art that the terms "H1" and "H2" are arbitrary designations, and that "H1" and "H2" in any of the embodiments above can be reversed. That is, any of the mutations above described as being in the CH1 domain of H1 and CL domain of L can, alternatively, be in the CH1 domain of H2 and the CL domain of L2.

In certain other embodiments, the multispecific antigen-binding proteins further comprise modification(s) in the Fc region to facilitate heterodimerization of the two arms of the multispecific antigen-binding protein.

Strategy #1

In one aspect, it was surprisingly found that a single amino acid modification to position S183 (EU numbering) in the CH1 domain of a heavy chain and a single amino acid modification to position V133 (EU numbering) in the CL domain of a light chain demonstrates preferential pairing between the modified heavy chain and the modified light chain and reducing pairing between, e.g., the modified heavy chain and a non-modified light chain, or, e.g., a non-modified heavy chain and the modified light chain. These residues were selected by expression data and confirmed by the knowledge and studies of the structure and function of the heavy chain CH1 domain and light chain CL domain. See FIGS. 1-3, 11C and 12C.

Thus, in certain embodiments, there is provided a multispecific antigen-binding protein comprising: (a) a first heavy chain/light chain pair capable of binding to a first antigen, the first heavy chain/light chain pair comprising a first heavy chain polypeptide (H1) and a first light chain poly peptide (L1), and (b) a second heavy chain/light chain pair capable of binding to a second antigen, the second heavy chain/light chain pair comprising a second heavy chain polypeptide (H2) and a second light chain polypeptide (L2), wherein each H1 and H2 comprises a heavy chain variable domain (VH) and a heavy chain constant domain (CH1), and each L1 and L2 comprises a light chain variable domain (VL) and a light chain constant domain (CL); wherein the CH1 domain of H1 comprises an amino acid substitution at position S183 (EU numbering), and wherein the CL domain comprises an amino acid substitution mutation at position V133 (EU numbering). In certain embodiments, the CH1 domain of H1 consists of (such as consists essentially of) an amino acid substitution at position S183 (EU numbering), and wherein the CL domain consists of (such as consists essentially of) an amino acid substitution mutation at position V133 (EU numbering). In certain embodiments, the first antigen and the second antigen are the same. In certain embodiments, the first heavy chain/light chain pair and the second heavy chain/light chain pair each bind to a different epitope on the same antigen. In certain embodiments, the first antigen and the second antigen are different. In certain embodiments, the multispecific antigen-binding protein is a bispecific antibody that binds two different antigens. In certain embodiments, the bispecific antibody is an antagonist or an agonist antibody. In certain embodiments, the bispecific antibody is an antagonist to one or both antigens; while in other embodiments, the bispecific antibody is an agonist to one or both antigens. Antigen-binding fragments of the multispecific antigen-binding proteins (such as bispecific antibodies) provided herein are also contemplated.

In certain embodiments, the amino acid at position S183 (EU numbering) on the CH1 domain of H1 of the multispecific antigen-binding protein is replaced with a positively charged amino acid residue, and the amino acid at position V133 (EU numbering) on the CL domain of the multispecific antigen-binding protein is replaced with a negatively charged residue. In certain embodiments, the amino acid at position S183 (EU numbering) on the CH1 domain of H1 is replaced with a negatively charged amino acid residue, and the amino acid at position V133 (EU numbering) on the CL domain is replaced with a positively charged residue. In certain embodiments, the positively charged residue is selected from the group consisting of R or K. In certain embodiments, the negatively charged residue is selected from the group consisting of D and E.

In certain embodiments, the CH1 domain of the multispecific antigen-binding protein comprises an amino acid substitution selected from the group consisting of S183A, S183T, S183V, S183Y, S183F, S183H, S183N, S183D, S183E, S183R, and S183K (EU numbering), and wherein the CL domain comprises an amino acid substitution selected from the group consisting of V133E, V133S, V133L, V133W, V133K, V133R, and V133D (EU numbering).

In certain embodiments, the CH1 domain of the multispecific antigen-binding protein consists of (such as consists essentially of) an amino acid substitution selected from the group consisting of: S183A, S183T, S183V, S183Y, S183F, S183H, S183N, S183D, S183E, S183R. and S183K (EU numbering), and wherein the CL domain consists of (such as consists essentially of) an amino acid substitution selected from the group consisting of V133E, V133S, V133L, V133W, V133K, V133R, and V133D (EU numbering).

It will be apparent to those of ordinary skill in the art that the terms "H1" and "H2" are arbitrary designations, and that "H1" and "H2" in any of the embodiments above can be reversed. That is, any of the mutations above described as being in the CH1 domain of H1 and CL domain of L1 can, alternatively, be in the CH1 domain of H2 and the CL domain of L2.

Thus, all possible pair-wise combinations of substitution mutations at position S183 (EU numbering) on the CH1 domain of H1 and at position V133 (EU numbering) on the CL domain of L1 are contemplated. In certain embodiments, specific combinations of substitution mutations at position S183 (EU numbering) on the CH1 domain of H1 and at position V133 (EU numbering) on the CL domain of L are contemplated. Such combinations include, but are not limited to, those provided in Table 1 below:

TABLE 1

| S183D/ | S183A/ | S183T/ | S183V/ | S183Y/ | S183F/ | S183F/ |
|---|---|---|---|---|---|---|
| V133K | V133K | V133W | V133L | V133S | V133E | V133D |
| S183E/ | S183A/ | S183T/ | S183V/ | S183Y/ | S183F/ | S183H/ |
| V133K | V133R | V133K | V133W | V133L | V133S | V133S |
| S183A/ | S183A/ | S183T/ | S183V/ | S183Y/ | S183F | S183H/ |
| V133E | V133D | V133K | V133K | V133W | V133L | V133L |
| S183A/ | S183T/ | S183T/ | S183V/ | S183Y/ | S183F/ | S183H/ |
| V133S | V133E | V133D | V133R | V133K | V133W | V133W |
| S183A/ | S183T/ | S183V/ | S183V/ | S183Y/ | S183F/ | S183N/ |
| V133L | V133S | V133E | V133D | V133R | V133K | V133L |
| S183A/ | S183T/ | S183V/ | S183Y/ | S183Y/ | S183F/ | S183E/ |
| V133W | V133L | V133S | V133E | V133D | V133R | V133L |
| S183T/ | S183K/ | S183Y/ | | | | |
| V133K | V133E | V133K | | | | |

In certain embodiments, the multispecific antigen-binding protein comprises a CH1 domain of H1 comprising the S183D or SI 83E mutation (EU numbering), and a CL domain of L1 comprising the V133K mutation (EU numbering). In certain embodiments, the multispecific antigen-binding protein comprises a CH1 domain of H1 and a CL domain of L1, wherein the CH1 domain consists of the S183D or S183E mutation (EU numbering), and a CL domain of L1 consists of the V133K mutation (EU numbering).

Two exemplary IgG1 CH1 domain amino acid sequences (SEQ ID NO: 53 and SEQ ID NO: 109), an exemplary IgG2 CH1 domain amino acid sequence (SEQ ID NO: 109), an exemplary IgG2 CH1 domain sequence (SEQ ID NO: 110), an exemplary IgG3 CH1 domain amino acid sequence (SEQ ID NO: 111), an exemplary IgG4 CH1 domain amino acid sequence (SEQ ID NO: 112), an exemplary lambda CL domain amino acid sequence (SEQ ID NO: 113) and an exemplary kappa CL domain amino acid sequence (SEQ ID NO: 54) are provided below:

```
                                   (SEQ ID NO: 53)
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKKV
                                   (SEQ ID NO: 109)
TKGPSVFPLA PSSKSTSGGT AALGCLVKDY FPEPVTVSWN

SGALTSGVHT FPAVLQSSGL YSLSSVVTVP SSSLGTQTYI

CN
                                   (SEQ ID NO: 110)
TKGPSVFPLA PCSRSTSEST AALGCLVKDY FPEPVTVSWN

SGALTSGVHT FAPVLQSSGL YSLSSVVTVP SSNFGTQTYT

CN
                                   (SEQ ID NO: 111)
TKGPSVFPLA PCSRSTSGGT AALGCLVKDY FPEPVTVSWN

SGALTSGVHT FAPVLQSSGL YSLSSVVTVP SSSLGTQTYT

CN
                                   (SEQ ID NO: 112)
TKGPSVFPLA PCSRSTSEST AALGCLVKDY FPEPVTVSWN

SGALTSGVHT FPAVLQSSGL YSLSSVVTVP SSSLGTKTYT

CN
                                   (SEQ ID NO: 113)
GQPKAAPSVT LFPPSSEELQ ANKATLVCLI SDFYPGAVTV

AWKADSSPVK AGVETTIPSK QSNNKYAASS YL forth in SEQ ID NO: 1 or the amino acids 11-116 in the sequence set forth in SEQ ID NO: 1. In certain embodiments, the multispecific antigen-binding protein comprises a CL domain of L1 comprising the amino acid sequence set forth in SEQ ID NO: 2 or the amino acids 11-116 in the sequence set forth in SEQ ID NO: 2. In certain embodiments, the multispecific antigen-binding protein comprises a CL domain of L1 comprising the amino acid sequence set forth in SEQ ID NO: 3 or the amino acids 11-116 in the sequence set forth in SEQ ID NO: 3. In certain embodiments, the multispecific antigen-binding protein comprises a CL domain of L1 comprising the amino acid sequence set forth in SEQ ID NO: 4 or the amino acids 11-116 in the sequence set forth in SEQ ID NO: 4. In certain embodiments, the multispecific antigen-binding protein comprises a CL domain of L1 comprising the amino acid sequence set forth in SEQ ID NO: 5 or the amino acids 11-116 in the sequence set forth in SEQ ID NO: 5. In certain embodiments, the multispecific antigen-binding protein comprises a CL domain of L1 comprising the amino acid sequence set forth in SEQ ID NO: 6 or the amino acids 11-116 in the sequence set forth in SEQ ID NO: 6. In certain embodiments, the multispecific antigen-binding protein comprises a CL domain of L1 comprising the amino acid sequence set forth in SEQ ID NO: 7 or the amino acids 11-116 in the sequence set forth in SEQ ID NO: 7.

The amino acid sequences of SEQ ID NOs: 1-7 are provided in Table 2A below. In certain embodiments, the multispecific antigen-binding protein comprises a first light chain polypeptide L1 comprising a CL domain as set forth in any of these sequences. The CL domain as set forth in SEQ ID NO: 54 corresponds to amino acids 11-116 of SEQ ID NOs: 1-7. Accordingly, L1 may comprise a CL domain comprising amino acids 11-116 as set forth in any of SEQ ID Nos: 1-7.

TABLE 2A

| | |
|---|---|
| V133E SEQ ID NO: 1 | GQGTKVEIKR TVAAPSVFIF PPSDEQLKSG TASVECLLNN FYPREAKVQW KVDNALQSGN SQESVTEQDS KDSTYSLSST LTLSKADYEK HKVYACEVTH QGLSSPVTKS FNRGEC |
| V133S SEQ ID NO: 2 | GQGTKVEIKR TVAAPSVFIF PPSDEQLKSG TASVSCLLNN FYPREAKVQW KVDNALQSGN SQESVTEQDS KDSTYSLSST LTLSKADYEK HKVYACEVTH QGLSSPVTKS FNRGEC |
| V133L SEQ ID NO: 3 | GQGTKVEIKR TVAAPSVFIF PPSDEQLKSG TASVLCLLNN FYPREAKVQW KVDNALQSGN SQESVTEQDS KDSTYSLSST LTLSKADYEK HKVYACEVTH QGLSSPVTKS FNRGEC |
| V133W SEQ ID NO: 4 | GQGTKVEIKR TVAAPSVFIF PPSDEQLKSG TASVWCLLNN FYPREAKVQW KVDNALQSGN SQESVTEQDS KDSTYSLSST LTLSKADYEK HKVYACEVTH QGLSSPVTKS FNRGEC |
| V133K SEQ ID NO: 5 | GQGTKVEIKR TVAAPSVFIF PPSDEQLKSG TASVKCLLNN FYPREAKVQW KVDNALQSGN SQESVTEQDS KDSTYSLSST LTLSKADYEK HKVYACEVTH QGLSSPVTKS FNRGEC |
| V133R SEQ ID NO: 6 | GQGTKVEIKR TVAAPSVFIF PPSDEQLKSG TASVRCLLNN FYPREAKVQW KVDNALQSGN SQESVTEQDS KDSTYSLSST LTLSKADYEK HKVYACEVTH QGLSSPVTKS FNRGEC |
| V133D SEQ ID NO: 7 | GQGTKVEIKR TVAAPSVFIF PPSDEQLKSG TASVDCLLNN FYPREAKVQW KVDNALQSGN SQESVTEQDS KDSTYSLSST LTLSKADYEK HKVYACEVTH QGLSSPVTKS FNRGEC |

Amino acid position 133 (EU numbering) in the CL domain of a kappa light chain corresponds to amino acid position 35 in SEQ ID NOs: 1-7.

In certain embodiments, the multispecific antigen-binding protein comprises a lambda light chain. In certain embodiments, the multispecific antigen-binding protein comprises a CL domain of L1 comprising the amino acid sequence set forth in SEQ ID NO: 114. In certain embodiments, the multispecific antigen-binding protein comprises a CL domain of L1 comprising the amino acid sequence set forth in SEQ ID NO: 115. In certain embodiments, the multispecific antigen-binding protein comprises a CL domain of L1 comprising the amino acid sequence set forth in SEQ ID NO: 116. In certain embodiments, the multispecific antigen-binding protein comprises a CL domain of L1 comprising the amino acid sequence set forth in SEQ ID NO: 117. In certain embodiments, the multispecific antigen-binding protein comprises a CL domain of L1 comprising the amino acid sequence set forth in SEQ ID NO: 118. In certain embodiments, the multispecific antigen-binding protein comprises a CL domain of L1 comprising the amino acid sequence set forth in SEQ ID NO: 119. In certain embodiments, the multispecific antigen-binding protein comprises a CL domain of L1 comprising the amino acid sequence set forth in SEQ ID NO: 120.

The amino acid sequences of SEQ ID NOs: 114-120 are provided in Table 2B below:

TABLE 2B

| | |
|---|---|
| V133E SEQ ID NO: 114 | GQPKAAPSVT LFPPSSEELQ ANKATLECLI SDFYPGAVTV AWKADSSPVK AGVETTTPSK QSNNKYAASS YLSLTPEQWK SHKSYSCQVT HEGSTVEKTV APTECS |
| V133S SEQ ID NO: 115 | GQPKAAPSVT LFPPSSEELQ ANKATLSCLI SDFYPGAVTV AWKADSSPVK AGVETTTPSK QSNNKYAASS YLSLTPEQWK SHKSYSCQVT HEGSTVEKTV APTECS |
| V133L SEQ ID NO: 116 | GQPKAAPSVT LFPPSSEELQ ANKATLLCLI SDFYPGAVTV AWKADSSPVK AGVETTTPSK QSNNKYAASS YLSLTPEQWK SHKSYSCQVT HEGSTVEKTV APTECS |
| V133W SEQ ID NO: 117 | GQPKAAPSVT LFPPSSEELQ ANKATLWCLI SDFYPGAVTV AWKADSSPVK AGVETTTPSK QSNNKYAASS YLSLTPEQWK SHKSYSCQVT HEGSTVEKTV APTECS |
| V133K SEQ ID NO: 118 | GQPKAAPSVT LFPPSSEELQ ANKATLKCLI SDFYPGAVTV AWKADSSPVK AGVETTTPSK QSNNKYAASS YLSLTPEQWK SHKSYSCQVT HEGSTVEKTV APTECS |
| V133R SEQ ID NO: 119 | GQPKAAPSVT LFPPSSEELQ ANKATLRCLI SDFYPGAVTV AWKADSSPVK AGVETTTPSK QSNNKYAASS YLSLTPEQWK SHKSYSCQVT HEGSTVEKTV APTECS |
| V133D SEQ ID NO: 120 | GQPKAAPSVT LFPPSSEELQ ANKATLDCLI SDFYPGAVTV AWKADSSPVK AGVETTTPSK QSNNKYAASS YLSLTPEQWK SHKSYSCQVT HEGSTVEKTV APTECS |

Amino acid position 133 (EU numbering) in the CL domain of a kappa light chain corresponds to amino acid position 133 (Kabat numbering) in the CL domain of a lambda light chain, which corresponds to amino acid position 27 in SEQ ID NOs: 114-120.

In certain embodiments, the multispecific antigen-binding protein comprises an IgG1 heavy chain, an IgG2 heavy chain, an IgG3 heavy chain, or an IgG4 heavy chain. In certain embodiments, the multispecific antigen-binding protein comprises a CH1 domain of H1 comprising the amino acid sequence set forth in SEQ ID NO: 8. In certain embodiments, the multispecific antigen-binding protein comprises a CH1 domain of H1 comprising the amino acid sequence set forth in SEQ ID NO: 9. In certain embodiments, the multispecific antigen-binding protein comprises a CH1 domain of H1 comprising the amino acid sequence set forth in SEQ ID NO: 10. In certain embodiments, the multispecific antigen-binding protein comprises a CH1 domain of H1 comprising the amino acid sequence set forth in SEQ ID NO: 11. In certain embodiments, the multispecific antigen-binding protein comprises a CH1 domain of H1 comprising the amino acid sequence set forth in SEQ ID NO: 12. In certain embodiments, the multispecific antigen-binding protein comprises a CH1 domain of H1 comprising the amino acid sequence set forth in SEQ ID NO: 13. In certain embodiments, the multispecific antigen-binding protein comprises a CH1 domain of H1 comprising the amino acid sequence set forth in SEQ ID NO: 14. In certain embodiments, the multispecific antigen-binding protein comprises a CH1 domain of H1 comprising the amino acid sequence set forth in SEQ ID NO: 15. In certain embodiments, the multispecific antigen-binding protein comprises a CH1 domain of H1 comprising the amino acid sequence set forth in SEQ ID NO: 16. In certain embodiments, the multispecific antigen-binding protein comprises a CH1 domain of H1 comprising the amino acid sequence set forth in SEQ ID NO: 101. In certain embodiments, the multispecific antigen-binding protein comprises a CH1 domain of H1 comprising the amino acid sequence set forth in SEQ ID NO: 102. In certain embodiments, the multispecific antigen-binding protein comprises a CH1 domain of H1 comprising the amino acid sequence set forth in SEQ ID NO: 121. In certain embodiments, the multispecific antigen-binding protein comprises a CH1 domain of H1 comprising the amino acid sequence set forth in SEQ ID NO: 122. In certain embodiments, the multispecific antigen-binding protein comprises a CH1 domain of H1 comprising the amino acid sequence set forth in SEQ ID NO: 123. In certain embodiments, the multispecific antigen-binding protein comprises a CH1 domain of H1 comprising the amino acid sequence set forth in SEQ ID NO: 124. In certain embodiments, the multispecific antigen-binding protein comprises a CH1 domain of H1 comprising the amino acid sequence set forth in SEQ ID NO: 125. In certain embodiments, the multispecific antigen-binding protein comprises a CH1 domain of H1 comprising the amino acid sequence set forth in SEQ ID NO: 126.

The amino acid sequences of SEQ ID NOs: 8-16, 101-102, and 121-126 are provided in Table 3 below:

TABLE 3

| | |
|---|---|
| S183A<br>SEQ ID NO: 8 | TKGPSVFPLA PSSKSTSGGT AALGCLVKDY<br>FPEPVTVSWN SGALTSGVHT FPAVLQSSGL<br>YSLA SVVTVP SSSLGTQTYI CN |
| S183T<br>SEQ ID NO: 9 | TKGPSVFPLA PSSKSTSGGT AALGCLVKDY<br>FPEPVTVSWN SGALTSGVHT FPAVLQSSGL<br>YSLT SVVTVP SSSLGTQTYI CN |
| S183V<br>SEQ ID NO: 10 | TKGPSVFPLA PSSKSTSGGT AALGCLVKDY<br>FPEPVTVSWN SGALTSGVHT FPAVLQSSGL<br>YSLV SVVTVP SSSLGTQTYI CN |
| S183Y<br>SEQ ID NO: 11 | TKGPSVFPLA PSSKSTSGGT AALGCLVKDY<br>FPEPVTVSWN SGALTSGVHT FPAVLQSSGL<br>YSLY SVVTVP SSSLGTQTYI CN |
| S183F<br>SEQ ID NO: 12 | TKGPSVFPLA PSSKSTSGGT AALGCLVKDY<br>FPEPVTVSWN SGALTSGVHT FPAVLQSSGL<br>YSLF SVVTVP SSSLGTQTYI CN |
| S183H<br>SEQ ID NO: 13 | TKGPSVFPLA PSSKSTSGGT AALGCLVKDY<br>FPEPVTVSWN SGALTSGVHT FPAVLQSSGL<br>YSLH SVVTVP SSSLGTQTYI CN |
| S183N<br>SEQ ID NO: 14 | TKGPSVFPLA PSSKSTSGGT AALGCLVKDY<br>FPEPVTVSWN SGALTSGVHT FPAVLQSSGL<br>YSLN SVVTVP SSSLGTQTYI CN |
| S183E IgG1<br>SEQ ID NO: 15 | TKGPSVFPLA PSSKSTSGGT AALGCLVKDY<br>FPEPVTVSWN SGALTSGVHT FPAVLQSSGL<br>YSLE SVVTVP SSSLGTQTYI CN |
| S183D<br>SEQ ID NO: 16 | TKGPSVFPLA PSSKSTSGGT AALGCLVKDY<br>FPEPVTVSWN SGALTSGVHT FPAVLQSSGL<br>YSLD SVVTVP SSSLGTQTYI CN |
| S183E IgG2<br>SEQ ID NO: 121 | TKGPSVFPLA PCSRSTSEST AALGCLVKDY<br>FPEPVTVSWN SGALTSGVHT FPAVLQSSGL<br>YSLE SVVTVP SSNFGTQTYT CN |
| S183E IgG3<br>SEQ ID NO: 122 | TKGPSVFPLA PCSRSTSGGT AALGCLVKDY<br>FPEPVTVSWN SGALTSGVHT FPAVLQSSGL<br>YSLE SVVTVP SSNFGTQTYT CN |
| S183E IgG4<br>SEQ ID NO: 123 | TKGPSVFPLA PCSRSTSEST AALGCLVKDY<br>FPEPVTVSWN SGALTSGVHT FAPVLQSSGL<br>YSLE SVVTVP SSSLGTKTYT CN |
| S183R<br>SEQ ID NO: 101 | TKGPSVFPLA PSSKSTSGGT AALGCLVKDY<br>FPEPVTVSWN SGALTSGVHT FPAVLQSSGL<br>YSLR SVVTVP SSSLGTQTYI CN |
| S183K IgG1<br>SEQ ID NO: 102 | TKGPSVFPLA PSSKSTSGGT AALGCLVKDY<br>FPEPVTVSWN SGALTSGVHT FPAVLQSSGL<br>YSLK SVVTVP SSSLGTQTYI CN |
| S183K IgG2<br>SEQ ID NO: 124 | TKGPSVFPLA PCSRSTSEST AALGCLVKDY<br>FPEPVTVSWN SGALTSGVHT FPAVLQSSGL<br>YSLK SVVTVP SSNFGTQTYT CN |
| S183K IgG3<br>SEQ ID NO: 125 | TKGPSVFPLA PCSRSTSGGT AALGCLVKDY<br>FPEPVTVSWN SGALTSGVHT FPAVLQSSGL<br>YSLK SVVTVP SSNFGTQTYT CN |
| S183K IgG4<br>SEQ ID NO: 126 | TKGPSVFPLA PCSRSTSEST AALGCLVKDY<br>FPEPVTVSWN SGALTSGVHT FPAVLQSSGL<br>YSLK SVVTVP SSNFGTKTYT CN |

Amino acid position 183 in the CH1 domain of IgG1, IgG2, IgG3, and IgG4 corresponds to amino acid position 64 in SEQ ID NOs: 8-16, 101-102, and 121-126.

All possible pair-wise combinations of SEQ ID NOs: 1-7 or amino acids 11-116 of SEQ ID Nos: 1-7 and 114-120 with SEQ ID NOs: 8-15, 101-102, and 121-126 are contemplated. In certain embodiments, specific combinations of SEQ ID NOs: 1-7 or amino acids 11-116 of SEQ ID Nos: 1-7 and 114-120 with SEQ ID NOs 8-15 and 101 and 102 are contemplated. Such combinations include, but are not limited to, those provided in Table 4 below (HC is IgG1 HC unless indicated otherwise):

TABLE 4

| SEQ ID NO: 16/<br>SEQ ID NO: 5* | SEQ ID NO: 8/<br>SEQ ID NO: 5* | SEQ ID NO: 9/<br>SEQ ID NO: 4* | SEQ ID NO: 10/<br>SEQ ID NO: 3* |
|---|---|---|---|

TABLE 4-continued

| | | | |
|---|---|---|---|
| S183D/V133K kappa | S183A/V133K kappa | S183T/V133W kappa | S183V/V133L kappa |
| SEQ ID NO: 15/ | SEQ ID NO: 8/ | SEQ ID NO: 9/ | SEQ ID NO: 10/ |
| SEQ ID NO: 5* | SEQ ID NO: 6* | SEQ ID NO: 5* | SEQ ID NO: 4* |
| S183E/V133K IGg1/kappa | S183A/V133R kappa | S183T/V133K kappa | S183V/V133W kappa |
| SEQ ID NO: 8/ | SEQ ID NO: 8/ | SEQ ID NO: 9/ | SEQ ID NO: 10/ |
| SEQ ID NO: 1* | SEQ ID NO: 7* | SEQ ID NO: 6* | SEQ ID NO: 5* |
| S183A/V133E kappa | S183A/V133D kappa | S183T/V133R kappa | S183V/V133K kappa |
| SEQ ID NO: 8/ | SEQ ID NO: 9/ | SEQ ID NO: 9/ | SEQ ID NO: 10/ |
| SEQ ID NO: 2* | SEQ ID NO: 1* | SEQ ID NO: 7* | SEQ ID NO: 6* |
| S183A/V133S kappa | S183T/V133E kappa | S183T/V133D kappa | S183V/V133R kappa |
| SEQ ID NO: 8/ | SEQ ID NO: 9/ | SEQ ID NO: 9/ | SEQ ID NO: 10/ |
| SEQ ID NO: 3* | SEQ ID NO: 2* | SEQ ID NO: 1* | SEQ ID NO: 7* |
| S183A/V133L kappa | S183T/V133S kappa | S183V/V133E kappa | S183V/V133D kappa |
| SEQ ID NO: 8/ | SEQ ID NO: 9/ | SEQ ID NO: 10/ | SEQ ID NO: 11/ |
| SEQ ID NO: 4* | SEQ ID NO: 3* | SEQ ID NO: 2* | SEQ ID NO: 1* |
| S183A/V133W kappa | S183T/V133L kappa | S183V/V133S kappa | S183Y/V133E kappa |
| SEQ ID NO: 11/ | SEQ ID NO: 12/ | SEQ ID NO: 12/ | SEQ ID NO: 11/ |
| SEQ ID NO: 2* | SEQ ID NO: 1* | SEQ ID NO: 7* | SEQ ID NO: 3* |
| S183Y/V133S kappa | S183F/V133E kappa | S183F/V133D kappa | S183Y/V133L kappa |
| SEQ ID NO: 12/ | SEQ ID NO: 13/ | SEQ ID NO: 11/ | SEQ ID NO: 12/ |
| SEQ ID NO: 2* | SEQ ID NO: 2* | SEQ ID NO: 4* | SEQ ID NO: 3* |
| S183F/V133S kappa | S183H/V133S kappa | S183Y/V133W kappa | S183F/V133L kappa |
| SEQ ID NO: 13/ | SEQ ID NO: 11/ | SEQ ID NO: 12/ | SEQ ID NO: 13/ |
| SEQ ID NO: 3* | SEQ ID NO: 5* | SEQ ID NO: 4* | SEQ ID NO: 4* |
| S183H/V133L kappa | S183Y/V133K kappa | S183F/V133W kappa | S183H/V133W kappa |
| SEQ ID NO: 11/ | SEQ ID NO: 12/ | SEQ ID NO: 14/ | SEQ ID NO: 11/ |
| SEQ ID NO: 6* | SEQ ID NO: 5* | SEQ ID NO: 3* | SEQ ID NO: 7* |
| S183Y/V133R kappa | S183F/V133K kappa | S183N/V133L kappa | S183Y/V133D kappa |
| SEQ ID NO: 12/ | SEQ ID NO: 15/ | SEQ ID NO: 102/ | SEQ ID NO: 9/ |
| SEQ ID NO: 6* | SEQ ID NO: 3* | SED ID NO: 1* | SEQ ID NO: 5* |
| S183F/V133R kappa | S183E/V133L kappa | S183K/V133E kappa | S183T/V133K kappa |
| SEQ ID NO: 8/ | SEQ ID NO: 9/ | SEQ ID NO: 10/ | SEQ ID NO: 11/ |
| SEQ ID NO: 114 | SEQ ID NO: 114 | SEQ ID NO: 114 | SEQ ID NO: 114 |
| S183A/V133E lambda | S183T/V133E lambda | S183V/V133E lambda | S183Y/V133E lambda |
| SEQ ID NO: 12/ | SEQ ID NO: 102/ | SEQ ID NO: 16/ | SEQ ID NO: 8/ |
| SEQ ID NO: 114 | SED ID NO: 114 | SEQ ID NO: 118 | SEQ ID NO: 118 |
| S183F/V133E lambda | S183K/V133E IgG1/lambda | S183D/V133K lambda | S183A/V133K lambda |
| SEQ ID NO: 15/ | SEQ ID NO: 9/ | SEQ ID NO: 10/ | SEQ ID NO: 11/ |
| SEQ ID NO: 118 | SEQ ID NO: 118 | SEQ ID NO: 118 | SEQ ID NO: 118 |
| S183E/V133K IgG1/lambda | S183T/V133K lambda | S183V/V133K lambda | S183Y/V133K lambda |
| SEQ ID NO: 12/ | SEQ ID NO: 9/ | SEQ ID NO: 121/ | SEQ ID NO: 122/ |
| SEQ ID NO: 118 | SEQ ID NO: 118 | SEQ ID NO: 5 | SEQ ID NO: 5 |
| S183F/V133K lambda | S183T/V133K lambda | S183E/V133K IgG2/kappa | S183E/V133K IgG3/kappa |
| SEQ ID NO: 123/ | SEQ ID NO: 121/ | SEQ ID NO: 122/ | SEQ ID NO: 123/ |
| SEQ ID NO: 5 | SEQ ID NO: 118 | SEQ ID NO: 118 | SEQ ID NO: 118 |
| S183E/V133K IgG4/kappa | S183E/V133K IgG2/lambda | S183E/V133K IgG3/lambda | S183E/V133K IgG4/lambda |
| SEQ ID NO: 124/ | SEQ ID NO: 125/ | SEQ ID NO: 126/ | SEQ ID NO: 124/ |
| SED ID NO: 1 | SED ID NO: 1 | SED ID NO: 1 | SED ID NO: 114 |
| S183K/V133E IgG2/kappa | S183K/V133E IgG3/kappa | S183K/V133E IgG4/kappa | S183K/V133E IgG2/lambda |
| SEQ ID NO: 125/ | SEQ ID NO: 126/ | | |
| SED ID NO: 114 | SED ID NO: 114 | | |
| S183K/V133E IgG3/lambda | S183K/V133E IgG4/lambda | | |

*or amino acids 11-116 of the corresponding sequence

The first SEQ ID NO in each pair in Table 4 refers to a CH1 domain sequence, and the second SEQ ID NO in each pair in Table 4 refers to a CL domain sequence.

It will be apparent to those of ordinary skill in the art that the terms "H1" and "H2" are arbitrary designations, and that "H1" and "H2" in any of the embodiments above can be reversed. That is, any of the mutations above described as being in the CH1 domain of H1 and CL domain of L1 can, alternatively, be in the CH1 domain of H2 and the CL domain of L2.

In certain embodiments, the multispecific antigen-binding proteins comprise CH1/CL mutations and demonstrate correct protein folding and/or expression levels that are comparable or superior to the multispecific antigen-binding proteins without the mutations or each parental monospecific antigen-binding proteins without the mutations.

In certain embodiments, the CH1 domain of H2 and the CL domain of L2 of the multispecific antigen-binding protein do not comprise an amino acid substitution. In certain embodiments, the CH1 of H2 of the multispecific antigen-binding protein does not comprise a substitution at S183 (EU numbering), and the CL of L2 of the multispecific antigen-binding protein does not comprise a substitution at V133 (EU numbering).

In certain embodiments, the parental H1 from which an H1 of a multispecific antigen-binding protein provided herein is derived does not show a significant preference for a parental L1 from which an L1 of a multispecific antigen-binding protein provided herein is derived. In certain embodiments. In certain embodiments, the parental H1 from which an H1 of a multispecific antigen-binding protein provided herein is derived shows a preference for a parental L1 from which an L1 of a multispecific antigen-binding protein provided herein is derived.

It will be apparent to those of ordinary skill in the art that the terms "H1" and "H2" are arbitrary designations, and that "H1" and "H2" in any of the embodiments above can be reversed. That is, any of the mutations above described as being in the CH1 domain of H1 and CL domain of L can, alternatively, be in the CH1 domain of H2 and the CL domain of L2.

Strategy #2

Using a second strategy aided by computer-guided and human-guided designs, Applicants redesigned the interacting surfaces of a CH1 domain of a heavy chain and a CL domain of a light chain to generate CH1/CL mutant pairs that are sterically compatible (such as conformationally compatible) with each other. The modified CH1 domains in each CH1/CL mutant pair are less sterically compatible (such as conformationally compatible) with wild-type CL, and demonstrate decreased pairing to wild-type CL. Correspondingly, the modified CL domains in each CH1/CL mutant pair are less sterically compatible (such as conformationally compatible) with wild-type CH1, and demonstrate decreased pairing to wild-type CH1. It was surprisingly discovered that the Tm of the Fabs comprising the modifications at the interface of the CH1 and CL domains were the same or substantially the same as the Tm of the Fabs without the corresponding mutations in the CH1/CL domains.

The mutations identified using the design strategy described below can be used independently of or in addition to the S183/V133 mutations discussed above (i.e., Strategy #1).

Figure 11B:
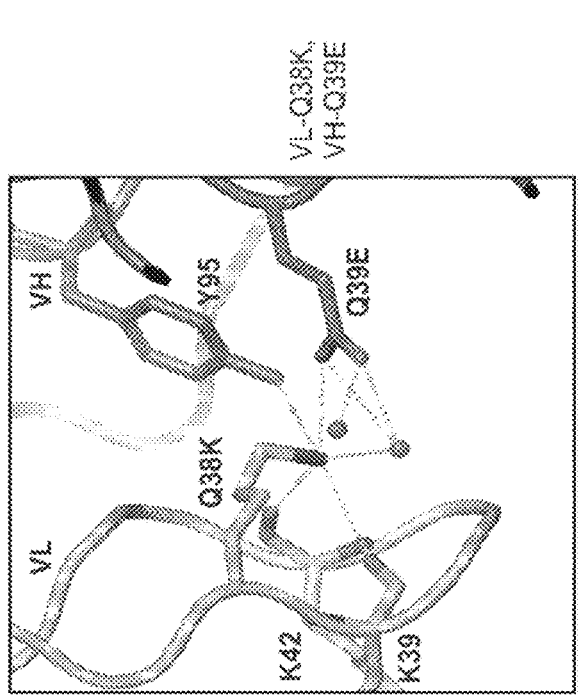
FIG. 11B shows the bonds (e.g., salt bridges and hydrogen bonds) formed by VL-Q38K and VH-Q39E in the modified 4D5 Fab.
Figure 11C:
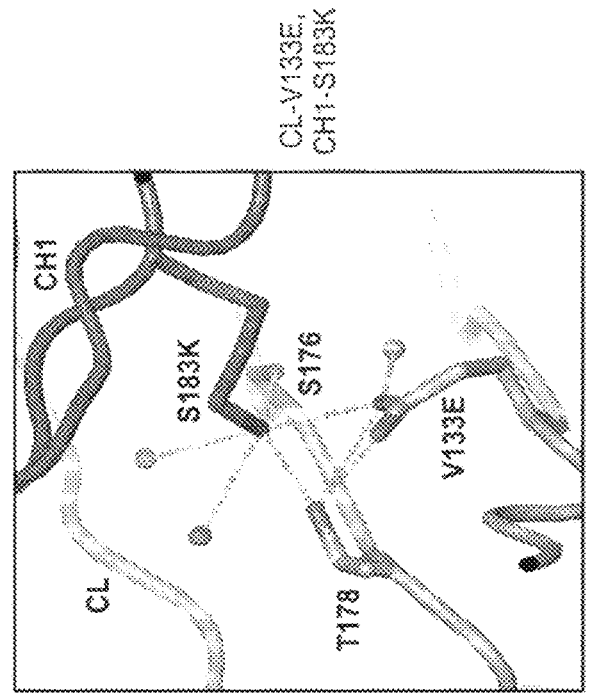
FIG. 11C shows the bonds (e.g., salt bridges and hydrogen bonds) formed by CL-V133E and CH1-S183K in the modified 4D5 Fab.
Figure 11A:
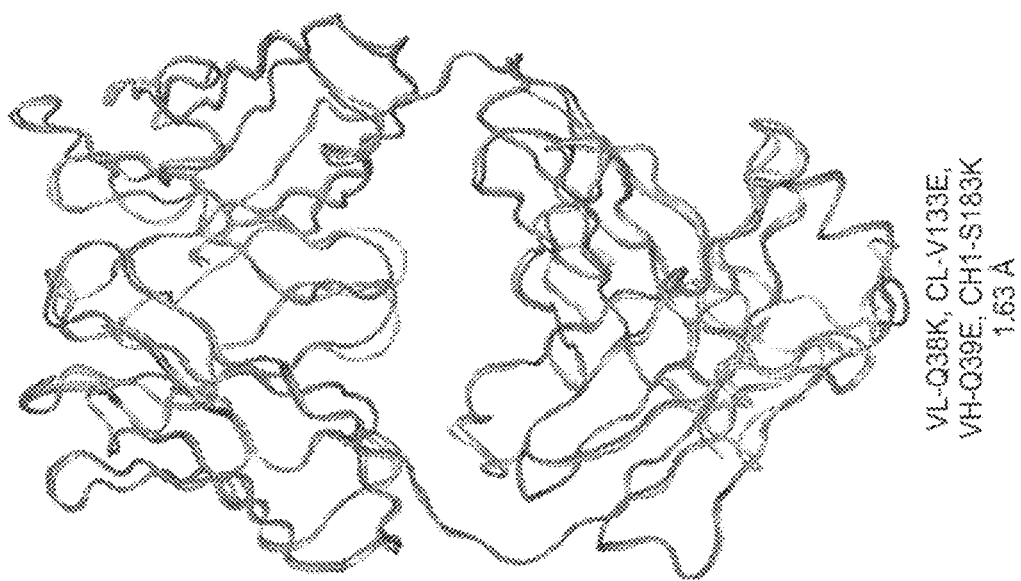
FIG. 11A shows the overlapping crystal structures of the wild type 4D5 Fab and the 4D5 Fab modified to have VL-Q38K. CL-V133E, VH-Q39E, and CH1-S183K mutations.

In a first approach (i.e., "Approach A"), one or more amino acid substitution mutations were introduced to the CL domain of a light chain to create a "knob" (or protuberance) on the surface of the CL domain that interacts with the CH1 domain. Correspondingly, one or more amino acid substitution mutations were introduced to the CH1 domain of a heavy chain to create a "hole" (or cavity) on the surface of the CH1 domain that interacts with the CL domain. See, e.g., FIG. 11A. In certain embodiments, the multispecific antigen-binding proteins comprising the modified CH1/CL sequences result in preferential pairing of the heavy and light chains with the amino acid substitution mutations in the CH1 and CL domains. In certain embodiments, the multispecific antigen-binding proteins comprising the modified CH1/CL sequences demonstrate increased protein expression levels as compared to the multispecific antigen-binding proteins without the corresponding CH1/CL mutations. In certain embodiments, the substituted amino acid(s) are not replaced with charged residue(s).

In a second approach (i.e., "Approach B"), two or more amino acid substitution mutations were introduced to the CL domain of a light chain to create a "knob" (or protuberance) and a "hole" (or cavity) on the surface of the CL domain that interacts with the CH1 domain. Correspondingly, two or more mutations were introduced to the CH1 domain of a heavy chain to create a "hole" and a "knob" at the surface of the CH1 domain that interacts with the CL domain. See, e.g., FIG. 11B. In certain embodiments, the multispecific antigen-binding proteins comprising the modified CH1/CL sequences show preferential pairing of the heavy and light chains with the amino acid substitution mutations in the CH1 and CL domains. In certain embodiments, the multispecific antigen-binding proteins comprising the modified CH1/CL sequences show increased protein expression as compared to the multispecific antigen-binding proteins without the corresponding CH1/CL mutations. In certain embodiments, the substituted amino acid(s) are not replaced with charged residue(s).

Multispecific antigen-binding proteins comprising a modified CH1 domain of H1 and a modified CL domain of L1 demonstrate improved stability and improved specificity with regard to heavy chain/light chain pairing. Provided herein is a multispecific antigen-binding protein comprising: a) a first heavy chain/light chain pair capable of binding to a first antigen, the first heavy chain/light chain pair comprising a first heavy chain polypeptide (H1) and a first light chain polypeptide (L1), and b) a second heavy chain/light chain pair capable of binding to a second antigen, the second heavy chain/light chain pair comprising a second heavy chain polypeptide (H2) and a second light chain polypeptide (L2), wherein each H1 and H2 comprises a heavy chain variable domain (VH) and a heavy chain constant domain (CH1), and each L1 and L2 comprises a light chain variable domain (VL) and a light chain constant domain (CL); wherein the CH1 domain of H1 comprises an amino acid substitution at position F170 (EU numbering), and wherein the CL domain comprises an amino acid substitution at position S176 (EU numbering). In certain embodiments, the first antigen and the second antigen are the same. In certain embodiments, the first heavy chain/light chain pair and the second heavy chain/light chain pair each bind to a different epitope on the same antigen. In certain embodiments, the first antigen and the second antigen are different. In certain embodiments, the CH1 domain of H1 of the multispecific antigen-binding protein further comprises one or more amino acid substitutions selected from the group consisting of: A141, S181, S183, and V185 (all EU numbering). In certain embodiments, the CL domain of L1 of the multispecific antigen-binding protein further comprises one or more amino acid substitutions selected from the group consisting of F116, S131, V133, L135, S162, S174, and T178 (all EU numbering). In certain embodiments, the CL domain of L of the multispecific antigen-binding protein further comprises one or more amino acid substitutions selected from the group consisting of F116, V133, L135, S162, S174, and T178 (all EU numbering). In certain embodiments, the CL domain of L1 of the multispecific antigen-binding protein further comprises one or more amino acid substitutions selected from the group consisting of F116, S131, L135, S162, S174, and T178 (all EU numbering). In certain embodiments, the CL domain of L1 of the multispecific antigen-binding protein further comprises one or more amino acid substitutions selected from the group consisting of F116, L135, S174, and T178 (all EU numbering). In certain embodiments, the CL domain of L1 of the multispecific antigen-binding protein further comprises one or more amino acid substitutions selected from the group consisting of F116, L135, S162, S174, and T178 (all EU numbering). In certain embodiments, the amino acid substitutions result in steric complementarity. In certain embodiments, the amino acid substitutions result in conformational complementarity. In certain embodiments, the substituted amino acid(s) are not replaced with charged residue(s).

In certain embodiments, the CH1 domain of H1 of the multispecific antigen-binding protein comprises (such as consists of or consists essentially of) one or more amino acid substitutions selected from the group consisting of: A141 and F170 (all EU numbering). In certain embodiments, the CL domain of L1 of the multispecific antigen-binding protein comprises one or more amino acid substitutions selected from the group consisting of F116, L135, S176, and T178 (all EU numbering). In certain embodiments, the amino acid substitutions result in steric complementarity. In certain embodiments, the amino acid substitutions result in conformational complementarity.

In certain embodiments, the CH1 domain of H1 of the multispecific antigen-binding protein comprises (such as consists of or consists essentially of) one or more amino acid substitutions selected from the group consisting of: F170, S181, and S183 (all EU numbering). In certain embodiments, the CL domain of L1 of the multispecific antigen-binding protein comprises one or more amino acid substitutions selected from the group consisting of F116 and S176 (all EU numbering). In certain embodiments, the amino acid substitutions result in steric complementarity. In certain embodiments, the amino acid substitutions result in conformational complementarity.

In certain embodiments, the CH1 domain of H1 of the multispecific antigen-binding protein comprises (such as consists of or consists essentially of) the amino acid substitution F170 (EU numbering). In certain embodiments, the CL domain of L1 of the multispecific antigen-binding protein comprises one or more amino acid substitutions selected from the group consisting of F116, L135, S174, S176, and T178 (all EU numbering). In certain embodiments, the amino acid substitutions result in steric complementarity. In certain embodiments, the amino acid substitutions result in conformational complementarity.

In certain embodiments, the CH1 domain of H1 of the multispecific antigen-binding protein comprises (such as consists of or consists essentially of) one or more amino acid substitutions selected from the group consisting of: F170, S183, and V185 (all EU numbering). In certain embodiments, the CL domain of L of the multispecific antigen-binding protein comprises one or more amino acid substitutions selected from the group consisting of F116, S176, and T178 (all EU numbering). In certain embodiments, the amino acid substitutions result in steric complementarity. In certain embodiments, the amino acid substitutions result in conformational complementarity.

In certain embodiments, the CH1 domain of H1 of the multispecific antigen-binding protein comprises (such as consists of or consists essentially of) one or more amino acid substitutions selected from the group consisting of: F170, S181, and V185 (all EU numbering). In certain embodiments, the CL domain of L1 of the multispecific antigen-binding protein comprises one or more amino acid substitutions selected from the group consisting of F116, L135, and S176 (all EU numbering). In certain embodiments, the amino acid substitutions result in steric complementarity. In certain embodiments, the amino acid substitutions result in conformational complementarity.

In certain embodiments, the CH1 domain of H1 of the multispecific antigen-binding protein comprises (such as consists of or consists essentially of) one or more amino acid substitutions selected from the group consisting of: A141 and F170 (all EU numbering). In certain embodiments, the CL domain of L1 of the multispecific antigen-binding protein comprises one or more amino acid substitutions selected from the group consisting of F116, L135, S174, S176, and T178 (all EU numbering). In certain embodiments, the amino acid substitutions result in steric complementarity. In certain embodiments, the amino acid substitutions result in conformational complementarity.

In certain embodiments, the CH1 domain of H1 of the multispecific antigen-binding protein comprises (such as consists of or consists essentially of) one or more amino acid substitutions selected from the group consisting of: A141, F170, and S181 (all EU numbering). In certain embodiments, the CL domain of L of the multispecific antigen-binding protein comprises one or more amino acid substitutions selected from the group consisting of F116, L135, S174, S176, and T178 (all EU numbering). In certain embodiments, the amino acid substitutions result in steric complementarity. In certain embodiments, the amino acid substitutions result in conformational complementarity.

In certain embodiments, the CH1 domain of H1 of the multispecific antigen-binding protein comprises (such as consists of or consists essentially of) one or more amino acid substitutions selected from the group consisting of: F170, S181, S183, and V185 (all EU numbering). In certain embodiments, the CL domain of L1 of the multispecific antigen-binding protein comprises one or more amino acid substitutions selected from the group consisting of L135, S174, S176, and T178 (all EU numbering). In certain embodiments, the amino acid substitutions result in steric complementarity. In certain embodiments, the amino acid substitutions result in conformational complementarity.

In certain embodiments, the CH1 domain of H1 of the multispecific antigen-binding protein comprises (such as consists of or consists essentially of) one or more amino acid substitutions selected from the group consisting of: A141, F170, S183, and V185 (all EU numbering). In certain embodiments, the CL domain of L1 of the multispecific antigen-binding protein comprises one or more amino acid substitutions selected from the group consisting of F116, S174, S176, and T178 (all EU numbering). In certain embodiments, the amino acid substitutions result in steric complementarity. In certain embodiments, the amino acid substitutions result in conformational complementarity.

In certain embodiments, the CH1 domain of H1 of the multispecific antigen-binding protein comprises (such as consists of or consists essentially of) one or more amino acid substitutions selected from the group consisting of: A141, F170, S181, and V185 (all EU numbering). In certain embodiments, the CL domain of L1 of the multispecific antigen-binding protein comprises one or more amino acid substitutions selected from the group consisting of F116, L135, S176, and T178 (all EU numbering). In certain embodiments, the amino acid substitutions result in steric complementarity. In certain embodiments, the amino acid substitutions result in conformational complementarity.

In certain embodiments, the CH1 domain of H1 of the multispecific antigen-binding protein comprises (such as consists of or consists essentially of) one or more amino acid substitutions selected from the group consisting of A141, F170, S181, and S183 (all EU numbering). In certain embodiments, the CL domain of L1 of the multispecific antigen-binding protein comprises one or more amino acid substitutions selected from the group consisting of F116, L135, S174, and S176 (all EU numbering). In certain embodiments, the amino acid substitutions result in steric complementarity. In certain embodiments, the amino acid substitutions result in conformational complementarity.

In certain embodiments, the CH1 domain of H1 of the multispecific antigen-binding protein comprises (such as consists of or consists essentially of) the amino acid substitution F170 (EU numbering). In certain embodiments, the CL domain of L1 of the multispecific antigen-binding protein comprises one or more amino acid substitutions selected from the group consisting of F116, L135, S176, and T178 (all EU numbering). In certain embodiments, the amino acid substitutions result in steric complementarity. In certain embodiments, the amino acid substitutions result in conformational complementarity.

In certain embodiments, the CH1 domain of H1 of the multispecific antigen-binding protein comprises (such as consists of or consists essentially of) one or more amino acid substitutions selected from the group consisting of: A141 F170, and V185 (EU numbering). In certain embodiments, the CL domain of L1 of the multispecific antigen-binding protein comprises one or more amino acid substitutions selected from the group consisting of F116 and S176 mutations (all EU numbering). In certain embodiments, the amino acid substitutions result in conformational complementarity.

In certain embodiments, the CH1 domain of H1 of the multispecific antigen-binding protein comprises (such as consists of or consists essentially of) one or more amino acid substitutions selected from the group consisting of: A141, F170, and S183 (EU numbering). In certain embodiments, the CL domain of L1 of the multispecific antigen-binding protein comprises one or more amino acid substitutions selected from the group consisting of F116 and S176 mutations (all EU numbering). In certain embodiments, the amino acid substitutions result in conformational complementarity.

In certain embodiments, the CH1 domain of H1 of the multispecific antigen-binding protein comprises (such as consists of or consists essentially of) one or more amino acid substitutions selected from the group consisting of: F170 and V185 (EU numbering). In certain embodiments, the CL domain of L of the multispecific antigen-binding protein comprises one or more amino acid substitutions selected from the group consisting of F116 and S176 mutations (all EU numbering). In certain embodiments, the amino acid substitutions result in conformational complementarity.

In certain embodiments, the CH1 domain of H1 and CL domain of L1 of the multispecific antigen-binding protein are altered so that within the CH1/CL interface, one or more amino acid residues of the CH1 domain are replaced with an equivalent number of amino acid residues, some or all having a larger side chain volume, thereby generating a protuberance on the surface of the CH1 domain, and one or more amino acid residues of the CL domain are replaced with an equivalent number of amino acid residues, some or all having a smaller side chain volume, thereby generating a cavity on the surface of the CL domain. In certain embodiments, the modifications on the CH1 and CL domains provide steric complementarity at the CH1/CL interface. In certain embodiments, the modifications on the CH1 and CL domains provide conformational complementarity at the CH1/CL interface.

In certain embodiments, the CH1 domain of H1 and the CL domain of L1 of the multispecific antigen-binding protein are altered so that within the CH1/Cl interface, one or more amino acid residues of the CL domain are replaced with an equivalent number of amino acid residues, some or all having a larger side chain volume, thereby generating a protuberance on the surface of the CL domain, and one or more amino acid residues of the CH1 domain are replaced with an equivalent number of amino acid residues, some or all having a smaller side chain volume, thereby generating a cavity on the surface of the CH1 domain. In certain embodiments, the one or more substituted amino acid residues of the CL domain comprise S176. In certain embodiments, the one or more substituted amino acid residues of the CH1 domain comprise F170. In certain embodiments, the modifications on the CH1 and CL domains provide steric complementarity at the interface. In certain embodiments, the modifications on the CH1 and CL domains provide conformational complementarity at the interface.

In certain embodiments, the CH1 domain of H1 comprises an amino acid substitution selected from the group consisting of F170S and F170A (EU numbering), and wherein the CL domain of L comprises an amino acid substitution selected from the group consisting of S176F (EU numbering).

In certain embodiments, the CH1 domain of H1 comprises the F170S mutation (EU numbering), and the CL domain of L1 comprises the S176F mutation (EU numbering). In certain embodiments, the CH1 domain of H1 comprises the F170A mutation (EU numbering), and the CL domain of L1 comprises the S176F mutation (EU numbering).

In certain embodiments a multispecific antigen-binding protein comprises a CH1 domain of H1 comprising (including consisting of and consisting essentially of) A141I, F170S, S181M, S183V, and V185A mutations (EU numbering), and a CL domain of L1 comprising (including consisting of or consisting essentially of) F116A, V133I, L135V, S162M, S174A, S176F, and T178V mutations (EU numbering).

In certain embodiments a multispecific antigen-binding protein comprises a CH1 domain of H1 comprising (including consisting of and consisting essentially of) A141I, F170S, S181M, S183A, and V185A mutations (EU numbering) and a CL domain of L1 comprising (including consisting of or consisting essentially of) F116A, S131D, L135V, S162A, S174A, S176F, and T178I mutations (EU numbering).

In certain embodiments a multispecific antigen-binding protein comprises a CH1 domain of H1 comprising (including consisting of and consisting essentially of) A141I, F170S, S181M, S183A, and V185A mutations (EU numbering) and a CL domain of L1 comprising (including consisting of or consisting essentially of) F116A, L135V, S174A, S176F, and T178V mutations (EU numbering). In certain embodiments a multispecific antigen-binding protein comprises a CH1 domain of H1 consisting of (such as consisting essentially of) A141I, F170S, S181M, S183A, and V185A mutations (EU numbering) and a CL domain of L1 consisting of (such as consisting essentially of) F116A, L135V, S174A, S176F, and T178V mutations (EU numbering).

In certain embodiments a multispecific antigen-binding protein comprises a CH1 domain of H1 comprising (including consisting of and consisting essentially of) A141I, F170A, S181M, S183V, and V185A mutations (EU numbering) and a CL domain of L1 comprising (including consisting of or consisting essentially of) F116A, L135V, S162M, S174A, S176F, and T178V mutations (EU numbering).

In certain embodiments a multispecific antigen-binding protein comprises a CH1 domain of H1 comprising (including consisting of and consisting essentially of) F170S, S181M, S183A, and V185A mutations (EU numbering) and a CL domain of L1 comprising (including consisting of or consisting essentially of) L135V, S174A, S176F, and T178V mutations (EU numbering).

In certain embodiments a multispecific antigen-binding protein comprises a CH1 domain of H1 comprising (including consisting of and consisting essentially of) A141I, F170S, S183A, and V185A mutations (EU numbering) and a CL domain of L1 comprising (including consisting of or consisting essentially of) F116A, S174A, S176F, and T178V mutations (EU numbering).

In certain embodiments a multispecific antigen-binding protein comprises a CH1 domain of H1 comprising (including consisting of and consisting essentially of) A141I, F170S, S181M, and V185A mutations (EU numbering) and a CL domain of L1 comprising (including consisting of or consisting essentially of) F116A, L135V, S176F, and T178V mutations (EU numbering).

In certain embodiments a multispecific antigen-binding protein comprises a CH1 domain of H1 comprising (including consisting of and consisting essentially of) A141I, F170S. S181M, and S183A mutations (EU numbering) and a CL domain of L1 comprising (including consisting of or consisting essentially of) F116A, L135V, S174A, and S176F mutations (EU numbering).

In certain embodiments a multispecific antigen-binding protein comprises a CH1 domain of H1 comprising (including consisting of and consisting essentially of) F170S, S183A, and V185A mutations (EU numbering) and a CL domain of L1 comprising (including consisting of or consisting essentially of) F116A, S176F, and T178V mutations (EU numbering).

In certain embodiments a multispecific antigen-binding protein comprises a CH1 domain of H1 comprising (including consisting of and consisting essentially of) F170S, S181M, and V185A mutations (EU numbering) and a CL domain of L1 comprising (including consisting of or consisting essentially of) F116A, L135V, and S176F mutations (EU numbering).

In certain embodiments a multispecific antigen-binding protein comprises a CH1 domain of H1 comprising (including consisting of and consisting essentially of) F170S, S181M, and S183A mutations (EU numbering) and a CL domain of L1 comprising (including consisting of or consisting essentially of) F116A and S176F mutations (EU numbering).

In certain embodiments a multispecific antigen-binding protein comprises a CH1 domain of H1 comprising (including consisting of and consisting essentially of) A141I, F170S, and V185A mutations (EU numbering) and a CL domain of L1 comprising (including consisting of or consisting essentially of) F116A and S176F mutations.

In certain embodiments a multispecific antigen-binding protein comprises a CH1 domain of H1 comprising (including consisting of and consisting essentially of) A141I, F170S, and S183A mutations (EU numbering) and a CL domain of L1 comprising (including consisting of or consisting essentially of) F116A and S176F mutations.

In certain embodiments a multispecific antigen-binding protein comprises a CH1 domain of H1 comprising (including consisting of and consisting essentially of) A141I, F170S, and S181M mutations (EU numbering) and a CL domain of L1 comprising (including consisting of or consisting essentially of) F116A, L135V, S174A, S176F, and T178V mutations EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering).

In certain embodiments a multispecific antigen-binding protein comprises a CH1 domain of H1 comprising (including consisting of and consisting essentially of) F170S and V185A mutations (EU numbering) and a CL domain of L1 comprising (including consisting of or consisting essentially of) F116A and S176F mutations.

In certain embodiments a multispecific antigen-binding protein comprises a CH1 domain of H1 comprising (including consisting of and consisting essentially of) A141I and F170S mutations (EU numbering) and a CL domain of L1 comprising (including consisting of or consisting essentially of) F116A, L135V, S174A, S176F, and T178V mutations (EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering).

In certain embodiments a multispecific antigen-binding protein comprises a CH1 domain of H1 comprising (including consisting of and consisting essentially of) A141I and F170S mutations (EU numbering) and a CL domain of L1 comprising (including consisting of or consisting essentially of) F116A, L135V, S176F, and T178V mutations (EU numbering).

In certain embodiments a multispecific antigen-binding protein comprises a CH1 domain of H1 comprising (including consisting of and consisting essentially of) A141I and F170S mutations (EU numbering) and a CL domain of L1 comprising (including consisting of or consisting essentially of) F116A, L135V, S174A, and S176F mutations (EU numbering).

In certain embodiments a multispecific antigen-binding protein comprises a CH1 domain of H1 comprising (including consisting of and consisting essentially of) A141I and F170S mutations (EU numbering) and a CL domain of L1 comprising (including consisting of or consisting essentially of) F116A, S176F, and T178V mutations (EU numbering).

In certain embodiments a multispecific antigen-binding protein comprises a CH1 domain of H1 comprising (including consisting of and consisting essentially of) A141I and F170S mutations (EU numbering) and a CL domain of L1 comprising (including consisting of or consisting essentially of) F116A, L135V, and S176F mutations (EU numbering).

In certain embodiments a multispecific antigen-binding protein comprises a CH1 domain of H1 comprising (including consisting of and consisting essentially of) A141I and F170S mutations (EU numbering) and a CL domain of L1 comprising (including consisting of or consisting essentially of) F116A and S176F mutations (EU numbering).

In certain embodiments a multispecific antigen-binding protein comprises a CH1 domain of H1 comprising (including consisting of and consisting essentially of) an F170S mutation (EU numbering), and a CL domain of L1 comprising (including consisting of or consisting essentially of) F116A, L135V, S174A, S176F, and T178V mutations (EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering).

In certain embodiments a multispecific antigen-binding protein comprises a CH1 domain of H1 comprising (including consisting of and consisting essentially of) an F170S mutation (EU numbering), and a CL domain of L1 comprising (including consisting of or consisting essentially of) F116A, L135V, S176F, and T178V mutations (EU numbering).

In certain embodiments a multispecific antigen-binding protein comprises a CH1 domain of H1 comprising (including consisting of and consisting essentially of) an F170S mutation (EU numbering) and a CL domain of L1 comprising (including consisting of or consisting essentially of) F116A, L135V, S174A, and S176F mutations (EU numbering).

In certain embodiments a multispecific antigen-binding protein comprises a CH1 domain of H1 comprising (including consisting of and consisting essentially of) an F170S mutation (EU numbering) and a CL domain of L1 comprising (including consisting of or consisting essentially of) F116A, S176F, and T178V mutations (EU numbering).

In certain embodiments a multispecific antigen-binding protein comprises a CH1 domain of H1 comprising (including consisting of and consisting essentially of) an F170S mutation (EU numbering) and a CL domain of L1 comprising (including consisting of or consisting essentially of) F116A, L135V, and S176F mutations (EU numbering).

In certain embodiments a multispecific antigen-binding protein comprises a CH1 domain of H1 comprising (including consisting of and consisting essentially of) an F170S mutation (EU numbering) and a CL domain of L1 comprising (including consisting of or consisting essentially of) F116A and S176F mutations (EU numbering).

In certain embodiments a multispecific antigen-binding protein comprises CH1 domain of H1 comprising no more than 1, no more than two, no more than three, no more than four, or no more than five amino acid mutations selected from the group consisting of: A141I, F170S, S181M, S183V, and V185A mutations (EU numbering).

In certain embodiments a multispecific antigen-binding protein comprises CH1 domain of H1 comprising no more than one, no more than two, no more than three, no more than four, or no more than five amino acid mutations selected from the group consisting of: A141I, F170S, S181M, S183A, and V185A mutations (EU numbering).

In certain embodiments a multispecific antigen-binding protein comprises CH1 domain of H1 consisting of no more than one, no more than two, no more than three, no more than four, or no more than five amino acid mutations selected from the group consisting of: A141I, F170S, S181M, S183A, and V185A mutations (EU numbering).

In certain embodiments a multispecific antigen-binding protein comprises CH1 domain of H1 comprising no more than one, no more than two, no more than three, no more than four, or no more than five amino acid mutations selected from the group consisting of: A141I, F170A, S181M, S183V, and V185A mutations (EU numbering).

In certain embodiments a multispecific antigen-binding protein comprises a CL domain of L1 comprising no more than one, no more than two, no more than three, no more than four, no more than five, no more than six, or no more than seven amino acid mutations selected from the group consisting of: F116A, V133I, L135V, S162M, S174A, S176F, and T178V mutations (EU numbering).

In certain embodiments a multispecific antigen-binding protein comprises a CL domain of L comprising no more than one, no more than two, no more than three, no more than four, no more than five, no more than six, or no more than seven amino acid mutations selected from the group consisting of: F116A, S131D, L135V, S162A, S174A, S176F, and T178I mutations (EU numbering).

In certain embodiments a multispecific antigen-binding protein comprises a CL domain of L1 comprising no more than one, no more than two, no more than three, no more than four, or no more than five amino acid mutations selected from the group consisting of: F116A, L135V, S174A, S176F, and T178V mutations (EU numbering).

In certain embodiments a multispecific antigen-binding protein comprises a CL domain of L consisting of no more than one, no more than two, no more than three, no more than four, or no more than five amino acid mutations selected from the group consisting of: F116A, L135V, S174A, S176F, and T178V mutations (EU numbering).

In certain embodiments a multispecific antigen-binding protein comprises a CL domain of L1 comprising no more than one, no more than two, no more than three, no more than four, no more than five, or no more than six amino acid mutations selected from the group consisting of: F116A, L135V, S162M, S174A, S176F, and T178V mutations (EU numbering).

All possible pair-wise combinations of CH1 domains and L1 domains described above are contemplated.

In certain embodiments, the multispecific antigen-binding protein comprises a kappa light chain. In certain embodiments, the multispecific antigen-binding protein comprises a first light chain polypeptide L1 comprising a CL domain as set forth in any of SEQ ID Nos: 17-27. The CL domain as set forth in SEQ ID NO: 54 corresponds to amino acids 11-116 of SEQ ID NOs: 17-27. Accordingly, L1 may comprise a CL domain comprising amino acids 11-116 as set forth in any of SEQ ID Nos: 17-27. In certain embodiments, the multispecific antigen-binding protein comprises a CL domain of L1 comprising the amino acid sequence set forth in SEQ ID NO: 17 or the amino acids 11-116 in the sequence set forth in SEQ ID NO: 17. In certain embodiments, the multispecific antigen-binding protein comprises a CL domain of L1 comprising the amino acid sequence set forth in SEQ ID NO: 18 or the amino acids 11-116 in the sequence set forth in SEQ ID NO: 18. In certain embodiments, the multispecific antigen-binding protein comprises a CL domain of L1 comprising the amino acid sequence set forth in SEQ ID NO: 19 or the amino acids 11-116 in the sequence set forth in SEQ ID NO: 19. In certain embodiments, the multispecific antigen-binding protein comprises a CL domain of L1 comprising the amino acid sequence set forth in SEQ ID NO: 20 or the amino acids 11-116 in the sequence set forth in SEQ ID NO: 20. In certain embodiments, the multispecific antigen-binding protein comprises a CL domain of L comprising the amino acid sequence set forth in SEQ ID NO: 21 or the amino acids 11-116 in the sequence set forth in SEQ ID NO: 21. In certain embodiments, the multispecific antigen-binding protein comprises a CL domain of L1 comprising the amino acid sequence set forth in SEQ ID NO: 22 or the amino acids 11-116 in the sequence set forth in SEQ ID NO: 22. In certain embodiments, the multispecific antigen-binding protein comprises a CL domain of L1 comprising the amino acid sequence set forth in SEQ ID NO: 23 or the amino acids 11-116 in the sequence set forth in SEQ ID NO: 23. In certain embodiments, the multispecific antigen-binding protein comprises a CL domain of L1 comprising the amino acid sequence set forth in SEQ ID NO: 24 or the amino acids 11-116 in the sequence set forth in SEQ ID NO: 24. In certain embodiments, the multispecific antigen-binding protein comprises a CL domain of L1 comprising the amino acid sequence set forth in SEQ ID NO: 25 or the amino acids 11-116 in the sequence set forth in SEQ ID NO: 25. In certain embodiments, the multispecific antigen-binding protein comprises a CL domain of L1 comprising the amino acid sequence set forth in SEQ ID NO: 26 or the amino acids G1-116 in the sequence set forth in SEQ ID NO: 26. In certain embodiments, the multispecific antigen-binding protein comprises a CL domain of L1 comprising the amino acid sequence set forth in SEQ ID NO: 27 or the amino acids 11-116 in the sequence set forth in SEQ ID NO 27.

In certain embodiments, the multispecific antigen-binding protein comprises a lambda light chain. In certain embodiments, the multispecific antigen-binding protein comprises a CL domain of L comprising the amino acid sequence set forth in SEQ ID NO; 127.

The amino acid sequences of SEQ ID NOs: 17-27 and 127 are provided in Table 5 below (LC is kappa LC unless indicated otherwise):

TABLE 5

| | |
|---|---|
| YS08 LC SEQ ID NO: 17 | GQGTKVEIKR TVAAPSVAIF PPSDEQLKSG TASVICVLNN FYPREAKVQW KVDNALQSGN SQEMVTEQDS KDSTYALFSV LTLSKADYEK HKVYACEVTH QGLSSPVTKS FNRGEC |
| YS18 LC SEQ ID NO: 18 | GQGTKVEIKR TVAAPSVAIF PPSDEQLKSG TADVVCVLNN FYPREAKVQW KVDNALQSGN SQEAVTEQDS KDSTYALFSI LTLSKADYEK HKVYACEVTH QGLSSPVTKS FNRGEC |
| YT65 LC kappa SEQ ID NO: 19 | GQGTKVEIKR TVAAPSVAIF PPSDEQLKSG TASVVCVLNN FYPREAKVQW KVDNALQSGN SQESVTEQDS KDSTYALFSV LTLSKADYEK HKVYACEVTH QGLSSPVTKS FNRGEC |
| YT65.1 LC SEQ ID NO: 20 | GQGTKVEIKR TVAAPSVFIF PPSDEQLKSG TASVVCVLNN FYPREAKVQW KVDNALQSGN SQESVTEQDS KDSTYALFSV LTLSKADYEK HKVYACEVTH QGLSSPVTKS FNRGEC |
| YT65.2 LC SEQ ID NO: 21 | GQGTKVEIKR TVAAPSVAIF PPSDEQLKSG TASVVCLLNN FYPREAKVQW KVDNALQSGN SQESVTEQDS KDSTYALFSV LTLSKADYEK HKVYACEVTH QGLSSPVTKS FNRGEC |
| YT65.3 LC SEQ ID NO: 22 | GQGTKVEIKR TVAAPSVAIF PPSDEQLKSG TASVVCVLNN FYPREAKVQW KVDNALQSGN SQESVTEQDS KDSTYSLFSV LTLSKADYEK HKVYACEVTH QGLSSPVTKS FNRGEC |
| YT65.4 LC SEQ ID NO: 23 | GQGTKVEIKR TVAAPSVAIF PPSDEQLKSG TASVVCVLNN FYPREAKVQW KVDNALQSGN SQESVTEQDS KDSTYALFST LTLSKADYEK HKVYACEVTH QGLSSPVTKS FNRGEC |
| YT65.5 LC SEQ ID NO: 24 | GQGTKVEIKR TVAAPSVAIF PPSDEQLKSG TASVVCLLNN FYPREAKVQW KVDNALQSGN SQESVTEQDS KDSTYSLFSV LTLSKADYEK HKVYACEVTH QGLSSPVTKS FNRGEC |
| YT65.6 LC SEQ ID NO: 25 | GQGTKVEIKR TVAAPSVAIF PPSDEQLKSG TASVVCVLNN FYPREAKVQW KVDNALQSGN SQESVTEQDS KDSTYALFST LTLSKADYEK HKVYACEVTH QGLSSPVTKS FNRGEC |
| YT65.7 LC SEQ ID NO: 26 | GQGTKVEIKR TVAAPSVAIF PPSDEQLKSG TASVVCLLNN FYPREAKVQW KVDNALQSGN SQESVTEQDS KDSTYSLFST LTLSKADYEK HKVYACEVTH QGLSSPVTKS FNRGEC |
| YT34 LC SEQ ID NO: 27 | GQGTKVEIKR TVAAPSVAIF PPSDEQLKSG TASVVCVLNN FYPREAKVQW KVDNALQSGN SQEMVTEQDS KDSTYALFSV LTLSKADYEK HKVYACEVTH QGLSSPVTKS FNRGEC |
| YT65 lambda SEQ ID NO: 127 | GQPKAAPSVA LFPPSSEELQ ANKATLVCVI SDFYPGAVTV AWKADSSPVK AGVETTTPSK QSNNKYAAFS VLSLTPEQWK SHKSYSCQVT HEGSTVEKTV APTECS |

Amino acid positions 116, 118, 131, 133, 135, 162, 164, 174, 176, and 178 in CL (EU numbering) correspond to amino acid positions 18, 20, 33, 35, 37, 64, 66, 76, 78, and 80 in SEQ ID NOs: 17-27, respectively. Amino acid positions 116, 118, 131, 133, 135, 162, 164, 174, 176, and 178 (EU numbering) in the CL domain of a kappa chain correspond to amino acid positions 116, 118, 131, 133, 135, 162, 164, 174, 176, and 178 (Kabat numbering) in the CL domain of a lambda light chain. Amino acid positions 116, 118, 131, 133, 135, 162, 164, 174, 176, and 178 (Kabat numbering) in the CL domain of a lambda light chain correspond to amino acid positions 10, 12, 25, 27, 29, 56, 59, 67, 69, and 71 in SEQ ID NO: 127, respectively.

In certain embodiments, the multispecific antigen-binding protein comprises an IgG1, IgG2, IgG3, or IgG4 heavy chain. In certain embodiments, the multispecific antigen-binding protein comprises a CH1 domain of H1 comprising the amino acid sequence set forth in SEQ ID NO: 28. In certain embodiments, the multispecific antigen-binding protein comprises a CH1 domain of H1 comprising the amino acid sequence set forth in SEQ ID NO: 29. In certain embodiments, the multispecific antigen-binding protein comprises a CH1 domain of H1 comprising the amino acid sequence set forth in SEQ ID NO: 31. In certain embodiments, the multispecific antigen-binding protein comprises a CH1 domain of H1 comprising the amino acid sequence set forth in SEQ ID NO: 32. In certain embodiments, the multispecific antigen-binding protein comprises a CH1 domain of H1 comprising the amino acid sequence set forth in SEQ ID NO: 33. In certain embodiments, the multispecific antigen-binding protein comprises a CH1 domain of H1 comprising the amino acid sequence set forth in SEQ ID NO: 34. In certain embodiments, the multispecific antigen-binding protein comprises a CH1 domain of H1 comprising the amino acid sequence set forth in SEQ ID NO: 35. In certain embodiments, the multispecific antigen-binding protein comprises a CH1 domain of H1 comprising the amino acid sequence set forth in SEQ ID NO: 36. In certain embodiments, the multispecific antigen-binding protein comprises a CH1 domain of H1 comprising the amino acid sequence set forth in SEQ ID NO: 37. In certain embodiments, the multispecific antigen-binding protein comprises a CH1 domain of H1 comprising the amino acid sequence set forth in SEQ ID NO: 38. In certain embodiments, the multispecific antigen-binding protein comprises a CH1 domain of H1 comprising the amino acid sequence set forth in SEQ ID NO: 39. In certain embodiments, the multispecific antigen-binding protein comprises a CH1 domain of H1 comprising the amino acid sequence set forth in SEQ ID NO: 40. In certain embodiments, the multispecific antigen-binding protein comprises a CH1 domain of H1 comprising the amino acid sequence set forth in SEQ ID NO: 41. In certain embodiments, the multispecific antigen-binding protein comprises a CH1 domain of H1 comprising the amino acid sequence set forth in SEQ ID NO: 42. In certain embodiments, the multispecific antigen-binding protein comprises a CH1 domain of H1 comprising the amino acid sequence set forth in SEQ ID NO: 43. In certain embodiments, the multispecific antigen-binding protein comprises a CH1 domain of H1 comprising the amino acid sequence set forth in SEQ ID NO: 44. In certain embodiments, the multispecific antigen-binding protein comprises a CH1 domain of H1 comprising the amino acid sequence set forth in SEQ ID NO: 103. In certain embodiments, the multispecific antigen-binding protein comprises a CH1 domain of H1 comprising the amino acid sequence set forth in SEQ ID NO: 104. In certain embodiments, the multispecific antigen-binding protein comprises a CH1 domain of H1 comprising the amino acid sequence set forth in SEQ ID NO: 105.

The amino acid sequences of SEQ ID NOs: 28-44 are provided in Table 6 below (HC is of IgG1 isotype unless indicated otherwise):

TABLE 6

| | |
|---|---|
| YS08 HC<br>SEQ ID NO: 28 | TKGPSVFPLA PSSKSTSGGT AILGCLVKDY<br>FPEPVTVSWN SGALTSGVHT SPAVLQSSGL<br>YMLVSAVTVP SSSLGTQTYI CN |
| YS18 HC/<br>YT65 HC<br>IgG1<br>SEQ ID NO: 29 | TKGPSVFPLA PSSKSTSGGT AILGCLVKDY<br>FPEPVTVSWN SGALTSGVHT SPAVLQSSGL<br>YMLASAVTVP SSSLGTQTYI CN |
| YS18 HC/<br>YT65 HC<br>IgG2<br>SEQ ID NO: 103 | TKGPSVFPLA PCSRSTSEST AILGCLVKDY<br>FPEPVTVSWN SGALTSGVHT SPAVLQSSGL<br>YMLASAVTVP SSNFGTQTYT CN |
| YS18 HC/<br>YT65 HC<br>IgG3<br>SEQ ID NO: 104 | TKGPSVFPLA PCSRSTSGGT AILGCLVKDY<br>FPEPVTVSWN SGALTSGVHT SPAVLQSSGL<br>YMLASAVTVP SSSLGTQTYT CN |
| YS18 HC/<br>YT65 HC<br>IgG4<br>SEQ ID NO: 105 | TKGPSVFPLA PCSRSTSEST AILGCLVKDY<br>FPEPVTVSWN SGALTSGVHT SPAVLQSSGL<br>YMLASAVTVP SSSLGTKTYT CN |
| YT65.1 HC<br>SEQ ID NO: 31 | TKGPSVFPLA PSSKSTSGGT AALGCLVKDY<br>FPEPVTVSWN SGALTSGVHT SPAVLQSSGL<br>YMLASAVTVP SSSLGTQTYI CN |

TABLE 6-continued

| | |
|---|---|
| YT65.2 HC<br>SEQ ID NO: 32 | TKGPSVFPLA PSSKSTSGGT AILGCLVKDY<br>FPEPVTVSWN SGALTSGVHT SPAVLQSSGL<br>YSLASAVTVP SSSLGTQTYI CN |
| YT65.3 HC<br>SEQ ID NO: 33 | TKGPSVFPLA PSSKSTSGGT AILGCLVKDY<br>FPEPVTVSWN SGALTSGVHT SPAVLQSSGL<br>YMLSSAVTVP SSSLGTQTYI CN |
| YT65.4 HC<br>SEQ ID NO: 34 | TKGPSVFPLA PSSKSTSGGT AILGCLVKDY<br>FPEPVTVSWN SGALTSGVHT SPAVLQSSGL<br>YMLASVVTVP SSSLGTQTYI CN |
| YT65.5 HC<br>SEQ ID NO: 35 | TKGPSVFPLA PSSKSTSGGT ALLGCLVKDY<br>FPEPVTVSWN SGALTSGVHT SPAVLQSSGL<br>YSLASAVTVP SSSLGTQTYI CN |
| YT65.6 HC<br>SEQ ID NO: 36 | TKGPSVFPLA PSSKSTSGGT AALGCLVKDY<br>FPEPVTVSWN SGALTSGVHT SPAVLQSSGL<br>YMLSSAVTVP SSSLGTQTYI CN |
| YT65.7 HC<br>SEQ ID NO: 37 | TKGPSVFPLA PSSKSTSGGT AALGCLVKDY<br>FPEPVTVSWN SGALTSGVHT SPAVLQSSGL<br>YMLASVVTVP SSSLGTQTYI CN |
| YT65.8 HC<br>SEQ ID NO: 38 | TKGPSVFPLA PSSKSTSGGT AILGCLVKDY<br>FPEPVTVSWN SGALTSGVHT SPAVLQSSGL<br>YSLSSAVTVP SSSLGTQTYI CN |
| YT65.9 HC<br>SEQ ID NO: 39 | TKGPSVFPLA PSSKSTSGGT AILGCLVKDY<br>FPEPVTVSWN SGALTSGVHT SPAVLQSSGL<br>YSLASVVTVP SSSLGTQTYI CN |
| YT65.10 HC<br>SEQ ID NO: 40 | TKGPSVFPLA PSSKSTSGGT AILGCLVKDY<br>FPEPVTVSWN SGALTSGVHT SPAVLQSSGL<br>YMLSSVVTVP SSSLGTQTYI CN |
| YT65.11 HC<br>SEQ ID NO: 41 | TKGPSVFPLA PSSKSTSGGT AALGCLVKDY<br>FPEPVTVSWN SGALTSGVHT SPAVLQSSGL<br>YSLSSAVTVP SSSLGTQTYI CN |
| YT65.12 HC<br>SEQ ID NO: 42 | TKGPSVFPLA PSSKSTSGGT AILGCLVKDY<br>FPEPVTVSWN SGALTSGVHT SPAVLQSSGL<br>YSLSSVVTVP SSSLGTQTYI CN |
| YT65.13 HC<br>SEQ ID NO: 43 | TKGPSVFPLA PSSKSTSGGT AALGCLVKDY<br>FPEPVTVSWN SGALTSGVHT SPAVLQSSGL<br>YSLSSVVTVP SSSLGTQTYI CN |
| YT34 HC<br>SEQ ID NO: 44 | TKGPSVFPLA PSSKSTSGGT AILGCLVKDY<br>FPEPVTVSWN SGALTSGVHT APAVLQSSGL<br>YMLVSAVTVP SSSLGTQTYI CN |

Amino acid positions 141, 170, 181, 183, and 185 (EU numbering) in CH1 correspond to amino acid positions 22, 51, 62, 64, and 66 of SEQ ID NOs: 28-44 and 103-105, respectively.

All possible pair-wise combinations of SEQ ID NOs: 17-27 or amino acids 11-116 of SEQ ID Nos: 17-27 and 127 with SEQ ID NOs: 28-44 and 103-105 described above are contemplated. In certain embodiments, specific combinations of SEQ ID NOs: 17-27 or amino acids 11-116 of SEQ ID Nos: 17-27 and 127 with SEQ ID NOs: 28-44 and 103-105 are contemplated. Such combinations include, but are not limited to, those provided in Table 7 below:

TABLE 7

| | | |
|---|---|---|
| SEQ ID NO: 28/<br>SEQ ID NO: 17*<br>YS08HC/YS08LC | SEQ ID NO: 40/<br>SEQ ID NO: 19*<br>YT65.10HC/YT65LC | SEQ ID NO: 36/<br>SEQ ID NO: 25*<br>YT65.6HC/YT65.6LC |
| SEQ ID NO: 29/<br>SEQ ID NO: 18*<br>YS18HC/YS18LC | SEQ ID NO: 42/<br>SEQ ID NO: 19*<br>YT65.12HC/YT65LC | SEQ ID NO: 32/<br>SEQ ID NO: 21*<br>YT65.2HC/YT65.2LC |
| SEQ ID NO: 29/<br>SEQ ID NO: 19* | SEQ ID NO: 43/<br>SEQ ID NO: 19* | SEQ ID NO: 43/<br>SEQ ID NO: 22* |

TABLE 7-continued

| | | |
|---|---|---|
| YT65HC/YT65LC IgG1/kappa | YT65.13HC/YT65LC | YT65.13HC/ YT65.3LC |
| SEQ ID NO: 34/ | SEQ ID NO: 44/ | SEQ ID NO: 37/ |
| SEQ ID NO: 23* | SEQ ID NO: 27* | SEQ ID NO: 26* |
| YT65.4HC/YT65.4LC | YT34HC/YT34LC | YT65.7HC/YT65.7LC |
| SEQ ID NO: 35/ | SEQ ID NO: 31/ | SEQ ID NO: 33/ |
| SEQ ID NO: 24* | SEQ ID NO: 20* | SEQ ID NO: 22* |
| YT65.5HC/YT65.5LC | YT65.1HC/YT651 LC | YT65.3HC/YT65.3LC |
| SEQ ID NO: 42/ | SEQ ID NO: 38/ | SEQ ID NO: 39/ |
| SEQ ID NO: 22 | SEQ ID NO: 26 | SEQ ID NO: 26 |
| YT65.12HC/YT65.3LC | YT65.8HC/YT65.7LC | YT65.9HC/YT65.7LC |
| SEQ ID NO: 41/ | SEQ ID NO: 103/ | SEQ ID NO: 104/ |
| SEQ ID NO: 26 | SEQ ID NO: 19 | SEQ ID NO: 19 |
| YT65.11HC/YT65.7LC | YT65HC/YT65LC IgG2/kappa | YT65HC IgG3/YT65LC IgG3/kappa |
| SEQ ID NO: 105/ | SEQ ID NO: 29/ | SEQ ID NO: 103/ |
| SEQ ID NO: 19 | SEQ ID NO: 127 | SEQ ID NO: 127 |
| YT65HC/YT65LC IgG4/kappa | YT65HC/YT65LC IgG1/lambda | YT65HC/YT65LC IgG2/kappa |
| SEQ ID NO: 104/ | SEQ ID NO: 105/ | |
| SEQ ID NO: 127 | SEQ ID NO: 127 | |
| YT65HC IgG3/YT65LC IgG3/kappa | YT65HC/YT65LC IgG4/lambda | |

*or amino acids 11-116 of the corresponding sequence

The first SEQ ID NO in each pair in Table 7 refers to a CH1 domain sequence, and the second SEQ ID NO in each pair in Table 7 refers to a CL domain sequence.

In a related aspect, provided is a multispecific antigen binding protein comprising: a) a first heavy chain/light chain pair capable of binding a first antigen, the first heavy chain/light chain pair comprising a first heavy chain sequence (H1) and a first light chain sequence (L1), and b) a second heavy chain/light chain pair comprising a second heavy chain sequence (H2) and a second light chain sequence (L2), wherein each H1 and H2 comprises a heavy chain variable domain (VH) and a heavy chain constant domain (CH1), and each L1 and L2 comprises a light chain variable domain (VL) and a light chain constant domain (CL); wherein the CH1 domain of H1 and the CL domain of L1 of the multispecific antigen-binding protein are altered so that within the CH1/CL interface, one or more amino acid residues of the CH1 domain are replaced with an equivalent number of amino acid residues, some having a larger side chain volume and some having a smaller side chain volume, thereby generating a protuberance and a cavity on the surface of the CH1 domain, and one or more amino acid residues of the CL domain are replaced with an equivalent number of amino acid residues, some having a smaller side chain volume and some having a larger side chain volume, thereby generating a cavity and a protuberance on the surface of the CL domain. In certain embodiments, the modifications on the CH1 and CL domains provide steric complementarity (such as conformational complementarity) at the interface.

In certain embodiments, the CH1 domain of H1 comprises an amino acid substitutions at positions L128, and wherein the CL domain of L1 comprises an amino acid substitution at positions F118 and L135 (EU numbering). In certain embodiments, the first antigen and the second antigen are the same. In certain embodiments, the first heavy chain/light chain pair and the second heavy chain/light chain pair each bind to a different epitope on the same antigen. In certain embodiments, the first antigen and the second antigen are different. In certain embodiments, the CH1 domain of H1 comprises an amino acid substitutions at positions L128 and V185 (EU numbering), and wherein the CL domain of L1 comprises an amino acid substitution at positions F118 and L135 (EU numbering). In certain embodiments, the first antigen and the second antigen are the same. In certain embodiments, the first heavy chain/light chain pair and the second heavy chain/light chain pair each bind to a different epitope on the same antigen. In certain embodiments, the first antigen and the second antigen are different. In certain embodiments, the CH1 domain of H1 of the multispecific antigen-binding protein further comprises one or more amino acid substitutions selected from the group consisting of: A141, F170, S181, and S183 (all EU numbering). In certain embodiments, the CL domain of L1 of the multispecific antigen-binding protein further comprises one or more amino acid substitutions selected from the group consisting of S131, V133, S162, S176 and T178 (all EU numbering). In certain embodiments, the amino acid substitutions result in steric complementarity (such as conformational complementarity) comparable or greater than that of the wild-type sequences. In certain embodiments, the CL domain of L1 of the multispecific antigen-binding protein further comprises one or more amino acid substitutions selected from the group consisting of S131, V133, S162, T164, S176 and T178 (all EU numbering).

In certain embodiments the multispecific antigen-binding protein comprises a CH1 domain of H1 comprising (including consisting of and consisting essentially of) one or more amino acid substitution selected from F128, A141, F170, S181, and S183 (EU numbering). In certain embodiments the multispecific antigen-binding protein comprises a CL domain of L1 comprising (including consisting of or consisting essentially of) one or more amino acid substitution selected from V118, S131, V133, S135, S162, T164, S176 and T178 (EU numbering). In certain embodiments, the amino acid substitutions result in steric complementarity (such as conformational complementarity) comparable or greater than that of the wild-type sequences.

In certain embodiments the multispecific antigen-binding protein comprises a CH1 domain of H1 comprising (including consisting of and consisting essentially of) one or more amino acid substitution selected from F128, A141, F170, S181, S183, and V185 (EU numbering). In certain embodiments the multispecific antigen-binding protein comprises a CL domain of L1 comprising (including consisting of or consisting essentially of) one or more amino acid substitution selected from V118, S131, V133, S135, S162, T164, S176 and T178 (EU numbering). In certain embodiments, the amino acid substitutions result in steric complementarity (such as conformational complementarity) comparable or greater than that of the wild-type sequences.

In certain embodiments the multispecific antigen-binding protein comprises a CH1 domain of H1 comprising (including consisting of and consisting essentially of) one or more amino acid substitution selected from F128, A141, F170, S181, S183, and V185 (EU numbering). In certain embodiments the multispecific antigen-binding protein comprises a CL domain of L comprising (including consisting of or consisting essentially of) one or more amino acid substitution selected from V118, S131, V133, S135, S162, S176 and T178 (EU numbering). In certain embodiments, the amino acid substitutions result in steric complementarity (such as conformational complementarity) comparable or greater than that of the wild-type sequences.

In certain embodiments the multispecific antigen-binding protein comprises a CH1 domain of H1 comprising (including consisting of and consisting essentially of) L128F, A141M, F170M, S181I and S183A mutations (EU numbering) and a CL domain of L1 comprising (including consisting of or consisting essentially of) F118V, S131T, V133A, L135Y, S162A, T164S, S176M, and T178L mutations (EU numbering).

In certain embodiments the multispecific antigen-binding protein comprises a CH1 domain of H1 comprising (including consisting of and consisting essentially of) L128F, A141M, F170Y, S181I, S183A, and V185A mutations (EU numbering) and a CL domain of L1 comprising (including consisting of or consisting essentially of) F118V, S131T, V133A, L135F, S162A, S176A, and T178L mutations (EU numbering).

In certain embodiments the multispecific antigen-binding protein comprises a CH1 domain of H1 comprising (including consisting of and consisting essentially of) L128F, A141T, F170M, S181T, S183A, and V185L mutations (EU numbering) and a CL domain of L1 comprising (including consisting of or consisting essentially of) F118V, S131T, V133A, L135F, S162A, T164S, S176T, and T178L mutations (EU numbering).

In certain embodiments the multispecific antigen-binding protein comprises a CH1 domain of H1 comprising (including consisting of and consisting essentially of) L128F, A141M, F170M, S181I, and S183A mutations (EU numbering), and a CL domain of L1 comprising (including consisting of or consisting essentially of) F118V, S131T, V133A, L135F, S162M, T164S, S176M, and T178L mutations (EU numbering).

In certain embodiments the multispecific antigen-binding protein comprises CH1 domain of H1 comprising no more than one, no more than two, no more than three, no more than four, or no more than five amino acid mutations selected from the group consisting of: L128F, A141M, F170M, S181I and S183A mutations (EU numbering).

In certain embodiments a multispecific antigen-binding protein comprises CH1 domain of H1 comprising no more than one, no more than two, no more than three, no more than four, no more than five, or no more than six amino acid mutations selected from the group consisting of: L128F, A141M, F170Y, S181I, S183A, and V185A mutations (EU numbering).

In certain embodiments a multispecific antigen-binding protein comprises CH1 domain of H1 comprising no more than one, no more than two, no more than three, no more than four, no more than five, or no more than six amino acid mutations selected from the group consisting of: L128F, A141T, F170M, S181T, S183A, and V185L mutations (EU numbering).

In certain embodiments a multispecific antigen-binding protein comprises CH1 domain of H1 comprising no more than one, no more than two, no more than three, no more than four, or no more than five amino acid mutations selected from the group consisting of: L128F, A141M, F170M, S181T, and S183A mutations (EU numbering).

In certain embodiments a multispecific antigen-binding protein comprises a CL domain of L1 comprising no more than one, no more than two, no more than three, no more than four, no more than five, no more than six, no more than seven, or no more than eight amino acid mutations selected from the group consisting of: F118V, S131T, V133A, L135Y, S162A, T164S, S176M, and T178L mutations (EU numbering).

In certain embodiments a multispecific antigen-binding protein comprises a CL domain of L1 comprising no more than one, no more than two, no more than three, no more than four, no more than five, no more than six, or no more than seven amino acid mutations selected from the group consisting of: F118V, S131T, V133A, L135F, S162A, S176A, and T178L mutations (EU numbering).

In certain embodiments a multispecific antigen-binding protein comprises a CL domain of L1 comprising no more than one, no more than two, no more than three, no more than four, no more than five, no more than six, no more than seven, or no more than eight amino acid mutations selected from the group consisting of: F118V, S131T, V133A, L135F, S162A, T164S, S176T, and T178L mutations (EU numbering).

In certain embodiments a multispecific antigen-binding protein comprises a CL domain of L1 comprising no more than one, no more than two, no more than three, no more than four, no more than five, no more than six, no more than seven, or no more than eight amino acid mutations selected from the group consisting of: F118V, S131T, V133A, L135F, S162M, T164S, S176M, and T178L mutations (EU numbering).

All possible pair-wise combinations of the CH1 and L1 domains described above are contemplated.

In certain embodiments, the multispecific antigen-binding protein comprises a kappa light chain. In certain embodiments, the multispecific antigen-binding protein comprises a first light chain polypeptide L1 comprising a CL domain as set forth in any of SEQ ID NO:45-48. The CL domain as set forth in SEQ ID NO: 54 corresponds to amino acids 11-116 of SEQ ID NOs: 45-48. Accordingly, L1 may comprise a CL domain comprising amino acids 11-116 as set forth in any of SEQ ID Nos: 45-48. In certain embodiments, the multispecific antigen-binding protein comprises a CL domain of L1 comprising the amino acid sequence set forth in SEQ ID NO: 45 or the amino acids 11-116 in the sequence set forth in SEQ ID NO: 45. In certain embodiments, the multispecific antigen-binding protein comprises a CL domain of L1 comprising the amino acid sequence set forth in SEQ ID NO: 46 or the amino acids 11-116 in the sequence set forth in SEQ ID NO: 46. In certain embodiments, the multispecific antigen-binding protein comprises a CL domain of L comprising the amino acid sequence set forth in SEQ ID NO: 47 or the amino acids 11-116 in the sequence set forth in SEQ ID NO: 47. In certain embodiments, the multispecific antigen-binding protein comprises a CL domain of L1 comprising the amino acid sequence set forth in SEQ ID NO: 48 or the amino acids 11-116 in the sequence set forth in SEQ ID NO: 48.

In certain embodiments, the multispecific antigen binding protein comprises a lamba light chain. In certain embodiments, the multispecific antigen-binding protein comprises a CL domain of L1 comprising the amino acid sequence set forth in SEQ ID NO: 128.

In certain embodiments, the multispecific antigen-binding protein comprises an IgG1, IgG2, IgG3, or IgG4 heavy chain. In certain embodiments, the multispecific antigen-binding protein comprises a CH1 domain of H1 comprising the amino acid sequence set forth in SEQ ID NO: 49. In certain embodiments, the multispecific antigen-binding protein comprises a CH1 domain of H1 comprising the amino acid sequence set forth in SEQ ID NO: 50. In certain embodiments, the multispecific antigen-binding protein comprises a CH1 domain of H1 comprising the amino acid sequence set forth in SEQ ID NO: 51. In certain embodiments, the multispecific antigen-binding protein comprises a CH1 domain of H1 comprising the amino acid sequence set forth in SEQ ID NO: 52. In certain embodiments, the multispecific antigen-binding protein comprises a CH1 domain of H1 comprising the amino acid sequence set forth in SEQ ID NO: 106. In certain embodiments, the multispecific antigen-binding protein comprises a CH1 domain of H1 comprising the amino acid sequence set forth in SEQ ID NO: 107. In certain embodiments, the multispecific antigen-binding protein comprises a CH1 domain of H1 comprising the amino acid sequence set forth in SEQ ID NO: 108. The amino acid sequences of SEQ ID NOs: 45-52 and 106-108 are provided in Table 8 below (LC is kappa LC unless indicated otherwise; HC is of IgG1 iotype unless indicated otherwise).

TABLE 8

| | |
|---|---|
| JS20 LC<br>SEQ ID NO: 45 | GQGTKVEIKR TVAAPSVFI V PPSDEQLKSG<br>TATVACYLNN FYPREAKVQW KVDNALQSGN<br>SQEAVSEQDS KDSTYSLMSL LTLSKADYEK<br>HKVYACEVTH QGLSSPVTKS FNRGEC |
| JS78 LC<br>kappa<br>SEQ ID NO: 46 | GQGTKVEIKR TVAAPSVFI V PPSDEQLKSG<br>TATVACFLNN FYPREAKVQW KVDNALQSGN<br>SQEAVTEQDS KDSTYSLASL LTLSKADYEK<br>HKVYACEVTH QGLSSPVTKS FNRGEC |
| JS78 LC<br>lambda<br>SEQ ID NO: 128 | GQPKAAPSVT LVPPSSEELQ ANKATLACFI<br>SDFYPGAVTV AWKADSSPVK AGVETATPSK<br>QSNNKYAAAS LLSLTPEQWK SHKSYSCQVT<br>HEGSTVEKTV APTECS |
| JT20 LC<br>SEQ ID NO: 47 | GQGTKVEIKR TVAAPSVFI V PPSDEQLKSG<br>TATVACFLNN FYPREAKVQW KVDNALQSGN<br>SQEAVSEQDS KDSTYSLTSL LTLSKADYEK<br>HKVYACEVTH QGLSSPVTKS FNRGEC |
| JT25 LC<br>SEQ ID NO: 48 | GQGTKVEIKR TVAAPSVFI V PPSDEQLKSG<br>TATVACFLNN FYPREAKVQW KVDNALQSGN<br>SQEMVSEQDS KDSTYSLMSL LTLSKADYEK<br>HKVYACEVTH QGLSSPVTKS FNRGEC |
| JS20 HC<br>SEQ ID NO: 49 | TKGPSVFPFA PSSKSTSGGT AMLGCLVKDY<br>FPEPVTVSWN SGALTSGVHT MPAVLQSSGL<br>YILASVVTVP SSSLGTQTYI CN |
| JS78 HC IgG1<br>SEQ ID NO: 50 | TKGPSVFPFA PSSKSTSGGT AMLGCLVKDY<br>FPEPVTVSWN SGALTSGVHT YPAVLQSSGL<br>YILASAVTVP SSSLGTQTYI CN |
| JS78 HC IgG2<br>SEQ ID NO: 106 | TKGPSVFPFA PCSRSTSEST AMMLGCLVKDY<br>FPEPVTVSWN SGALTSGVHT YPAVLQSSGL<br>YILASAVTVP SSNFGTQTYT CN |
| JS78 HC IgG3<br>SEQ ID NO: 107 | TKGPSVFPFA PCSRSTSGGT AMLGCVKDY<br>FPEPVTVSWN SGALTSGVHT YPAVLQSSGL<br>YILASAVTVP SSSLGTQTYT CN |
| JS78 HC IgG4<br>SEQ ID NO: 108 | TKGPSVFPFA PCSRSTSEST AMLGCLVKDY<br>FPEPVTVSWN SGALTSGVHT FPAVLQSSGL<br>YILASAVTVP SSSLGTKTYT CN |
| JT20 HC<br>SEQ ID NO: 51 | TKGPSVFPFA PSSKSTSGGT ATLGCLVKDY<br>FPEPVTVSWN SGALTSGVHT MPAVLQSSGL<br>YTLASLVTVP SSSLGTQTYI CN |
| JT25 HC<br>SEQ ID NO: 52 | TKGPSVFPFA PSSKSTSGGT AMLGCLVKDY<br>FPEPVTVSWN SGALTSGVHT MPAVLQSSGL<br>YTLASVVTVP SSSLGTQTYI CN |

Amino acid positions 116, 118, 131, 133, 135, 162, 164, 174, 176, and 178 in CL (EU numbering) correspond to amino acid positions 18, 20, 33, 35, 37, 64, 66, 76, 78, and 80 in SEQ ID NOs: 4548, respectively. Amino acid positions 116, 118, 131, 133, 135, 162, 164, 174, 176, and 178 (EU numbering) in the CL domain of a kappa chain correspond to amino acid positions 116, 118, 131, 133, 135, 162, 164, 174, 176, and 178 (Kabat numbering) in the CL domain of a lambda light chain. Amino acid positions 116, 118, 131, 133, 135, 162, 164, 174, 176, and 178 (Kabat numbering) in the CL domain of a lambda light chain correspond to amino acid positions 10, 12, 25, 27, 29, 56, 59, 67, 69, and 71 in SEQ ID NO: 128, respectively.

Amino acid positions 128, 141, 170, 181, 183, and 185 (EU numbering) in CH1 correspond to amino acid positions 9, 22, 51, 62, 64, and 66 of SEQ ID NOs: 49-52 and 106-108, respectively.

All possible pair-wise combinations of SEQ ID NOs: 45-48 or amino acids 11-116 of SEQ ID Nos: 45-48 and SEQ ID NOs: 49-52 are contemplated. In certain embodiments, the multispecific antigen-binding protein comprises a first light chain polypeptide L1 comprising a CL domain as set forth in any of SEQ ID NOs: 45-48. The CL domain as set forth in SEQ ID NO: 54 corresponds to amino acids 11-116 of SEQ ID NOs: 45-48. Accordingly, L1 may comprise a CL domain comprising amino acids 11-116 as set forth in any of SEQ ID Nos: 45-48. In certain embodiments, specific combinations of SEQ ID NOs: 45-48 or amino acids 11-116 of SEQ ID Nos: 45-48 and 128 with SEQ ID NOs: 49-52 and 106-108 are contemplated. Such combinations include, but are not limited to, SEQ ID NO: 49/SEQ ID NO: 45 or amino acids 11-116 of SEQ ID NO: 45; SEQ ID NO: 50/SEQ ID NO: 46 or amino acids 11-116 of SEQ ID NO: 46; SEQ ID NO: 106/SEQ ID NO: 46 or amino acids 11-116 of SEQ ID NO: 46; SEQ ID NO: 107/SEQ ID NO: 46 or amino acids 11-116 of SEQ ID NO: 46; SEQ ID NO: 108/SEQ ID NO: 46 or amino acids 11-116 of SEQ ID NO: 46; SEQ ID NO: 51/SEQ ID NO: 47 or amino acids 11-116 of SEQ ID NO: 47; SEQ ID NO: 50/SEQ ID NO: 128; SEQ ID NO: 106/SEQ ID NO: 128; SEQ ID NO: 107/SEQ ID NO: 128; SEQ ID NO: 108/SEQ ID NO: 128; and SEQ ID NO: 52/SEQ ID NO:48 or amino acids 11-116 of SEQ ID NO: 48.

It will be apparent to those of ordinary skill in the art that the terms "H1" and "H2" are arbitrary designations, and that "H1" and "H2" in any of the embodiments above can be reversed. That is, any of the mutations above described as being in the CH1 domain of H1 and CL domain of L1 can, alternatively, be in the CH1 domain of H2 and the CL domain of L2.

As noted above, the mutations in the CH1/CL interface identified by Strategy #2 can be used independently of or in addition to the mutations in the CH1/CL interface identified by Strategy #1.

Thus, for example, provided herein is a multispecific antigen-binding protein comprising a CH1 domain of H1 that comprises A141I, F170S, S181M, S183A, and V185A substitution mutations (EU numbering), a CL domain of L1 that comprises F116A, L135V, S174A, S176F, and T178V substitution mutations (EU numbering), a CH1 domain of H2 that comprises an S183E substitution mutation (EU numbering), and a CL domain of L2 that comprises a V133K substitution mutation (EU numbering). Additionally, in certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the multispecific antigen-binding protein comprises a CH1 domain of H1 that comprises A141I, F170S, S181M, S183A, and V185A substitution mutations (EU numbering), a CL domain of L1 that comprises F116A, L135V, S174A, S176F, and T178V substitution mutations (EU numbering), a CH1 domain of H2 that consists of an S183E substitution mutation (EU numbering), and a CL domain of L2 that consists of a V133K substitution mutation (EU numbering). Additionally, in certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the multispecific antigen-binding protein comprises a CH1 domain of H1 that consists of A141I, F170S, S181M, S183A, and V185A substitution mutations (EU numbering), a CL domain of L1 that consists of F116A, L135V, S174A, S176F, and T178V substitution mutations (EU numbering), a CH1 domain of H2 that consists of an S183E substitution mutation (EU numbering), and a CL domain of L2 that consists of a V133K substitution mutation (EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering). In certain embodiments, the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). Additionally, in certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering). In certain embodiments, the multispecific antigen-binding protein comprises a CH1 domain of H1 that comprises (or consisting of or consisting essentially of) the amino acid sequence of SEQ ID NO: 29, a CL domain of L1 that comprises (or consisting of or consisting essentially of) SEQ ID NO: 19 or the amino acids 11-116 in the sequence set forth in SEQ ID NO: 19, a CH1 domain of H2 that comprises (or consists of or consisting essentially of) the amino acid sequence of SEQ ID NO: 15, and a CL domain of L2 that comprises (or consists of or consisting essentially of) SEQ ID NO: 5 or the amino acids 11-116 in the sequence set forth in SEQ ID NO: 5.

In certain embodiments, the multispecific antigen-binding protein comprises a CH1 domain of H1 that comprises A141I, F170S, S181M, S183A, and V185A substitution mutations (EU numbering), a CL domain of L1 that comprises F116A, L135V, S174A, S176F, and T178V substitution mutations (EU numbering), a CH1 domain of H2 that comprises an S183K substitution mutation (EU numbering), and a CL domain of L2 that comprises a V133E substitution mutation (EU numbering). In certain embodiments, the multispecific antigen-binding protein comprises a CH1 domain of H1 that comprises A141I, F170S, S181M, S183A, and V185A substitution mutations (EU numbering), a CL domain of L1 that comprises F116A, L135V, S174A, S176F, and T178V substitution mutations (EU numbering), a CH1 domain of H2 that consists of an S183K substitution mutation (EU numbering), and a CL domain of L2 that consists of a V133E substitution mutation (EU numbering). In certain embodiments, the multispecific antigen-binding protein comprises a CH1 domain of H1 that consists of A141I, F170S, S181M, S183A, and V185A substitution mutations (EU numbering), a CL domain of L1 that consists of F116A, L135V, S174A, S176F, and T178V substitution mutations (EU numbering), a CH1 domain of H2 that consists of an S183K substitution mutation (EU numbering), and a CL domain of L2 that consists of a V133E substitution mutation (EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering). In certain embodiments, the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering).

In certain embodiments, the multispecific antigen-binding protein comprises a CH1 domain of H1 that comprises A141I, F170S, S181M, S183A, and V185A substitution mutations (EU numbering), a CL domain of L1 that comprises F116A, L135V, S174A, S176F, and T178V substitution mutations (EU numbering), a CH1 domain of H2 that comprises L128F, A141M, F170M, S181I, and S183A substitution mutations (EU numbering), and a CL domain of L2 that comprises F118V, S131T, V133A, L135Y, S162A, T164S, S176M, and S178L substitution mutations (EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering).

In certain embodiments, the multispecific antigen-binding protein comprises a CH1 domain of H1 that comprises A141I, F170S, S181M, S183A, and V185A substitution mutations (EU numbering), a CL domain of L1 that comprises F116A, L135V, S174A, S176F, and T178V substitution mutations (EU numbering), a CH1 domain of H2 that comprises L128F, A141M, F170Y, S181I, S183A, and V185A substitution mutations (EU numbering), and a CL domain of L2 that comprises F118V, S131T, V133A, L135F, S162A, S176A, and T178L substitution mutations (EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering).

In certain embodiments, the multispecific antigen-binding protein comprises a CH1 domain of H1 that comprises A141I, F170S, S181M, S183A, and V185A mutations (EU numbering), a CL domain of L1 that comprises F116A, L135V, S174A, S176F, and T178V mutations (EU numbering), a CH1 domain of H2 that comprises L128F, A141T, F170M, S181T, S183A, and V185L substitution mutations (EU numbering), and a CL domain of L2 that comprises F118V, S131T, V133A, L135F, S162A, T164S, S176T, and T178L substitution mutations (EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering).

In certain embodiments, the multispecific antigen-binding protein comprises a CH1 domain of H1 that comprises A141I, F170S, S181M, S183A, and V185A substitution mutations (EU numbering), a CL domain of L1 that comprises F116A, L135V, S174A, S176F, and T178V substitution mutations (EU numbering), a CH1 domain of H2 that comprises L128F, A141M, F170M, S181T, and S183A substitution mutations (EU numbering), and a CL domain of L2 that comprises F118V, S131T, V133A, L135F, S162M, T164S, S176M, and T178L substitution mutations (EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering).

In certain embodiments, the multispecific antigen-binding protein comprises a CH1 domain of H1 that comprises A141I, F170S, S181M, S183A, and V185A substitution mutations (EU numbering), a CL domain of L1 that comprises F116A, L135V, S174A, S176F, and T178V substitution mutations (EU numbering), a CH1 domain of H2 that comprises A141I, F170S, S181M, S183V, and V185A substitution mutations (EU numbering), and a CL domain of L2 that comprises F116A, V133I, L135V, S162M, S174A, S176F, and T178V substitution mutations (EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering).

In certain embodiments, the multispecific antigen-binding protein comprises a CH1 domain of H1 that comprises A141I, F170S, S181M, S183A, and V185A substitution mutations (EU numbering), a CL domain of L1 that comprises F116A, L135V, S174A, S176F, and T178V substitution mutations (EU numbering), a CH1 domain of H2 that comprises A141I, F170S, S181M, S183A, and V185A substitution mutations (EU numbering), and a CL domain of L2 that comprises F116A, S131D, L135V, S162A, S174A, S176F, and T178I substitution mutations (EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering).

In certain embodiments, the multispecific antigen-binding protein comprises a CH1 domain of H1 that comprises A141I, F170S, S181M, S183A, and V185A substitution mutations (EU numbering), a CL domain of L1 that comprises F116A, L135V, S174A, S176F, and T178V substitution mutations (EU numbering), a CH1 domain of H2 that comprises A141I, F170A, S181M, S183V, and V185A substitution mutations (EU numbering), and a CL domain of L2 that comprises F116A, L135V, S162M, S174A, S176F, and T178V substitution mutations (EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering).

In certain embodiments, the multispecific antigen-binding protein comprises a CH1 domain of H1 that comprises L128F, A141M, F170Y, S181I, S183A, and V185A mutations (EU numbering), a CL domain of L1 that comprises F118V, S131T, V133A, L135F, S162A, S176A, and T178L mutations (EU numbering), a CH1 domain of H2 that comprises an S183E substitution mutation (EU numbering), and a CL domain of L2 that comprises a V133K substitution mutation (EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering).

In certain embodiments, the multispecific antigen-binding protein comprises a CH1 domain of H1 that comprises L128F, A141M, F170Y, S181I, S183A, and V185A mutations (EU numbering), a CL domain of L1 that comprises F118V, S131T, V133A, L135F, S162A, S176A, and T178L mutations (EU numbering), a CH1 domain of H2 that comprises an S183K substitution mutation (EU numbering), and a CL domain of L2 that comprises a V133E substitution mutation (EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering).

In certain embodiments, the multispecific antigen-binding protein comprises a CH1 domain of H1 that comprises L128F, A141M, F170Y, S181I, S183A, and V185A substitution mutations (EU numbering), a CL domain of L1 that comprises F118V, S131T, V133A, L135F, S162A, S176A, and T178L substitution mutations (EU numbering), a CH1 domain of H2 that comprises L128F, A141M, F170M, S181I, and S183A substitution mutations (EU numbering), and a CL domain of L2 that comprises F118V, S131T, V133A, L135Y, S162A, T164S, S176M, and S178L substitution mutations (EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering).

In certain embodiments, the multispecific antigen-binding protein comprises a CH1 domain of H1 that comprises L128F, A141M, F170Y, S181I, S183A, and V185A substitution mutations (EU numbering), a CL domain of L1 that comprises F118V, S131T, V133A, L135F, S162A, S176A, and T178L substitution mutations (EU numbering), a CH1 domain of H2 that comprises A141I, F170S, S181M, S183A, and V185A substitution mutations (EU numbering), a CL domain of L2 that comprises F116A, L135V, S174A, S176F, and T178V substitution mutations (EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering).

In certain embodiments, the multispecific antigen-binding protein comprises a CH1 domain of H1 that comprises L128F, A141M, F170Y, S181I, S183A, and V185A substitution mutations (EU numbering), a CL domain of L1 that comprises F118V, S131T, V133A, L135F, S162A, S176A, and T178L substitution mutations (EU numbering), a CH1 domain of H2 that comprises L128F, A141T, F170M, S181T, S183A, and V185L substitution mutations (EU numbering), and a CL domain of L2 that comprises F118V, S131T, V133A, L135F, S162A, T164S, S176T, and T178L substitution mutations (EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering).

In certain embodiments, the multispecific antigen-binding protein comprises a CH1 domain of H1 that comprises L128F, A141M, F170Y, S181I, S183A, and V185A substitution mutations (EU numbering), a CL domain of L1 that comprises F118V, S131T, V133A, L135F, S162A, S176A, and T178L substitution mutations (EU numbering), a CH1 domain of H2 that comprises L128F, A141M, F170M, S181T, and S183A substitution mutations (EU numbering), and a CL domain of L2 that comprises F118V, S131T, V133A, L135F, S162M, T164S, S176M, and T178L substitution mutations (EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering).

In certain embodiments, the multispecific antigen-binding protein comprises a CH1 domain of H1 that comprises L128F, A141M, F170Y, S181I, S183A, and V185A substitution mutations (EU numbering), a CL domain of L1 that comprises F118V, S131T, V133A, L135F, S162A, S176A, and T178L substitution mutations (EU numbering), a CH1 domain of H2 that comprises A141I, F170S, S181M, S183V, and V185A substitution mutations (EU numbering), and a CL domain of L2 that comprises F116A, V133I, L135V, S162M, S174A, S176F, and T178V substitution mutations (EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering).

It will be apparent to those of ordinary skill in the art that the terms "H1" and "H2" are arbitrary designations, and that "H1" and "H2" in any of the embodiments above can be reversed. That is, any of the mutations above described as being in the CH1 domain and/or the VH domain of H1 and CL domain and/or the VL domain of L1 can, alternatively, be in the CH1 domain and/or VH domain of H2 and the CL domain and/or VL domain of L2.

In certain embodiments, the multispecific antigen-binding protein comprises a CH1 domain of H1 that comprises L128F, A141M, F170Y, S181I, S183A, and V185A substitution mutations (EU numbering), a CL domain of L that comprises F118V, S131T, V133A, L135F, S162A, S176A, and T178L substitution mutations (EU numbering), a CH1 domain of H2 that comprises A141I, F170S, S181M, S183A, and V185A substitution mutations (EU numbering), and a CL domain of L2 that comprises F116A, S131D, L135V, S162A, S174A, S176F, and T178I substitution mutations (EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering).

In certain embodiments, the multispecific antigen-binding protein comprises a CH1 domain of H1 that comprises L128F, A141M, F170Y, S181I, S183A, and V185A substitution mutations (EU numbering), a CL domain of L1 that comprises F118V, S131T, V133A, L135F, S162A, S176A, and T178L substitution mutations (EU numbering), a CH1 domain of H2 that comprises A141I, F170A, S181M, S183V, and V185A substitution mutations (EU numbering), and a CL domain of L2 that comprises F116A, L135V, S162M, S174A, S176F, and T178V substitution mutations (EU numbering). In certain embodiments, the VL domain of L1 the multispecific antigen-binding protein comprises a Q38K substitution mutation (Kabat numbering), the VH domain of H1 of the multispecific antigen-binding protein comprises a Q39E substitution mutation (Kabat numbering), the VL domain of L2 of the multispecific antigen-binding protein comprises a Q38E substitution mutation (Kabat numbering), and the VH domain of H2 of the multispecific antigen-binding protein comprises a Q39K substitution mutation (Kabat numbering). In certain embodiments, the VL domain of L1 the multispecific antigen-binding protein comprises a Q38E substitution mutation (Kabat numbering), the VH domain of H1 of the multispecific antigen-binding protein comprises a Q39K substitution mutation (Kabat numbering), the VL domain of L2 of the multispecific antigen-binding protein comprises a Q38K substitution mutation (Kabat numbering), and the VH domain of H2 of the multispecific antigen-binding protein comprises a Q39E substitution mutation (Kabat numbering).

It will be apparent to those of ordinary skill in the art that the terms "H1" and "H2" are arbitrary designations, and that "H1" and "H2" in any of the embodiments above can be reversed. That is, any of the mutations above described as being in the CH1 domain and/or the VH domain of H1 and CL domain and/or the VL domain of L1 can, alternatively, be in the CH1 domain and/or VH domain of H2 and the CL domain and/or VL domain of L2.

In certain embodiments, a multispecific antigen-binding protein provided herein comprises a CH1 domain of H1 comprising no more than 1 amino acid substitution mutation, no more than 2 amino acid substitution mutations, no more than 3 amino acid substitution mutations, no more than 5 amino acid substitution mutations, or no more than 6 amino acid substitutions, no more than 7 amino acid substitutions, no more than 8 amino acid substitutions, no more than 9 amino acid substitutions, no more than 10 amino acid substitutions, no more than 11 amino acid substitutions, or no more than 12 amino acid substitutions.

In certain embodiments, a multispecific antigen-binding protein provided herein comprises a CL domain of L1 comprising no more than 1 amino acid substitution mutation, no more than 2 amino acid substitution mutations, no more than 3 amino acid substitution mutations, no more than 5 amino acid substitution mutations, or no more than 6 amino acid substitutions, no more than 7 amino acid substitutions, no more than 8 amino acid substitutions, or no more than 9 amino acid substitutions, no more than 10 amino acid substitutions, no more than 11 amino acid substitutions, or no more than 12 amino acid substitutions.

In certain embodiments the CH1 domain of H1 has at least about 701%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to a human germline or allotype heavy chain CH1 domain. See Jefferis et al. (2009) Mabs 1: 332-338. Provided below are the amino acid sequences of human IgG1 CH1 domain (i.e., SEQ ID NO: 57) and human IgG4 S228P CH1 domain (i.e., SEQ ID NO: 58). ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSPEE MTKNQVSLTC LVKGFYPSDI AVEWESNGQP ENNYKTTPPV LDSDGSFFLY SKLTVDKSRW QQGNVFSCSV MHEALHNHYT QKSLSLSPGK (SEQ ID NO. 57) ASTKGPSVFP LAPCSRSTSE STAALGCLVK DYFPEPVTVS WNSGALTSGV HTFPAVLQSS GLYSLSSVVT VPSSSLGTKT YTCNVDHKPS NTKVDKPVES KYGPPCPPCP APEFLGGPSV FLFPPKPKDT LMISRTPEVT CVVVDVSQED PEVQFNWYVD GVEVHNAKTK PREEQFNSTY PVVSVLTVLH QDWLNGKEYK CKVSNKGLPS SIEKTISKAK GQPPEPQVYT LPPSQEEMTK NQVSLTCLVK GFYPSDIAVE WESNGQPENN YKTTPPVLDS DGSFFLYSRL TVDKSPWQEG NVFSCSVMHE ALHNHYTQKS LSLSLGK (SEQ ID NO. 58)

In some embodiments, LC1 is a kappa light chain. In some embodiments, the CL domain of LC1 has at least about 70%, at least about 710%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to a human germline or allotype kappa chain CL domain. Provided below is the amino acid sequence of human kappa light chain constant domain (i.e., SEQ ID NO: 59).

RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC (SEQ ID NO: 59) In some embodiments, LC1 is a lambda light chain. In some embodiments, the CL domain of LC1 has at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to a human germline or allotype lambda CL domain. Provided below is the amino acid sequence of a human lambda light chain constant domain (i.e., SEQ ID NO: 113).

(SEQ ID NO: 113)
GQPKAAPSVT LFPPSSEELQ ANKATLVCLI SDFYPGAVTV

AWKADSSPVK AGVETTTPSK QSNNKYAASS YLSLTPEQWK

SHKSYSCQVT HEGSTVEKTV SPTECS

In certain embodiments, the parental H1 from which an H1 of a multispecific antigen-binding protein provided herein is derived does not show a significant preference for a parental L1 from which an L1 of a multispecific antigen-binding protein provided herein is derived. In certain embodiments. In certain embodiments, the parental H1 from which an H1 of a multispecific antigen-binding protein provided herein is derived shows a preference for a parental L1 from which an L1 of a multispecific antigen-binding protein provided herein is derived.

It will be apparent to those of ordinary skill in the art that the terms "H1" and "H2" are arbitrary designations, and that "H1" and "H2" in any of the embodiments above can be reversed. That is, any of the mutations above described as being in the CH1 domain and/or the VH domain of H1 and CL domain and/or the VL domain of L1 can, alternatively, be in the CH1 domain and/or VH domain of H2 and the CL domain and/or VL domain of L2.

Modifications to the VH and VL Domains

In certain embodiments, the multispecific antigen-binding protein, or an antigen-binding fragment thereof, comprises amino acid modifications in the VH and VL domain(s), i.e., independently of modifications in the CH1 and CL domains described herein. In certain embodiments, the multispecific antigen-binding proteins provided herein additionally comprise amino acid modifications in the VH and VL domain(s), i.e., in combination with mutations in the CH1/CL interface identified by Strategy #1 and/or the mutations in the CH1/CL interface identified by Strategy #1.

In certain embodiments, the VH domain of H1 of the multispecific antigen-binding protein comprises an amino acid substitution at position Q39 (Kabat numbering), and the VL domain of L1 of the multispecific antigen-binding protein comprises an amino acid substitution at position Q38 (Kabat numbering). In certain embodiments, the amino acid at position Q39 (Kabat numbering) in the VH domain of H1 is replaced with a positively charged residue, and the amino acid at position Q38 (Kabat numbering) in the VL domain of L1 is replaced with a negatively charged residue. In certain embodiments, the amino acid at position Q39 (Kabat numbering) in the VH domain of H1 is replaced with a negatively charged residue, and wherein the amino acid at position Q38 (Kabat numbering) in the VL domain of L1 is replaced with a positively charged residue. In certain embodiments, the positively charged residue is selected from the group consisting of R, H, and K. In certain embodiments, the negatively charged residue is selected from the group consisting of D and E.

Additionally or alternatively, in certain embodiments, the VH domain of H2 of the multispecific antigen-binding protein comprises an amino acid substitution at position Q39 (Kabat numbering), and the VL domain of L2 of the multispecific antigen-binding protein comprises an amino acid substitution at position Q38 (Kabat numbering). In certain embodiments, the amino acid at position Q39 (Kabat numbering) in the VH domain of H2 is replaced with a positively charged residue, and wherein the amino acid at position Q38 (Kabat numbering) in the VL domain of L2 is replaced with a negatively charged residue. In certain embodiments, the amino acid at position Q39 (Kabat numbering) in the VH domain of H2 is replaced with a negatively charged residue, and wherein the amino acid at position Q38 (Kabat numbering) in the VL domain of L2 is replaced with a positively charged residue. In certain embodiments, the positively charged residue is selected from the group consisting of R, H, and K. In certain embodiments, the negatively charged residue is selected from the group consisting of D and E.

In certain embodiments, specific combinations of substitution mutations at position Q39 (Kabat numbering) on the VH domain of H land at position Q38 (Kabat numbering) on the VL domain of L1 and/or at position Q39 (Kabat numbering) on the VH domain of H2 and at position Q38 (Kabat numbering) on the VL domain of L2 are contemplated. Such combinations include, but not limited, to those shown in Tables 9A and 9B below:

TABLE 9A

| | |
|---|---|
| Q39D/Q38K | Q39R/Q38D |
| Q39E/Q38K | Q39K/Q38D |
| Q39D/Q38R | Q39R/Q38E |
| Q39E/Q38R | Q39K/Q38E |
| Q39D/Q38H | Q39H/Q38D |
| Q39E/Q38H | Q39H/Q38E |

The first mutation in each pair in Table 9A refers to a modification in the VH domain sequence, and the second mutation in each pair in Table 9A refers to a modification in the VL domain sequence.

TABLE 9B

| | | | |
|---|---|---|---|
| EKKE | KEEK | EKKD | KDEK |
| ERKE | KEER | ERKD | KDER |
| DKKE | KEDK | DKKD | KDDK |
| DRKE | KEDR | DRKD | KDDR |
| EKRE | REEK | EKRD | RDEK |
| ERRE | REER | ERRD | RDER |
| DKRE | REDK | DKRD | RDDK |
| DRRE | REDR | DRRD | RDDR |

The four letter mutations in Table 9B refer to the amino acid substitutions at $Q39X_{HV1}/Q38X_{VL1}/Q39X_{VH2}/Q38X_{VL2}$, where "VH1" refers to the VH domain of H1, "VL" refers to the VL domain of L1, "VH2" refers to the VH domain of H2, and "VL2" refers to the VL domain of L2. It will be apparent to those of ordinary skill in the art that the terms "H1"/"L1" and "H2"/"L2" are arbitrary designations, and that "H1" and "L1" in any of the embodiments above can be reversed with "H2" and "L2," respectively. That is, any of the mutations above described as being in the VH domain of H1 and VL domain of L1 can, alternatively, be in the VH domain of H2 and the VL domain of L2.

In certain embodiments, the VH domain of H1 of the multispecific antigen-binding protein comprises an amino acid substitution at position Q39E (Kabat numbering), and the VL domain of L1 of the multispecific antigen-binding protein comprises an amino acid substitution at position Q38K (Kabat numbering). In certain embodiments, the VH domain of H2 of the multispecific antigen-binding protein comprises an amino acid substitution at position Q39K (Kabat numbering), and the VL domain of L2 of the multispecific antigen-binding protein comprises an amino acid substitution at position Q38E (Kabat numbering). In certain embodiments, the VH domain of H1 of the multispecific antigen-binding protein comprises an amino acid substitution at position Q39K (Kabat numbering), and the VL domain of L1 of the multispecific antigen-binding protein comprises an amino acid substitution at position Q38E (Kabat numbering). In certain embodiments, the VH domain of H2 of the multispecific antigen-binding protein comprises an amino acid substitution at position Q39E (Kabat numbering), and the VL domain of L2 of the multispecific antigen-binding protein comprises an amino acid substitution at position Q38K (Kabat numbering). In certain embodiments, the VH domain of H1 of the multispecific antigen-binding protein comprises an amino acid substitution at position Q39E (Kabat numbering), the VL domain of L1 of the multispecific antigen-binding protein comprises an amino acid substitution at position Q38K (Kabat numbering), the VH domain of H2 of the multispecific antigen-binding protein comprises an amino acid substitution at position Q39K (Kabat numbering), and the VL domain of L2 of the multispecific antigen-binding protein comprises an amino acid substitution at position Q38E (Kabat numbering). In certain embodiments, the VH domain of H1 of the multispecific antigen-binding protein comprises an amino acid substitution at position Q39K (Kabat numbering), the VL domain of L1 of the multispecific antigen-binding protein comprises an amino acid substitution at position Q38E (Kabat numbering), the VH domain of H2 of the multispecific antigen-binding protein comprises an amino acid substitution at position Q39E (Kabat numbering), and the VL domain of L2 of the multispecific antigen-binding protein comprises an amino acid substitution at position Q38K (Kabat numbering).

In certain embodiments, the VH domain of H1 of the multispecific antigen-binding protein comprises a Q39E substitution mutation (Kabat numbering), the VL domain of L of the multispecific antigen-binding protein comprises a Q38R substitution mutation (Kabat numbering), the VH domain of H2 of the multispecific antigen-binding protein comprises a Q39K substitution mutation (Kabat numbering), and the VL domain of L2 of the multispecific antigen-binding protein comprises a Q38E substitution mutation (Kabat numbering).

In certain embodiments, the VH domain of H1 of the multispecific antigen-binding protein comprises a Q39D substitution mutation (Kabat numbering), the VL domain of L1 of the multispecific antigen-binding protein comprises a Q38K substitution mutation (Kabat numbering), the VH domain of H2 of the multispecific antigen-binding protein comprises a Q39K substitution mutation (Kabat numbering), and the VL domain of L2 of the multispecific antigen-binding protein comprises a Q38E substitution mutation (Kabat numbering).

In certain embodiments, the VH domain of H1 of the multispecific antigen-binding protein comprises a Q39D substitution mutation (Kabat numbering), the VL domain of L1 of the multispecific antigen-binding protein comprises a Q38R substitution mutation (Kabat numbering), the VH domain of H2 of the multispecific antigen-binding protein comprises a Q39K substitution mutation (Kabat numbering), and the VL domain of L2 of the multispecific antigen-binding protein comprises a Q38E substitution mutation (Kabat numbering).

In certain embodiments, the VH domain of H1 of the multispecific antigen-binding protein comprises a Q39E substitution mutation (Kabat numbering), the VL domain of L1 of the multispecific antigen-binding protein comprises a Q38K substitution mutation (Kabat numbering), the VH domain of H2 of the multispecific antigen-binding protein comprises a Q39R substitution mutation (Kabat numbering), and the VL domain of L2 of the multispecific antigen-binding protein comprises a Q38E substitution mutation (Kabat numbering).

In certain embodiments, the VH domain of H1 of the multispecific antigen-binding protein comprises a Q39E substitution mutation (Kabat numbering), the VL domain of L1 of the multispecific antigen-binding protein comprises a Q38R substitution mutation (Kabat numbering), the VH domain of H2 of the multispecific antigen-binding protein comprises a Q39R substitution mutation (Kabat numbering), and the VL domain of L2 of the multispecific antigen-binding protein comprises a Q38E substitution mutation (Kabat numbering).

In certain embodiments, the VH domain of H1 of the multispecific antigen-binding protein comprises a Q39D substitution mutation (Kabat numbering), the VL domain of L1 of the multispecific antigen-binding protein comprises a Q38K substitution mutation (Kabat numbering), the VH domain of H2 of the multispecific antigen-binding protein comprises a Q39R substitution mutation (Kabat numbering), and the VL domain of L2 of the multispecific antigen-binding protein comprises a Q38E substitution mutation (Kabat numbering).

In certain embodiments, the VH domain of H1 of the multispecific antigen-binding protein comprises a substitution mutation Q39D (Kabat numbering), the VL domain of L1 of the multispecific antigen-binding protein comprises a Q38R substitution mutation (Kabat numbering), the VH domain of H2 of the multispecific antigen-binding protein comprises a Q39R substitution mutation (Kabat numbering), and the VL domain of L2 of the multispecific antigen-binding protein comprises a Q38E substitution mutation (Kabat numbering).

In certain embodiments, the VH domain of H1 of the multispecific antigen-binding protein comprises a Q39E substitution mutation (Kabat numbering), the VL domain of L1 of the multispecific antigen-binding protein comprises a Q38K substitution mutation (Kabat numbering), the VH domain of H2 of the multispecific antigen-binding protein comprises a Q39K substitution mutation (Kabat numbering), and the VL domain of L2 of the multispecific antigen-binding protein comprises a Q38D substitution mutation (Kabat numbering).

In certain embodiments, the VH domain of H1 of the multispecific antigen-binding protein comprises a Q39E substitution mutation (Kabat numbering), the VL domain of L1 of the multispecific antigen-binding protein comprises a Q38R substitution mutation (Kabat numbering), the VH domain of H2 of the multispecific antigen-binding protein comprises a Q39K substitution mutation (Kabat numbering), and the VL domain of L2 of the multispecific antigen-binding protein comprises a Q38D substitution mutation (Kabat numbering).

In certain embodiments, the VH domain of H1 of the multispecific antigen-binding protein comprises a Q39D substitution mutation (Kabat numbering), the VL domain of L1 of the multispecific antigen-binding protein comprises a Q38K substitution mutation (Kabat numbering), the VH domain of H2 of the multispecific antigen-binding protein comprises a Q39K substitution mutation (Kabat numbering), and the VL domain of L2 of the multispecific antigen-binding protein comprises a Q38D substitution mutation (Kabat numbering).

In certain embodiments, the VH domain of H1 of the multispecific antigen-binding protein comprises a Q39D substitution mutation (Kabat numbering), the VL domain of L1 of the multispecific antigen-binding protein comprises a Q38R substitution mutation (Kabat numbering), the VH domain of H2 of the multispecific antigen-binding protein comprises a Q39K substitution mutation (Kabat numbering), and the VL domain of L2 of the multispecific antigen-binding protein comprises a Q38D substitution mutation (Kabat numbering).

In certain embodiments, the VH domain of H1 of the multispecific antigen-binding protein comprises a Q39E substitution mutation (Kabat numbering), the VL domain of L1 of the multispecific antigen-binding protein comprises a Q38K substitution mutation (Kabat numbering), the VH domain of H2 of the multispecific antigen-binding protein comprises a Q39R substitution mutation (Kabat numbering), and the VL domain of L2 of the multispecific antigen-binding protein comprises a Q38D substitution mutation (Kabat numbering).

In certain embodiments, the VH domain of H1 of the multispecific antigen-binding protein comprises a Q39E substitution mutation (Kabat numbering), the VL domain of L1 of the multispecific antigen-binding protein comprises a Q38R substitution mutation (Kabat numbering), the VH domain of H2 of the multispecific antigen-binding protein comprises a Q39R substitution mutation (Kabat numbering), and the VL domain of L2 of the multispecific antigen-binding protein comprises a Q38D substitution mutation (Kabat numbering).

In certain embodiments, the VH domain of H1 of the multispecific antigen-binding protein comprises a Q39D substitution mutation (Kabat numbering), the VL domain of L1 of the multispecific antigen-binding protein comprises a Q38K substitution mutation (Kabat numbering), the VH domain of H2 of the multispecific antigen-binding protein comprises a Q39R substitution mutation (Kabat numbering), and the VL domain of L2 of the multispecific antigen-binding protein comprises a Q38D substitution mutation (Kabat numbering).

In certain embodiments, the VH domain of H1 of the multispecific antigen-binding protein comprises a Q39D substitution mutation (Kabat numbering), the VL domain of L1 of the multispecific antigen-binding protein comprises a Q38R substitution mutation (Kabat numbering), the VH domain of H2 of the multispecific antigen-binding protein comprises a Q39R substitution mutation (Kabat numbering), and the VL domain of L2 of the multispecific antigen-binding protein comprises a Q38D substitution mutation (Kabat numbering).

In certain embodiments, the VH domain of H1 of the multispecific antigen-binding protein comprises a Q39K substitution mutation (Kabat numbering), the VL domain of L1 of the multispecific antigen-binding protein comprises a Q38E substitution mutation (Kabat numbering), the VH domain of H2 of the multispecific antigen-binding protein comprises a Q39E substitution mutation (Kabat numbering), and the VL domain of L2 of the multispecific antigen-binding protein comprises a Q38R substitution mutation (Kabat numbering).

In certain embodiments, the VH domain of H1 of the multispecific antigen-binding protein comprises a Q39K substitution mutation (Kabat numbering), the VL domain of L1 of the multispecific antigen-binding protein comprises a Q38E substitution mutation (Kabat numbering), the VH domain of H2 of the multispecific antigen-binding protein comprises a Q39D substitution mutation (Kabat numbering), and the VL domain of L2 of the multispecific antigen-binding protein comprises a Q38K substitution mutation (Kabat numbering).

In certain embodiments, the VH domain of H1 of the multispecific antigen-binding protein comprises a Q39K substitution mutation (Kabat numbering), the VL domain of L of the multispecific antigen-binding protein comprises a Q38E substitution mutation (Kabat numbering), the VH domain of H2 of the multispecific antigen-binding protein comprises a Q39D substitution mutation (Kabat numbering), and the VL domain of L2 of the multispecific antigen-binding protein comprises a Q38R substitution mutation (Kabat numbering).

In certain embodiments, the VH domain of H1 of the multispecific antigen-binding protein comprises a Q39R substitution mutation (Kabat numbering), the VL domain of L1 of the multispecific antigen-binding protein comprises a Q38E substitution mutation (Kabat numbering), the VH domain of H2 of the multispecific antigen-binding protein comprises a Q39E substitution mutation (Kabat numbering), and the VL domain of L2 of the multispecific antigen-binding protein comprises a Q38K substitution mutation (Kabat numbering).

In certain embodiments, the VH domain of H1 of the multispecific antigen-binding protein comprises a Q39R substitution mutation (Kabat numbering), the VL domain of L1 of the multispecific antigen-binding protein comprises a Q38E substitution mutation (Kabat numbering), the VH domain of H2 of the multispecific antigen-binding protein comprises a Q39E substitution mutation (Kabat numbering), and the VL domain of L2 of the multispecific antigen-binding protein comprises a Q38R substitution mutation (Kabat numbering).

In certain embodiments, the VH domain of H1 of the multispecific antigen-binding protein comprises a Q39R substitution mutation (Kabat numbering), the VL domain of L1 of the multispecific antigen-binding protein comprises a Q38E substitution mutation (Kabat numbering), the VH domain of H2 of the multispecific antigen-binding protein comprises a Q39D substitution mutation (Kabat numbering), and the VL domain of L2 of the multispecific antigen-binding protein comprises a Q38K substitution mutation (Kabat numbering).

In certain embodiments, the VH domain of H1 of the multispecific antigen-binding protein comprises a Q39R substitution mutation (Kabat numbering), the VL domain of L1 of the multispecific antigen-binding protein comprises a Q38E substitution mutation (Kabat numbering), the VH domain of H2 of the multispecific antigen-binding protein comprises a Q39D substitution mutation (Kabat numbering), and the VL domain of L2 of the multispecific antigen-binding protein comprises a Q38R substitution mutation (Kabat numbering).

In certain embodiments, the VH domain of H1 of the multispecific antigen-binding protein comprises a Q39K substitution mutation (Kabat numbering), the VL domain of L of the multispecific antigen-binding protein comprises a Q38D substitution mutation (Kabat numbering), the VH domain of H2 of the multispecific antigen-binding protein comprises a Q39E substitution mutation (Kabat numbering), and the VL domain of L2 of the multispecific antigen-binding protein comprises a Q38K substitution mutation (Kabat numbering).

In certain embodiments, the VH domain of H1 of the multispecific antigen-binding protein comprises a Q39K substitution mutation (Kabat numbering), the VL domain of L1 of the multispecific antigen-binding protein comprises a Q38D substitution mutation (Kabat numbering), the VH domain of H2 of the multispecific antigen-binding protein comprises a Q39E substitution mutation (Kabat numbering), and the VL domain of L2 of the multispecific antigen-binding protein comprises a Q38R substitution mutation (Kabat numbering).

In certain embodiments, the VH domain of H1 of the multispecific antigen-binding protein comprises a Q39K substitution mutation (Kabat numbering), the VL domain of L1 of the multispecific antigen-binding protein comprises a Q38D substitution mutation (Kabat numbering), the VH domain of H2 of the multispecific antigen-binding protein comprises a Q39D substitution mutation (Kabat numbering), and the VL domain of L2 of the multispecific antigen-binding protein comprises a Q38K substitution mutation (Kabat numbering).

In certain embodiments, the VH domain of H1 of the multispecific antigen-binding protein comprises a Q39K substitution mutation (Kabat numbering), the VL domain of L1 of the multispecific antigen-binding protein comprises a Q38D substitution mutation (Kabat numbering), the VH domain of H2 of the multispecific antigen-binding protein comprises a Q39D substitution mutation (Kabat numbering), and the VL domain of L2 of the multispecific antigen-binding protein comprises a Q38R substitution mutation (Kabat numbering).

In certain embodiments, the VH domain of H1 of the multispecific antigen-binding protein comprises a Q39R substitution mutation (Kabat numbering), the VL domain of L1 of the multispecific antigen-binding protein comprises a Q38D substitution mutation (Kabat numbering), the VH domain of H2 of the multispecific antigen-binding protein comprises a Q39E substitution mutation (Kabat numbering), and the VL domain of L2 of the multispecific antigen-binding protein comprises a Q38K substitution mutation (Kabat numbering).

In certain embodiments, the VH domain of H1 of the multispecific antigen-binding protein comprises a Q39R substitution mutation (Kabat numbering), the VL domain of L1 of the multispecific antigen-binding protein comprises a Q38D substitution mutation (Kabat numbering), the VH domain of H2 of the multispecific antigen-binding protein comprises a Q39E substitution mutation (Kabat numbering), and the VL domain of L2 of the multispecific antigen-binding protein comprises a Q38R substitution mutation (Kabat numbering).

In certain embodiments, the VH domain of H1 of the multispecific antigen-binding protein comprises a Q39R substitution mutation (Kabat numbering), the VL domain of L1 of the multispecific antigen-binding protein comprises a Q38D substitution mutation (Kabat numbering), the VH domain of H2 of the multispecific antigen-binding protein comprises a Q39D substitution mutation (Kabat numbering), and the VL domain of L2 of the multispecific antigen-binding protein comprises a Q38K substitution mutation (Kabat numbering).

In certain embodiments, the VH domain of H1 of the multispecific antigen-binding protein comprises a Q39R substitution mutation (Kabat numbering), the VL domain of L1 of the multispecific antigen-binding protein comprises a Q38D substitution mutation (Kabat numbering), the VH domain of H2 of the multispecific antigen-binding protein comprises a Q39D substitution mutation (Kabat numbering), and the VL domain of L2 of the multispecific antigen-binding protein comprises a Q38R substitution mutation (Kabat numbering).

In certain embodiments, the VH domain of H1 of the multispecific antigen-binding protein comprises a Q39H substitution mutation (Kabat numbering), the VL domain of L1 of the multispecific antigen-binding protein comprises a Q38D substitution mutation (Kabat numbering), the VH domain of H2 of the multispecific antigen-binding protein comprises a Q39D substitution mutation (Kabat numbering), and the VL domain of L2 of the multispecific antigen-binding protein comprises a Q38H substitution mutation (Kabat numbering).

In certain embodiments, the VH domain of H1 of the multispecific antigen-binding protein comprises a Q39H substitution mutation (Kabat numbering), the VL domain of L1 of the multispecific antigen-binding protein comprises a Q38E substitution mutation (Kabat numbering), the VH domain of H2 of the multispecific antigen-binding protein comprises a Q39E substitution mutation (Kabat numbering), and the VL domain of L2 of the multispecific antigen-binding protein comprises a Q38H substitution mutation (Kabat numbering).

In certain embodiments, the VH domain of H1 of the multispecific antigen-binding protein comprises a Q39D substitution mutation (Kabat numbering), the VL domain of L of the multispecific antigen-binding protein comprises a Q38H substitution mutation (Kabat numbering), the VH domain of H2 of the multispecific antigen-binding protein comprises a Q39H substitution mutation (Kabat numbering), and the VL domain of L2 of the multispecific antigen-binding protein comprises a Q38D substitution mutation (Kabat numbering).

In certain embodiments, the VH domain of H1 of the multispecific antigen-binding protein comprises a Q39E substitution mutation (Kabat numbering), the VL domain of L1 of the multispecific antigen-binding protein comprises a Q38H substitution mutation (Kabat numbering), the VH domain of H2 of the multispecific antigen-binding protein comprises a Q39H substitution mutation (Kabat numbering), and the VL domain of L2 of the multispecific antigen-binding protein comprises a Q38E substitution mutation (Kabat numbering).

It will be apparent to those of ordinary skill in the art that the terms "H1"/"L1" and "H2"/"L2" are arbitrary designations, and that "H1" and "L1" in any of the embodiments above can be reversed with "H2" and "L2," respectively. That is, any of the mutations above described as being in the VH domain of H1 and VL domain of L1 can, alternatively, be in the VH domain of H2 and the VL domain of L2.

As noted elsewhere herein, the multispecific antigen-binding proteins provided herein in some embodiments comprise amino acid modifications in the VH and VL domain(s), i.e., such as the amino acid modifications described above, in combination with mutations in the CH1/CL interface identified by Strategy #1 and/or the mutations in the CH1/CL interface identified by Strategy #2.

In certain embodiments, the VH domain of H1 of the multispecific antigen-binding protein comprises a Q39E substitution mutation (Kabat numbering), the VL domain of L1 the multispecific antigen-binding protein comprises a Q38K substitution mutation (Kabat numbering), the CH1 domain of H2 of the multispecific antigen-binding protein comprises (such as consists of or consists essentially of) an S183E substitution mutation (EU numbering), and the CL domain of L2 of the multispecific antigen-binding protein comprises (such as consists of or consists essentially of) a V133K substitution mutation (EU numbering).

In certain embodiments, the VH domain of H1 of the multispecific antigen-binding protein comprises a Q39K substitution mutation (Kabat numbering), the VL domain of L1 the multispecific antigen-binding protein comprises a Q38E substitution mutation (Kabat numbering), the CH1 domain of H2 of the multispecific antigen-binding protein comprises (such as consists of or consists essentially of) an S183E substitution mutation (EU numbering), and the CL domain of L2 of the multispecific antigen-binding protein comprises (such as consists of or consists essentially of) a V133K substitution mutation (EU numbering).

In certain embodiments, the VH domain of H1 of the multispecific antigen-binding protein comprises a Q39E substitution mutation (Kabat numbering), the VL domain of L1 the multispecific antigen-binding protein comprises a Q38K substitution mutation (Kabat numbering), the CH1 domain of H1 of the multispecific antigen-binding protein comprises (such as consists of or consists essentially of) an S183E substitution mutation (EU numbering), and the CL domain of L1 of the multispecific antigen-binding protein comprises (such as consists of or consists essentially of) a V133K substitution mutation (EU numbering).

In certain embodiments, the VH domain of H1 of the multispecific antigen-binding protein comprises a Q39K substitution mutation (Kabat numbering), the VL domain of L1 the multispecific antigen-binding protein comprises a Q38E substitution mutation (Kabat numbering), the CH1 domain of H1 of the multispecific antigen-binding protein comprises (such as consists of or consists essentially of) an S183E substitution mutation (EU numbering), and the CL domain of L1 of the multispecific antigen-binding protein comprises (such as consists of or consists essentially of) a V133K substitution mutation (EU numbering).

In certain embodiments, the VH domain of H1 of the multispecific antigen-binding protein comprises a Q39E substitution mutation (Kabat numbering), the VL domain of L1 the multispecific antigen-binding protein comprises a Q38K substitution mutation (Kabat numbering), the CH1 domain of H2 of the multispecific antigen-binding protein comprises (such as consists of or consists essentially of) an S183E substitution mutation (EU numbering), and the CL domain of L2 of the multispecific antigen-binding protein comprises (such as consists of or consists essentially of) a V133K substitution mutation (EU numbering).

In certain embodiments, the VH domain of H1 of the multispecific antigen-binding protein comprises a Q39E substitution mutation (Kabat numbering), the VL domain of L the multispecific antigen-binding protein comprises a Q38K substitution mutation (Kabat numbering), the CH1 domain of H1 of the multispecific antigen-binding protein comprises (such as consists of or consists essentially of) an S183K substitution mutation (EU numbering), and the CL domain of L1 of the multispecific antigen-binding protein comprises (such as consists of or consists essentially of) a V133E substitution mutation (EU numbering).

In certain embodiments, the VH domain of H1 of the multispecific antigen-binding protein comprises a Q39E substitution mutation (Kabat numbering), the VL domain of L the multispecific antigen-binding protein comprises a Q38K substitution mutation (Kabat numbering), the VH domain of H2 the multispecific antigen-binding protein comprises a Q39K substitution mutation (Kabat numbering), the CH1 domain of H2 of the multispecific antigen-binding protein comprises (such as consists of or consists essentially of) an S183E substitution mutation (EU numbering), the VL domain of L2 of the multispecific antigen-binding protein comprises a Q38E substitution mutation (Kabat numbering), and the CL domain of L2 of the multispecific antigen-binding protein comprises (such as consists of or consists essentially of) a V133K substitution mutation (EU numbering).

In certain embodiments, the VH domain of H1 of the multispecific antigen-binding protein comprises a Q39K substitution mutation (Kabat numbering), the VL domain of L1 the multispecific antigen-binding protein comprises a Q38E substitution mutation (Kabat numbering), the VH domain of H2 the multispecific antigen-binding protein comprises a Q39E substitution mutation (Kabat numbering), the CH1 domain of H2 of the multispecific antigen-binding protein comprises (such as consists of or consists essentially of) an S183E substitution mutation (EU numbering), the VL domain of L2 of the multispecific antigen-binding protein comprises a Q38K substitution mutation (Kabat numbering), and the CL domain of L2 of the multispecific antigen-binding protein comprises (such as consists of or consists essentially of) a V133K substitution mutation (EU numbering).

In certain embodiments, the VH domain of H1 of the multispecific antigen-binding protein comprises a Q39K substitution mutation (Kabat numbering), the VL domain of L1 the multispecific antigen-binding protein comprises a Q38E substitution mutation (Kabat numbering), the VH domain of H2 the multispecific antigen-binding protein comprises a Q39E substitution mutation (Kabat numbering), the CH1 domain of H2 of the multispecific antigen-binding protein comprises (such as consists of or consists essentially of) an S183F substitution mutation (EU numbering), the VL domain of L2 of the multispecific antigen-binding protein comprises a Q38K substitution mutation (Kabat numbering), and the CL domain of L2 of the multispecific antigen-binding protein comprises (such as consists of or consists essentially of) a V133K substitution mutation (EU numbering).

In certain embodiments, the VH domain of H1 of the multispecific antigen-binding protein comprises a Q39K substitution mutation (Kabat numbering), the CH1 domain of H1 of the multispecific antigen-binding protein comprises (such as consists of or consists essentially of) an S183E substitution mutation (EU numbering), the VL domain of L1 the multispecific antigen-binding protein comprises a Q38E substitution mutation (Kabat numbering), the VH domain of H2 the multispecific antigen-binding protein comprises a Q39E substitution mutation (Kabat numbering), the CH1 domain of H2 of the multispecific antigen-binding protein comprises (such as consists of or consists essentially of) an S183F substitution mutation (EU numbering), the VL domain of L2 of the multispecific antigen-binding protein comprises a Q38K substitution mutation (Kabat numbering), and the CL domain of L2 of the multispecific antigen-binding protein comprises (such as consists of or consists essentially of) a V133K substitution mutation (EU numbering).

In certain embodiments, the VH domain of H1 of the multispecific antigen-binding protein comprises a Q39K substitution mutation (Kabat numbering), the VL domain of L1 the multispecific antigen-binding protein comprises a Q38E substitution mutation (Kabat numbering), the VH domain of H2 the multispecific antigen-binding protein comprises a Q39E substitution mutation (Kabat numbering), the CH1 domain of H2 of the multispecific antigen-binding protein comprises (such as consists of or consists essentially of) an S183T substitution mutation (EU numbering), the VL domain of L2 of the multispecific antigen-binding protein comprises a Q38K substitution mutation (Kabat numbering), and the CL domain of L2 of the multispecific antigen-binding protein comprises (such as consists of or consists essentially of) a V133K substitution mutation (EU numbering).

In certain embodiments, the VH domain of H1 of the multispecific antigen-binding protein comprises a Q39K substitution mutation (Kabat numbering), the CH1 domain of H1 of the multispecific antigen-binding protein comprises (such as consists of or consists essentially of) an S183E substitution mutation (EU numbering), the VL domain of L1 the multispecific antigen-binding protein comprises a Q38E substitution mutation (Kabat numbering), the VH domain of H2 the multispecific antigen-binding protein comprises a Q39E substitution mutation (Kabat numbering), the CH1 domain of H2 of the multispecific antigen-binding protein comprises (such as consists of or consists essentially of) an S183T substitution mutation (EU numbering), the VL domain of L2 of the multispecific antigen-binding protein comprises a Q38K substitution mutation (Kabat numbering), and the CL domain of L2 of the multispecific antigen-binding protein comprises (such as consists of or consists essentially of) a V133K substitution mutation (EU numbering).

In certain embodiments, the VH domain of H1 of the multispecific antigen-binding protein comprises a Q39K substitution mutation (Kabat numbering), the VL domain of L1 the multispecific antigen-binding protein comprises a Q38E substitution mutation (Kabat numbering), the VH domain of H2 the multispecific antigen-binding protein comprises a Q39E substitution mutation (Kabat numbering), the CH1 domain of H2 of the multispecific antigen-binding protein comprises (such as consists of or consists essentially of) an S183Y substitution mutation (EU numbering), the VL domain of L2 of the multispecific antigen-binding protein comprises a Q38K substitution mutation (Kabat numbering), and the CL domain of L2 of the multispecific antigen-binding protein comprises (such as consists of or consists essentially of) a V133K substitution mutation (EU numbering).

In certain embodiments, the VH domain of H1 of the multispecific antigen-binding protein comprises a Q39K substitution mutation (Kabat numbering), the CH1 domain of H1 of the multispecific antigen-binding protein comprises (such as consists of or consists essentially of) an S183E substitution mutation (EU numbering), the VL domain of L1 the multispecific antigen-binding protein comprises a Q38E substitution mutation (Kabat numbering), the VH domain of H2 the multispecific antigen-binding protein comprises a Q39E substitution mutation (Kabat numbering), the CH1 domain of H2 of the multispecific antigen-binding protein comprises (such as consists of or consists essentially of) an S183Y substitution mutation (EU numbering), the VL domain of L2 of the multispecific antigen-binding protein comprises a Q38K substitution mutation (Kabat numbering), and the CL domain of L2 of the multispecific antigen-binding protein comprises (such as consists of or consists essentially of) a V133K substitution mutation (EU numbering).

In certain embodiments, the VH domain of H1 of the multispecific antigen-binding protein comprises a Q39K substitution mutation (Kabat numbering), the CL domain of L1 of the multispecific antigen-binding protein comprises (such as consists of or consists essentially of) a V133E substitution mutation (EU numbering), the VL domain of L1 the multispecific antigen-binding protein comprises a Q38E substitution mutation (Kabat numbering), the VH domain of H2 the multispecific antigen-binding protein comprises a Q39E substitution mutation (Kabat numbering), the CH1 domain of H2 of the multispecific antigen-binding protein comprises (such as consists of or consists essentially of) an S183E substitution mutation (EU numbering), the VL domain of L2 of the multispecific antigen-binding protein comprises a Q38K substitution mutation (Kabat numbering), and the CL domain of L2 of the multispecific antigen-binding protein comprises (such as consists of or consists essentially of) a V133K substitution mutation (EU numbering).

In certain embodiments, the VH domain of H1 of the multispecific antigen-binding protein comprises a Q39K substitution mutation (Kabat numbering), the VL domain of L the multispecific antigen-binding protein comprises a Q38E substitution mutation (Kabat numbering), the VH domain of H2 the multispecific antigen-binding protein comprises a Q39E substitution mutation (Kabat numbering), the CH1 domain of H2 of the multispecific antigen-binding protein comprises (such as consists of or consists essentially of) an S183K substitution mutation (EU numbering), the VL domain of L2 of the multispecific antigen-binding protein comprises a Q38K substitution mutation (Kabat numbering), and the CL domain of L2 of the multispecific antigen-binding protein comprises (such as consists of or consists essentially of) a V133E substitution mutation (EU numbering).

In certain embodiments, the VH domain of H1 of the multispecific antigen-binding protein comprises a Q39E substitution mutation (Kabat numbering), the VL domain of L1 the multispecific antigen-binding protein comprises a Q38K substitution mutation (Kabat numbering), the VH domain of H2 the multispecific antigen-binding protein comprises a Q39K substitution mutation (Kabat numbering), the CH1 domain of H2 of the multispecific antigen-binding protein comprises (such as consists of or consists essentially of) an S183K substitution mutation (EU numbering), the VL domain of L2 of the multispecific antigen-binding protein comprises a Q38E substitution mutation (Kabat numbering), and the CL domain of L2 of the multispecific antigen-binding protein comprises (such as consists of or consists essentially of) a V133E substitution mutation (EU numbering).

In certain embodiments, the VH domain of H1 of the multispecific antigen-binding protein comprises a Q39E substitution mutation (Kabat numbering), the CH1 domain of H1 of the multispecific antigen-binding protein comprises (such as consists of or consists essentially of) an S183E substitution mutation (EU numbering), the VL domain of L1 the multispecific antigen-binding protein comprises a Q38K substitution mutation (Kabat numbering), the CL domain of L1 of the multispecific antigen-binding protein comprises (such as consists of or consists essentially of) a V133K substitution mutation (EU numbering), the VH domain of H2 the multispecific antigen-binding protein comprises a Q39K substitution mutation (Kabat numbering), and the VL domain of L2 of the multispecific antigen-binding protein comprises a Q38E substitution mutation (Kabat numbering).

In certain embodiments, the VH domain of H1 of the multispecific antigen-binding protein comprises a Q39K substitution mutation (Kabat numbering), the CH1 domain of H1 of the multispecific antigen-binding protein comprises (such as consists of or consists essentially of) an S183E substitution mutation (EU numbering), the VL domain of L1 the multispecific antigen-binding protein comprises a Q38E substitution mutation (Kabat numbering), CL domain of L1 of the multispecific antigen-binding protein comprises (such as consists of or consists essentially of) a V133K substitution mutation (EU numbering), the VH domain of H2 the multispecific antigen-binding protein comprises a Q39E substitution mutation (Kabat numbering), and the VL domain of L2 of the multispecific antigen-binding protein comprises a Q38K substitution mutation (Kabat numbering).

In certain embodiments, the VH domain of H1 of the multispecific antigen-binding protein comprises a Q39E substitution mutation (Kabat numbering), the CH1 domain of H1 of the multispecific antigen-binding protein comprises (such as consists of or consists essentially of) an S183K substitution mutation (EU numbering), the VL domain of L1 the multispecific antigen-binding protein comprises a Q38K substitution mutation (Kabat numbering), the CL domain of L of the multispecific antigen-binding protein comprises (such as consists of or consists essentially of) a V133E substitution mutation (EU numbering), the VH domain of H2 the multispecific antigen-binding protein comprises a Q39K substitution mutation (Kabat numbering), and the VL domain of L2 of the multispecific antigen-binding protein comprises a Q38E substitution mutation (Kabat numbering).

In certain embodiments, the VH domain of H1 of the multispecific antigen-binding protein comprises a Q39K substitution mutation (Kabat numbering), the VL domain of L1 the multispecific antigen-binding protein comprises a Q38E substitution mutation (Kabat numbering), the CH1 domain of H1 of the multispecific antigen-binding protein comprises (such as consists of or consists essentially of) an S183K substitution mutation (EU numbering), and the CL domain of L1 of the multispecific antigen-binding protein comprises (such as consists of or consists essentially of) a V133E substitution mutation (EU numbering).

In certain embodiments, the VH domain of H1 of the multispecific antigen-binding protein comprises a Q39K substitution mutation (Kabat numbering), the CH1 domain of H1 of the multispecific antigen-binding protein comprises (such as consists of or consists essentially of) an S183K substitution mutation (EU numbering), the VL domain of L1 the multispecific antigen-binding protein comprises a Q38E substitution mutation (Kabat numbering), the CL domain of L1 of the multispecific antigen-binding protein comprises (such as consists of or consists essentially of) a V133E substitution mutation (EU numbering), the VH domain of H2 the multispecific antigen-binding protein comprises a Q39E substitution mutation (Kabat numbering), and the VL domain of L2 of the multispecific antigen-binding protein comprises a Q38K substitution mutation (Kabat numbering).

In certain embodiments, the CH1 domain of H1 of the multispecific antigen-binding protein comprises a S183K substitution mutation (EU numbering), the CL domain of L1 of the multispecific antigen-binding protein comprises a V133E substitution mutation (EU numbering), the CH1 domain of H2 of the multispecific antigen-binding protein comprises an S183E substitution mutation (EU numbering), and the CL domain of L2 of the multispecific antigen-binding protein comprises a V133K substitution mutation (EU numbering). In certain embodiments, the CH1 domain of H1 of the multispecific antigen-binding protein consists of a S183K substitution mutation (EU numbering), the CL domain of L1 of the multispecific antigen-binding protein consists of a V133E substitution mutation (EU numbering), the CH1 domain of H2 of the multispecific antigen-binding protein consists of an S183E substitution mutation (EU numbering), and the CL domain of L2 of the multispecific antigen-binding protein consists of a V133K substitution mutation (EU numbering).

In certain embodiments, the VH domain of H1 of the multispecific antigen-binding protein comprises a Q39E substitution mutation (Kabat numbering), the VL domain of L1 the multispecific antigen-binding protein comprises a Q38K substitution mutation (Kabat numbering), the CL domain of L1 of the multispecific antigen-binding protein comprises a V133E substitution mutation (EU numbering), the CH1 domain of H2 of the multispecific antigen-binding protein comprises an S183E substitution mutation (EU numbering), and the CL domain of L2 of the multispecific antigen-binding protein comprises a V133K substitution mutation (EU numbering).

In certain embodiments, the CH1 domain of H1 of the multispecific antigen-binding protein comprises a S183K substitution mutation (EU numbering), the CL domain of L1 of the multispecific antigen-binding protein comprises a V133E substitution mutation (EU numbering), the VH domain of H2 the multispecific antigen-binding protein comprises a Q39K substitution mutation (Kabat numbering), the CH1 domain of H2 of the multispecific antigen-binding protein comprises an S183E substitution mutation (EU numbering), the VL domain of L2 of the multispecific antigen-binding protein comprises a Q38E substitution mutation (Kabat numbering), and the CL domain of L2 of the multispecific antigen-binding protein comprises a V133K substitution mutation (EU numbering).

In certain embodiments, the VH domain of H1 of the multispecific antigen-binding protein comprises a Q39E substitution mutation (Kabat numbering), the CH1 domain of H1 of the multispecific antigen-binding protein comprises a S183K substitution mutation (EU numbering), the VL domain of L1 the multispecific antigen-binding protein comprises a Q38K substitution mutation (Kabat numbering), the CL domain of L1 of the multispecific antigen-binding protein comprises a V133E substitution mutation (EU numbering), the VH domain of H2 the multispecific antigen-binding protein comprises a Q39K substitution mutation (Kabat numbering), the CH1 domain of H2 of the multispecific antigen-binding protein comprises an S183E substitution mutation (EU numbering), the VL domain of L2 of the multispecific antigen-binding protein comprises a Q38E substitution mutation (Kabat numbering), and the CL domain of L2 of the multispecific antigen-binding protein comprises a V133K substitution mutation (EU numbering).

In certain embodiments, the VH domain of H1 of the multispecific antigen-binding protein comprises a Q39E substitution mutation (Kabat numbering), the CH1 domain of H1 of the multispecific antigen-binding protein consists of a S183K substitution mutation (EU numbering), the VL domain of L1 the multispecific antigen-binding protein comprises a Q38K substitution mutation (Kabat numbering), the CL domain of L1 of the multispecific antigen-binding protein consists of a V133E substitution mutation (EU numbering), the VH domain of H2 the multispecific antigen-binding protein comprises a Q39K substitution mutation (Kabat numbering), the CH1 domain of H2 of the multispecific antigen-binding protein consists of an S183E substitution mutation (EU numbering), the VL domain of L2 of the multispecific antigen-binding protein comprises a Q38E substitution mutation (Kabat numbering), and the CL domain of L2 of the multispecific antigen-binding protein consists of a V133K substitution mutation (EU numbering).

In certain embodiments, the VH domain of H1 of the multispecific antigen-binding protein comprises a Q39K substitution mutation (Kabat numbering), the CH1 domain of H1 of the multispecific antigen-binding protein comprises a S183K substitution mutation (EU numbering), the VL domain of L1 the multispecific antigen-binding protein comprises a Q38E substitution mutation (Kabat numbering), the CL domain of L1 of the multispecific antigen-binding protein comprises a V133E substitution mutation (EU numbering), the VH domain of H2 the multispecific antigen-binding protein comprises a Q39E substitution mutation (Kabat numbering), the CH1 domain of H2 of the multispecific antigen-binding protein comprises an S183E substitution mutation (EU numbering), the VL domain of L2 of the multispecific antigen-binding protein comprises a Q38K substitution mutation (Kabat numbering), and the CL domain of L2 of the multispecific antigen-binding protein comprises a V133K substitution mutation (EU numbering).

In certain embodiments, the VH domain of H1 of the multispecific antigen-binding protein comprises a Q39K substitution mutation (Kabat numbering), the CH1 domain of H1 of the multispecific antigen-binding protein consists of a S183K substitution mutation (EU numbering), the VL domain of L1 the multispecific antigen-binding protein comprises a Q38E substitution mutation (Kabat numbering), the CL domain of L1 of the multispecific antigen-binding protein consists of a V133E substitution mutation (EU numbering), the VH domain of H2 the multispecific antigen-binding protein comprises a Q39E substitution mutation (Kabat numbering), the CH1 domain of H2 of the multispecific antigen-binding protein consists of an S183E substitution mutation (EU numbering), the VL domain of L2 of the multispecific antigen-binding protein comprises a Q38K substitution mutation (Kabat numbering), and the CL domain of L2 of the multispecific antigen-binding protein consists of a V133K substitution mutation (EU numbering).

In certain embodiments, the CH1 domain of H1 of the multispecific antigen-binding protein comprises a S183E substitution mutation (EU numbering), the CL domain of L1 of the multispecific antigen-binding protein comprises a V133K substitution mutation (EU numbering), the CH1 domain of H2 of the multispecific antigen-binding protein comprises an S183K substitution mutation (EU numbering), and the CL domain of L2 of the multispecific antigen-binding protein comprises a V133E substitution mutation (EU numbering).

In certain embodiments, the CH1 domain of H1 of the multispecific antigen-binding protein consists of a S183E substitution mutation (EU numbering), the CL domain of L1 of the multispecific antigen-binding protein consists of a V133K substitution mutation (EU numbering), the CH1 domain of H2 of the multispecific antigen-binding protein consists of an S183K substitution mutation (EU numbering), and the CL domain of L2 of the multispecific antigen-binding protein consists of a V133E substitution mutation (EU numbering).

In certain embodiments, the VH domain of H1 of the multispecific antigen-binding protein comprises a Q39E substitution mutation (Kabat numbering), the CH1 domain of H1 of the multispecific antigen-binding protein comprises a S183E substitution mutation (EU numbering), the VL domain of L1 the multispecific antigen-binding protein comprises a Q38K substitution mutation (Kabat numbering), the CL domain of L1 of the multispecific antigen-binding protein comprises a V133K substitution mutation (EU numbering), the VH domain of H2 the multispecific antigen-binding protein comprises a Q39K substitution mutation (Kabat numbering), the CH1 domain of H2 of the multispecific antigen-binding protein comprises an S183K substitution mutation (EU numbering), the VL domain of L2 of the multispecific antigen-binding protein comprises a Q38E substitution mutation (Kabat numbering), and the CL domain of L2 of the multispecific antigen-binding protein comprises a V133E substitution mutation (EU numbering).

In certain embodiments, the VH domain of H1 of the multispecific antigen-binding protein comprises a Q39E substitution mutation (Kabat numbering), the CH1 domain of H1 of the multispecific antigen-binding protein consists of a S183E substitution mutation (EU numbering), the VL domain of L1 the multispecific antigen-binding protein comprises a Q38K substitution mutation (Kabat numbering), the CL domain of L1 of the multispecific antigen-binding protein consists of a V133K substitution mutation (EU numbering), the VH domain of H2 the multispecific antigen-binding protein comprises a Q39K substitution mutation (Kabat numbering), the CH1 domain of H2 of the multispecific antigen-binding protein consists of an S183K substitution mutation (EU numbering), the VL domain of L2 of the multispecific antigen-binding protein comprises a Q38E substitution mutation (Kabat numbering), and the CL domain of L2 of the multispecific antigen-binding protein consists of a V133E substitution mutation (EU numbering).

In certain embodiments, the VH domain of H1 of the multispecific antigen-binding protein comprises a Q39K substitution mutation (Kabat numbering), the CH1 domain of H1 of the multispecific antigen-binding protein comprises a S183E substitution mutation (EU numbering), the VL domain of L1 the multispecific antigen-binding protein comprises a Q38E substitution mutation (Kabat numbering), the CL domain of L1 of the multispecific antigen-binding protein comprises a V133K substitution mutation (EU numbering), the VH domain of H2 the multispecific antigen-binding protein comprises a Q39E substitution mutation (Kabat numbering), the CH1 domain of H2 of the multispecific antigen-binding protein comprises an S183K substitution mutation (EU numbering), the VL domain of L2 of the multispecific antigen-binding protein comprises a Q38K substitution mutation (Kabat numbering), and the CL domain of L2 of the multispecific antigen-binding protein comprises a V133E substitution mutation (EU numbering).

In certain embodiments, the VH domain of H1 of the multispecific antigen-binding protein comprises a Q39K substitution mutation (Kabat numbering), the CH1 domain of H1 of the multispecific antigen-binding protein consists of a S183E substitution mutation (EU numbering), the VL domain of L1 the multispecific antigen-binding protein comprises a Q38E substitution mutation (Kabat numbering), the CL domain of L1 of the multispecific antigen-binding protein consists of a V133K substitution mutation (EU numbering), the VH domain of H2 the multispecific antigen-binding protein comprises a Q39E substitution mutation (Kabat numbering), the CH1 domain of H2 of the multispecific antigen-binding protein consists of an S183K substitution mutation (EU numbering), the VL domain of L2 of the multispecific antigen-binding protein comprises a Q38K substitution mutation (Kabat numbering), and the CL domain of L2 of the multispecific antigen-binding protein consists of a V133E substitution mutation (EU numbering).

In certain embodiments, the VH domain of H1 of the multispecific antigen-binding protein comprises a Q39E substitution mutation (Kabat numbering), the VL domain of L1 the multispecific antigen-binding protein comprises a Q38K substitution mutation (Kabat numbering), the CL domain of L of the multispecific antigen-binding protein comprises a V133E substitution mutation (EU numbering), the VH domain of H2 the multispecific antigen-binding protein comprises a Q39K substitution mutation (Kabat numbering), the CH1 domain of H2 of the multispecific antigen-binding protein comprises an S183E substitution mutation (EU numbering), the VL domain of L2 of the multispecific antigen-binding protein comprises a Q38E substitution mutation (Kabat numbering), and the CL domain of L2 of the multispecific antigen-binding protein comprises a V133K substitution mutation (EU numbering).

In certain embodiments, the VH domain of H1 of the multispecific antigen-binding protein comprises a Q39E substitution mutation (Kabat numbering), the VL domain of L the multispecific antigen-binding protein comprises a Q38K substitution mutation (Kabat numbering), the VH domain of H2 the multispecific antigen-binding protein comprises a Q39K substitution mutation (Kabat numbering), the CH1 domain of H2 of the multispecific antigen-binding protein comprises an S183F substitution mutation (EU numbering), the VL domain of L2 of the multispecific antigen-binding protein comprises a Q38E substitution mutation (Kabat numbering), and the CL domain of L2 of the multispecific antigen-binding protein comprises a V133K substitution mutation (EU numbering).

In certain embodiments, the VH domain of H1 of the multispecific antigen-binding protein comprises a Q39E substitution mutation (Kabat numbering), the VL domain of L1 the multispecific antigen-binding protein comprises a Q38K substitution mutation (Kabat numbering), the VH domain of H2 the multispecific antigen-binding protein comprises a Q39K substitution mutation (Kabat numbering), the CH1 domain of H2 of the multispecific antigen-binding protein comprises an S183T substitution mutation (EU numbering), the VL domain of L2 of the multispecific antigen-binding protein comprises a Q38E substitution mutation (Kabat numbering), and the CL domain of L2 of the multispecific antigen-binding protein comprises a V133K substitution mutation (EU numbering).

In certain embodiments, the VH domain of H1 of the multispecific antigen-binding protein comprises a Q39E substitution mutation (Kabat numbering), the VL domain of L1 the multispecific antigen-binding protein comprises a Q38K substitution mutation (Kabat numbering), the VH domain of H2 the multispecific antigen-binding protein comprises a Q39K substitution mutation (Kabat numbering), the CH1 domain of H2 of the multispecific antigen-binding protein comprises an S183Y substitution mutation (EU numbering), the VL domain of L2 of the multispecific antigen-binding protein comprises a Q38E substitution mutation (Kabat numbering), and the CL domain of L2 of the multispecific antigen-binding protein comprises a V133K substitution mutation (EU numbering).

In certain embodiments, the VH domain of H1 of the multispecific antigen-binding protein comprises a Q39E substitution mutation (Kabat numbering), the VL domain of L1 the multispecific antigen-binding protein comprises a Q38K substitution mutation (Kabat numbering), the CL domain of L1 of the multispecific antigen-binding protein comprises a V133E substitution mutation (EU numbering), the VH domain of H2 the multispecific antigen-binding protein comprises a Q39K substitution mutation (Kabat numbering), the CH1 domain of H2 of the multispecific antigen-binding protein comprises an S183F substitution mutation (EU numbering), the VL domain of L2 of the multispecific antigen-binding protein comprises a Q38E substitution mutation (Kabat numbering), and the CL domain of L2 of the multispecific antigen-binding protein comprises a V133K substitution mutation (EU numbering).

In certain embodiments, the VH domain of H1 of the multispecific antigen-binding protein comprises a Q39E substitution mutation (Kabat numbering), the VL domain of L1 the multispecific antigen-binding protein comprises a Q38K substitution mutation (Kabat numbering), the CL domain of L of the multispecific antigen-binding protein comprises a V133E substitution mutation (EU numbering), the VH domain of H2 the multispecific antigen-binding protein comprises a Q39K substitution mutation (Kabat numbering), the CH1 domain of H2 of the multispecific antigen-binding protein comprises an S183T substitution mutation (EU numbering), the VL domain of L2 of the multispecific antigen-binding protein comprises a Q38E substitution mutation (Kabat numbering), and the CL domain of L2 of the multispecific antigen-binding protein comprises a V133K substitution mutation (EU numbering).

In certain embodiments, the VH domain of H1 of the multispecific antigen-binding protein comprises a Q39E substitution mutation (Kabat numbering), the VL domain of L the multispecific antigen-binding protein comprises a Q38K substitution mutation (Kabat numbering), the CL domain of L1 of the multispecific antigen-binding protein comprises a V133E substitution mutation (EU numbering), the VH domain of H2 the multispecific antigen-binding protein comprises a Q39K substitution mutation (Kabat numbering), the CH1 domain of H2 of the multispecific antigen-binding protein comprises an S183Y substitution mutation (EU numbering), the VL domain of L2 of the multispecific antigen-binding protein comprises a Q38E substitution mutation (Kabat numbering), and the CL domain of L2 of the multispecific antigen-binding protein comprises a V133K substitution mutation (EU numbering).

In certain embodiments, the VH domain of H1 the multispecific antigen-binding protein comprises a Q39E substitution mutation (Kabat numbering), the CH1 domain of H1 of the multispecific antigen-binding protein comprises an S183T substitution mutation (EU numbering) the VL domain of L1 of the multispecific antigen-binding protein comprises a Q38K substitution mutation (Kabat numbering), and the CL domain of L1 of the multispecific antigen-binding protein comprises a V133K substitution mutation (EU numbering). In certain embodiments, the VH domain of H2 the multispecific antigen-binding protein comprises a Q39K substitution mutation (Kabat numbering), the CH1 domain of H2 of the multispecific antigen-binding protein comprises an S183K substitution mutation (EU numbering) the VL domain of L2 of the multispecific antigen-binding protein comprises a Q38E substitution mutation (Kabat numbering), and the CL domain of L2 of the multispecific antigen-binding protein comprises a V133T substitution mutation (EU numbering).

In certain embodiments, the VH domain of H1 the multispecific antigen-binding protein comprises a Q39E substitution mutation (Kabat numbering), the CH1 domain of H1 of the multispecific antigen-binding protein comprises an S183E substitution mutation (EU numbering) the VL domain of L1 of the multispecific antigen-binding protein comprises a Q38K substitution mutation (Kabat numbering), and the CL domain of L1 of the multispecific antigen-binding protein comprises a V133K substitution mutation (EU numbering). In certain embodiments, the VH domain of H2 the multispecific antigen-binding protein comprises a Q39K substitution mutation (Kabat numbering), the CH1 domain of H2 of the multispecific antigen-binding protein comprises an S183K substitution mutation (EU numbering) the VL domain of L2 of the multispecific antigen-binding protein comprises a Q38E substitution mutation (Kabat numbering), and the CL domain of L2 of the multispecific antigen-binding protein comprises a V133E substitution mutation (EU numbering).

In certain embodiments, the VH domain of H1 the multispecific antigen-binding protein comprises a Q39K substitution mutation (Kabat numbering), the CH1 domain of H1 of the multispecific antigen-binding protein comprises an S183E substitution mutation (EU numbering) the VL domain of L1 of the multispecific antigen-binding protein comprises a Q38E substitution mutation (Kabat numbering), and the CL domain of L1 of the multispecific antigen-binding protein comprises a V133K substitution mutation (EU numbering). In certain embodiments, the VH domain of H2 the multispecific antigen-binding protein comprises a Q39E substitution mutation (Kabat numbering), the CH1 domain of H2 of the multispecific antigen-binding protein comprises an S183K substitution mutation (EU numbering) the VL domain of L2 of the multispecific antigen-binding protein comprises a Q38K substitution mutation (Kabat numbering), and the CL domain of L2 of the multispecific antigen-binding protein comprises a V133E substitution mutation (EU numbering).

In certain embodiments, the VH domain of H1 the multispecific antigen-binding protein comprises a Q39K substitution mutation (Kabat numbering), the CH1 domain of H1 of the multispecific antigen-binding protein comprises an S183T substitution mutation (EU numbering) the VL domain of L1 of the multispecific antigen-binding protein comprises a Q38E substitution mutation (Kabat numbering), and the CL domain of L1 of the multispecific antigen-binding protein comprises a V133K substitution mutation (EU numbering). In certain embodiments, the VH domain of H2 the multispecific antigen-binding protein comprises a Q39E substitution mutation (Kabat numbering), the CH1 domain of H2 of the multispecific antigen-binding protein comprises an S183K substitution mutation (EU numbering) the VL domain of L2 of the multispecific antigen-binding protein comprises a Q38K substitution mutation (Kabat numbering), and the CL domain of L2 of the multispecific antigen-binding protein comprises a V133T substitution mutation (EU numbering).

In certain embodiments, the VH domain of H1 of the multispecific antigen-binding protein comprises a Q39E substitution mutation (Kabat numbering), the VL domain of L1 the multispecific antigen-binding protein comprises a Q38K substitution mutation (Kabat numbering), the CH1 domain of H1 of the multispecific antigen-binding protein comprises A141I, F170S, S181M, S183A, and V185A mutations (EU numbering), the CL domain of L1 of the multispecific antigen-binding protein comprises F116A, L135V, S174A, S176F, and T178V mutations (EU numbering).

In certain embodiments, the CH1 domain of H1 of the multispecific antigen-binding protein comprises A141I, F170S, S181M, S183A, and V185A mutations (EU numbering), the CL domain of L1 of the multispecific antigen-binding protein comprises F116A, L135V, S174A, S176F, and T178V mutations (EU numbering), the VH domain of H2 the multispecific antigen-binding protein comprises a Q39K substitution mutation (Kabat numbering), and the VL domain of L2 of the multispecific antigen-binding protein comprises a Q38E substitution mutation (Kabat numbering).

In certain embodiments, the VH domain of H1 of the multispecific antigen-binding protein comprises a Q39E substitution mutation (Kabat numbering), the VL domain of L1 the multispecific antigen-binding protein comprises a Q38K substitution mutation (Kabat numbering), the CH1 domain of H1 of the multispecific antigen-binding protein comprises A141I, F170S, S181M, S183A, and V185A mutations (EU numbering), the CL domain of L1 of the multispecific antigen-binding protein comprises F116A, L135V, S174A, S176F, and T178V mutations (EU numbering), the VH domain of H2 the multispecific antigen-binding protein comprises a Q39K substitution mutation (Kabat numbering), and the VL domain of L2 of the multispecific antigen-binding protein comprises a Q38E substitution mutation (Kabat numbering).

In certain embodiments, the VH domain of H1 of the multispecific antigen-binding protein comprises a Q39E substitution mutation (Kabat numbering), the VL domain of L1 the multispecific antigen-binding protein comprises a Q38K substitution mutation (Kabat numbering), the CH1 domain of H1 of the multispecific antigen-binding protein consists of A141I, F170S, S181M, S183A, and V185A mutations (EU numbering), the CL domain of L1 of the multispecific antigen-binding protein consists of F116A, L135V, S174A, S176F, and T178V mutations (EU numbering), the VH domain of H2 the multispecific antigen-binding protein comprises a Q39K substitution mutation (Kabat numbering), and the VL domain of L2 of the multispecific antigen-binding protein comprises a Q38E substitution mutation (Kabat numbering).

In certain embodiments, the VH domain of H1 of the multispecific antigen-binding protein comprises a Q39K substitution mutation (Kabat numbering), the VL domain of L1 the multispecific antigen-binding protein comprises a Q38E substitution mutation (Kabat numbering), the CH1 domain of H1 of the multispecific antigen-binding protein comprises A141I, F170S, S181M, S183A, and V185A mutations (EU numbering), the CL domain of L1 of the multispecific antigen-binding protein comprises F116A, L135V, S174A, S176F, and T178V mutations (EU numbering), the VH domain of H2 the multispecific antigen-binding protein comprises a Q39E substitution mutation (Kabat numbering), and the VL domain of L2 of the multispecific antigen-binding protein comprises a Q38K substitution mutation (Kabat numbering).

In certain embodiments, the VH domain of H1 of the multispecific antigen-binding protein comprises a Q39K substitution mutation (Kabat numbering), the VL domain of L1 the multispecific antigen-binding protein comprises a Q38E substitution mutation (Kabat numbering), the CH1 domain of H1 of the multispecific antigen-binding protein consists of A141I, F170S, S181M, S183A, and V185A mutations (EU numbering), the CL domain of L1 of the multispecific antigen-binding protein consists of F116A, L135V, S174A, S176F, and T178V mutations (EU numbering), the VH domain of H2 the multispecific antigen-binding protein comprises a Q39E substitution mutation (Kabat numbering), and the VL domain of L2 of the multispecific antigen-binding protein comprises a Q38K substitution mutation (Kabat numbering).

In certain embodiments, the CH1 domain of H1 of the multispecific antigen-binding protein comprises A141I, F170S, S181M, S183A, and V185A mutations (EU numbering), the CL domain of L1 of the multispecific antigen-binding protein comprises F116A, L135V, S174A, S176F, and T178V mutations (EU numbering), the CH1 domain of H2 of the multispecific antigen-binding protein comprises an S183E substitution mutation (EU numbering), and the CL domain of L2 of the multispecific antigen-binding protein comprises a V133K substitution mutation (EU numbering).

In certain embodiments, the CH1 domain of H1 of the multispecific antigen-binding protein comprises A141I, F170S, S181M, S183A, and V185A mutations (EU numbering), the CL domain of L1 of the multispecific antigen-binding protein comprises F116A, L135V, S174A, S176F, and T178V mutations (EU numbering), the CH1 domain of H2 of the multispecific antigen-binding protein consists of an S183E substitution mutation (EU numbering), and the CL domain of L2 of the multispecific antigen-binding protein consists of a V133K substitution mutation (EU numbering).

In certain embodiments, the CH1 domain of H1 of the multispecific antigen-binding protein consists of A141I, F170S, S181M, S183A, and V185A mutations (EU numbering), the CL domain of L1 of the multispecific antigen-binding protein consists of F116A, L135V, S174A, S176F, and T178V mutations (EU numbering), the CH1 domain of H2 of the multispecific antigen-binding protein consists of an S183E substitution mutation (EU numbering), and the CL domain of L2 of the multispecific antigen-binding protein consists of a V133K substitution mutation (EU numbering).

In certain embodiments, the VH domain of H1 of the multispecific antigen-binding protein comprises a Q39E substitution mutation (Kabat numbering), the VL domain of L the multispecific antigen-binding protein comprises a Q38K substitution mutation (Kabat numbering), the CH1 domain of H1 of the multispecific antigen-binding protein comprises A141I, F170S, S181M, S183A, and V185A mutations (EU numbering), the CL domain of L1 of the multispecific antigen-binding protein comprises F116A, L135V, S174A, S176F, and T178V mutations (EU numbering), the CH1 domain of H2 of the multispecific antigen-binding protein comprises an S183E substitution mutation (EU numbering), and the CL domain of L2 of the multispecific antigen-binding protein comprises a V133K substitution mutation (EU numbering).

In certain embodiments, the VH domain of H1 of the multispecific antigen-binding protein comprises a Q39E substitution mutation (Kabat numbering), the VL domain of L1 the multispecific antigen-binding protein comprises a Q38K substitution mutation (Kabat numbering), the CH1 domain of H1 of the multispecific antigen-binding protein comprises A141I, F170S, S181M, S183A, and V185A mutations (EU numbering), the CL domain of L1 of the multispecific antigen-binding protein comprises F116A, L135V, S174A, S176F, and T178V mutations (EU numbering), the VH domain of H2 the multispecific antigen-binding protein comprises a Q39K substitution mutation (Kabat numbering), the CH1 domain of H2 of the multispecific antigen-binding protein comprises an S183E substitution mutation (EU numbering), the VL domain of L2 of the multispecific antigen-binding protein comprises a Q38E substitution mutation (Kabat numbering), and the CL domain of L2 of the multispecific antigen-binding protein comprises a V133K substitution mutation (EU numbering).

In certain embodiments, the VH domain of H1 of the multispecific antigen-binding protein comprises a Q39E substitution mutation (Kabat numbering), the VL domain of L1 the multispecific antigen-binding protein comprises a Q38K substitution mutation (Kabat numbering), the CH1 domain of H1 of the multispecific antigen-binding protein comprises A141I, F170S, S181M, S183A, and V185A mutations (EU numbering), the CL domain of L1 of the multispecific antigen-binding protein comprises F116A, L135V, S174A, S176F, and T178V mutations (EU numbering), the VH domain of H2 the multispecific antigen-binding protein comprises a Q39K substitution mutation (Kabat numbering), the CH1 domain of H2 of the multispecific antigen-binding protein consists of an S183E substitution mutation (EU numbering), the VL domain of L2 of the multispecific antigen-binding protein comprises a Q38E substitution mutation (Kabat numbering), and the CL domain of L2 of the multispecific antigen-binding protein consists of a V133K substitution mutation (EU numbering).

In certain embodiments, the VH domain of H1 of the multispecific antigen-binding protein comprises a Q39E substitution mutation (Kabat numbering), the VL domain of L1 the multispecific antigen-binding protein comprises a Q38K substitution mutation (Kabat numbering), the CH1 domain of H1 of the multispecific antigen-binding protein consists of A141I, F170S, S181M, S183A, and V185A mutations (EU numbering), the CL domain of L1 of the multispecific antigen-binding protein consists of F116A, L135V, S174A, S176F, and T178V mutations (EU numbering), the VH domain of H2 the multispecific antigen-binding protein comprises a Q39K substitution mutation (Kabat numbering), the CH1 domain of H2 of the multispecific antigen-binding protein consists of an S183E substitution mutation (EU numbering), the VL domain of L2 of the multispecific antigen-binding protein comprises a Q38E substitution mutation (Kabat numbering), and the CL domain of L2 of the multispecific antigen-binding protein consists of a V133K substitution mutation (EU numbering).

In certain embodiments, the VH domain of H1 of the multispecific antigen-binding protein comprises a Q39K substitution mutation (Kabat numbering), the VL domain of L1 the multispecific antigen-binding protein comprises a Q38E substitution mutation (Kabat numbering), the CH1 domain of H1 of the multispecific antigen-binding protein comprises A141I, F170S, S181M, S183A, and V185A mutations (EU numbering), the CL domain of L1 of the multispecific antigen-binding protein comprises F116A, L135V, S174A, S176F, and T178V mutations (EU numbering), the VH domain of H2 the multispecific antigen-binding protein comprises a Q39E substitution mutation (Kabat numbering), the CH1 domain of H2 of the multispecific antigen-binding protein comprises an S183E substitution mutation (EU numbering), the VL domain of L2 of the multispecific antigen-binding protein comprises a Q38K substitution mutation (Kabat numbering), and the CL domain of L2 of the multispecific antigen-binding protein comprises a V133K substitution mutation (EU numbering).

In certain embodiments, the VH domain of H1 of the multispecific antigen-binding protein comprises a Q39K substitution mutation (Kabat numbering), the VL domain of L1 the multispecific antigen-binding protein comprises a Q38E substitution mutation (Kabat numbering), the CH1 domain of H1 of the multispecific antigen-binding protein comprises A141I, F170S, S181M, S183A, and V185A mutations (EU numbering), the CL domain of L1 of the multispecific antigen-binding protein comprises F116A, L135V, S174A, S176F, and T178V mutations (EU numbering), the VH domain of H2 the multispecific antigen-binding protein comprises a Q39E substitution mutation (Kabat numbering), the CH1 domain of H2 of the multispecific antigen-binding protein consists of an S183E substitution mutation (EU numbering), the VL domain of L2 of the multispecific antigen-binding protein comprises a Q38K substitution mutation (Kabat numbering), and the CL domain of L2 of the multispecific antigen-binding protein consists of a V133K substitution mutation (EU numbering).

In certain embodiments, the VH domain of H1 of the multispecific antigen-binding protein comprises a Q39K substitution mutation (Kabat numbering), the VL domain of L1 the multispecific antigen-binding protein comprises a Q38E substitution mutation (Kabat numbering), the CH1 domain of H1 of the multispecific antigen-binding protein consists of A141I, F170S, S181M, S183A, and V185A mutations (EU numbering), the CL domain of L1 of the multispecific antigen-binding protein consists of F116A, L135V, S174A, S176F, and T178V mutations (EU numbering), the VH domain of H2 the multispecific antigen-binding protein comprises a Q39E substitution mutation (Kabat numbering), the CH1 domain of H2 of the multispecific antigen-binding protein consists of an S183E substitution mutation (EU numbering), the VL domain of L2 of the multispecific antigen-binding protein comprises a Q38K substitution mutation (Kabat numbering), and the CL domain of L2 of the multispecific antigen-binding protein consists of a V133K substitution mutation (EU numbering).

In certain embodiments, the CH1 domain of H1 of the multispecific antigen-binding protein comprises A141I, F170S, S181M, S183A, and V185A mutations (EU numbering), the CL domain of L1 of the multispecific antigen-binding protein comprises F116A, L135V, S174A, S176F, and T178V mutations (EU numbering), the CH1 domain of H2 of the multispecific antigen-binding protein comprises an S183K substitution mutation (EU numbering), and the CL domain of L2 of the multispecific antigen-binding protein comprises a V133E substitution mutation (EU numbering).

In certain embodiments, the CH1 domain of H1 of the multispecific antigen-binding protein comprises A141I, F170S, S181M, S183A, and V185A mutations (EU numbering), the CL domain of L1 of the multispecific antigen-binding protein comprises F116A, L135V, S174A, S176F, and T178V mutations (EU numbering), the CH1 domain of H2 of the multispecific antigen-binding protein consists of an S183K substitution mutation (EU numbering), and the CL domain of L2 of the multispecific antigen-binding protein consists of a V133E substitution mutation (EU numbering).

In certain embodiments, the CH1 domain of H1 of the multispecific antigen-binding protein consists of A141I, F170S, S181M, S183A, and V185A mutations (EU numbering), the CL domain of L1 of the multispecific antigen-binding protein consists of F116A, L135V, S174A, S176F, and T178V mutations (EU numbering), the CH1 domain of H2 of the multispecific antigen-binding protein consists of an S183K substitution mutation (EU numbering), and the CL domain of L2 of the multispecific antigen-binding protein consists of a V133E substitution mutation (EU numbering).

In certain embodiments, the VH domain of H1 of the multispecific antigen-binding protein comprises a Q39E substitution mutation (Kabat numbering), the VL domain of L the multispecific antigen-binding protein comprises a Q38K substitution mutation (Kabat numbering), the CH1 domain of H1 of the multispecific antigen-binding protein comprises A141I, F170S, S181M, S183A, and V185A mutations (EU numbering), the CL domain of L of the multispecific antigen-binding protein comprises F116A, L135V, S174A, S176F, and T178V mutations (EU numbering), the VH domain of H2 the multispecific antigen-binding protein comprises a Q39K substitution mutation (Kabat numbering), the CH1 domain of H2 of the multispecific antigen-binding protein comprises an S183K substitution mutation (EU numbering), the VL domain of L2 of the multispecific antigen-binding protein comprises a Q38E substitution mutation (Kabat numbering), and the CL domain of L2 of the multispecific antigen-binding protein comprises a V133E substitution mutation (EU numbering).

In certain embodiments, the VH domain of H1 of the multispecific antigen-binding protein comprises a Q39E substitution mutation (Kabat numbering), the VL domain of L1 the multispecific antigen-binding protein comprises a Q38K substitution mutation (Kabat numbering), the CH1 domain of H1 of the multispecific antigen-binding protein comprises A141I, F170S, S181M, S183A, and V185A mutations (EU numbering), the CL domain of L1 of the multispecific antigen-binding protein comprises F116A, L135V, S174A, S176F, and T178V mutations (EU numbering), the VH domain of H2 the multispecific antigen-binding protein comprises a Q39K substitution mutation (Kabat numbering), the CH1 domain of H2 of the multispecific antigen-binding protein consists of an S183K substitution mutation (EU numbering), the VL domain of L2 of the multispecific antigen-binding protein comprises a Q38E substitution mutation (Kabat numbering), and the CL domain of L2 of the multispecific antigen-binding protein consists of a V133E substitution mutation (EU numbering).

In certain embodiments, the VH domain of H1 of the multispecific antigen-binding protein comprises a Q39E substitution mutation (Kabat numbering), the VL domain of L the multispecific antigen-binding protein comprises a Q38K substitution mutation (Kabat numbering), the CH1 domain of H1 of the multispecific antigen-binding protein consists of A141I, F170S, S181M, S183A, and V185A mutations (EU numbering), the CL domain of L of the multispecific antigen-binding protein consists of F116A, L135V, S174A, S176F, and T178V mutations (EU numbering), the VH domain of H2 the multispecific antigen-binding protein comprises a Q39K substitution mutation (Kabat numbering), the CH1 domain of H2 of the multispecific antigen-binding protein consists of an S183K substitution mutation (EU numbering), the VL domain of L2 of the multispecific antigen-binding protein comprises a Q38E substitution mutation (Kabat numbering), and the CL domain of L2 of the multispecific antigen-binding protein consists of a V133E substitution mutation (EU numbering).

In certain embodiments, the VH domain of H1 of the multispecific antigen-binding protein comprises a Q39K substitution mutation (Kabat numbering), the VL domain of L1 the multispecific antigen-binding protein comprises a Q38E substitution mutation (Kabat numbering), the CH1 domain of H1 of the multispecific antigen-binding protein comprises A141I, F170S, S181M, S183A, and V185A mutations (EU numbering), the CL domain of L1 of the multispecific antigen-binding protein comprises F116A, L135V, S174A, S176F, and T178V mutations (EU numbering), the VH domain of H2 the multispecific antigen-binding protein comprises a Q39E substitution mutation (Kabat numbering), the CH1 domain of H2 of the multispecific antigen-binding protein comprises an S183K substitution mutation (EU numbering), the VL domain of L2 of the multispecific antigen-binding protein comprises a Q38K substitution mutation (Kabat numbering), and the CL domain of L2 of the multispecific antigen-binding protein comprises a V133E substitution mutation (EU numbering).

In certain embodiments, the VH domain of H1 of the multispecific antigen-binding protein comprises a Q39K substitution mutation (Kabat numbering), the VL domain of L1 the multispecific antigen-binding protein comprises a Q38E substitution mutation (Kabat numbering), the CH1 domain of H1 of the multispecific antigen-binding protein comprises A141I, F170S, S181M, S183A, and V185A mutations (EU numbering), the CL domain of L of the multispecific antigen-binding protein comprises F116A, L135V, S174A, S176F, and T178V mutations (EU numbering), the VH domain of H2 the multispecific antigen-binding protein comprises a Q39E substitution mutation (Kabat numbering), the CH1 domain of H2 of the multispecific antigen-binding protein consists of an S183K substitution mutation (EU numbering), the VL domain of L2 of the multispecific antigen-binding protein comprises a Q38K substitution mutation (Kabat numbering), and the CL domain of L2 of the multispecific antigen-binding protein consists of a V133E substitution mutation (EU numbering).

In certain embodiments, the VH domain of H1 of the multispecific antigen-binding protein comprises a Q39K substitution mutation (Kabat numbering), the VL domain of L1 the multispecific antigen-binding protein comprises a Q38E substitution mutation (Kabat numbering), the CH1 domain of H1 of the multispecific antigen-binding protein consists of A141I, F170S, S181M, S183A, and V185A mutations (EU numbering), the CL domain of L1 of the multispecific antigen-binding protein consists of F116A, L135V, S174A, S176F, and T178V mutations (EU numbering), the VH domain of H2 the multispecific antigen-binding protein comprises a Q39E substitution mutation (Kabat numbering), the CH1 domain of H2 of the multispecific antigen-binding protein consists of an S183K substitution mutation (EU numbering), the VL domain of L2 of the multispecific antigen-binding protein comprises a Q38K substitution mutation (Kabat numbering), and the CL domain of L2 of the multispecific antigen-binding protein consists of a V133E substitution mutation (EU numbering).

Additional combinations of mutations in the CH1/CL interface identified by Strategy #2, mutations in the CH1/CL interface identified by Strategy #1, and mutations in the VH and VL domains. i.e., not limited to those described above, are also contemplated.

It will be apparent to those of ordinary skill in the art that the terms "H1" and "H2" are arbitrary designations, and that "H1" and "H2" in any of the embodiments above can be reversed. That is, any of the mutations above described as being in the CH1 domain and/or the VH domain of H1 and CL domain and/or the VL domain of L1 can, alternatively, be in the CH1 domain and/or VH domain of H2 and the CL domain and/or VL domain of L2.

Fc Mutations

In certain embodiments, each of H1 and H2 of the multispecific antigen-binding protein comprises an Fc region comprising a CH2 and a CH3 domain. In certain embodiments, the Fc region of H1 and/or H2 is IgG1, IgG2 or IgG4 Fc. In certain embodiments, the CH3 domains of H1 and H2 each meet at an interface, and each of the CH3 domains comprises an amino acid substitution such that the Fc region of H1 preferentially pairs with that of H2 as compared to H1. In certain embodiments, the amino acid substitutions in the CH3 domains results in greater electrostatic complementarity than wild type without the substitutions in the CH3 domains. Methods of measuring electrostatic complementarity at protein/protein interfaces are known in the art and described in, e.g., McCoy et al. (1997) *J Mol Biol* 268, 570-584; Lee et al., (2001) Protein Sci. 10, 362-377; and Chau et al. (1994) *J Comp Mol Des* 8, 51325 In certain embodiments, the amino acid substitutions in the CH3 domains results in greater steric complementarity than wild type without the substitutions in the CH3 domains. Methods of measuring electrostatic complementarity at protein/protein interfaces are known in the art and described in, e.g., Lawrence et al. (1993) *J Mol Biol* 234, 946-950; Walls et al. (1992) *J Mol Biol* 228, 277-297; and Schueler-Furman et al. (2005) *Proteins* 60, 187-194.

In certain embodiments, the CH3 domains of H1 and H2 (e.g., H1 and H2 of any of the embodiments described herein) are altered, so that within the CH3/CH3 interface, one or more amino acid residues in the CH3 domain of H1 are replaced with one or more amino acid residues having a larger side chain volume, thereby generating a protuberance (or a knob) on the surface of the CH3 domain of H1, and one or more, preferably two or three, amino acid residues in the CH3 domain of H2 that interacts with the CH3 domain of H1 are modified and replaced with amino acid residues having a small side chain volume, thereby generating a cavity (or a hole) on the surface of the CH3 domain of H2 that interacts with the CH3 domain of H1. In certain embodiments, the CH3 domains of H1 and H2 (e.g., H1 and H2 of any of the embodiments described herein) are altered, so that within the interface one or two amino acid residues in the CH3 domain of H2 are replaced with an equivalent number of amino acid residues having a larger side chain volume, thereby generating a protuberance (or a knob) within the interface of the CH3 domain of H2 which is positionable in a cavity (or a hole) within the surface of the CH3 domain of H1 and the CH3 domain of H1 is altered so that within the surface of the CH3 domain of H2 that meets the interface of the CH3 domain of H2 two or three amino acid residues are replaced with an equivalent number of amino acid residues having a smaller side chain volume, thereby generating a cavity within the interface of the CH3 domain of H1 within which a protuberance within the interface of the CH3 domain of H2 is positionable. In certain embodiments, the import residue with a larger side chain volume is phenylalanine (F), tyrosine (Y), arginine (R) or tryptophan (W). In certain embodiments, the protuberance or knob mutation comprises replacement of threonine at position 366 with tryptophan, amino acid numbering according to the EU numbering scheme of Kabat et al. (pp. 688-696 in Sequences of proteins of immunological interest, 5th ed., Vol. 1 (1991; NIH. Bethesda, MD)). In certain embodiments, the import residue with a smaller side chain volume is serine (S), alanine (A), valine (V), or threonine (T). In certain embodiments, the original residue is threonine. In certain embodiments, the original residue is leucine. In certain embodiments, the original residue is tyrosine. In certain embodiments, the import residue is not cysteine (C). In one embodiment, the import residue is alanine (A). A cavity can be generated by replacing one or more original residues of the CH3 domain. For example, in one embodiment, the CH3 domain comprising a cavity comprises replacement of two or more original amino acids selected from the group consisting of threonine, leucine and tyrosine. In certain embodiments, the CH3 domain comprising a cavity comprises two or more import residues selected from the group consisting of alanine, serine, threonine and valine. In certain embodiments, the modification for the knob mutation is T366W, and the modifications for the hole mutation is at least one, or at least two of T366S, L368A, and Y407V. In certain embodiments, the modification for the knob mutation is T366W, and the modifications for the hole mutation is T366S, L368A, and Y407V. See, e.g., U.S. Pat. Nos. 5,731, 168, 5,807,706, 7,183,076, each incorporated herein by reference in its entirety.

Transferability

Although the specific amino acid modifications to CH1 domain of H1 and CL domain of L1 above have been described with respect to the EU numbering system, it is contemplated and that these amino acid modifications are transferable to other immunoglobulin heavy and light chains, resulting in similar patterns of preferential pairing of one immunoglobulin heavy chain with one of the two immunoglobulin light chains in view of the following.

The CH1/CL interface residues in the interface between immunoglobulin heavy and light chains are relatively well conserved (Padlan et al., 1986, Mol. Immunol. 23(9): 951-

960). This sequence conservation, a result of evolutionary constraints, increases the likelihood that functionally active antibody binding domains will be formed during combinatorial pairing of light and heavy chains. As a result of this sequence conservation, it follows that sequence modifications noted above which drive preferential pairing could transfer to other heavy and light chain pairs, as this region displays high sequence conservation across antibodies.

In certain embodiments, the amino acid modifications described herein are transferable to the immunoglobulin heavy and light chains of antibodies based on human or humanized IgG1/κ. In certain embodiments, the amino acid modifications described herein are transferable to the immunoglobulin heavy and light chains of antibodies based on human or humanized IgG2/κ. In certain embodiments, the amino acid modifications described herein are transferable to the immunoglobulin heavy and light chains of antibodies based on human or humanized IgG3/κ. In certain embodiments, the amino acid modifications described herein are transferable to the immunoglobulin heavy and light chains of antibodies based on human or humanized IgG4/κ. In certain embodiments, the amino acid modifications described herein are transferable to the immunoglobulin heavy and light chains of antibodies based on human or humanized IgA1/κ. In certain embodiments, the amino acid modifications described herein are transferable to the immunoglobulin heavy and light chains of antibodies based on human or humanized IgA2/κ. In certain embodiments, the amino acid modifications described herein are transferable to the immunoglobulin heavy and light chains of antibodies based on human or humanized IgD/κ. In certain embodiments, the amino acid modifications described herein are transferable to the immunoglobulin heavy and light chains of antibodies based on human or humanized IgE/κ. In certain embodiments, the amino acid modifications described herein are transferable to the immunoglobulin heavy and light chains of antibodies based on human or humanized IgG/κ. In certain embodiments, the amino acid modifications described herein are transferable to the immunoglobulin heavy and light chains of antibodies based on human or humanized IgM/κ.

In certain embodiments, the amino acid modifications described herein are transferable to the immunoglobulin heavy and light chains of antibodies based on human or humanized IgG1/λ. In certain embodiments, the amino acid modifications described herein are transferable to the immunoglobulin heavy and light chains of antibodies based on human or humanized IgG2/λ. In certain embodiments, the amino acid modifications described herein are transferable to the immunoglobulin heavy and light chains of antibodies based on human or humanized IgG3/λ. In certain embodiments, the amino acid modifications described herein are transferable to the immunoglobulin heavy and light chains of antibodies based on human or humanized IgG4/λ. In certain embodiments, the amino acid modifications described herein are transferable to the immunoglobulin heavy and light chains of antibodies based on human or humanized IgA1/λ. In certain embodiments, the amino acid modifications described herein are transferable to the immunoglobulin heavy and light chains of antibodies based on human or humanized IgA2/λ. In certain embodiments, the amino acid modifications described herein are transferable to the immunoglobulin heavy and light chains of antibodies based on human or humanized IgD/λ. In certain embodiments, the amino acid modifications described herein are transferable to the immunoglobulin heavy and light chains of antibodies based on human or humanized IgE/λ. In certain embodiments, the amino acid modifications described herein are transferable to the immunoglobulin heavy and light chains of antibodies based on human or humanized IgG/λ. In certain embodiments, the amino acid modifications described herein are transferable to the immunoglobulin heavy and light chains of antibodies based on human or humanized IgM/λ. In certain embodiments, the amino acid modifications described herein are transferable to the immunoglobulin heavy and light chains of antibodies having a framework close to germline. In certain embodiments, the amino acid modifications described herein are transferable to the immunoglobulin heavy and light chains of antibodies having canonical CL and CH1 domains.

In certain embodiments, the amino acid modifications described herein are introduced to the immunoglobulin heavy and light chains of mouse antibodies. In certain embodiments, the amino acid modifications described herein are introduced to the immunoglobulin heavy and light chains of antibodies based on mouse IgG2a/λ. In certain embodiments, the amino acid modifications described herein are introduced to the immunoglobulin heavy and light chains of antibodies based on mouse IgG2a/κ.

The amino acid sequence of the mouse IgG2a constant region is set forth in SEQ ID NO: 60 below:

```
                                              (SEQ ID NO: 60)
AKTTAPSVYP LAPVCGDTTG SSVTLGCLVK GYFPEPVTLT

WNSGSLSSGV HTFPAVLQSD LYTLSSSVTV TSSTWPSQSI

TCNVAHPASS TKVDKKIEPR GPTIKPCPPC KCPAPNLLGG

PSVFIFPPKI KDVLMISLSP IVTCVVVDVS EDDPDVQISW

FVNNVEVHTA QTQTHREDYN STLRVVSALP IQHQDWMSGK

EFKCKVNNKD LPAPIERTIS KPKGSVRAPQ VYVLPPPEEE

MTKKQVTLTC MVTDFMPEDI YVEWTNNGKT ELNYKNTEPV

LDSDGSYFMY SKLRVEKKNW VERNSYSCSV VHEGLHNHHT

TKSFSRTPGK
```

The amino acid sequence of the mouse kappa light chain is set forth in SEQ ID NO: 61 below:

```
                                              (SEQ ID NO: 61)
RADAAPTVSI FPPSSEQLTS GGASVVCFLN NFYPKDINVK

WKIDGSERQN GVLNSWTDQD SKDSTYSMSS TLTLTKDEYE

RHNSYTCEAT HKTSTSPIVK SFNRNEC
```

The amino acid sequence of the mouse lambda 1 light chain is set forth in SEQ ID NO: 62 below:

```
                                              (SEQ ID NO: 62)
GQPKSSPSVT LFPPSSEELE TNKATLVCTI TDFYPGVVTV

DWKVDGTPVT QGMETTQPSK QSNNYKMASS YLTLTARAWE

RHSSYSCQVT HEGHTVEKSL SRADCS
```

The amino acid sequence of the mouse lambda 2 light chain is set forth in SEQ ID NO: 63 below:

```
                                    (SEQ ID NO: 63)
GQPKSTPTLT VFPPSSEELK ENKATLVCLI SNFSPSGVTV

AWKANGTPIT QGVDTSNPTK EGNKFMASSF LHLTSDQWRS

HNSFTCQVTH EGDTVEKSLS PAECL
```

The amino acid sequence of the mouse lambda 3 light chain is set forth in SEQ ID NO: 64 below:

```
                                    (SEQ ID NO: 64)
GQPKSTPTLT MFPPSPEELQ ENKATLVCLI SNFSPSGVTV

AWKANGTPIT QGVDTSNPTK EDNKYMASSF LHLTSDQWRS

HNSFTCQVTH EGDTVEKSLS PAECL
```

In certain embodiments, the amino acid modifications that are that are transferable (such as to any of the immunoglobulin heavy and light chains described above) comprise the following combination of substitution mutations: position Q39 (Kabat numbering) on the VH domain of H1; position Q38 on the VL domain of L1; position Q39 (Kabat numbering) on the VH domain of H2; position S183 (EU numbering) on the CH1 domain of H2; position Q38 (Kabat numbering) on the VL domain of L2; and position V133 (EU numbering) on the CL domain of L2.

In certain embodiments, the amino acid modifications that are that are transferable (such as to any of the immunoglobulin heavy and light chains described above) comprise the following combination of substitution mutations: position Q39 (Kabat numbering) on the VH domain of H1; position S183 (EU numbering) on the CH1 domain of H1; position Q38 on the VL domain of L1; position V133 (EU numbering) on the CL domain of L1; position Q39 (Kabat numbering) on the VH domain of H2; position S183 (EU numbering) on the CH1 domain of H2; position Q38 (Kabat numbering) on the VL domain of L2; and position V133 (EU numbering) on the CL domain of L2.

In certain embodiments, the amino acid modifications that are transferable (such as to any of the immunoglobulin heavy and light chains described above) comprise (such as consist or consist essentially of) the following combination of substitution mutations: position Q39E (Kabat numbering) on the VH domain of H1; position Q38K on the VL domain of L1; position Q39K (Kabat numbering) on the VH domain of H2; position S183K (EU numbering) on the CH1 domain of H2; position Q38E (Kabat numbering) on the VL domain of L1; and V133E (EU numbering) on the CL domain of L2.

In certain embodiments, the amino acid modifications that are transferable (such as to any of the immunoglobulin heavy and light chains described above) comprise (such as consist or consist essentially of) the following combination of substitution mutations: position Q39K (Kabat numbering) on the VH domain of H1; position Q38E on the VL domain of L1; position Q39E (Kabat numbering) on the VH domain of H2; position S183K (EU numbering) on the CH1 domain of H2; position Q38K (Kabat numbering) on the VL domain of L1; and V133E (EU numbering) on the CL domain of L2.

In certain embodiments, the amino acid modifications that are transferable (such as to any of the immunoglobulin heavy and light chains described above) comprise (such as consist or consist essentially of) the following combination of substitution mutations: position Q39E (Kabat numbering) on the VH domain of H1; position Q38K on the VL domain of L1; position Q39K (Kabat numbering) on the VH domain of H2; position S183E (EU numbering) on the CH1 domain of H2; position Q38E (Kabat numbering) on the VL domain of L1; and V133K (EU numbering) on the CL domain of L2.

In certain embodiments, the amino acid modifications that are transferable (such as to any of the immunoglobulin heavy and light chains described above) comprise (such as consist or consist essentially of) the following combination of substitution mutations: position Q39K (Kabat numbering) on the VH domain of H1; position Q38E on the VL domain of L1; position Q39E (Kabat numbering) on the VH domain of H2; position S183E (EU numbering) on the CH1 domain of H2; position Q38K (Kabat numbering) on the VL domain of L1; and V133K (EU numbering) on the CL domain of L2.

In certain embodiments, the amino acid modifications that are introduced to different IgG molecules (such as to any of the immunoglobulin heavy and light chains described above) comprise a Q39E substitution mutation (Kabat numbering) in the VH domain of HL a Q38K substitution mutation (Kabat numbering) in the VL domain of L1; A141I, F170S, S181M, S183A, and V185A mutations (EU numbering) in the CH1 domain of H1; F116A, L135V, S174A, S176F, and T178V mutations (EU numbering) in the CL domain of L1; a Q39K substitution mutation (Kabat numbering) in the VH domain of H2; and a Q38E substitution mutation (Kabat numbering) in the VL domain of L2.

In certain embodiments, the amino acid modifications that are introduced to different IgG molecules (such as to any of the immunoglobulin heavy and light chains described above) comprise a Q39E substitution mutation (Kabat numbering) in the VH domain of H1; comprise a Q38K substitution mutation (Kabat numbering) in the VL domain of L1; consist of A141I, F170S, S181M, S183A, and V185A mutations (EU numbering) in the CH1 domain of H1; consist of F116A, L135V, S174A, S176F, and T178V mutations (EU numbering) in the CL domain of L1; comprise a Q39K substitution mutation (Kabat numbering) in the VH domain of H2; and comprise a Q38E substitution mutation (Kabat numbering) in the VL domain of L2.

In certain embodiments, the amino acid modifications that are introduced to different IgG molecules (such as to any of the immunoglobulin heavy and light chains described above) comprise: a Q39K substitution mutation (Kabat numbering) in the VH domain of H1; a Q38E substitution mutation (Kabat numbering) in the VL domain of L1; A141I, F170S, S181M, S183A, and V185A mutations (EU numbering) in the CH1 domain of H1; F116A, L135V, S174A, S176F, and T178V mutations (EU numbering) in the CL domain of L1; a Q39E substitution mutation (Kabat numbering) in the VH domain of H2; and a Q38K substitution mutation (Kabat numbering) in the VL domain of L2.

In certain embodiments, the amino acid modifications that are introduced to different IgG molecules (such as to any of the immunoglobulin heavy and light chains described above) comprise a Q39K substitution mutation (Kabat numbering) in the VH domain of H1; comprise a Q38E substitution mutation (Kabat numbering) in the VL domain of L1; consist of A141I, F170S, S181M, S183A, and V185A mutations (EU numbering) in the CH1 domain of H1; consist of F116A, L135V, S174A, S176F, and T178V mutations (EU numbering) in the CL domain of L1; comprise a Q39E substitution mutation (Kabat numbering) in the VH domain of H2; and comprise a Q38K substitution mutation (Kabat numbering) in the VL domain of L2.

In certain embodiments, the amino acid modifications that are introduced to different IgG molecules (such as to any of the immunoglobulin heavy and light chains described above) comprise: A141I, F170S, S181M, S183A, and V185A mutations (EU numbering) in the CH1 domain of H1; F116A, L135V, S174A, S176F, and T178V mutations (EU numbering) in the CL domain of L1, an S183E substitution mutation (EU numbering) in the CH1 domain of H2; and a V133K substitution mutation (EU numbering) in the CL domain of L2.

In certain embodiments, the amino acid modifications that are introduced to different IgG molecules (such as to any of the immunoglobulin heavy and light chains described above) comprise A141I, F170S, S181M, S183A, and V185A mutations (EU numbering) in the CH1 domain of H1; comprise F116A, L135V, S174A, S176F, and T178V mutations (EU numbering) in the CL domain of L1, consist of an S183E substitution mutation (EU numbering) in the CH1 domain of H2; and consist of a V133K substitution mutation (EU numbering) in the CL domain of L2.

In certain embodiments, the amino acid modifications that are introduced to different IgG molecules (such as to any of the immunoglobulin heavy and light chains described above) consist of A141I, F170S, S181M, S183A, and V185A mutations (EU numbering) in the CH1 domain of H1; F116A, L135V, S174A, S176F, and T178V mutations (EU numbering) in the CL domain of L1, of an S183E substitution mutation (EU numbering) in the CH1 domain of H2; and a V133K substitution mutation (EU numbering) in the CL domain of L2.

In certain embodiments, the amino acid modifications that are introduced to different IgG molecules (such as to any of the immunoglobulin heavy and light chains described above) comprise: a Q39E substitution mutation (Kabat numbering) in the VH domain of H1; a Q38K substitution mutation (Kabat numbering) in the VL domain of L1; A141I, F170S, S181M, S183A, and V185A mutations (EU numbering) in the CH1 of H1; F116A, L135V, S174A, S176F, and T178V mutations (EU numbering) in the CL domain of H1; a Q39K substitution mutation (Kabat numbering) in the VH domain of H2; an S183E substitution mutation (EU numbering) in the CH1 of H2; a Q38E substitution mutation (Kabat numbering) in the VL domain of L2; and a V133K substitution mutation (EU numbering) in the CL domain of L2.

In certain embodiments, the amino acid modifications that are introduced to different IgG molecules (such as to any of the immunoglobulin heavy and light chains described above) comprise a Q39E substitution mutation (Kabat numbering) in the VH domain of H1; comprise a Q38K substitution mutation (Kabat numbering) in the VL domain of L1; comprise A141I, F170S, S181M, S183A, and V185A mutations (EU numbering) in the CH1 of H1; comprise F116A, L135V, S174A, S176F, and T178V mutations (EU numbering) in the CL domain of H1; comprise a Q39K substitution mutation (Kabat numbering) in the VH domain of H2; consist of an S183E substitution mutation (EU numbering) in the CH1 of H2; comprise a Q38E substitution mutation (Kabat numbering) in the VL domain of L2; and consist of a V133K substitution mutation (EU numbering) in the CL domain of L2.

In certain embodiments, the amino acid modifications that are introduced to different IgG molecules (such as to any of the immunoglobulin heavy and light chains described above) comprise a Q39E substitution mutation (Kabat numbering) in the VH domain of H1; comprise a Q38K substitution mutation (Kabat numbering) in the VL domain of L1; consist of A141I, F170S, S181M, S183A, and V185A mutations (EU numbering) in the CH1 of H1; consist of F116A, L135V, S174A, S176F, and T178V mutations (EU numbering) in the CL domain of H1; comprise a Q39K substitution mutation (Kabat numbering) in the VH domain of H2; consist of an S183E substitution mutation (EU numbering) in the CH1 of H2; comprise a Q38E substitution mutation (Kabat numbering) in the VL domain of L2; and consist of a V133K substitution mutation (EU numbering) in the CL domain of L2.

In certain embodiments, the amino acid modifications that are introduced to different IgG molecules (such as to any of the immunoglobulin heavy and light chains described above) comprise a Q39K substitution mutation (Kabat numbering) in the VH domain of H1; a Q38E substitution mutation (Kabat numbering) in the VL domain of L1; A141I, F170S, S181M, S183A, and V185A mutations (EU numbering) in the CH1 domain of H1; F116A, L135V, S174A, S176F, and T178V mutations (EU numbering) in the CL domain of L1; a Q39E substitution mutation (Kabat numbering) in the VH domain of H2: an S183E substitution mutation (EU numbering) in the CH1 domain of H2; a Q38K substitution mutation (Kabat numbering) in the VL domain of L2; and a V133K substitution mutation (EU numbering) in the CL of L2.

In certain embodiments, the amino acid modifications that are introduced to different IgG molecules (such as to any of the immunoglobulin heavy and light chains described above) comprise a Q39K substitution mutation (Kabat numbering) in the VH domain of H1; comprise a Q38E substitution mutation (Kabat numbering) in the VL domain of L1; comprise A141I, F170S, S181M, S183A, and V185A mutations (EU numbering) in the CH1 domain of H1; comprise F116A, L135V, S174A, S176F, and T178V mutations (EU numbering) in the CL domain of L1 comprise a Q39E substitution mutation (Kabat numbering) in the VH domain of H2; consist of an S183E substitution mutation (EU numbering) in the CH1 domain of H2; comprise a Q38K substitution mutation (Kabat numbering) in the VL domain of L2; and consist of a V133K substitution mutation (EU numbering) in the CL of L2.

In certain embodiments, the amino acid modifications that are introduced to different IgG molecules (such as to any of the immunoglobulin heavy and light chains described above) comprise a Q39K substitution mutation (Kabat numbering) in the VH domain of H1; comprise a Q38E substitution mutation (Kabat numbering) in the VL domain of L1; consist of A141I, F170S, S181M, S183A, and V185A mutations (EU numbering) in the CH1 domain of H1; consist of F116A, L135V, S174A, S176F, and T178V mutations (EU numbering) in the CL domain of L1; comprise a Q39E substitution mutation (Kabat numbering) in the VH domain of H2; consist of an S183E substitution mutation (EU numbering) in the CH1 domain of H2; comprise a Q38K substitution mutation (Kabat numbering) in the VL domain of L2; and consist of a V133K substitution mutation (EU numbering) in the CL of L2.

In certain embodiments, the amino acid modifications that are introduced to different IgG molecules (such as to any of the immunoglobulin heavy and light chains described above) comprise A141I, F170S, S181M, S183A, and V185A mutations (EU numbering) in the CH1 domain of H1; F116A, L135V, S174A, S176F, and T178V mutations (EU numbering) in the CL domain of L1, an S183K substitution mutation (EU numbering) in the CH1 domain of H2, and a V133E substitution mutation (EU numbering) in the CL domain of L2.

In certain embodiments, the amino acid modifications that are introduced to different IgG molecules (such as to any of the immunoglobulin heavy and light chains described above) comprise A141I, F170S, S181M, S183A, and V185A mutations (EU numbering) in the CH1 domain of H1; comprise F116A, L135V, S174A, S176F, and T178V mutations (EU numbering) in the CL domain of L1, consist of an S183K substitution mutation (EU numbering) in the CH1 domain of H2, and consist of a V133E substitution mutation (EU numbering) in the CL domain of L2.

In certain embodiments, the amino acid modifications that are introduced to different IgG molecules (such as to any of the immunoglobulin heavy and light chains described above) consist of A141I, F170S, S181M, S183A, and V185A mutations (EU numbering) in the CH1 domain of H1; F116A, L135V, S174A, S176F, and T178V mutations (EU numbering) in the CL domain of L1, consist of an S183K substitution mutation (EU numbering) in the CH1 domain of H2, and consist of a V133E substitution mutation (EU numbering) in the CL domain of L2

In certain embodiments, the amino acid modifications that are introduced to different IgG molecules (such as to any of the immunoglobulin heavy and light chains described above) comprise a Q39E substitution mutation (Kabat numbering) in the VH domain of H1; a Q38K substitution mutation (Kabat numbering) in the VL domain of L1; A141I, F170S, S181M, S183A, and V185A mutations (EU numbering) in the CH1 domain of H1; F116A, L135V, S174A, S176F, and T178V mutations (EU numbering) in the CL domain of L1, a Q39K substitution mutation (Kabat numbering) in the VH domain of H2, an S183K substitution mutation (EU numbering) in the CH1 domain of H2, a Q38E substitution mutation (Kabat numbering) in the VL domain of L2, and a V133E substitution mutation (EU numbering) in the CL domain of L2.

In certain embodiments, the amino acid modifications that are introduced to different IgG molecules (such as to any of the immunoglobulin heavy and light chains described above) comprise a Q39E substitution mutation (Kabat numbering) in the VH domain of H1; comprise a Q38K substitution mutation (Kabat numbering) in the VL domain of L1; comprise A141I, F170S, S181M, S183A, and V185A mutations (EU numbering) in the CH1 domain of H1; comprise F116A, L135V, S174A, S176F, and T178V mutations (EU numbering) in the CL domain of L1; comprise a Q39K substitution mutation (Kabat numbering) in the VH domain of H2; consist of an S183K substitution mutation (EU numbering) in the CH1 domain of H2; comprise a Q38E substitution mutation (Kabat numbering) in the VL domain of L2; and consist of a V133E substitution mutation (EU numbering) in the CL domain of L2.

In certain embodiments, the amino acid modifications that are introduced to different IgG molecules (such as to any of the immunoglobulin heavy and light chains described above) comprise a Q39E substitution mutation (Kabat numbering) in the VH domain of H1; comprise a Q38K substitution mutation (Kabat numbering) in the VL domain of L1; consist of A141I, F170S, S181M, S183A, and V185A mutations (EU numbering) in the CH1 domain of H1; consist of F116A, L135V, S174A, S176F, and T178V mutations (EU numbering) in the CL domain of L1; comprise a Q39K substitution mutation (Kabat numbering) in the VH domain of H2; consist of an S183K substitution mutation (EU numbering) in the CH1 domain of H2; comprise a Q38E substitution mutation (Kabat numbering) in the VL domain of L2; and consist of a V133E substitution mutation (EU numbering) in the CL domain of L2.

In certain embodiments, the amino acid modifications that are introduced to different IgG molecules (such as to any of the immunoglobulin heavy and light chains described above) comprise a Q39K substitution mutation (Kabat numbering) in the VH domain of H1; a Q38E substitution mutation (Kabat numbering) in the VL domain of L1; A141I, F170S, S181M, S183A, and V185A mutations (EU numbering) in the CH1 domain of H1; F116A, L135V, S174A, S176F, and T178V mutations (EU numbering) in the CL domain of L1; a Q39E substitution mutation (Kabat numbering) in the VH domain of H2, an S183K substitution mutation (EU numbering) in the CH1 domain of H2; a Q38K substitution mutation (Kabat numbering) in the VL domain of L2; and a V133E substitution mutation (EU numbering) in the CL domain of L2.

In certain embodiments, the amino acid modifications that are introduced to different IgG molecules (such as to any of the immunoglobulin heavy and light chains described above) comprise a Q39K substitution mutation (Kabat numbering) in the VH domain of H1; comprise a Q38E substitution mutation (Kabat numbering) in the VL domain of L1; comprise A141I, F170S, S181M, S183A, and V185A mutations (EU numbering) in the CH1 domain of H1; comprise F116A, L135V, S174A, S176F, and T178V mutations (EU numbering) in the CL domain of L1 comprise a Q39E substitution mutation (Kabat numbering) in the VH domain of H2, consist of an S183K substitution mutation (EU numbering) in the CH1 domain of H2; comprise a Q38K substitution mutation (Kabat numbering) in the VL domain of L2; and consist of a V133E substitution mutation (EU numbering) in the CL domain of L2.

In certain embodiments, the amino acid modifications that are introduced to different IgG molecules (such as to any of the immunoglobulin heavy and light chains described above) comprise a Q39K substitution mutation (Kabat numbering) in the VH domain of H1; comprise a Q38E substitution mutation (Kabat numbering) in the VL domain of L1; consist of A141I, F170S, S181M, S183A, and V185A mutations (EU numbering) in the CH1 domain of H1; consist of F116A, L135V, S174A, S176F, and T178V mutations (EU numbering) in the CL domain of L1; comprise a Q39E substitution mutation (Kabat numbering) in the VH domain of H2, consist of an S183K substitution mutation (EU numbering) in the CH1 domain of H2; comprise a Q38K substitution mutation (Kabat numbering) in the VL domain of L2; and consist of a V133E substitution mutation (EU numbering) in the CL domain of L2.

In certain embodiments, the amino acid modifications that are introduced to different IgG molecules (such as to any of the immunoglobulin heavy and light chains described above) comprise (such as consist or consist essentially of) the following combination of substitution mutations: L128F, A141M, F170M, S181I and S183A mutations (EU numbering) on the CH1 domain of H1 and F118V, S131T, V133A, L135Y, S162A, T164S, S176M, and T178L mutations (EU numbering) on the CL domain of L1.

In certain embodiments, the amino acid modifications that are introduced to different IgG molecules (such as to any of the immunoglobulin heavy and light chains described above) comprise (such as consist or consist essentially of) the following combination of substitution mutations: L128F, A141M, F170Y, S181I, S183A, and V185A mutations (EU numbering) on the CH1 domain of H1 and F118V, S131T, V133A, L135F, S162A, S176A, and T178L mutations (EU numbering) on the CL domain of L1.

In certain embodiments, the amino acid modifications that are introduced to different IgG molecules (such as to any of the immunoglobulin heavy and light chains described above) comprise (such as consist or consist essentially of) the following combination of substitution mutations: L128F, A141T, F170M, S181T, S183A, and V185L mutations (EU numbering) on the CH1 domain of H1 and F118V, S131T, V133A, L135F, S162A, T164S, S176T, and T178L mutations (EU numbering) on the CL domain of L1.

In certain embodiments, the amino acid modifications that are introduced to different IgG molecules (such as to any of the immunoglobulin heavy and light chains described above) comprise (such as consist or consist essentially of) the following combination of substitution mutations: L128F, A141M, F170M, S181T, and S183A mutations (EU numbering) on the CH1 domain of H1 and F118V, S131T, V133A, L135F, S162M, T164S, S176M, and T178L mutations (EU numbering) on the CL domain of L1.

In certain embodiments, the amino acid modifications that are introduced to different IgG molecules (such as to any of the immunoglobulin heavy and light chains described above) comprise (such as consist or consist essentially of) the following combination of substitution mutations: A141I, F170S, S181M, S183V, and V185A mutations (EU numbering) on the CH1 domain of H1 and F116A, V133I, L135V, S162M, S174A, S176F, and T178V mutations (EU numbering) on the CL domain of L1.

In certain embodiments, the amino acid modifications that are introduced to different IgG molecules (such as to any of the immunoglobulin heavy and light chains described above) comprise (such as consist or consist essentially of) the following combination of substitution mutations: A141I, F170S, S181M, S183A, and V185A mutations (EU numbering) on the CH1 domain of H1 and F116A, S131D, L135V, S162A, S174A, S176F, and T178I mutations (EU numbering) on the CL domain of L1.

In certain embodiments, the amino acid modifications that are introduced to different IgG molecules (such as to any of the immunoglobulin heavy and light chains described above) comprise the following combination of substitution mutations: A141I, F170S, S181M, S183A, and V185A mutations (EU numbering) on the CH1 domain of H1 and F116A, L135V, S174A, S176F, and T178V mutations (EU numbering) on the CL domain of L1.

In certain embodiments, the amino acid modifications that are introduced to different IgG molecules (such as to any of the immunoglobulin heavy and light chains described above) consist of the following combination of substitution mutations: A141I, F170S, S181M, S183A, and V185A mutations (EU numbering) on the CH1 domain of H1 and F116A, L135V, S174A, S176F, and T178V mutations (EU numbering) on the CL domain of L1.

In certain embodiments, the amino acid modifications that are introduced to different IgG molecules (such as to any of the immunoglobulin heavy and light chains described above) comprise (such as consist or consist essentially of) the following combination of substitution mutations: A141I, F170A, S181M, S183V, and V185A mutations (EU numbering) on the CH1 domain of H1 and F116A, L135V, S162M, S174A, S176F, and T178V mutations (EU numbering) on the CL domain of L1.

Additional combinations of mutations in the CH/CL interface identified by Strategy #2, mutations in the CH1/CL interface identified by Strategy #1, and mutations in the VH and VL domains. i.e., not limited to those described above, are also contemplated. Such combinations include, but are not limited to those described below:

It will be apparent to those of ordinary skill in the art that the terms "H1" and "H2" are arbitrary designations, and that "H1" and "H2" in any of the embodiments above can be reversed. That is, any of the mutations above described as being in the CH1 domain and/or the VH domain of H1 and CL domain and/or the VL domain of L1 can, alternatively, be in the CH1 domain and/or VH domain of H2 and the CL domain and/or VL domain of L2.

Properties

Preferential Pairing/Preferential Assembly

"Preferential pairing" describes the pairing pattern of a first polypeptide (such as H1) with a second polypeptide (such as L1) when one or more additional, distinct polypeptides are present at the same time as the pairing occurs between the first and second polypeptide. Preferential pairing occurs between, e.g., H1 and L1 of a multispecific antigen-binding protein provided herein, if the amount of the H1-L1 heavy chain-light chain pairing is greater than the amount of the H1-L2 pairing when H1 is co-expressed with at least L1, and L2. Likewise, preferential pairing occurs between, e.g., H2 and L2 of a multispecific antigen-binding protein provided herein, if the amount of the H2-L2 heavy chain-light chain pairing was greater than the amount of the H2-L1 pairing when H2 is co-expressed with at least L1, and L2. In certain embodiments, the preferential pairing is resulted from amino acid modifications of the VH/VL domains and/or CH1/CL domains.

In certain embodiments, the H1 of a multispecific antigen-binding protein provided herein preferentially pairs with the L1. In certain embodiments, the H2 of a multispecific antigen-binding protein provided herein preferentially pairs with the L2. In certain embodiments, the H1 of a multispecific antigen-binding protein provided herein preferentially pairs with the L1 and the H2 of the multispecific antigen-binding protein herein preferentially pairs with the L2. In certain embodiments, when H1 of a multispecific antigen-binding protein described herein is co-expressed with H2, L1, and L2, the multispecific antigen-binding protein comprising the desired pairings (e.g., H1-L1 and H2-L2) is produced with a relative yield of at least about 30%, at least about 35%, at least about 40%, at least about 45%, at least about 50%, at least about 55%, at least about 60%, at least about 70%, at least about 71%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more than about 99%, including any range in between these values. The relative yield of a multispecific antigen-binding protein comprising the desired pairings (e.g., H1-L1 and H2-L2) can be determined using, e.g., mass spectrometry, as described in the Examples.

In certain embodiments, the expressed polypeptides of a multispecific antigen-binding protein provided herein assemble with improved specificity to reduce generation of mispaired heavy chains and light chains. In certain embodiments, the CH1 domain of H1 of a multispecific antigen-binding protein provided herein assembles with the CL domain of L1 during production.

Methods of Assessing Preferential Pairing/Preferential Assembly

Preferential pairing and/or preferential assembly of the CH1 domain of H1 with the CL domain of L1 of the multispecific antigen-binding protein can be determined using any one of a variety of methods well known to those of ordinary skill in the art. For example, the degree of preferential pairing of the CH1 domain of H1 with the CL domain of L1 in a multispecific antigen-binding protein can be determined via Light Chain Competition Assay (LCCA). International patent application PCT/US2013/063306, filed Oct. 3, 2013, describes various embodiments of LCCA and is herein incorporated by reference in its entirety for all purposes. The method allows quantitative analysis of the pairing of heavy chains with specific light chains within the mixture of co-expressed proteins and can be used to determine if one particular immunoglobulin heavy chain selectively associates with either one of two immunoglobulin light chains when the heavy chain and light chains are co-expressed. The method is briefly described as follows: At least one heavy chain and two different light chains are co-expressed in a cell, in ratios such that the heavy chain is the limiting pairing reactant; optionally separating the secreted proteins from the cell; separating the immunoglobulin light chain polypeptides bound to heavy chain from the rest of the secreted proteins to produce an isolated heavy chain paired fraction; detecting the amount of each different light chain in the isolated heavy chain fraction; and analyzing the relative amount of each different light chain in the isolated heavy chain fraction to determine the ability of the at least one heavy chain to selectively pair with one of the light chains.

In certain embodiments, preferential pairing of the CH1 domain of H1 with the CL domain of L1 of the multispecific antigen-binding protein is determined via mass spectrometry (such as liquid chromatography-mass spectrometry (LC-MS) native mass spectrometry, acidic mass spectrometry, etc.). Mass spectrometry is used to quantify the relative heterodimer populations including each light chain using differences in their molecular weight to identify each distinct species.

In certain embodiments, preferential pairing of the CH1 domain of H1 with the CL domain of L1 of the multispecific antigen-binding protein is determined by assaying the thermal stability of the heavy/light chain pairs of a multispecific antigen-binding protein provided herein. The thermal stability of a heavy/light chain pair in a multispecific antigen-binding protein can be determined according to methods known in the art. The melting temperature of a heavy/light chain pair in a multispecific antigen-binding protein is indicative of its thermal stability. The melting point of the heavy/light chain pair may be measured using techniques such as differential scanning calorimetry (Chen et al (2003) Pharm Res 20:1952-60; Ghirlando et al (1999) Immunol Lett 68:47-52). Alternatively, the thermal stability of the heavy/light chain pair may be measured using circular dichroism (Murray et al. (2002) J. Chromatogr Sci 40:343-9).

In certain embodiments, preferential pairing of the CH1 domain of H1 with the CL domain of L1 of the multispecific antigen-binding protein is determined via binding affinity of the heavy/light chain pairs for their respective targets. The on-rate and off-rate of the interaction can be determined by competitive binding assays according to methods well known in the art. In certain embodiments, the competitive binding assay is a radioimmunoassay comprising the incubation of labeled target (e.g., $^3$H or $^{125}$I) with a multispecific antigen-binding protein provided herein in the presence of increasing amounts of unlabeled target, and the detection of the multispecific antigen-binding protein bound to the labeled target. In certain embodiments, the affinity of the multispecific antigen-binding protein for the target and the binding off-rates can be determined from the saturation data by Scatchard analysis.

In certain embodiments, preferential pairing of the CH1 domain of H1 with the CL domain of L of the multispecific antigen-binding protein is determined by measuring kinetic parameters, such as $K_D$, $k_{off}$, $k_{on}$, $R_{max}$. In certain embodiments, kinetic parameters are determined via surface plasmon resonance (SPR) based assays known in the art (e.g., BIAcore kinetic analysis). For a review of SPR-based technology see Mullet et al., 2000, Methods 22: 77-91; Dong et al., 2002, Review in Mol. Biotech., 82: 303-23; Fivash et al., 1998, Current Opinion in Biotechnology 9: 97-101; Rich et al., 2000, Current Opinion In Biotechnology 11: 54-61. Additionally, any of the SPR instruments and SPR based methods for measuring protein-protein interactions described in U.S. Pat. Nos. 6,373,577; 6,289,286; 5,322,798; 5,341,215; 6,268,125 are contemplated.

In certain embodiments, fluorescence-activated cell sorting (FACS) is used to measure the affinity of a multispecific antigen-binding protein for its target(s), according to methods well known in the art. Other methods of assaying preferential pairing of CH1 domain of H1 with the CL domain of L1 are described in, e.g., WO 2014/081955, WO 2014/082179, and WO 2014/150973, which are herein incorporated by reference in their entireties for all purposes.

Stability

In certain embodiments, the one or more amino acid substitution(s) present on the CH1 domain of H1 and the one or more amino acid substitution mutation(s) present on the CL of L1 do not decrease the stability of a multispecific antigen-binding protein provided herein. In certain embodiments, the one or more amino acid substitution(s) present on the CH1 domain of H1, the one or more amino acid substitution mutation(s) present on the CL of L1, the amino acid substitution mutation at position Q39 (Kabat numbering) on the VH of H1, and the amino acid substitution mutation at position Q38 (Kabat numbering) of the VL of L1 do not decrease the stability of a multispecific antigen-binding protein provided herein. In certain embodiments, the one or more amino acid substitution(s) present on the CH1 domain of H1, the one or more amino acid substitution mutation(s) present on the CL of L1, the amino acid substitution mutation at position Q39 (Kabat numbering) on the VH of H1, the amino acid substitution mutation at position Q38 (Kabat numbering) of the VL of L1, the amino acid substitution mutation at position Q39 (Kabat numbering) on the VH of H2, and the amino acid substitution mutation at position Q38 (Kabat numbering) of the VL of L2, do not decrease the stability of a multispecific antigen-binding protein provided herein.

In certain embodiments, the stability of a multispecific antigen-binding protein provided herein is at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more than about 99% of the stability of a multispecific antigen-binding protein without the amino acid substitution mutations.

The stability of a multispecific antigen-binding protein can be determined using any one of a variety of techniques for assessing protein stability known to those of ordinary skill in the art. For example, circular dichroism (CD) is a spectroscopic technique widely that measures the absorption of circularly polarized light. As structures such as alpha helices and beta sheets are chiral, the absorption of circularly polarized light acts as a marker of the degree of foldedness of the protein ensemble. This technique has been used to measure equilibrium unfolding of the protein by measuring the change in this absorption as a function of temperature. The temperature at the transition midpoint, where the concentration of native and denatured states is 1, is known as the melting temperature (Tm) of a protein. Further details regarding CD are described in, e.g., Kelly et al. (2000) *Curr Prot and Peptide Sci* 1, 349-384; Correa et al. (2009) *African J Biochem Res* 3, 164-173; and Greenfield (2006) *Nat Protoc.* 1, 2527-2535.

In certain embodiments, a multispecific antigen-binding protein described herein (e.g., comprising the CH1/CL modifications and/or VH/VL modifications described herein) has a melting temperature that is no more than about 10° C., no more than about 9.5° C., no more than about 9° C. no more than about 8.5° C., no more than about 8° C., no more than about 7.5° C., no more than about 7.0° C., no more than about 6.5° C. no more than about 6.0° C., no more than about 5.5° C., no more than about 5.0° C., no more than about 4.5° C., no more than about 4° C., no more than about 3.5° C., no more than about 3° C., no more than about 2.5° C. no more than about 2° C. no more than about 1.5° C., no more than about 1° C., no more than about 0.5° C., or less than about 0.5° C. lower than the Tm of a wild type multispecific antigen binding protein that comprises no amino acid substitution mutations in the CH1/CL and/or VH/VL domains. In certain embodiments, a Fab of the multispecific antigen-binding protein described herein (e.g., comprising the CH1/CL modifications and/or VH/VL modifications described herein) has a melting temperature that is no more than about 10° C., no more than about 9.5° C., no more than about 9° C., no more than about 8.5° C., no more than about 8° C., no more than about 7.5° C., no more than about 7.0° C. no more than about 6.5° C., no more than about 6.0° C., no more than about 5.5° C. no more than about 5.0° C., no more than about 4.5° C., no more than about 4° C., no more than about 3.5° C., no more than about 3° C., no more than about 2.5° C. no more than about 2° C., no more than about 1.5° C., no more than about 1° C., no more than about 0.5° C., or less than about 0.5° C. lower than the Tm of a Fab of a wild type parent antibody of the multispecific antigen binding protein that comprises no amino acid substitution mutations in the CH1/CL and/or VH/VL domains.

Alternatively, the stability of a multispecific antigen-binding protein can be determined using, e.g., differential scanning calorimetry (DSC), which measures the thermodynamic parameters that control non-covalent bond formation in proteins. Further details regarding DSC are described in, e.g., Ionescu et al. (2008) *J Pharm Sci* 97, 1414-1426. The stability of a multispecific antigen-binding protein can also be determined using, e.g., differential scanning fluorimetry (DSF or thermal shift assay), which measures the thermal stability of a target protein and the change in protein melting temperature upon the binding of the protein to, e.g., a ligand or a second protein. Further details regarding DSF are described in, e.g., Niesen, et al. (2007) *Nat Protoc* 2, 2212-2221.

Binding Affinity

In certain embodiments, the one or more amino acid substitution(s) present on the CH1 domain of H1 and the one or more amino acid substitution mutation(s) present on the CL of L1 do not decrease the binding affinity of a multispecific antigen-binding protein provided herein to an antigen. In certain embodiments, the one or more amino acid substitution(s) present on the CH1 domain of H1, the one or more amino acid substitution mutation(s) present on the CL of L1, the amino acid substitution mutation at position Q39 (Kabat numbering) on the VH of H1, and the amino acid substitution mutation at position Q38 (Kabat numbering) of the VL of L1 do not decrease the binding affinity of a multispecific antigen-binding protein provided herein to an antigen. In certain embodiments, the one or more amino acid substitution(s) present on the CH1 domain of H1, the one or more amino acid substitution mutation(s) present on the CL of L1, the amino acid substitution mutation at position Q39 (Kabat numbering) on the VH of H1, the amino acid substitution mutation at position Q38 (Kabat numbering) of the VL of L1, the amino acid substitution mutation at position Q39 (Kabat numbering) on the VH of H2, and the amino acid substitution mutation at position Q38 (Kabat numbering) of the VL of L2, do not decrease the binding affinity of a multispecific antigen-binding protein provided herein to an antigen.

Methods of Measuring Binding Affinity

As noted elsewhere herein, antigen binding of a multispecific antigen binding protein provided herein can be assessed by measuring any one of a variety of binding kinetic parameters, including Kd, $k_{on}$, and/or $k_{off}$. Kd can be measured by using surface plasmon resonance assays using a BIAcorer™-T100 or a BIAcore™-T200 (GE Healthcare, Piscataway, NJ) at 25° C. with immobilized target (e.g., antigen) CM5 chips at 100 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 µg/ml (~0.2 µM) before injection at a flow rate of 5 µl/minute to achieve approximately 100 response units (RU) of coupled protein. Following the injection of antigen, 1M ethanolamine is injected to block unreacted groups. For kinetics measurements, two-fold serial dilutions of Fab (e.g., 0.78 nM to 500 nM) are injected in PBS with 0.05% Tween 20 (PBST) at 25° C. at a flow rate of approximately 25 µl/min. Association rates ($k_{on}$) and dissociation rates ($k_{off}$) are calculated using a simple one-to-one Langmuir binding model (BIAcore Evaluation Software) by simultaneous fitting the association and dissociation sensorgram. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

In certain embodiments, the Kd of a multispecific antigen binding protein provided herein is at least no less than about 10%, about 15%, about 20%, about 25%, about 30%, about 35%, about 40%, about 45%, about 50%, or more than about 50% of the Kd of a wild type binding protein comprising no mutations at the CH1/CL interface.

Immunogenicity

In certain embodiments, a multispecific antigen-binding protein provided herein is non-immunogenic or substantially non-immunogenic in a human. In certain embodiments, the modification (such as one or more amino acid substitutions) of the CH1 region is non-immunogenic or substantially non-immunogenic in a human. In certain embodiments, the modification (such as one or more amino acid substitutions) of the CL region is non-immunogenic or substantially non-immunogenic in a human. In certain embodiments, the modification (such as one or more amino acid substitutions) of the CH1 region does not result in a human T-cell epitope. In certain embodiments, the modification (such as one or more amino acid substitutions) of the CL region does not result in a human T-cell epitope. The immunogenicity a multispecific antigen-binding protein provided herein can be evaluated using methods well known to those of ordinary skill in the art. In certain embodiments, the immunogenicity a multispecific antigen-binding protein provided herein is assessed via ELISA (see, e.g., Yin et al. (2015) Cell Immunol. 295, 118-126). See also, e.g., Hartmann et al. (2001) Clin Cancer Res. 7, 1873-1881.

Pharmacokinetic Properties

In certain embodiments, the one or more amino acid substitution(s) present on the CH1 domain of H1 and the one or more amino acid substitution mutation(s) present on the CL of L1 do not significantly affect the pharmacokinetic properties of a multispecific antigen-binding protein provided herein, as compared to a multispecific antigen-binding protein that does not comprise such amino acid substitutions. In certain embodiments, the one or more amino acid substitution(s) present on the CH1 domain of H1, the one or more amino acid substitution mutation(s) present on the CL of L1, the amino acid substitution mutation at position Q39 (Kabat numbering) on the VH of H1, and the amino acid substitution mutation at position Q38 (Kabat numbering) of the VL of L1 do not significantly affect the pharmacokinetic properties of a multispecific antigen-binding protein provided herein, as compared to a multispecific antigen-binding protein that does not comprise such amino acid substitutions. In certain embodiments, the one or more amino acid substitution(s) present on the CH1 domain of H1, the one or more amino acid substitution mutation(s) present on the CL of L1, the amino acid substitution mutation at position Q39 (Kabat numbering) on the VH of H1, the amino acid substitution mutation at position Q38 (Kabat numbering) of the VL of L1, the amino acid substitution mutation at position Q39 (Kabat numbering) on the VH of H2, and the amino acid substitution mutation at position Q38 (Kabat numbering) of the VL of L2, do not significantly affect the pharmacokinetic properties of a multispecific antigen-binding protein provided herein, as compared to a multispecific antigen-binding protein that does not comprise such amino acid substitutions. Such pharmacokinetic properties include, e.g., Cmax, AUC, CL (i.e., drug clearance), $t_{1/2, \square}$, $V_1$, and $V_{ss}$. In certain embodiments, Cmax of a multispecific antigen-binding protein provided herein is about any one of 50%, 60%, 70%, 80%, 90%, 100%, 110%, 120%, 130%, 140%, 150%, or 160% (including any range in between these values) of a multispecific antigen-binding protein that does not comprise amino acid substitutions in the CH1 of H1, the VH of H1, the CL of L1, the VL of L1, the CH1 of H2, the VH of H2, the CL of L2, and/or the VL of L2. In certain embodiments, AUC of a multispecific antigen-binding protein provided herein is about any one of 50%, 60%, 70%, 80%, 90%, 100%, 110%, 120%, 130%, 140%, 150%, or 160% (including any range in between these values) of a multispecific antigen-binding protein that does not comprise amino acid substitutions in the CH1 of H1, the VH of H1, the CL of L1, the VL of L1, the CH1 of H2, the VH of H2, the CL of L2, and/or the VL of L2. In certain embodiments, CL (i.e., drug clearance) of a multispecific antigen-binding protein provided herein is about any one of 50%, 60%, 70%, 80%, 90%, 100%, 110%, 120%, 130%, 140%, 150%, or 160% (including any range in between these values) of a multispecific antigen-binding protein that does not comprise amino acid substitutions in the CH1 of H1, the VH of H1, the CL of L1, the VL of L1, the CH1 of H2, the VH of H2, the CL of L2, and/or the VL of L2. In certain embodiments, $t_{1/2, \square}$ of a multispecific antigen-binding protein provided herein is about any one of 50%, 60%, 70%, 80%, 90%, 100%, 110%, 120%, 130%, 140%, 150%, or 160% (including any range in between these values) of a multispecific antigen-binding protein that does not comprise amino acid substitutions in the CH1 of H1, the VH of H1, the CL of L1, the VL of L1, the CH1 of H2, the VH of H2, the CL of L2, and/or the VL of L2. In certain embodiments, the $V_1$ of a multispecific antigen-binding protein provided herein is about any one of 50%, 60%, 70%, 80%, 90%, 100%, 110%, 120%, 130%, 140%, 150%, or 160% (including any range in between these values) of a multispecific antigen-binding protein that does not comprise amino acid substitutions in the CH1 of H1, the VH of H1, the CL of L1, the VL of L1, the CH1 of H2, the VH of H2, the CL of L2, and/or the VL of L2. In certain embodiments, the $V_{ss}$ of a multispecific antigen-binding protein provided herein is about any one of 50%, 60%, 70%, 80%, 90%, 100%, 110%, 120%, 130%, 140%, 150%, or 160% (including any range in between these values) of a multispecific antigen-binding protein that does not comprise amino acid substitutions in the CH1 of H1, the VH of H1, the CL of L1, the VL of L1, the CH1 of H2, the VH of H2, the CL of L2, and/or the VL of L2.

Multispecific Antibody Formats

The multispecific antigen-binding proteins provided herein can be used with any one of a variety of bispecific or multispecific antibody formats known in the art. Numerous formats have been developed in the art to address therapeutic opportunities afforded by molecules with multiple binding specificities. Several approaches have been described to prepare bi-specific antibodies in which specific antibody light chains or fragment pair with specific antibody heavy chains or fragments.

For example, International Patent Application No. PCT/EP2011/056388 (WO 2011/131746) describes an in vitro method for generating a heterodimeric protein in which asymmetrical mutations are introduced into the CH3 regions of two monospecific starting proteins in order to drive directional "Fab-arm" or "half-molecule" exchange between two monospecific IgG4 or IgG4-like antibodies upon incubation under reducing conditions.

Schaefer et al. (Roche Diagnostics GmbH), describe a method to assemble two heavy and two light chains, derived from two existing antibodies, into human bivalent bispecific IgG antibodies without use of artificial linkers (PNAS (2011) 108(27): 11187-11192 and US 2009/0232811). The method involves exchanging one or more heavy chain and light chain domains within the antigen-binding fragment (Fab) of one half of the bi-specific antibody (CrossMab). Based on the knobs-into-holes technology that enables heterodimerization of the heavy chains, correct association of the light chains and their cognate heavy chains is achieved by exchange of heavy-chain and light-chain domains within the antigen binding fragment (Fab) of one half of the bispecific antibody. This "crossover" retains the antigen-binding affinity but makes the two arms so different that light-chain mispairing can no longer occur. See WO2009/080251, WO2009/080252, WO2009/080253, and WO2009/080254, each incorporated herein by reference in its entirety.

Knobs-into-holes is a heterodimerization technology for the CH3 domain of an antibody. Previously, knobs-into-holes technology has been applied to the production of human full-length bispecific antibodies with a single common light chain (LC) (Merchant et al. "An efficient route to human bispecific IgG." Nat Biotechnol. 1998; 16:677-81; Jackman et al. "Development of a two-part strategy to identify a therapeutic human bispecific antibody that inhibits IgE receptor signaling." J Biol Chem. 2010:285:20850-9.) See also WO1996027011, which is herein incorporated by reference in its entirety for all purposes.

Strop et al. (Rinat-Pfizer Inc.), describe a method of producing stable bi-specific antibodies by expressing and purifying two antibodies of interest separately, and then mixing them together under specified redox conditions (J. Mol. Biol. (2012) 420:204-19).

Other heterodimerization domain having a strong preference for forming heterodimers over homodimers can be incorporated into the instant multispecific antigen-binding proteins. Illustrative examples include but are not limited to, for example, WO2007147901 (Kjærgaard et al.—Novo Nordisk: describing ionic interactions); WO 2009089004 (Kannan et al.—Amgen: describing electrostatic steering effects): WO 2010/034605 (Christensen et al.—Genentech; describing coiled coils). See also, for example, Pack, P. & Plueckthun, A., Biochemistry 31, 1579-1584 (1992) describing leucine zipper or Pack et al., Bio/Technology 11, 1271-1277 (1993) describing the helix-turn-helix motif. The phrase "heteromultimerization domain" and "heterodimerization domain" are used interchangeably herein. In certain embodiments, the multispecific antigen-binding protein comprises one or more heterodimerization domains.

Zhu et al. (Genentech) have engineered mutations in the VL/VH interface of a diabody construct consisting of variant domain antibody fragments completely devoid of constant domains, and generated a heterodimeric diabody (Protein Science (1997) 6:781-788). Similarly, Igawa et al. (Chugai) have also engineered mutations in the VL/VH interface of a single-chain diabody to promote selective expression and inhibit conformational isomerization of the diabody (Protein Engineering, Design & Selection (2010) 23:667-677).

US Patent Publication No. 2009/0182127 (Novo Nordisk, Inc.) describes the generation of bi-specific antibodies by modifying amino acid residues at the Fc interface and at the CH1:CL interface of light-heavy chain pairs that reduce the ability of the light chain of one pair to interact with the heavy chain of the other pair.

Another format, used for Bispecific T cell Engager (BiTE) molecules (see, e.g., Wolf et al. (2005) Drug Discovery Today 10:1237-1244)), is based on single chain variable fragment (scFv) modules. An scFv consists of an antibody's light and heavy chain variable regions fused via a flexible linker, which generally can fold appropriately and so that the regions can bind the cognate antigen. A BiTE concatenates two scFv's of different specificities in tandem on a single chain. This configuration precludes the production of molecules with two copies of the same heavy chain variable region. In addition, the linker configuration is designed to ensure correct pairing of the respective light and heavy chains.

Reviews of various bispecific and multispecific antibody formats are provided in Klein et al., (2012) mAbs 4:6, 653-663 and Spiess et al. (2015) "Alternative molecular formats and therapeutic applications for bispecific antibodies." Mol. Immunol. Published online Jan. 27, 2015; doi: 10.1016/j.molimm.2015.01.003.

The multispecific antigen-binding proteins described herein can be incorporated into any one of the formats described above. In certain embodiments, the CH1/CL and VH/VL mutations described herein can be combined with the CrossMab technology to further ensure correct heavy/light chain pairing.

Polynucleotides, Vectors, and Host Cells

Polynucleotides

Provided herein are nucleic acids encoding heavy and/or light chain constant and/or variable domains described herein. In certain embodiments, an isolated nucleic acid provided herein encodes at least one polypeptide sequence of a multispecific antigen-binding protein described herein. In certain embodiments, an isolated nucleic acid provided herein encodes at least two polypeptide sequences of a multispecific antigen-binding protein described herein. In certain embodiments, an isolated nucleic acid provided herein encodes at least three polypeptide sequences of a multispecific antigen-binding protein described herein. In certain embodiments, an isolated nucleic acid provided herein encodes at least four polypeptide sequences of a multispecific antigen-binding protein described herein. In certain embodiments, an isolated nucleic acid provided herein encodes more than four polypeptide sequences of a multispecific antigen-binding protein described herein.

Nucleic acid molecules provided herein include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The nucleic acid molecules provide herein include full-length genes or cDNA molecules as well as a combination of fragments thereof. In certain embodiments, the nucleic acids provided herein are derived from human sources. In certain embodiments, the nucleic acids provided herein are derived from mouse sources.

As noted elsewhere herein, an "isolated" nucleic acid is a nucleic acid that has been separated from adjacent genetic sequences present in the genome of the organism from which the nucleic acid was isolated, in the case of nucleic acids isolated from naturally-occurring sources. In the case of nucleic acids synthesized enzymatically from a template or chemically, such as PCR products, cDNA molecules, or oligonucleotides for example, it is understood that the nucleic acids resulting from such processes are isolated nucleic acids. An isolated nucleic acid molecule refers to a nucleic acid molecule in the form of a separate fragment or as a component of a larger nucleic acid construct.

In certain embodiments, the nucleic acids are substantially free from contaminating endogenous material. The nucleic acid molecule has preferably been derived from DNA or RNA isolated at least once in substantially pure form and in a quantity or concentration enabling identification, manipulation, and recovery of its component nucleotide sequences by standard biochemical methods (such as those outlined in Sambrook et al., Molecular Cloning: A Laboratory Manual, 2nd ed., Cold Spring Harbor Laboratory. Cold Spring Harbor, NY (1989)). Such sequences are preferably provided and/or constructed in the form of an open reading frame uninterrupted by internal non-translated sequences, or intrans, that are typically present in eukaryotic genes. Sequences of nontranslated DNA can be present 5' or 3' from an open reading frame, where the same do not interfere with manipulation or expression of the coding region.

Nucleic acid variants are ordinarily prepared by site specific mutagenesis of nucleotides in the DNA encoding the polypeptide, using cassette or PCR mutagenesis or other techniques well known in the art, to produce DNA encoding the variant, and thereafter expressing the recombinant DNA in cell culture as outlined herein. However, antibodies or antigen-binding fragments thereof comprising variant CDRs having up to about 100-150 residues may be prepared by in vitro synthesis using established techniques. The variants typically exhibit the same qualitative biological activity as the naturally occurring analogue, e.g., binding to antigen, although variants can also be selected which have modified characteristics.

As will be appreciated by those in the art, due to the degeneracy of the genetic code, an extremely large number of nucleic acids may be made, all of which encode the CDRs and heavy and light chains or other components of a multimeric antigen-binding protein described herein. Thus, having identified a particular amino acid sequence, those skilled in the art could make any number of different nucleic acids, by simply modifying the sequence of one or more codons in a way which does not change the amino acid sequence of the encoded multimeric antigen-binding protein.

Vectors

Provided are expression systems and constructs in the form of plasmids, expression vectors, transcription or expression cassettes which comprise at least one polynucleotide described herein. In certain embodiments, a plasmid, expression vector, transcription or expression cassette provided herein comprises a polynucleotide encoding at least one polypeptide (e.g., a first heavy chain, a first light chain, a second heavy chain, or a second light chain) of a multispecific antigen-binding protein provided herein. In certain embodiments, a plasmid, expression vector, transcription or expression cassette provided herein comprises a polynucleotide encoding at least two polypeptides (e.g., a first heavy chain and a first light chain, or a second heavy chain and a second light chain) of a multispecific antigen-binding protein provided herein. In certain embodiments, a plasmid, expression vector, transcription or expression cassette provided herein comprises a polynucleotide encoding at least four polypeptides (e.g., a first heavy chain, a first light chain, a second heavy chain, and a second light chain) of a multispecific antigen-binding protein provided herein.

Typically, expression vectors used in the host cells will contain sequences for plasmid maintenance and for cloning and expression of exogenous nucleotide sequences. Such sequences, collectively referred to as "flanking sequences," in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule typically located at the 5' or 3' end of the polypeptide coding sequence; the oligonucleotide sequence encodes polyHis (such as hexaHis (SEQ ID NO: 66)), or another "tag" such as FLAG, HA (hemaglutinin influenza virus), or myc, for which commercially available antibodies exist. This tag is typically fused to the polypeptide upon expression of the polypeptide, and can serve as a means for affinity purification or detection of the polypeptide from the host cell. Affinity purification can be accomplished, for example, by column chromatography using antibodies against the tag as an affinity matrix. Optionally, the tag can subsequently be removed from the purified polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors provided herein may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, CA), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, MA) is suitable for most gram-negative bacteria, and various viral origins (e.g., SV40, polyoma, adenovirus, vesicular stomatitis virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antibody light or heavy chain. As a result, increased quantities of a polypeptide are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed. In certain embodiments, one or more coding regions may be operably linked to an internal ribosome binding site (IRES), allowing translation of two open reading frames from a single RNA transcript.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors provided herein will typically contain a promoter that is recognized by the host organism and operably linked to the molecule encoding the polypeptide. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe gene to which they are operably linked, that is, with little or no control over gene expression. A large number of promoters, recognized by a variety of potential host cells, are well known. A suitable promoter is operably linked to the DNA encoding e.g., heavy chain or light chain, by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981. Nature 290:304-310); CMV promoter (Thomsen et al., 1984, Proc. Natl. Acad. U.S.A. 81:659-663); the promoter contained in the 3' long terminal repeat of Rous sarcoma virus (Yamamoto et al., 1980. Cell 22:787-797); herpes thymidine kinase promoter (Wagner et al., 1981, Proc. Natl. Acad. Sci. U.S.A. 78:1444-1445); promoter and regulatory sequences from the metallothionein gene Prinster et al., 1982, Nature 296:39-42); and prokaryotic promoters such as the beta-lactamase promoter (Villa-Kamaroff et al., 1978, Proc. Natl. Acad. Sci. U.S.A. 75:3727-3731); or the tac promoter (DeBoer et al., 1983, Proc. Natl. Acad. Sci. U.S.A. 80:21-25). Also of interest are the following animal transcriptional control regions, which exhibit tissue specificity and have been utilized in transgenic animals: the elastase I gene control region that is active in pancreatic acinar cells (Swift et al., 1984, Cell 38:639-646; Omitz et al., 1986, Cold Spring Harbor Symp. Quant. Biol. 50:399409; MacDonald, 1987, Hepatology 7:425-515); the insulin gene control region that is active in pancreatic beta cells (Hanahan, 1985, Nature 315: 115-122); the immunoglobulin gene control region that is active in lymphoid cells (Grosschedl et al., 1984, Cell 38:647-658; Adames et al., 1985, Nature 318:533-538; Alexander et al., 1987, Mol. Cell. Biol. 7:1436-1444); the mouse mammary tumor virus control region that is active in testicular, breast, lymphoid and mast cells (Leder et al., 1986, Cell 45:485-495); the albumin gene control region that is active in liver (Pinkert et al., 1987, Genes and Devel. 1:268-276); the alpha-feta-protein gene control region that is active in liver (Krumlauf et al., 1985, Mol. Cell. Biol. 5:1639-1648; Hammer et al., 1987, Science 253:53-58); the alpha 1-antitrypsin gene control region that is active in liver (Kelsev et al., 1987. Genes and Devel. 1: 161-171): the beta-globin gene control region that is active in myeloid cells (Mogram et al., 1985, Nature 315:338-340: Kollias et al., 1986, Cell 46:89-94); the myelin basic protein gene control region that is active in oligodendrocyte cells in the brain (Readhead et al., 1987. Cell 48:703-712); the myosin light chain-2 gene control region that is active in skeletal muscle (Sani, 1985, Nature 314:283-286); and the gonadotropic releasing hormone gene control region that is active in the hypothalamus (Mason et al., 1986, Science 234: 1372-1378).

An enhancer sequence may be inserted into the vector to increase transcription of DNA encoding a light chain or a heavy chain provided herein by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alphafeto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the multispecific antigen-binding protein. The choice of signal peptide or leader depends on the type of host cells in which the multispecific antigen-binding protein is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, Nature 312:768; the interleukin-4 receptor signal peptide described in EP Patent No. 0367 566; the type I interleukin-I receptor signal peptide described in U.S. Pat. No. 4,968,607; the type II interleukin-I receptor signal peptide described in EP Patent No. 0 460 846.

The vector may contain one or more elements that facilitate expression when the vector is integrated into the host cell genome. Examples include an EASE element (Aldrich et al. 2003 Biotechnol Prog. 19: 1433-38) and a matrix attachment region (MAR). MARs mediate structural organization of the chromatin and may insulate the integrated vector from "position" effect. Thus. MARs are particularly useful when the vector is used to create stable transfectants. A number of natural and synthetic MAR-containing nucleic acids are known in the art, e.g., U.S. Pat. Nos. 6,239,328; 7,326,567; 6,177,612; 6,388,066; 6,245,974; 7,259,010; 6,037,525; 7,422,874; 7,129,062.

Expression vectors provided herein may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding a light chain, a heavy chain, or a light chain and a heavy chain sequence has been inserted into the proper site of the vector, the completed vector may be inserted into a suitable host cell for amplification and/or polypeptide expression. The transformation of an expression vector into a selected host cell may be accomplished by well-known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra. In certain embodiments, one or more vectors capable of expressing a first heavy chain, a first light chain, a second heavy chain and a first light chain are introduced into a host cell.

Host Cells

In addition, provided are host cells comprising the expression systems or constructs described above. In certain embodiments, the multispecific antigen-binding protein is expressed from a single host cell. A host cell, when cultured under appropriate conditions, synthesizes multispecific antigen-binding protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule. A host cell may be eukaryotic or prokaryotic.

Mammalian cell lines available as hosts for expression are well known in the art and include, but are not limited to, immortalized cell lines available from the American Type Culture Collection (ATCC) and any cell lines used in an expression system known in the art can be used to make the recombinant polypeptides provided herein. In general, host cells are transformed with a recombinant expression vector that comprises DNA encoding a desired multispecific antigen-binding protein. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, or their derivatives such as Veggie CHO and related cell lines which grow in serum-free media (Rasmussen et al., 1998, Cytotechnology 28: 31), HeLa cells, BHK (ATCC CRL10) cell lines, and the CVI/EBNA cell line derived from the African green monkey kidney cell line CVI (ATCC CCL 70) as described by McMahan et al., 1991, EMBO J. 10: 2821, human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Optionally, mammalian cell lines such as HepG2/3B, KB, NIH 3T3 or S49, for example, can be used for expression of the polypeptide when it is desirable to use the polypeptide in various signal transduction or reporter assays. Alternatively, it is possible to produce the polypeptide in lower eukaryotes such as yeast or in prokaryotes such as bacteria. Suitable yeasts include *Saccharomyces cerevisiae, Schizosaccharomyces pombe, Kluyveromyces* strains, *Candida* strains, *Pichia* strains, or any yeast strain capable of expressing heterologous polypeptides. Suitable bacterial strains include *Escherichia coli, Bacillus subtilis, Salmonella typhimurium*, or any bacterial strain capable of expressing heterologous polypeptides.

In certain embodiments, provided is a cell line expressing a multispecific antigen-binding protein described herein. In certain embodiments, the cell line is a prokaryotic cell line. In certain embodiments, the cell line is an *E. coli* cell line. In certain embodiments, HC1, LC1, HC2, and LC2 are coexpressed in the same prokaryotic cell. In certain embodiments, HC1, LC1, HC2, and LC2 are coexpressed m the same *E. coli* cell. In certain embodiments, HC1, LC1, HC2, and LC2 are coexpressed in the same eukaryotic cell. In certain embodiments, the cell line is an eukaryotic cell line. In certain embodiments, the cell line is a stable cell line. In certain embodiments, the stable cell line is a mammalian cell line. In certain embodiments, the stable cell line is a CHO cell line. In certain embodiments, at least about 85%, about 86%, about 87%, about 88%, about 89%, about 90%, about 91%, about 92% about 93%, about 94%, about 95%, about 96%, about 97%, about 98%, about 99%, or more than about 99% of the multispecific antigen-binding protein expressed by the stable cell line is correctly assembled (i.e., wherein LC1 is paired with HC1, and wherein LC2 is paired with HC2). Stable cell line can be generated by methods known in the art. In certain embodiments, the stable cell line is generated by random or targeted integration of polynucleotide(s) expressing HC1, LC1, HC2, and LC2 into the host cell genome.

If the multispecific antigen-binding protein made in yeast or bacteria, it may be desirable to modify the product produced therein, for example by phosphorylation or glycosylation of the appropriate sites, in order to obtain a functional product. Such covalent attachments can be accomplished using known chemical or enzymatic methods. A polypeptide can also be produced by operably linking the isolated nucleic acid provided herein to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac kit), and such methods are well known in the art, as described in Summers and Smith, Texas Agricultural Experiment Station Bulletin No. 1555 (1987), and Luckow and Summers, Bio/Technology 6:47 (1988). Cell-free translation systems could also be employed to produce polypeptides, such as antibodies or fragments, using RNAs derived from nucleic acid constructs disclosed herein. Appropriate cloning and expression vectors for use with bacterial, fungal, yeast, and mammalian cellular hosts are described by Pouwels et al. (Cloning Vectors: A Laboratory Manual, Elsevier, New York, 1985). A host cell that comprises an isolated nucleic acid provided herein, preferably operably linked to at least one expression control sequence, is a "recombinant host cell".

In certain embodiments, cell lines may be selected through determining which cell lines have high expression levels and constitutively produce multispecific antigen-binding proteins with the desired binding properties. In another embodiment, a cell line from the B cell lineage that does not make its own antibody but has a capacity to make and secrete a heterologous multispecific antigen-binding protein can be selected.

Production and Purification of Multispecific Antigen-Binding Proteins

Culturing Host Cells

In certain embodiments, provided is a method of producing a multispecific antigen-binding protein described herein comprising (a) introducing a set of polynucleotides encoding H1, H2, L1, and L2 into a host cell; and (b) culturing the host cell to produce multispecific antigen-binding protein. In certain embodiments, the poly nucleotides encoding L1 and L2 are introduced into the host cell at a predetermined ratio (e.g., a molar ratio or a weight ratio). In certain embodiments, polynucleotides encoding L1 and L2 are introduced into the host cell such that the ratio (e.g., a molar ratio or a weight ratio) of L1:L2 is about 1:1, about 1:1.5, about 1:2, about 1:2.5, about 1:3, about 1:3.5, about 1:4, about 1:4.5, about 1:5, about 1:5.5, about 1.5:1, about 2:1, about 2.5:1, about 3:1, about 3.5:1, about 4:1, about 4.5:1, about 5:1, or about 5.5:1, including any range in between these values. In certain embodiments, the ratio is a molar ratio. In certain embodiments the ration is a weight ratio. In certain embodiments, the polynucleotides encoding H1 and H1 are introduced into the host cell at a predetermined ratio (e.g., a molar ratio or a weight ratio). In certain embodiments, polynucleotides encoding H1 and H2 are introduced into the host cell such that the ratio (e.g., a molar ratio or a weight ratio) of H1:H2 is about 1:1, about 1:1.5, about 1:2, about 1:2.5, about 1:3, about 1:3.5, about 1:4, about 1:4.5, about 1:5, about 1:5.5, about 1.5:1, about 2:1, about 2.5:1, about 3:1, about 3.5:1, about 4:1, about 4.5:1, about 5:1, or about 5.5:1, including any range in between these values. In certain embodiments, the ratio is molar ratio. In certain embodiments the ration is a weight ratio. In certain embodiments, the polynucleotides encoding H1, H2, L1 and L2 are introduced into the host cell at a predetermined ratio (e.g., a molar ratio or a weight ratio). In certain embodiments, polynucleotides encoding H1, H2, L1, and L2 are introduced into the host cell such that the ratio (e.g., a molar ratio or a weight ratio) of H1+H2:L1+L2 is about 5:1, about 5:2, about 5:3, about 5:4, about 1:1, about 4:5, about 3:5, about 2:5, or about 1:5, including any range in between these values. In certain embodiments, polynucleotides encoding LC1, LC2, HC1, and HC2 are introduced into the host cell such that the ratio (e.g., a molar ratio or a weight ratio) of LC1:LC2:HC1:HC2 is about 1:1:1:1, about 2.8:1:1:1, about 1.4:1:1:1, about 1:1.4:1, about 1:2.8:1:1, about 1:1:2.8:1, about 1:1:1.4:1, about 1:1:1:2.8, or about 1:1:1:1.4, including any range in between these values. In certain embodiments, the ratio is molar ratio. In certain embodiments the ration is a weight ratio.

In certain embodiments, the method of producing a multispecific antigen-binding protein further comprises determining an optimal ratio of the polynucleotides for introduction into the cell. In certain embodiments, mass spectrometry is used to determine multispecific antigen-binding protein yield (such as bispecific antibody yield), and optimal chain ratio is adjusted to maximize multispecific antigen-binding protein yield (such as bispecific antibody yield). In certain embodiments, dual antigen ELISA is used to determine multispecific antigen-binding protein yield (such as bispecific antibody yield), and optimal chain ratio is adjusted to maximize yield. In certain embodiments, the method of producing a multispecific antigen-binding protein further comprises harvesting or recovering the multispecific antigen-binding protein from the cell culture. In certain embodiments, the method of producing a multispecific antigen-binding protein further comprises purifying the harvested or recovered multispecific antigen-binding protein.

The host cells used to produce a desired multispecific antigen-binding protein (such as bispecific antibody) provided herein may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. No. 4,767,704; 4,657,866; 4,927,762; 4,560,655; or 5,122,469; WO 90/03430: WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Harvesting or Recovering and Purifying Multispecific Antigen-Binding Proteins

In a related aspect, provided is a method of producing a multispecific antigen-binding protein described herein comprising culturing a host cell described above under conditions that allow expression of the multispecific antigen-binding protein and recovering (such as harvesting) the multispecific antigen-binding protein. In certain embodiments, the method further comprises purifying the recovered multispecific antigen-binding protein (such as a bispecific antibody) to obtain a preparation that is substantially homogeneous, e.g., for further assays and uses.

A multispecific antigen-binding proteins provided herein can be produced intracellularly, or directly secreted into the medium. If the multispecific antigen-binding protein is produced intracellularly, as a first step, the particulate debris, either host cells or lysed fragments, are removed, for example, by centrifugation or ultrafiltration. Where the multispecific antigen-binding protein is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

Standard protein purification methods known in the art can be employed to obtain substantially homogeneous preparations of a multispecific antigen-binding protein from cells. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

Additionally or alternatively, a multispecific antigen-binding protein prepared can be purified using, for example, hydroxyapatite chromatography, gel electrophoresis, dialysis, and affinity chromatography, with affinity chromatography being the preferred purification technique.

In certain aspects, the preparation derived from the cell culture medium as described above is applied onto the Protein A immobilized solid phase to allow specific binding of the multispecific antigen-binding protein of interest to Protein A. The solid phase is then washed to remove contaminants non-specifically bound to the solid phase. The multispecific antigen-binding protein (such as a bispecific antibody) is recovered from the solid phase by elution into a solution containing a chaotropic agent or mild detergent. Exemplary chaotropic agents and mild detergents include, but are not limited to. Guanidine-HCl, urea, lithium perclorate, Arginine. Histidine, SDS (sodium dodecyl sulfate), Tween, Triton, and NP-40, all of which are commercially available.

The suitability of protein A as an affinity ligand depends on the species and isotype of any immunoglobulin Fc domain that is present in the multispecific antigen-binding protein. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the multispecific antigen-binding protein comprises a CH3 domain, the Bakerbond ABX™ resin Q. T. Baker, Phillipsburg, NJ) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the multispecific antigen-binding protein to be recovered.

Following any preliminary purification step(s), the mixture comprising a multispecific antigen-binding protein of interest and contaminants may be subjected to low pH hydrophobic interaction chromatography using an elution buffer at a pH between about 2.5-4.5, preferably performed at low salt concentrations (e.g., from about 0-0.25M salt). The production of the multispecific antigen-binding proteins can alternatively or additionally (to any of the foregoing particular methods) comprise dialyzing a solution comprising a mixture of the polypeptides.

Libraries of Multispecific Antigen-Binding Proteins

Provided herein are libraries comprising a plurality of multispecific antigen-binding proteins described herein. In certain embodiments, the library is a polynucleotide library (such as a plurality of any of the polynucleotides described herein). In certain embodiments, the library is a polypeptide library (such as a plurality of any of the polypeptides described herein). In certain embodiments, a polypeptide library provided herein is a polypeptide display library. Such polypeptide display libraries can be screened to select and/or evolve binding proteins with desired properties for a wide variety of utilities, including but not limited to therapeutic, prophylactic, veterinary, diagnostic, reagent, or material applications.

In certain embodiments, provided are libraries comprising at least 2, 3, 4, 5, 10, 30, 100, 250, 500, 750, 1000, 2500, 5000, 7500, 10000, 25000, 50000, 75000, 100000, 250000, 500000, 750000, 1000000, 2500000, 5000000, 7500000, 10000000, or more than 10000000 different multispecific antigen-binding proteins, each comprising an amino acid substitution mutation at position S183 (EU numbering) on the CH1 domain of H1 and an amino acid substitution mutation at position V133 (EU numbering) on the CL domain of L1. Additionally or alternatively, the multispecific antigen-binding proteins in the library comprise a CH1 domain of H1 comprising (including consisting of and consisting essentially of) A141I, F170S, S181M, S183V, and V185A mutations (EU numbering), and a CL domain of L1 comprising (including consisting of or consisting essentially of) F116A, V133I, L135V, S162M, S174A, S176F, and T178V mutations (EU numbering). Additionally or alternatively, the multispecific antigen-binding proteins in the library comprise a CH1 domain of H1 comprising (including consisting of and consisting essentially of) A141I, F170S, S181M, S183A, and V185A mutations (EU numbering) and a CL domain of L1 comprising (including consisting of or consisting essentially of) F116A, S131D, L135V, S162A, S174A, S176F, and T178I mutations (EU numbering). Additionally or alternatively, the multispecific antigen-binding proteins in the library comprise CH1 domain of H1 comprising (including consisting of and consisting essentially of) A141I, F170S, S181M, S183A, and V185A mutations (EU numbering) and a CL domain of L1 comprising (including consisting of or consisting essentially of) F116A, L135V, S174A, S176F, and T178V mutations (EU numbering). Additionally or alternatively, the multispecific antigen-binding proteins in the library comprise a CH1 domain of H1 comprising (including consisting of and consisting essentially of) A141I, F170A, S181M, S183V, and V185A mutations (EU numbering) and a CL domain of L1 comprising (including consisting of or consisting essentially of) F116A, L135V, S162M, S174A, S176F, and T178V mutations (EU numbering). Additionally or alternatively, the multispecific antigen-binding proteins in the library comprise a CH1 domain of H1 comprising (including consisting of and consisting essentially of) L128F, A141M, F170M, S181I and S183A mutations (EU numbering) and a CL domain of L1 comprising (including consisting of or consisting essentially of) F118V, S131T, V133A, L135Y, S162A, T164S, S176M, and T178L mutations (EU numbering). Additionally or alternatively, the multispecific antigen-binding proteins in the library comprise a CH1 domain of H1 comprising (including consisting of and consisting essentially of) L128F, A141M, F170Y, S181I, S183A, and V185A mutations (EU numbering) and a CL domain of L1 comprising (including consisting of or consisting essentially of) F118V, S131T, V133A, L135F, S162A, S176A, and T178L mutations (EU numbering). Additionally or alternatively, the multispecific antigen-binding proteins in the library comprise a CH1 domain of H1 comprising (including consisting of and consisting essentially of) L128F, A141T, F170M, S181T, S183A, and V185L mutations (EU numbering) and a CL domain of L comprising (including consisting of or consisting essentially of) F118V, S131T, V133A, L135F, S162A, T164S, S176T, and T178L mutations (EU numbering). Additionally or alternatively, the multispecific antigen-binding proteins in the library comprise a CH1 domain of H1 comprising (including consisting of and consisting essentially of) L128F, A141M, F170M, S181T, and S183A mutations (EU numbering), and a CL domain of L1 comprising (including consisting of or consisting essentially of) F118V, S131T, V133A, L135F, S162M, T164S, S176M, and T178L mutations (EU numbering).

Additionally or alternatively, the multispecific antigen-binding proteins in the library comprise a CH1 domain of H1 comprising (including consisting of and consisting essentially of) F170S, S181M, S183A, and V185A mutations (EU numbering) and a CL domain of L1 comprising (including consisting of or consisting essentially of) L135V, S174A, S176F, and T178V mutations (EU numbering). Additionally or alternatively, the multispecific antigen-binding proteins in the library comprise a CH1 domain of H1 comprising (including consisting of and consisting essentially of) A141I, F170S, S183A, and V185A mutations (EU numbering) and a CL domain of L comprising (including consisting of or consisting essentially of) F116A, S174A, S176F, and T178V mutations (EU numbering). Additionally or alternatively, the multispecific antigen-binding proteins in the library comprise a CH1 domain of H1 comprising (including consisting of and consisting essentially of) A141I, F170S, S181M, and V185A mutations (EU numbering) and a CL domain of L1 comprising (including consisting of or consisting essentially of) F116A, L135V, S176F, and T178V mutations (EU numbering). Additionally or alternatively, the multispecific antigen-binding proteins in the library comprise a CH1 domain of H1 comprising (including consisting of and consisting essentially of) A141I, F170S, S181M, and S183A mutations (EU numbering) and a CL domain of L1 comprising (including consisting of or consisting essentially of) F116A, L135V, S174A, and S176F mutations (EU numbering). Additionally or alternatively, the multispecific antigen-binding proteins in the library comprise a CH1 domain of H1 comprising (including consisting of and consisting essentially of) F170S, S183A, and V185A mutations (EU numbering) and a CL domain of L1 comprising (including consisting of or consisting essentially of) F116A, S176F, and T178V mutations (EU numbering). Additionally or alternatively, the multispecific antigen-binding proteins in the library comprise a CH1 domain of H1 comprising (including consisting of and consisting essentially of) F170S, S181M, and V185A mutations (EU numbering) and a CL domain of L1 comprising (including consisting of or consisting essentially of) F116A, L135V, and S176F mutations (EU numbering). Additionally or alternatively, the multispecific antigen-binding proteins in the library comprise a CH1 domain of H1 comprising (including consisting of and consisting essentially of) F170S, S181M, and S183A mutations (EU numbering) and a CL domain of L1 comprising (including consisting of or consisting essentially of) F116A and S176F mutations (EU numbering). Additionally or alternatively, the multispecific antigen-binding proteins in the library comprise a CH1 domain of H1 comprising (including consisting of and consisting essentially of) A141I, F170S, and V185A mutations (EU numbering) and a CL domain of L comprising (including consisting of or consisting essentially of) F116A and S176F mutations. Additionally or alternatively, the multispecific antigen-binding proteins in the library comprise a CH1 domain of H1 comprising (including consisting of and consisting essentially of) A141I, F170S, and S183A mutations (EU numbering) and a CL domain of L1 comprising (including consisting of or consisting essentially of) F116A and S176F mutations. Additionally or alternatively, the multispecific antigen-binding proteins in the library comprise a CH1 domain of H1 comprising (including consisting of and consisting essentially of) A141I, F170S, and S181M mutations (EU numbering) and a CL domain of L comprising (including consisting of or consisting essentially of) F116A, L135V, S174A, S176F, and T178V mutations EU numbering). Additionally or alternatively, the multispecific antigen-binding proteins in the library comprise a CH1 domain of H1 comprising (including consisting of and consisting essentially of) F170S and V185A mutations (EU numbering) and a CL domain of L1 comprising (including consisting of or consisting essentially of) F116A and S176F mutations. Additionally or alternatively, the multispecific antigen-binding proteins in the library comprise a CH1 domain of H1 comprising (including consisting of and consisting essentially of) A141I and F170S mutations (EU numbering) and a CL domain of L1 comprising (including consisting of or consisting essentially of) F116A, L135V, S174A, S176F, and T178V mutations (EU numbering). Additionally or alternatively, the multispecific antigen-binding proteins in the library comprise a CH1 domain of H1 comprising (including consisting of and consisting essentially of) an F170S mutation (EU numbering), and a CL domain of L1 comprising (including consisting of or consisting essentially of) F116A, L135V, S174A, S176F, and T178V mutations (EU numbering). Additionally or alternatively, the multispecific antigen-binding proteins in the library comprise a CH1 domain of H1 comprising (including consisting of and consisting essentially of) an F170S mutation (EU numbering), and a CL domain of L1 comprising (including consisting of or consisting essentially of) F116A, L135V, S176F, and T178V mutations (EU numbering). Additionally or alternatively, the multispecific antigen-binding proteins in the library comprise a CH1 domain of H1 comprising (including consisting of and consisting essentially of) an F170S mutation (EU numbering) and a CL domain of L1 comprising (including consisting of or consisting essentially of) F116A, L135V, S174A, and S176F mutations (EU numbering). Additionally or alternatively, the multispecific antigen-binding proteins in the library comprise a CH1 domain of H1 comprising (including consisting of and consisting essentially of) an F170S mutation (EU numbering) and a CL domain of L1 comprising (including consisting of or consisting essentially of) F116A, S176F, and T178V mutations (EU numbering). Additionally or alternatively, the multispecific antigen-binding proteins in the library comprise a CH1 domain of H1 comprising (including consisting of and consisting essentially of) an F170S mutation (EU numbering) and a CL domain of L1 comprising (including consisting of or consisting essentially of) F116A, L135V, and S176F mutations (EU numbering).

Additionally or alternatively, the multispecific antigen-binding proteins in the library comprise a CH1 domain of H1 comprising (including consisting of and consisting essentially of) an F170S mutation (EU numbering) and a CL domain of L1 comprising (including consisting of or consisting essentially of) F116A and S176F mutations (EU numbering). Additionally or alternatively, the multispecific antigen-binding proteins in the library comprise a CH1 domain of H1 comprising (including consisting of and consisting essentially of) A141I and F170S mutations (EU numbering) and a CL domain of L1 comprising (including consisting of or consisting essentially of) F116A, L135V, S176F, and T178V mutations (EU numbering). Additionally or alternatively, the multispecific antigen-binding proteins in the library comprise a CH1 domain of H1 comprising (including consisting of and consisting essentially of) A141I and F170S mutations (EU numbering) and a CL domain of L1 comprising (including consisting of or consisting essentially of) F116A, L135V, S174A, and S176F mutations (EU numbering). Additionally or alternatively, the multispecific antigen-binding proteins in the library comprise a CH1 domain of H1 comprising (including consisting of and consisting essentially of) A141I and F170S mutations (EU numbering) and a CL domain of L1 comprising (including consisting of or consisting essentially of) F116A, S176F, and T178V mutations (EU numbering). Additionally or alternatively, the multispecific antigen-binding proteins in the library comprise a CH1 domain of H1 comprising (including consisting of and consisting essentially of) A141I and F170S mutations (EU numbering) and a CL domain of L1 comprising (including consisting of or consisting essentially of) F116A, L135V, and S176F mutations (EU numbering). Additionally or alternatively, the multispecific antigen-binding proteins in the library comprise a CH1 domain of H1 comprising (including consisting of and consisting essentially of) A141I and F170S mutations (EU numbering) and a CL domain of L comprising (including consisting of or consisting essentially of) F116A and S176F mutations (EU numbering).

Additionally or alternatively, the multispecific antigen-binding proteins in the library comprise an amino acid substitution mutation at position Q39 (Kabat numbering) on the VH domain of H1 and an amino acid substitution mutation at position Q38 (Kabat numbering on the VL domain of L1. Additionally or alternatively, the multispecific antigen-binding proteins in the library comprise an amino acid substitution mutation at position Q39 (Kabat numbering) on the VH domain of H2 and an amino acid substitution mutation at position Q38 (Kabat numbering on the VL domain of L2.

In certain embodiments, provided are libraries comprising at least 2, 3, 4, 5, 10, 30, 100, 250, 500, 750, 1000, 2500, 5000, 7500, 10000, 25000, 50000, 75000, 100000, 250000, 500000, 750000, 1000000, 2500000, 5000000, 7500000, 10000000, or more than 10000000 multispecific antigen-binding proteins provided herein having unique sequences in their complementarity determining regions (CDRS), including any range in between these values. In certain embodiments, the multispecific antigen-binding protein library has a sequence diversity of about 2, about 5, about 10, about 50, about 100, about 250, about 500, about 750, about $10^3$, about $10^4$, about $10^1$, about $10^6$, about $10^7$, about $10^8$, about $10^9$, about $10^{10}$, about $10^{11}$, about $10^{12}$, about $10^{13}$, about $10^{14}$, or more than about $10^{14}$ (such as about $10^{15}$ or about $10^{16}$), including any range in between these values.

In certain embodiments, a multispecific antigen-binding protein library is generated via genetic engineering. A variety of methods for mutagenesis and subsequent library construction have been previously described (along with appropriate methods for screening or selection). Such mutagenesis methods include, but are not limited to, e.g., error-prone PCR, loop shuffling, or oligonucleotide-directed mutagenesis, random nucleotide insertion or other methods prior to recombination. Further details regarding these methods are described in, e.g., Abou-Nadler et al. (2010) *Bioengineered Bugs* 1, 337-340: Firth et al. (2005) *Bioinformatics* 21, 3314-3315; Cirino et al. (2003) *Methods. Mol Biol* 231, 3-9; Pirakitikulr (2010) *Protein Sci* 19, 2336-2346; Steffens et al. (2007) *J. Biomol Tech* 18, 147-149; and others. Accordingly, in certain embodiments, provided are multispecific antigen-binding protein libraries generated via genetic engineering techniques.

In certain embodiments, a multispecific antigen-binding protein library is generated via in vitro translation. Briefly, in vitro translation entails cloning the protein-coding sequence(s) into a vector containing a promoter, producing mRNA by transcribing the cloned sequence(s) with an RNA polymerase, and synthesizing the protein by translation of this mRNA in vitro, e.g., using a cell-free extract. A desired mutant protein can be generated simply by altering the cloned protein-coding sequence. Many mRNAs can be translated efficiently in wheat germ extracts or in rabbit reticulocyte lysates. Further details regarding in vitro translation are described in, e.g., Hope et al. (1985) *Cell* 43, 177-188; Hope et al. (1986) *Cell* 46, 885-894; Hope et al. (1987) *EMBO J.* 6, 2781-2784; Hope et al. (1988) *Nature* 333, 635-640; and Melton et al. (1984) *Nucl. Acids Res.* 12, 7057-7070.

Accordingly, provided is a plurality of nucleic acid molecules encoding a polypeptide display library described herein. An expression vector operably linked to the plurality of nucleic acid molecules is also provided herein.

In certain embodiments, a multispecific antigen-binding protein library is generated via chemical synthesis. Methods of solid phase and liquid phase peptide synthesis are well known in the art and described in detail in, e.g., Methods of Molecular Biology, 35, Peptide Synthesis Protocols, (M. W. Pennington and B. M. Dunn Eds), Springer, 1994; Welsch et al. (2010) *Curr Opin Chem Biol* 14, 1-15; Methods of Enzymology, 289. Solid Phase Peptide Synthesis, (G. B. Fields Ed.), Academic Press, 1997: Chemical Approaches to the Synthesis of Peptides and Proteins, (P. Lloyd-Williams, F. Albericio, and E. Giralt Eds), CRC Press, 1997; Fmoc Solid Phase Peptide Synthesis, A Practical Approach, (W. C.

Chan, P. D. White Eds), Oxford University Press, 2000; Solid Phase Synthesis. A Practical Guide. (S. F. Kates, F Albericio Eds), Marcel Dekker, 2000: P. Seneci, Solid-Phase Synthesis and Combinatorial Technologies, John Wiley & Sons, 2000; Synthesis of Peptides and Peptidomimetics (M. Goodman, Editor-in-chief, A. Felix, L. Moroder, C. Tmiolo Eds), Thieme, 2002: N. L. Benoiton, Chemistry of Peptide Synthesis, CRC Press, 2005; Methods in Molecular Biology, 298, Peptide Synthesis and Applications, (J. Howl Ed) Humana Press, 2005; and Amino Acids, Peptides and Proteins in Organic Chemistry, Volume 3, Building Blocks, Catalysts and Coupling Chemistry, (A. B. Hughs, Ed.) Wiley-VCH, 2011. Accordingly, in certain embodiments, provided is a multispecific antigen-binding protein library generated via chemical synthesis techniques.

In certain embodiments, the multispecific antigen-binding protein library comprises a display library. In certain embodiments, the display library is a phage display library, a phagemid display library, a virus display library, a bacterial display library, a yeast display library, a λgt11 library, a CIS display library, and in vitro compartmentalization library, or a ribosome display library. Methods of making and screening such display libraries are well known to those of skill in the art and described in, e.g., Molek et al. (2011) *Molecules* 16, 857-887; Boder et al., (1997) *Nat Biotechnol* 15, 553-557; Scott et al. (1990) *Science* 249, 386-390; Brisette et al. (2007) *Methods Mol Biol* 383, 203-213: Kenrick et al. (2010) *Protein Eng Des Sel* 23, 9-17; Freudl et al. (1986) *J Mol Biol* 188, 491-494; Getz et al. (2012) *Methods Enzymol* 503, 75-97; Smith et al. (2014) *Curr Drug Discov Technol* 11, 48-55; Hanes, et al. (1997) *Proc Natl Acad Sci USA* 94, 4937-4942; Lipovsek et al., (2004) *J Imm Methods* 290, 51-67: Ullman et al. (2011) Brief. Funct. Genomics, 10, 125-134; Odegrip et al. (2004) *Proc Natl Acad Sci USA* 101, 2806-2810; and Miller et al. (2006) Nat Methods 3, 561-570.

In certain embodiments, the multispecific antigen-binding protein library comprises an RNA-protein fusion library generated, for example, by the techniques described in Szostak et al., U.S. Pat. Nos. 6,258,558, 6,261,804, 5,643,768, and 5,658,754. In certain embodiments, the multispecific antigen-binding protein library comprises a DNA-protein library, as described, for example, in U.S. Pat. No. 6,416,950.

Directed Evolution of Multispecific Antigen-Binding Protein Libraries

The multispecific antigen binding proteins provided herein can be screened to identify, e.g., multivalent antigen binding proteins having improved binding affinity to two or more target ligands of interest. Accordingly, provided herein is a method of obtaining a multispecific antigen-binding protein that specifically binds at least two target ligands of interest (e.g., two or more targets ligands of interest described elsewhere herein).

In certain embodiments, the method comprises a) contacting a first target ligand with a library of multispecific antigen-binding proteins (such as a library described herein) under conditions that allow a multispecific antigen-binding protein: first target ligand complex to form, (b) detecting the formation of the multispecific antigen-binding protein: first target ligand complex, and (c) obtaining from the complex the multispecific antigen-binding protein that specifically binds the first target ligand.

Additionally or alternatively, in certain embodiments, the method comprises a) contacting a second target ligand with a library of multispecific antigen-binding proteins (such as a library described herein) under conditions that allow a multispecific antigen-binding protein: second target ligand complex to form, (b) detecting the formation of the multispecific antigen-binding protein: second target ligand complex, and (c) obtaining from the complex the multispecific antigen-binding protein that specifically binds the second target ligand.

In certain embodiments, provided is a complex comprising a multispecific antigen-binding protein provided herein and a first target ligand (i.e., a multispecific antigen-binding protein: target ligand complex). In certain embodiments, provided is a complex comprising a multispecific antigen-binding protein provided herein and a second target ligand. In certain embodiments, provided is a complex comprising a multispecific antigen-binding protein provided herein, a first target ligand, and a second target ligand. In certain embodiments, the provided is a multispecific antigen-binding protein capable of binding to two or more target ligands. In certain embodiments, the method further comprises (d) determining the nucleic acid sequence of the multispecific antigen-binding protein that specifically binds the two or more target ligands.

In certain embodiments, a multispecific antigen-binding protein that specifically binds two or more target ligands is subject to affinity maturation. In this process, a multispecific antigen-binding protein is subject to a scheme that selects for increased affinity for a first target and/or a second target (see Wu et al. (1998) *Proc Natl Acad Sci USA*. 95, 603742). In certain embodiments, a multispecific antigen-binding protein that specifically binds a first target ligand is further randomized after identification from a library screen. For example, in certain embodiments, the method of obtaining a multispecific antigen-binding protein that specifically binds a first target ligand further comprises (e) randomizing the CDR-H1, CDR-H2, CDR-H3, CDR-L1, CDR-L2, and/or CDR-L3 of the multispecific antigen-binding protein obtained from the multispecific antigen-binding protein: first target ligand complex identified previously to generate further multispecific antigen-binding proteins, (f) contacting the first target ligand with the further randomized multispecific antigen-binding proteins, (g) detecting the formation of the further randomized multispecific antigen-binding protein: first target ligand complex, and (h) obtaining from the complex the further randomized multispecific antigen-binding protein that specifically binds the first target ligand. Additionally or alternatively, in certain embodiments, steps (e)-(h) are repeated with a second target ligand.

In certain embodiments, the method further comprises (i) determining the nucleic acid sequence of the multispecific antigen-binding protein that specifically binds the first (and/or second) target ligand.

In certain embodiments, the further randomized multispecific antigen-binding proteins comprise at least one or at least two randomized CDRs which were not previously randomized in the first library. Multiple rounds of randomization, screening and selection can be performed until n multispecific antigen-binding protein(s) having sufficient affinity for the first and/or second target ligands are obtained. Thus, in certain embodiments, steps (e)-(h) or steps (e)-(i) are repeated one, two, three, four, five, six, seven, eight, nine, ten, or more than ten times in order to identify the multispecific antigen-binding protein that specifically binds a first target ligand. Additionally or alternatively, in certain embodiments, steps (e)-(h) or steps (e)-(i) are repeated one, two, three, four, five, six, seven, eight, nine, ten, or more than ten times in order to identify the multispecific antigen-binding protein that specifically binds a second target ligand.

In certain embodiments, the multispecific antigen-binding protein that has undergone at least two, three, four, five, six, seven, eight, nine, ten, or more than ten rounds of randomization, screening and selection binds the target ligand with an affinity that is at least as high as that of the multispecific antigen-binding protein that has undergone one round of randomization, screening, and selection. In certain embodiments, the multispecific antigen-binding protein that has undergone at least two, three, four, five, six, seven, eight, nine, ten, or more than ten rounds of randomization, screening and selection binds the first target ligand with an affinity that is higher than that of the multispecific antigen-binding protein that has undergone one round of randomization, screening, and selection. Additionally or alternatively, in certain embodiments, the multispecific antigen-binding protein that has undergone at least two, three, four, five, six, seven, eight, nine, ten, or more than ten rounds of randomization, screening and selection binds the second target ligand with an affinity that is higher than that of the multispecific antigen-binding protein that has undergone one round of randomization, screening, and selection.

It will be readily apparent to one of ordinary skill in the art that the methods described above can be repeated to identify a multispecific antigen-binding protein that specifically binds three target ligands of interest, four target ligands of interest, five target ligands of interest, or more than five target ligands of interest.

A library of multispecific antigen-binding proteins described herein may be screened by any technique known in the art for evolving new or improved binding proteins that specifically bind a target ligand. In certain embodiments, the target ligand is immobilized on a solid support (such as a column resin or microtiter plate well), and the target ligand is contacted with a library of candidate multispecific antigen-binding proteins (such as any library described herein). Selection techniques can be, for example, phage display (Smith (1985) *Science* 228, 1315-1317), mRNA display (Wilson et al. (2001) *Proc Natl Acad Sci USA* 98: 3750-3755) bacterial display (Georgiou, et al. (1997) *Nat Biotechnol* 15:29-34), yeast display (Boder and Wittrup (1997) *Nat. Biotechnol.* 15:553-5577) or ribosome display (Hanes and Pluckthun (1997) *Proc Natl Acad Sci USA* 94:4937-4942 and WO2008/068637).

In certain embodiments, the library of multispecific antigen-binding proteins is a phage display library. In certain embodiments, provided is a phage particle displaying a multispecific antigen-binding protein described herein. In certain embodiments, the provided is a phage particle displaying a multispecific antigen-binding protein described herein capable of binding to a target ligand.

Phage display is a technique by which a plurality of multispecific antigen-binding protein variants are displayed as fusion proteins to the coat protein on the surface of bacteriophage particles (Smith, G. P. (1985) *Science,* 228: 1315-7; Scott, J. K. and Smith, G. P. (1990) *Science* 249: 386; Sergeeva, A., et al. (2006) *Adv. Drug Deliv. Rev.* 58:1622-54). The utility of phage display lies in the fact that large libraries of selectively randomized protein variants (or randomly cloned cDNAs) can be rapidly and efficiently sorted for those sequences that bind to a target molecule with high affinity.

Display of peptides (Cwirla, S. E. et al. (1990) *Proc. Natl. Acad. Sci. USA,* 87:6378) or protein (Lowman, H. B. et al. (1991) *Biochemistry,* 30:10832; Clackson, T. et al. (1991) *Nature,* 352: 624; Marks, J. D. et al. (1991), *J. Mol. Biol.,* 222:581; Kang, A. S. et al. (1991) *Proc. Natl. Acad Sci. USA,* 88:8363) libraries on phage have been used for screening millions of polypeptides or oligopeptides for ones with specific binding properties (Smith, G. P. (1991) *Current Opin. Biotechnol.,* 2:668; Wu et al. (1998) *Proc Natl Acad Sci USA.* May 95, 6037-42). Polyvalent phage display methods have been used for displaying small random peptides and small proteins through fusions to either gene III or gene VIII of filamentous phage. (Wells and Lowman, *Curr. Opin. Struct. Biol.,* 3:355-362 (1992), and references cited therein.) In a monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. (Lowman and Wells, *Methods: A companion to Methods in Enzymology,* 3:205-0216 (1991).)

Sorting phage libraries of multispecific antigen-binding proteins entails the construction and propagation of a large number of variants, a procedure for affinity purification using the target ligand, and a means of evaluating the results of binding enrichments (see for example, U.S. Pat. Nos. 5,223,409, 5,403,484, 5,571,689, and 5,663,143).

Most phage display methods use filamentous phage (such as M13 phage). Lambdoid phage display systems (see WO1995/34683, U.S. Pat. No. 5,627,024), T4 phage display systems (Ren et al. (1998) *Gene* 215:439; Zhu et al. (1998) *Cancer Research,* 58:3209-3214; Jiang et al., (1997) *Infection & Immunity,* 65:4770-4777; Ren et al. (1997) *Gene,* 195:303-311; Ren (1996) *Protein Sci.,* 5:1833; Efimov et al. (1995) *Virus Genes,* 10:173) and T7 phage display systems (Smith and Scott (1993) *Methods in Enzymology,* 217: 228-257; U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 1998/14277) and phage display libraries have been used to analyze and control bimolecular interactions (WO 1998/20169; WO 1998/20159) and properties of constrained helical peptides (WO 1998/20036). WO 1997/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 1997/46251 describes a method of biopanning a random phage display library with an affinity purified antibody and then isolating binding phage, followed by a micropanning process using microplate wells to isolate high affinity binding phage. Such method can be applied to the multispecific antigen-binding proteins disclosed herein. The use of *Staphylococcus aureus* protein A as an affinity tag has also been reported (Li et al. (1998) *Mol Biotech.* 9:187). WO 1997/47314 describes the use of substrate subtraction libraries to distinguish enzyme specificities using a combinatorial library which may be a phage display library. Additional methods of selecting specific binding proteins are described in U.S. Pat. Nos. 5,498,538, 5,432,018, and WO 1998/15833. Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

Antigens/Target Molecules

Examples of molecules that may be targeted by a multispecific antigen-binding protein provided herein include, but are not limited to, soluble serum proteins and their receptors and other membrane bound proteins (e.g., adhesins). In another embodiment, a multispecific antigen-binding protein provided herein is capable of binding one, two or more cytokines, cytokine-related proteins, and cytokine receptors selected from the group consisting of 8MPI, 8MP2, 8MP38 (GDFIO), 8MP4, 8MP6, 8MP8, CSFI (M-CSF), CSF2 (GM-CSF), CSF3 (G-CSF), EPO, FGF1 (αFGF), FGF2 (βFGF), FGF3 (int-2), FGF4 (HST), FGF5, FGF6 (HST-2), FGF7 (KGF), FGF9, FGF10, FGF11, FGF12, FGF12B, FGF14, FGF16, FGF17, FGF19, FGF20, FGF21, FGF23, IGF1, IGF2, IFNA1, IFNA2, IFNA4, IFNA5, IFNA6, IFNA7, IFN81, IFNG, IFNWI, FEL1, FEL1 (EPSELON), FEL1 (ZETA), IL 1A, IL 1B, IL2, IL3, IL4, IL5, IL6, IL7, IL8, IL9, IL10, IL 11, IL 12A, IL 12B, IL 13, IL 14, IL 15, IL 16, IL 17, IL 17B, IL 18, IL 19, IL20, IL22, IL23, IL24, IL25, IL26, IL27, IL28A, IL28B, IL29, IL30, PDGFA, PDGFB, TGFA, TGFB1, TGFB2, TGFBb3, LTA (TNF-β), LTB, TNF (TNF-α), TNFSF4 (OX40 ligand), TNFSF5 (CD40 ligand). TNFSF6 (FasL), TNFSF7 (CD27 ligand), TNFSF8 (CD30 ligand), TNFSF9 (4-1 BB ligand), TNFSF10 (TRAIL), TNFSF11 (TRANCE), TNFSF12 (APO3L), TNFSF13 (April), TNFSF13B, TNFSF14 (HVEM-L), TNFSF15 (VEGI), TNFSF18, HGF (VEGFD), VEGF, VEGFB, VEGFC, IL1R1, IL1R2, IL1RL1, IL1RL2, IL2RA, IL2RB, IL2RG, IL3RA, IL4R, IL5RA, IL6R, IL7R, IL8RA, IL8RB, IL9R, IL10RA, IL10RB, IL 11RA, IL12RB1, IL12RB2, IL13RA1, IL13RA2, IL15RA, IL17R, IL18R1, IL20RA, IL21R, IL22R, IL1HY1, IL1RAP, IL1RAPL1, IL1RAPL2, IL1RN, IL6ST, IL18BP, IL18RAP, IL22RA2, AIF1, HGF, LEP (leptin), PTN, and THPO.

In another embodiment, a target molecule is a chemokine, chemokine receptor, or a chemokine-related protein selected from the group consisting of CCLI (1-309), CCL2 (MCP-1/MCAF), CCL3 (MIP-Iα), CCL4 (MIP-Iβ), CCL5 (RANTES), CCL7 (MCP-3), CCL8 (mcp-2), CCL11 (eotaxin), CCL 13 (MCP-4), CCL 15 (MIP-Iδ), CCL 16 (HCC-4), CCL 17 (TARC), CCL 18 (PARC), CCL 19 (MDP-3b), CCL20 (MIP-3α), CCL21 (SLC/exodus-2), CCL22 (MDC/STC-1), CCL23 (MPIF-1), CCL24 (MPIF-2/eotaxin-2), CCL25 (TECK), CCL26 (eotaxin-3), CCL27 (CTACK/ILC), CCL28, CXCLI (GROI), CXCL2 (GR02), CXCL3 (GR03), CXCL5 (ENA-78), CXCL6 (GCP-2), CXCL9 (MIG), CXCL 10 (IP 10), CXCL 11 (1-TAC), CXCL 12 (SDFI), CXCL 13, CXCL 14, CXCL 16, PF4 (CXCL4), PPBP (CXCL7), CX3CL 1 (SCYDI), SCYEI, XCLI (lymphotactin), XCL2 (SCM-Iβ), BLRI (MDR15), CCBP2 (D6/JAB61), CCRI (CKRI/HM145), CCR2 (mcp-IRB IRA), CCR3 (CKR3/CMKBR3), CCR4, CCR5 (CMKBR5/ChemR13), CCR6 (CMKBR6/CKR-L3/STRL22/DRY6), CCR7 (CKR7/EBII), CCR8 (CMKBR8/TER1/CKR-L1), CCR9 (GPR-9-6), CCRL1 (VSHK1), CCRL2 (L-CCR), XCR1 (GPR5/CCXCR1), CMKLR1, CMKOR1 (RDC1), CX3CR1 (V28), CXCR4, GPR2 (CCR10), GPR31, GPR81 (FKSG80), CXCR3 (GPR9/CKR-L2), CXCR6 (TYMSTR/STRL33/Bonzo), HM74, IL8RA (IL8Rα), IL8RB (IL8Rβ), LTB4R (GPR16), TCP10, CKLFSF2, CKLFSF3, CKLFSF4, CKLFSF5, CKLFSF6, CKLFSF7, CKLFSF8, BDNF, C5R1, CSF3, GRCC10 (C10), EPO, FY (DARC), GDF5, HDF1, HDF1α, DL8, PRL, RGS3, RGS13, SDF2, SLIT2, TLR2, TLR4, TREM1, TREM2, and VHL.

In another embodiment the multispecific antigen-binding proteins provided herein are capable of binding one or more targets selected from the group consisting of ABCF1; ACVR1; ACVR1B; ACVR2; ACVR2B; ACVRL1; ADORA2A; Aggrecan; AGR2; AICDA; AIF1; AIG1; AKAP1; AKAP2; AMH; AMHR2; ANGPTL; ANGPT2; ANGPTL3; ANGPTL4; ANPEP; APC; APOC1; AR; AZGP1 (zinc-a-glycoprotein); B7.1; B7.2; BAD; BAFF (BLys); BAG1; BAI1; BCL2; BCL6; BDNF; BLNK; BLRI (MDR15); BMP1: BMP2; BMP3B (GDF10); BMP4; BMP6; BMP8; BMPR1A; BMPR1B; BMPR2; BPAG1 (plectin); BRCA1; C19orf10 (IL27w); C3; C4A; C5; C5R1; CANT1; CASP1; CASP4; CAV1; CCBP2 (D6/JAB61); CCL1 (1-309); CCL11 (eotaxin); CCL13 (MCP-4); CCL15 (MIP1δ); CCL16 (HCC-4); CCL17 (TARC); CCL18 (PARC); CCL19 (MIP-3β); CCL2 (MCP-1); MCAF; CCL20 (MIP-3α); CCL21 (MTP-2); SLC; exodus-2; CCL22 (MDC/STC-1); CCL23 (MPIF-1); CCL24 (MPIF-2/eotaxin-2); CCL25 (TECK); CCL26 (eotaxin-3); CCL27 (CTACK/ILC); CCL28; CCL3 (MTP-Iα); CCL4 (MDP-Iβ); CCL5 (RANTES); CCL7 (MCP-3); CCL8 (mcp-2); CCNA1; CCNA2; CCND1; CCNE1; CCNE2; CCR1 (CKRI/HM145); CCR2 (mcp-IRβ/RA); CCR3 (CKR/CMKBR3); CCR4; CCR5 (CMKBR5/ChemR13); CCR6 (CMKBR6/CKR-L3-STRL22, DRY6); CCR7 (CKBR7/EB11); CCR8 (CMKBR8/TER1/CKR-L1); CCR9 (GPR-9-6); CCRL1 (VSHK1); CCRL2 (L-CCR); CD164; CD19; CD1C; CD20; CD200; CD22: CD24; CD28; CD3; CD37; CD38: CD3E; CD3G; CD3Z; CD4; CD40; CD40L; CD44; CD45RB; CD52; CD69; CD72; CD74; CD79A; CD79B; CD5; CD80; CD81; CD83; CD86; CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKN1A (p21/WAF1/Cip1); CDKN1B (p27/Kip1); CDKN1C; CDKN2A (P16INK4a); CDKN2B; CDKN2C; CDKN3; CEBPB; CER1; CHGA; CHGB; Chitinase; CHST10; CKLFSF2; CKLFSF3; CKLFSF4; CKLFSF5; CKLFSF6; CKLFSF7: CKLFSF8; CLDN3; CLDN7 (claudin-7); CLN3; CLU (clusterin); CMKLR1; CMKOR1 (RDC1); CNR1; COL 18A1; COL1A1; COL4A3; COL6A1; CR2; CRP; CSFI (M-CSF); CSF2 (GM-CSF); CSF3 (GCSF); CTLA4; CTNNB1 (b-catenin); CTSB (cathepsin B); CX3CL1 (SCYDI); CX3CR1 (V28); CXCL1 (GRO1); CXCL10 (IP-10); CXCL11 (I-TAC/IP-9); CXCL12 (SDF1); CXCL13; CXCL14; CXCL16; CXCL2 (GRO2); CXCL3 (GRO3); CXCL5 (ENA-78/LIX); CXCL6 (GCP-2); CXCL9 (MIG); CXCR3 (GPR9/CKR-L2); CXCR4; CXCR6 (TYMSTR/STRL33/Bonzo); CYB5; CYC1; CYSLTR1; DAB21P; DES; DKFZp451J0118; DNCLI; DPP4; E2F1; ECGF1; EDG1; EFNA1; EFNA3; EFNB2; EGF; EGFR; ELAC2; ENG; ENO1; ENO2; ENO3; EPHB4; EPO; ERBB2 (Her-2); EREG; ERK8; ESR1; ESR2; F3 (TF); FADD; FasL; FASN; FCER1A; FCER2; FCGR3A; FGF; FGF1 (αFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FEL1 (EPSILON); FIL1 (ZETA); FLJ12584; FLJ25530; FLRTI (fibronectin); FLT1; FOS; FOSL1 (FRA-1); FY (DARC); GABRP (GABAa); GAGEB1; GAGEC1; GALNAC4S-6ST; GATA3; GDF5; GFI1; GGT1; GM-CSF; GNASI; GNRHI; GPR2 (CCR10); GPR31; GPR44; GPR81 (FKSG80); GRCCIO (C10); GRP; GSN (Gelsolin); GSTP1; HAVCR2; HDAC4; HDAC5; HDAC7A; HDAC9; HGF; HIF1A; HOP1; histamine and histamine receptors; HLA-A; HLA-DRA; HM74; HMOXI; HUMCYT2A; ICEBERG; ICOSL; 1D2; IFN-a; IFNA1; IFNA2; IFNA4; IFNA5; IFNA6; IFNA7; IFNB1; IFNgamma; DFNW1; IGBP1; IGF1; IGF1R; IGF2; IGFBP2; IGFBP3; IGFBP6; IL-1; IL10; IL10RA; IL10RB; IL11; IL11RA; IL-12; IL12A; IL12B; IL12RB1; IL12RB2; IL13; IL13RA1; IL13RA2; IL14; IL15; IL15RA; IL16; IL17; IL17B; IL17C; IL17R;

IL18; IL18BP; IL18R1; IL18RAP; IL19; IL1A; IL1B; IL1F10; IL1F5; IL1F6; IL1F7; IL1F8; IL1F9; IL1HY1; IL1R1; IL1R2; IL1RAP; IL1RAPL1; IL1RAPL2; IL1RL1; IL1RL2, ILIRN; IL2; IL20; IL20RA; IL21 R; IL22; IL22; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); EL7; EL7R; EL8; IL8RA; DL8RB; IL8RB; DL9; DL9R; DLK; INHA; INHBA; INSL3; INSL4; IRAK1; ERAK2; ITGA1; ITGA2; ITGA3; ITGA6 (a6 integrin); ITGAV; ITGB3; ITGB4 (b4 integrin); JAG1; JAK1; JAK3; JUN; K6HF; KAI1; KDR; KITLG; KLF5 (GC Box BP); KLF6; KLKIO; KLK12; KLK13; KLK14; KLK15; KLK3; KLK4; KLK5; KLK6; KLK9; KRT1; KRT19 (Keratin 19); KRT2A; KHTHB6 (hair-specific type H keratin); LAMAS; LEP (leptin); Lingo-p75; Lingo-Troy; LPS; LTA (TNF-b); LTB; LTB4R (GPR16); LTB4R2; LTBR; MACMARCKS; MAG or OMgp; MAP2K7 (c-Jun); MDK; MIB1; midkine; MEF; MIP-2; MK167; (Ki-67); MMP2; MMP9; MS4A1; MSMB; MT3 (metallothionectin-111); MTSS1; MUC1 (mucin); MYC; MY088; NCK2; neurocan; NFKB1; NFKB2; NGFB (NGF); NGFR; NgR-Lingo; NgR-Nogo66 (Nogo); NgR-p75; NgR-Troy; NME1 (NM23A); NOX5; NPPB; NR0B1; NR0B2; NR1D1; NR1D2; NR1H2; NR1H3; NR1H4; NR112; NR113; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZI; OPRD1; P2RX7; PAP; PART1; PATE; PAWR; PCA3; PCNA; POGFA; POGFB; PECAMI; PF4 (CXCL4); PGF; PGR; phosphacan; PIAS2; PIK3CG; PLAU (uPA); PLG; PLXDCI; PPBP (CXCL7); PPID; PRI; PRKCQ; PRKDI; PRL; PROC; PROK2; PSAP; PSCA; PTAFR; PTEN; PTGS2 (COX-2); PTN; RAC2 (p21 Rac2); RARB; RGSI; RGS13; RGS3; RNF110 (ZNF144); ROBO2; S100A2; SCGB1D2 (lipophilin B), SCGB2A1 (mammaglobin2); SCGB2A2 (mammaglobin 1); SCYEI (endothelial Monocyte-activating cytokine); SDF2; SERPINA1; SERPINA3; SERPINB5 (maspin); SERPINE1 (PAI-1); SERPDMF1; SHBG; SLA2; SLC2A2; SLC33A1; SLC43A1; SLIT2; SPPI; SPRR1B (Sprl); ST6GAL1; STABI; STAT6; STEAP; STEAP2; TB4R2; TBX21; TCPIO; TOGFI; TEK; TGFA; TGFBI; TGFBII; TGFB2; TGFB3; TGFBI; TGFBRI; TGFBR2; TGFBR3; THIL; THBSI (thrombospondin-1); THBS4; THPO; TIE (Tie-1); TMP3; tissue factor; TLR1; TLR2; TLR3; TLR4; TLR5; TLR6; TLR7; TLR8; TLR9; TLR10; TNF; TNF-a; TNFAEP2 (B94); TNFAIP3; TNFRSFIIA; TNFRSF1A; TNFRSF1B; TNFRSF21; TNFRSF5; TNFRSF6 (Fas); TNFRSF7; TNFRSF8; TNFRSF9; TNFSF10 (TRAIL); TNFSF11 (TRANCE); TNFSF12 (AP03L); TNFSF13 (April); TNFSF13B; TNFSF14 (HVEM-L); TNFSF15 (VEGI); TNFSFI8; TNFSF4 (OX40 ligand); TNFSF5 (CD40 ligand); TNFSF6 (FasL); TNFSF7 (CD27 ligand); TNFSFS (CD30 ligand); TNFSF9 (4-1 BB ligand); TOLLIP; Toll-like receptors; TOP2A (topoisomerase Ea); TP53; TPM1; TPM2; TRADD; TRAF1; TRAF2; TRAF3; TRAF4; TRAF5; TRAF6; TREM1; TREM2; TRPC6; TSLP; TWEAK; VEGF; VEGFB; VEGFC; versican; VHL C5; VLA-4; XCL1 (lymphotactin); XCL2 (SCM-1b); XCRI (GPR5/CCXCRI); YY1; and ZFPM2.

Preferred molecular target molecules for antibodies provided herein include CD proteins such as CD3, CD4, CD5, CD16, CD19, CD20, CD34; CD64, CD200 members of the ErbB receptor family such as the EGF receptor, HER2, HER3 or HER4 receptor; cell adhesion molecules such as LFA-1, Mac1, p150.95, VLA-4, ICAM-1, VCAM, alpha4/beta7 integrin, and alphav/beta3 integrin including either alpha or beta subunits thereof (e.g., anti-CD11a, anti-CD18, or anti-CD11b antibodies); growth factors such as VEGF-A, VEGF-C; tissue factor (TF); alpha interferon (alphaIFN); TNFalpha, an interleukin, such as IL-1 beta, IL-3, IL-4, IL-5, IL-S, IL-9, IL-13, IL 17 AF, IL-1S, IL-13R alpha1, IL13R alpha2, IL-4R, IL-5R, IL-9R, IgE; blood group antigens; flk2/flt3 receptor; obesity (OB) receptor; mpl receptor; CTLA-4; RANKL, RANK, RSV F protein, protein C etc.

In one embodiment, the multispecific antigen-binding proteins provided herein bind low density lipoprotein receptor-related protein (LRP)-1 or LRP-8 or transferrin receptor, and at least one target selected from the group consisting of 1) beta-secretase (BACE1 or BACE2), 2) alpha-secretase, 3) gamma-secretase, 4) tau-secretase, 5) amyloid precursor protein (APP), 6) death receptor 6 (DR6), 7) amyloid beta peptide, 8) alpha-synuclein, 9) Parkin, 10) Huntingtin, 11) p75 NTR, and 12) caspase-6

In one embodiment, a multispecific antigen-binding proteins provided herein binds to at least two target molecules selected from the group consisting of: IL-1 alpha and IL-1 beta, IL-12 and IL-1S; IL-13 and IL-9; IL-13 and IL-4; IL-13 and IL-5; IL-5 and IL-4; IL-13 and IL-1beta; IL-13 and IL-25; IL-13 and TARC; IL-13 and MDC; IL-13 and MEF; IL-13 and TGF-~; IL-13 and LHR agonist; IL-12 and TWEAK, IL-13 and CL25; IL-13 and SPRR2a; IL-13 and SPRR2b; IL-13 and ADAMS, IL-13 and PED2, IL17A and IL 17F, CD3 and CD19, CD138 and CD20; CD138 and CD40; CD19 and CD20; CD20 and CD3; CD3S and CD13S; CD3S and CD20; CD3S and CD40; CD40 and CD20; CD-S and IL-6; CD20 and BR3, TNF alpha and TGF-beta, TNF alpha and IL-1 beta; TNF alpha and IL-2, TNF alpha and IL-3, TNF alpha and IL-4, TNF alpha and IL-5, TNF alpha and IL6, TNF alpha and IL8, TNF alpha and IL-9. TNF alpha and IL-10, TNF alpha and IL-11, TNF alpha and IL-12, TNF alpha and IL-13, TNF alpha and IL-14, TNF alpha and IL-15, TNF alpha and IL-16, TNF alpha and IL-17, TNF alpha and IL-18, TNF alpha and IL-19, TNF alpha and IL-20, TNF alpha and IL-23. TNF alpha and IFN alpha, TNF alpha and CD4. TNF alpha and VEGF. TNF alpha and MIF, TNF alpha and ICAM-1, TNF alpha and PGE4, TNF alpha and PEG2, TNF alpha and RANK ligand, TNF alpha and Te38, TNF alpha and BAFF, TNF alpha and CD22, TNF alpha and CTLA-4, TNF alpha and GP130, TNF a and IL-12p40, VEGF and HER2, VEGF-A and HER2, VEGF-A and PDGF, HER1 and HER2, VEGFA and ANG2, VEGF-A and VEGF-C. VEGF-C and VEGF-D, HER2 and DR5, VEGF and IL-8, VEGF and MET, VEGFR and MET receptor, EGFR and MET, VEGFR and EGFR, HER2 and CD64, HER2 and CD3, HER2 and CD16, HER2 and HER3; EGFR (HER1) and HER2, EGFR and HER3, EGFR and HER4, IL-14 and IL-13, IL-13 and CD40L, IL4 and CD40L, TNFR1 and IL-1 R, TNFR1 and IL-6R and TNFR1 and IL-18R, EpCAM and CD3. MAPG and CD28, EGFR and CD64, CSPGs and RGM A; CTLA-4 and BTN02; IGF1 and IGF2; IGF1/2 and Erb2B; MAG and RGM A; NgR and RGM A; NogoA and RGM A; OMGp and RGM A; POL-1 and CTLA-4; and RGM A and RGM B.

Soluble antigens or fragments thereof, optionally conjugated to other molecules, can be used as immunogens for generating antibodies. For transmembrane molecules, such as receptors, fragments of these (e.g., the extracellular domain of a receptor) can be used as the immunogen. Alternatively, cells expressing the transmembrane molecule can be used as the immunogen. Such cells can be derived from a natural source (e.g., cancer cell lines) or may be cells which have been transformed by recombinant techniques to express the transmembrane molecule. Other antigens and forms thereof useful for preparing antibodies will be apparent to those in the art.

Activity Assays

The multispecific antigen-binding proteins provided herein can be characterized for their physical/chemical properties and biological functions by various assays known in the art.

The purified multispecific antigen-binding proteins can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments, the multispecific antigen-binding proteins provided herein are analyzed for their biological activity. In some embodiments, the multispecific antigen-binding proteins are tested for their antigen-binding activity. The antigen-binding assays that are known in the art and can be used herein include, without limitation, any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. Exemplary antigen-binding assays are provided in the Examples below.

In one embodiment provided herein is an altered multispecific antigen-binding proteins provided that possesses some but not all effector functions, which make it a desired candidate for many applications in which the half-life of the multispecific antigen-binding protein in vivo is important yet certain effector functions (such as complement and ADCC) are unnecessary or deleterious. In certain embodiments, a multispecific antigen-binding protein provided herein exhibits decreased FcγR binding activity. In certain embodiments, a multispecific antigen-binding protein provided herein comprise at least one, at least two, or three mutations in the Fc region selected from the group consisting of K322A, L234A and L235A (EU numbering). In certain embodiments, a multispecific antigen-binding protein provided herein is an aglycosylated multispecific antigen-binding protein comprising an N297A substitution mutation in the Fc region. In certain embodiments, a multispecific antigen-binding protein provided herein is an aglycosylated multispecific antigen-binding protein comprising, e.g., an N297G substitution mutation in the Fc region. In certain embodiments, a multispecific antigen-binding protein provided herein comprises a deletion at the C-terminal lysine (ΔK447) of H1 and H2. In certain embodiments, the Fc activities of the produced multispecific antigen-binding proteins are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the multispecific antigen-binding protein lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al. *PNAS (USA)* 95:652-656 (1998). C1q binding assays may also be carried out to confirm that the multispecific antigen-binding protein is unable to bind C1q and hence lacks CDC activity. To assess complement activation, a CDC assay. e.g. as described in Gazzano-Santoro et al., *J. Immunol. Methods* 202:163 (1996), may be performed. FcRn binding and in vivo clearance/half-life determinations can also be performed using methods known in the art.

Conjugated Proteins

Also provided herein are conjugated proteins such as conjugated multispecific antigen-binding protein or immunoconjugates (for example, "antibody-drug conjugates" or "ADC"), comprising any of the multispecific antigen-binding proteins described herein (e.g., a multispecific antigen-binding protein made according to the methods described herein) w % here one of the constant regions of the light chain or the heavy chain is conjugated to a chemical molecule such as a dye or cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In particular, as described herein, the use of heteromultimerization domains enables the construction of antibodies containing two different heavy chains (HC1 and HC2) as well as two different light chains (LC1 and LC2). An immunoconjugate constructed using the methods described herein may contain the cytotoxic agent conjugated to a constant region of only one of the heavy chains (HC1 or HC2) or only one of the light chains (LC1 or LC2). Also, because the immunoconjugate can have the cytotoxic agent attached to only one heavy or light chain, the amount of the cytotoxic agent being administered to a subject is reduced relative to administration of a multispecific antigen-binding protein having the cytotoxic agent attached to heavy and/or light chains. Reducing the amount of cytotoxic agent being administered to a subject limits adverse side effects associated with the cytotoxic agent.

The use of multispecific antigen-binding protein-drug conjugates for the local delivery of cytotoxic or cytostatic agents, i.e., drugs to kill or inhibit tumor cells in the treatment of cancer (Syrigos and Epenetos, Anticancer Research 19:605-614 (1999); Niculescu-Duvaz and Springer. Adv. Drg. Del. Rev. 26:151-172 (1997); U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al. Lancet (Mar. 15, 1986):603-605 (1986); Thorpe, (1985) "Antibody Carriers Of Cytotoxic Agents In Cancer Therapy: A Review," in Monoclonal Antibodies '84: Biological And Clinical Applications, A. Pinchera et al. (eds.), pp. 475-506). Maximal efficacy with minimal toxicity is sought thereby. Both polyclonal antibodies and monoclonal antibodies have been reported as useful in these strategies (Rowland et al., Cancer Immunol. Immunother. 21: 183-187 (1986)). Drugs used in these methods include daunomycin, doxorubicin, methotrexate, and vindesine (Rowland et al. (1986) supra). Toxins used in antibody-toxin conjugates include bacterial toxins such as diphtheria toxin, plant toxins such as ricin, small molecule toxins such as geldanamycin (Mandler et al. Jour. of the Nat. Cancer Inst. 92(19):1573-1581 (2000); Mandler et al. Bioorganic & Med. Chem. Letters 10:1025-1028 (2000); Mandler et al. Bioconjugate Chem. 13:786-791 (2002)), maytansinoids (EP 1391213: Liu et al. Proc. Natl. Acad. Sci. USA 93:8618-8623 (1996)), and calicheamicin (Lode et al. Cancer Res. 58:2928 (1998); Hinman et al. Cancer Res. 53:3336-3342 (1993)). The toxins may affect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the multispecific antigen-binding protein and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (pazidobenzoyl) hexanediamine), bis-diazonium derivatives (such as bis-(pdiazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon-14-labeled 1-isothiocyanatobenzyl-3-methyldiethylene triaminepentaacetic acid (MX-DTPA) is an exemplary chelating agent for conjugation of radionuclide to an antibody. See, e.g., WO 94/11026.

Conjugates of a multispecific antigen-binding protein and one or more small molecule toxins, such as a calicheamicin, maytansinoids, dolastatins, aurostatins, a trichothecene, and CC1065, and the derivatives of these toxins that have toxin activity, are also contemplated herein.

Maytansine and Maytansinoids

In some embodiments, the immunoconjugate comprises a multispecific antigen-binding protein (full length or fragments) provided herein conjugated to one or more maytansinoid molecules. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814, 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the nondisulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 81, the disclosures of which are hereby expressly incorporated by reference. Liu et al. Proc. Natl. Acad. Sci. USA 93: 8618-8623 (19%) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al. Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA. 1-maytansinoid conjugate was tested in vitro on the human breast cancer cell line SK-BR-3, which expresses 3×10 HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Multispecific antigen-binding protein-maytansinoid conjugates are prepared by chemically linking a multispecific antigen-binding protein to a maytansinoid molecule without significantly diminishing the biological activity of either the multispecific antigen-binding protein or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making multispecific antigen-binding protein maytansinoid conjugates, including, for example, those disclosed in U.S. Pat. No. 5,208,020 or EP Patent 0 425 235 B1, Chari et al. Cancer Research 52:127-131 (1992), and U.S. Patent Application Publication No. 2005/0169933, the disclosures of which are hereby expressly incorporated by reference. Antibody-maytansinoid conjugates comprising the linker component SMCC may be prepared as disclosed in U.S. Patent Application Publication No. 2005/0169933. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of a multispecific antigen-binding protein and maytansinoid may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCI), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al. Biochem. J. 173:723-737 (1978)) and N-succinimidyl-4-(2-pyridylthio) pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Auristatins and Dolastatins

In some embodiments, the immunoconjugate comprises a multispecific antigen-binding protein provided herein conjugated to dolastatins or dolastatin peptidic analogs and derivatives, the auristatins (U.S. Pat. Nos. 5,635,483 and 5,780,588). Dolastatins and auristatins have been shown to interfere with microtubule dynamics, GTP hydrolysis, and nuclear and cellular division (Woyke et al. Antimicrob. Agents and Chemother. 45(12):3580-3584 (2001)) and have anticancer (U.S. Pat. No. 5,663,149) and antifungal activity (Pettit et al. Antimicrob. Agents Chemother. 42:2961-2965 (1998)). The dolastatin or auristatin drug moiety may be attached to the multispecific antigen-binding protein through the N- (amino) terminus or the C- (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands," U.S. Application Publication No. 2005/0238649, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lubke, "The Peptides," volume 1, pp. 76-136, 1965, Academic Press) that is well known in the field of peptide chemistry. The auristatin/dolastatin drug moieties may be prepared according to the methods of: U.S. Pat. Nos. 5,635,483 and 5,780,588; Pettit el al. J. Nat. Prod. 44:482-485 (1981); Pettit et al. Anti-Cancer Drug Design 13:47-66 (1998): Poncet, Curr. Pharm. Des. 5:139-162 (1999); and Pettit, Fortschr. Chem. Org. Naturst. 70:1-79 (1997). See also Doronina, Nat. Biotechnol. 21 (7):778-784 (2003); and "Monomethylvaline Compounds Capable of Conjugation to Ligands," U.S. Application Publication No. 2005/0238649, hereby incorporated by reference in its entirety (disclosing, e.g., linkers and methods of preparing monomethylvaline compounds such as MMAE and MMAF conjugated to linkers).

Calicheamicin

In other embodiments, the immunoconjugate comprises a multispecific antigen-binding protein provided herein conjugated to one or more calicheamicin molecules. The calicheamicin family of antibiotics are capable of producing double-stranded DNA breaks at subpicomolar concentrations. For the preparation of conjugates of the calicheamicin family, see U.S. Pat. Nos. 5,712,374; 5,714,586; 5,739,116; 5,767,285; 5,770,701; 5,770,710; 5,773,001; and 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al. Cancer Research 53:3336-3342 (1993). Lode et al. Cancer Research 58:2925-2928 (1998) and the aforementioned U.S. patents to American Cyanamid). Another antitumor drug to which the multispecific antigen-binding protein can be conjugated is QFA, which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the multispecific antigen-binding proteins provided herein include BCNU, streptozoicin, vincristine and 5-fluorouracil, the family of agents known collectively LL-E33288 complex described in U.S. Pat. Nos. 5,053,394 and 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca Americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes (see, for example, WO 93/21232, published Oct. 28, 1993).

Also provided is an immunoconjugate formed between a multispecific antigen-binding protein described herein and a compound with nucleolytic activity (e.g., a ribonuclease or a DNA endonuclease such as a deoxyribonuclease; DNase).

For selective destruction of a tumor, the multispecific antigen-binding protein may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example tc99m or I123, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$, and $In^{111}$ can be attached via a cysteine residue in the peptide. Yttrium-90 can be attached via a lysine residue. The IODOGEN method (Fraker et al. Biochem. Biophys. Res. Commun. 80:49-57 (1978)) can be used to incorporate iodine-123. "Monoclonal Antibodies in Immunoscintigraphy" (Chatal, CRC Press 1989) describes other methods in detail.

Conjugates of the multispecific antigen-binding protein and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCI), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al. Science 238:1098 (1987). Carbon-14-labeled 1-isothiocyanatobenzyl-3-methyldiethylene triaminepentaacetic acid (MX-DTPA) is an exemplary chelating agent for conjugation of radionuclide to the multispecific antigen-binding protein. See, e.g., WO 94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al. Cancer Research 52:127-131 (1992); U.S. Pat. No. 5,208,020) may be used.

Such compounds include, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL, U.S.A). See pages 467-498, 2003-2004 Applications Handbook and Catalog.

Preparation of Conjugated Multispecific Antigen-Binding Proteins

In certain embodiments, a multispecific antigen-binding protein provided herein is conjugated to one or more moieties (for example, drug moieties), e.g., about 1 to about 20 moieties per multispecific antigen-binding protein, optionally through a linker. The conjugated antibodies may be prepared by several routes, employing organic chemistry reactions, conditions, and reagents known to those skilled in the art, including: (1) reaction of a nucleophilic group of a multispecific antigen-binding protein with a bivalent linker reagent via a covalent bond, followed by reaction with a moiety of interest; and (2) reaction of a nucleophilic group of a moiety with a bivalent linker reagent via a covalent bond, followed by reaction with the nucleophilic group of a multispecific antigen-binding protein. Additional methods for preparing conjugated antibodies are described herein.

The linker reagent may be composed of one or more linker components. Exemplary linker components include 6-maleimidocaproyl ("MC"), maleimidopropanoyl ("MP"), p-aminobenzyloxycarbonyl ("PAB"), N-Succinimidyl 4-(2-pyridylthio) pentanoate ("SPP"), N-Succinimidyl 4-(N-maleimidomethyl) cyclohexane-1-carboxylate ("SMCC"), and N-Succinimidyl (4-iodo-acetyl) aminobenzoate ("SIAB"). Additional linker components are known in the art and some are described herein. See also "Monomethylvaline Compounds Capable of Conjugation to Ligands," U.S. Application Publication No. 2005/0238649, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g., lysine, (iii) side chain thiol groups, e.g., cysteine, and (iv) sugar hydroxyl or amino groups where the multispecific antigen-binding protein is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e., cysteine bridges. Antibodies may be made reactive for conjugation with linker reagents by treatment with a reducing agent such as OTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the multispecific antigen-binding protein (or fragment thereof) by introducing one, two, three, four, or more cysteine residues (e.g., preparing mutant antibodies comprising one or more non-native cysteine amino acid residues).

Conjugated multispecific antigen-binding proteins may also be produced by modification of the multispecific antigen-binding protein to introduce electrophilic moieties, which can react with nucleophilic substituents on the linker reagent or drug or other moiety. The sugars of glycosylated antibodies may be oxidized, e.g., with periodate oxidizing reagents, to form aldehyde or ketone groups which may react with the amine group of linker reagents or drug or other moieties. The resulting imine Schiff base groups may form a stable linkage, or may be reduced, e.g., by borohydride reagents to form stable amine linkages. In one embodiment, reaction of the carbohydrate portion of a glycosylated multispecific antigen-binding protein with either glactose oxidase or sodium meta-periodate may yield carbonyl (aldehyde and ketone) groups in the protein that can react with appropriate groups on the drug or other moiety (Hermanson, Bioconjugate Techniques). In another embodiment, proteins containing N-terminal serine or threonine residues can react with sodium meta-periodate, resulting in production of an aldehyde in place of the first amino acid (Geoghegan and Stroh, Bioconjugate Chem. 3:138-146 (1992); U.S. Pat. No. 5,362,852). Such aldehyde can be reacted with a drug moiety or linker nucleophile.

Likewise, nucleophilic groups on a moiety (such as a drug moiety) include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups.

Alternatively, a fusion protein comprising the multispecific antigen-binding protein and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate. In yet another embodiment, the multispecific antigen-binding protein may be conjugated to a "receptor" (such streptavidin) for utilization in tumor pre-targeting wherein the multispecific antigen-binding protein-receptor conjugate is administered to the individual, followed by removal of unbound conjugate from the circulation using a clearing agent and then administration of a "ligand" (e.g., avidin) which is conjugated to a cytotoxic agent (e.g., a radionucleotide).

Utility

The present methods provided herein find industrial applicability in the production of multispecific antigen-binding proteins. The multispecific antigen-binding proteins described herein find use in, for example, in vitro, ex vivo and in vivo therapeutic methods. Provided herein are various methods based on using one or more of these molecules. In certain pathological conditions, it is necessary and/or desirable to utilize multispecific antigen-binding proteins (such as bispecific antibodies). Provide herein are multispecific antigen-binding proteins, which can be used for a variety of purposes, for example as therapeutics, prophylactics and diagnostics. For example, provided are methods of treating a disease, said methods comprising administering to a subject in need of treatment a multispecific antigen-binding protein provided herein, whereby the disease is treated. Any of the multispecific antigen-binding proteins described herein can be used in therapeutic (or prophylactic or diagnostic) methods described herein.

For example, one valuable benefit of the multispecific antigen-binding proteins provided herein is the enhanced avidity they pose for its antigen. In addition to having intrinsic high affinity on a binding unit (i.e., a Fab) to antigen basis, normal IgG antibodies also exploit the avidity effect to increase their association with antigens as a result of their bivalent binding towards the targets.

In certain embodiments, a multispecific antigen-binding protein provided herein binds epitopes on two or more antigen molecules. In certain embodiments, a multispecific antigen-binding protein binds two or more epitopes on the same antigen molecule. A multispecific antigen-binding protein directed against two separate epitopes on the same antigen molecule may not only provide the benefit of enhanced binding avidity (because of bivalent binding), but may also acquire novel properties that are not associated with either of the parent antibodies. In certain embodiments, the multispecific antigen-binding proteins provided herein find use in, for example, the blocking of receptor-ligand interactions.

The multispecific antigen-binding proteins described herein also find use in the application of simultaneously blocking the signaling pathways of two targets with one molecule.

Therapeutic Uses

The multispecific antigen-binding proteins (such as antibodies and antibody fragments described herein) may be used for therapeutic applications. In certain embodiments, provided is a method of treating a disease in a subject comprising administering to the subject an effective amount of a multispecific antigen-binding protein described herein. In certain embodiments, provided is the use of a multispecific antigen-binding protein provided herein in the manufacture of a medicament for treating a disease. In certain embodiments, provided is a multispecific antigen-binding protein for use in treating a disease in a subject.

For example, such multispecific antigen-binding proteins can be used for the treatment of tumors, including pre-cancerous, non-metastatic, metastatic, and cancerous tumors (e.g., early stage cancer), for the treatment of allergic or inflammatory disorders, or for the treatment of autoimmune disease, or for the treatment of a subject at risk for developing cancer (for example, breast cancer, colorectal cancer, lung cancer, renal cell carcinoma, glioma, or ovarian cancer), an allergic or inflammatory disorder, or an autoimmune disease.

The term cancer embraces a collection of proliferative disorders, including but not limited to pre-cancerous growths, benign tumors, and malignant tumors. Benign invade, or metastasize to distant sites. Malignant tumors will invade and damage other tissues around them. They can also gain the ability to break off from where they started and spread to other parts of the body (metastasize), usually through the bloodstream or through the lymphatic system where the lymph nodes are located. Primary tumors are classified by the type of tissue from which they arise; metastatic tumors are classified by the tissue type from which the cancer cells are derived. Over time, the cells of a malignant tumor become more abnormal and appear less like normal cells. This change in the appearance of cancer cells is called the tumor grade and cancer cells are described as being well-differentiated, moderately differentiated, poorly-differentiated, or undifferentiated. Well-differentiated cells are quite normal appearing and resemble the normal cells from which they originated. Undifferentiated cells are cells that have become so abnormal that it is no longer possible to determine the origin of the cells.

The tumor can be a solid tumor or a non-solid or soft tissue tumor. Examples of soft tissue tumors include leukemia (e.g., chronic myelogenous leukemia, acute myelogenous leukemia, adult acute lymphoblastic leukemia, acute myelogenous leukemia, mature B-cell acute lymphoblastic leukemia, chronic lymphocytic leukemia, polymphocytic leukemia, or hairy cell leukemia), or lymphoma (e.g., non-Hodgkin's lymphoma, cutaneous T-cell lymphoma, or Hodgkin's disease). A solid tumor includes any cancer of body tissues other than blood, bone marrow, or the lymphatic system. Solid tumors can be further separated into those of epithelial cell origin and those of non-epithelial cell origin. Examples of epithelial cell solid tumors include tumors of the gastrointestinal tract, colon, breast, prostate, lung, kidney, liver, pancreas, ovary, head and neck, oral cavity, stomach, duodenum, small intestine, large intestine, anus, gall bladder, labium, nasopharynx, skin, uterus, male genital organ, urinary organs, bladder, and skin. Solid tumors of non-epithelial origin include sarcomas, brain tumors, and bone tumors.

Epithelial cancers generally evolve from a benign tumor to a preinvasive stage (e.g., carcinoma in situ), to a malignant cancer, which has penetrated the basement membrane and invaded the subepithelial stroma. Multispecific antigen-binding protein complexes can also be used in these therapeutic applications, and antibodies that bind HER2 can in particular be used to treat breast cancer, colorectal cancer, lung cancer, renal cell carcinoma, glioma, or ovarian cancer.

Other subjects that are candidates for receiving compositions provided herein have, or are at risk for developing, abnormal proliferation of fibrovascular tissue, acne rosacea, acquired immune deficiency syndrome, artery occlusion, atopic keratitis, bacterial ulcers, Bechets disease, blood borne tumors, carotid obstructive disease, choroidal neovascularization, chronic inflammation, chronic retinal detachment, chronic uveitis, chronic vitritis, contact lens overwear, corneal graft rejection, corneal neovascularization, corneal graft neovascularization, Crohn's disease, Eales disease, epidemic keratoconjunctivitis, fungal ulcers, Herpes simplex infections, Herpes zoster infections, hyperviscosity syndromes, Kaposi's sarcoma, leukemia, lipid degeneration. Lyme's disease, marginal keratolysis, Mooren ulcer, Mycobacteria infections other than leprosy, myopia, ocular neovascular disease, optic pits, Osler-Weber syndrome (Osier-Weber-Rendu), osteoarthritis, Paget's disease, pars planitis, pemphigoid, phylectenulosis, polyarteritis, post-laser complications, protozoan infections, pseudoxanthoma elasticum, pterygium keratitis sicca, radial keratotomy, retinal neovascularization, retinopathy of prematurity, retrolental fibroplasias, sarcoid, scleritis, sickle cell anemia, Sogren's syndrome, solid tumors, Stargart's disease, Steven's Johnson disease, superior limbic keratitis, syphilis, systemic lupus, Terrien's marginal degeneration, toxoplasmosis, tumors of Ewing sarcoma, tumors of neuroblastoma, tumors of osteosarcoma, tumors of retinoblastoma, tumors of rhabdomyosarcoma, ulcerative colitis, vein occlusion, Vitamin A deficiency, Wegener's sarcoidosis, undesired angiogenesis associated with diabetes, parasitic diseases, abnormal wound healing, hypertrophy following surgery, injury or trauma (e.g., acute lung injury/ARDS), inhibition of hair growth, inhibition of ovulation and corpus luteum formation, inhibition of implantation, and inhibition of embryo development in the uterus.

Examples of allergic or inflammatory disorders or autoimmune diseases or disorders that may be treated using a multispecific antigen-binding protein made according to the methods described herein include, but are not limited to arthritis (rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polvarthritis chronica primaria, reactive arthritis, and ankylosing spondylitis), inflammatory hyperproliferative skin diseases, psoriasis such as plaque psoriasis, guttate psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spinaoptical MS, primary progressive MS (PPMS), and relapsing remitting MS (RRMS), progressive systemic sclerosis, atherosclerosis, arteriosclerosis, sclerosis disseminata, and ataxic sclerosis, inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis, respiratory distress syndrome, including adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune mediated GN, membranous GN (membranous nephropathy), idiopathic membranous GN or idiopathic membranous nephropathy, membrane- or membranous proliferative GN (MPGN), including Type I and Type II, and rapidly progressive GN, allergic conditions, allergic reaction, eczema including allergic or atopic eczema, asthma such as asthma bronchiale, bronchial asthma, and auto-immune asthma, conditions involving infiltration of T-cells and chronic inflammatory responses, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extra-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis nodosa), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia. Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune\ neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, immune complex nephritis, antibody-mediated nephritis, neuromyelitis optica, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiffman or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barre syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS: Lou Gehrig's disease), coronary artery disease, autoimmune ear disease such as autoimmune inner ear disease (AIED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressier's syndrome, alopecia areata, CREST syndrome (calcinosis, Raynaud's phenomenon, esophageal dysmotility, sclerodactyly, and telangiectasia), male and female autoimmune infertility, mixed connective tissue disease, Chagas' disease, rheumatic fever, recurrent abortion, farmer's lung, erythema multiforme, postcardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetal is, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthalmopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermatogenesis, autoimmune hemolysis, Boeck's disease, cryoglobulinemia, Dupuytren's contracture, endophthalmitis phacoanaphylactica, enteritis allergica, erythema nodosum leprosum, idiopathic facial paralysis, chronic fatigue syndrome, febris rheumatica, Hamman-Rich's disease, sensoneural hearing loss, hemoglobinuria paroxistica, hypogonadism, ileitis regionalis, leucopenia, mononucleosis infectiosa, traverse myelitis, primary idiopathic myxedema, nephrosis, ophthalmia simpatica, orchitis granulomatosa, pancreatitis, polyradiculitis acuta, pyoderma gangrenosum, Quervain's thyreoiditis, acquired spenic atrophy, infertility due to antispermatozoan antobodies, non-malignant thymoma, vitiligo, SCID and Epstein-Barr virus-associated diseases, acquired immune deficiency syndrome (AIDS), parasitic diseases such as Leishmania, toxic shock syndrome, food poisoning, conditions involving infiltration of T-cells, leukocyte adhesion deficiency, immune responses associated with acute and delayed hypersensitivity mediated by cytokines and T-lymphocytes, diseases involving leukocyte diapedesis, multiple organ injury syndrome, antigen-antibody complex mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolysis bullosa acquisita (EBA), hemochromatosis, myocarditis, nephrotic syndrome, primary sclerosing cholangitis, purulent or non-purulent sinusitis, acute or chronic sinusitis, ethmoid, frontal, maxillary, or sphenoid sinusitis, an eosinophil-related disorder such as eosinophilia, pulmonary infiltration eosinophilia, eosinophiliamyalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polvendocrine autoimmune disease, sclerosing cholangitis, sclera, episclera, chronic mucocutaneous candidiasis, Bruton's syndrome, transient hypogammaglobulinemia of infancy, Wiskott-Aidrich syndrome, ataxia telangiectasia, autoimmune disorders associated with collagen disease, rheumatism, neurological disease, ischemic reperfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

In addition to therapeutic uses, the multispecific antigen-binding proteins provide herein can be used for other purposes, including diagnostic methods, such as diagnostic methods for the diseases and conditions described herein.
Dosages, Formulations, and Duration The proteins provided herein will be formulated, dosed, and administered in a fashion consistent with good medical practice. Factors for consideration in this context include the particular disorder being treated, the particular mammal being treated, the clinical condition of the individual subject, the cause of the disorder, the site of delivery of the agent, the method of administration, the scheduling of administration, and other factors known to medical practitioners. The "therapeutically effective amount" of the proteins to be administered will be governed by such considerations, and is the minimum amount necessary to prevent, ameliorate, or treat a particular disorder (for example, a cancer, allergic or inflammatory disorder, or autoimmune disorder). The proteins need not be, but are optionally, formulated with one or more agents currently used to prevent or treat the disorder. The effective amount of such other agents depends on the amount of proteins present in the formulation, the type of disorder or treatment, and other factors discussed above. These are generally used in the same dosages and with administration routes as used hereinbefore or about from 1 to 99% of the heretofore employed dosages. Generally, alleviation or treatment of a cancer involves the lessening of one or more symptoms or medical problems associated with the cancer. The therapeutically effective amount of the drug can accomplish one or a combination of the following: reduce (by at least 10%, 20%, 30%, 40%, 50%, 60%, 70%, 80%, 90%, 100% or more) the number of cancer cells; reduce or inhibit the tumor size or tumor burden; inhibit (i.e., to decrease to some extent and/or stop) cancer cell infiltration into peripheral organs; reduce hormonal secretion in the case of adenomas; reduce vessel density; inhibit tumor metastasis; reduce or inhibit tumor growth; and/or relieve to some extent one or more of the symptoms associated with the cancer. In some embodiments, the proteins are used to prevent the occurrence or reoccurrence of cancer or an autoimmune disorder in the subject.

In one embodiment, the compositions provided herein be used for increasing the duration of survival of a human subject susceptible to or diagnosed with a cancer or autoimmune disorder. Duration of survival is defined as the time from first administration of the drug to death. Duration of survival can also be measured by stratified hazard ratio (HR) of the treatment group versus control group, which represents the risk of death for a subject during the treatment.

In certain embodiments, the treatment significantly increases response rate in a group of human subjects susceptible to or diagnosed with a cancer who are treated with various anti-cancer therapies. Response rate is defined as the percentage of treated subjects who responded to the treatment. In one aspect, the combination treatment comprises use of multispecific antigen-binding proteins provided herein and surgery, radiation therapy, or one or more chemotherapeutic agents significantly increases response rate in the treated subject group compared to the group treated with surgery, radiation therapy, or chemotherapy alone, the increase having a Chi-square p-value of less than 0.005. Additional measurements of therapeutic efficacy in the treatment of cancers are described in U.S. Patent Application Publication No. 20050186208.
Pharmaceutical Compositions and Formulations The multispecific antigen-binding proteins disclosed herein can be formulated with suitable carriers or excipients so that they are suitable for administration. Suitable formulations of the multispecific antigen-binding proteins disclosed herein are obtained by mixing multispecific antigen-binding proteins disclosed herein having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins: hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary antibody formulations, which can be applied to the multispecific antigen-binding proteins provided herein, are described in WO98/56418, expressly incorporated herein by reference. Lyophilized formulations adapted for subcutaneous administration are described in WO97/04801. Such lyophilized formulations may be reconstituted with a suitable diluent to a high protein concentration and the reconstituted formulation may be administered subcutaneously to the mammal to be treated herein.

The formulation herein may also contain more than one active compound as necessary for the particular indication being treated, preferably those with complementary activities that do not adversely affect each other. For example, it may be desirable to further provide an anti-neoplastic agent, a growth inhibitory agent, a cytotoxic agent, or a chemotherapeutic agent. Such molecules are suitably present in combination in amounts that are effective for the purpose intended. The effective amount of such other agents depends on the amount of multispecific antigen-binding protein present in the formulation, the type of disease or disorder or treatment, and other factors discussed above. These are generally used in the same dosages and with administration routes as described herein or about from 1 to 99% of the heretofore employed dosages. The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in *Remington's Pharmaceutical*

Sciences 16th edition, Osol, A. Ed. (1980). Sustained-release preparations may be prepared. Suitable examples of sustained release preparations include semi-permeable matrices of solid hydrophobic polymers containing the antagonist, which matrices are in the form of shaped articles. e.g. films, or microcapsules. Examples of sustained-release matrices include polyesters, hydrogels (for example, poly(2-hydroxyethylmethacrylate), or poly(vinylalcohol)), polylactides (U.S. Pat. No. 3,773,919), copolymers of L-glutamic acid and, ethyl-L-glutamate, non-degradable ethylene-vinyl, degradable lactic acid-glycolic acid copolymers such as the LUPRON DEPOT™ (injectable microspheres composed of lactic acid-glycolic acid copolymer and leuprolide acetate), and poly-D-(−)-3-hydroxy butyric acid.

Lipofectins or liposomes can be used to deliver the multispecific antigen-binding proteins disclosed herein or compositions provided herein into cells.

Optionally, but preferably, the formulation contains a pharmaceutically acceptable salt, preferably sodium chloride, and preferably at about physiological concentrations. Optionally, the formulations can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations can include a pharmaceutically acceptable surfactant at a concentration of 0.005 to 0.02%.

Sustained-release preparations may be prepared. Suitable examples of sustained-release preparations include semipermeable matrices of solid hydrophobic polymers containing the multispecific antigen-binding protein, which matrices are in the form of shaped articles, e.g., films, or microcapsule. Examples of sustained-release matrices include polyesters, hydrogels (for example, poly(2-hydroxyethylmethacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated multispecific antigen-binding protein(s) remain in the body for a long time, they may denature or aggregate as a result of exposure to moisture at 37° C. resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The proteins described herein (e.g., a multispecific antigen-binding protein (such as an bispecific antibody) provided herein) are administered to a human subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration may be particularly desired if extensive side effects or toxicity is associated with antagonism to the target molecule recognized by the proteins. An ex vivo strategy can also be used for therapeutic applications. Ex vivo strategies involve transfecting or transducing cells obtained from the subject with a polynucleotide encoding a protein provided herein. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells.

In one example, the multispecific antigen-binding protein (such as a bispecific antibody) is administered locally, e.g., by direct injections, when the disorder or location of the tumor permits, and the injections can be repeated periodically. The protein complex can also be delivered systemically to the subject or directly to the tumor cells, e.g., to a tumor or a tumor bed following surgical excision of the tumor, in order to prevent or reduce local recurrence or metastasis.

Diagnosis and Imaging

Multispecific antigen-binding proteins (such as bispecific antibodies) provided herein can be used to assay protein levels in a biological sample using classical immunohistological methods known to those of skill in the art (e.g., see Jalkanen, et al., *J. Cell. Biol.* 101:976-985 (1985); Jalkanen, et al., *J. Cell. Biol.* 105:3087-3096 (1987)). Other antibody-based methods useful for detecting protein gene expression include immunoassays, such as the enzyme linked immunosorbent assay (ELISA) and the radioimmunoassay (RIA) can be adapted for use with a multispecific antigen-binding protein (such as an bispecific antibody) provided herein. Suitable assay labels are known in the art and include enzyme labels, such as, glucose oxidase; radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminol; and fluorescent labels, such as fluorescein and rhodamine, and biotin.

Techniques known in the art may be applied to multispecific antigen-binding proteins (such as bispecific antibodies) provided herein. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003). One can also study overexpression of one or more antigens of interest by measuring shed antigen(s) in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., *J. Immunol. Methods* 132: 73-80 (1990)) adapted for use with multispecific antigen-binding proteins (such as bispecific antibodies) provided herein. Aside from the above assays, various in vivo and ex vivo assays are available to the skilled practitioner. For example, one can expose cells within the body of the mammal to multispecific antigen-binding proteins (such as bispecific antibodies) provided herein which are optionally labeled with a detectable label, e.g., a radioactive isotope, and binding of the multispecific antigen-binding proteins (such as bispecific antibodies) to one or more antigen(s) of interest can be evaluated, e.g., by external scanning for radioactivity or by analyzing a sample (e.g., a biopsy or other biological sample) taken from a mammal previously exposed to the multispecific antigen-binding protein.

Articles of Manufacture and Kits

Also provided are articles of manufacture containing one or more multispecific antigen-binding proteins (such as bispecific antibodies) described herein, and materials useful for the treatment or diagnosis of a disorder (for example, an autoimmune disease or cancer). In certain embodiments, the article of manufacture comprises a container and a label or package insert on or associated with the container. Suitable containers include, for example, bottles, vials, syringes, etc. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). At least one active agent in the composition is a multispecific antigen-binding protein (such as a bispecific antibody) provided herein. The label or package insert indicates that the composition is used for treating the particular condition. The label or package insert will further comprise instructions for administering the multispecific antigen-binding protein composition to the subject. Articles of manufacture and kits comprising combinatorial therapies described herein are also contemplated.

"Package insert" refers to instructions customarily included in commercial packages of therapeutic products that contain information about the indications, usage, dosage, administration, contra indications and/or warnings concerning the use of such therapeutic products. In certain embodiments, the package insert indicates that the composition is used for treating breast cancer, colorectal cancer, lung cancer, renal cell carcinoma, glioma, or ovarian cancer.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials considered from a commercial and user standpoint, including other buffers, diluents, filters, needles, and syringes.

Kits are also provided that are useful for various purposes, e.g., for purification or immunoprecipitation of two or more target antigens from cells. For isolation and purification of two or more target antigens, the kit can contain a multispecific antigen-binding protein (e.g., an EGFR/HER2 antibody) coupled to beads (e.g., sepharose beads). Kits can be provided which contain the multispecific antigen-binding protein(s) for detection and quantitation of the antigen in vitro, e.g., in an ELISA or a Western blot. As with the article of manufacture, the kit comprises a container and a label or package insert on or associated with the container. The container holds a composition comprising at least one multispecific antigen-binding protein (such as a bispecific antibody) provided herein. Additional containers may be included that contain, e.g., diluents and buffers or control antibodies. The label or package insert may provide a description of the composition as well as instructions for the intended in vitro or diagnostic use.

Computer Implementation

Provided herein is a computer readable medium for evaluating a multispecific antigen binding protein comprising 1) a first heavy chain/light chain pair binding to a first antigen which comprises a first heavy chain sequence (H1) and a first light chain sequence (L1), and 2) a second heavy chain/light chain pair binding to a second antigen which comprises a second heavy chain sequence (H2) and a second light chain sequence (L2), wherein each H1 and H2 comprises a heavy chain variable domain (VH) and a heavy chain constant domain (CH1), and each L1 and L2 comprises a light chain variable domain (VL) and a light chain constant domain (CL).

In certain embodiments, the computer readable medium comprises a dataset comprising data representing amino acid substitutions in H1, L1, H2, and L2, wherein at least one of the amino acid substitutions in the CH1 domain of H1 comprises an amino acid substitution at position S183 with reference to SEQ ID NO:1, and wherein the CL domain comprises an amino acid substitution at position V133 with reference to SEQ ID NO:2. In certain embodiments, the computer readable medium comprises a dataset comprising data representing amino acid substitutions in H1, L1, H2, and L2, wherein at least one of the amino acid substitutions in the CH1 domain of H1 comprises an amino acid substitution at position F170 or L128 and V185 with reference to SEQ ID NO: 1, and wherein the CL domain comprises an amino acid substitution at position 5176 or F118 and L135 with reference to SEQ ID NO:2. In certain embodiments, the computer readable medium comprises a dataset comprising data representing amino acid substitutions in H1, L1, H2, and L2, wherein at least one of the amino acid substitutions in the CH1 domain of H1 comprises an amino acid substitution at position S182, F170 or L128, and V185 with reference to SEQ ID NO:1, wherein the CL domain comprises an amino acid substitution at position V13, S176 or F118, and L135 with reference to SEQ ID NO:2.

In certain embodiments, the computer readable medium for evaluating a multispecific antigen binding protein comprises computer executable code for determining the likelihood that H1 will preferentially pair with L1 as compared to L2 and/or H2 will preferentially pair with L2 as compared to L1.

In certain embodiments, a computer comprises at least one processor coupled to a chipset. Also coupled to the chipset are a memory, a storage device, a keyboard, a graphics adapter, a pointing device, and a network adapter. A display is coupled to the graphics adapter. In one embodiment, the functionality of the chipset is provided by a memory controller hub and an V/O controller hub. In another embodiment, the memory is coupled directly to the processor instead of the chipset.

The storage device is any device capable of holding data, like a hard drive, compact disk read-only memory (CD-ROM), DVD, or a solid-state memory device. The memory holds instructions and data used by the processor. The pointing device may be a mouse, track ball, or other type of pointing device, and is used in combination with the keyboard to input data into the computer system. The graphics adapter displays images and other information on the display. The network adapter couples the computer system to a local or wide area network.

As is known in the art, a computer can have different and/or other components than those described previously. In addition, the computer can lack certain components. Moreover, the storage device can be local and/or remote from the computer (such as embodied within a storage area network (SAN)).

As is known in the art, the computer is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device, loaded into the memory, and executed by the processor.

The foregoing written description is considered to be sufficient to enable one skilled in the art to practice the invention. The following Examples are offered for illustrative purposes only, and are not intended to limit the scope of the present invention in any way. Indeed, various modifications in addition to those shown and described herein will become apparent to those skilled in the art from the foregoing description and fall within the scope of the appended claims.

EXAMPLES

Example 1: Engineering Antibody Heavy Chain/Light Chain Pairs Using Strategy #1

Fab assembly is independently driven by VH/VL and CH1/CL domain interaction. CL destabilizing mutations may only have modest effect on antigen binding; yet disruption of the interaction between the CH1 and CL domains can interfere with the antibody folding and secretion in mammalian cells (data not shown). We generated a panel of CH1/CL mutation pairs to direct specific and correct HC and LC pairing and minimize HC/LC mispairing. The ability of CH1/CL mutation pairs to direct correct pairing was examined as described in further detail below.

Mutations at F118, V133, or L135 in the CL domain were found to perturb assembly with CH1 (data not shown). To identify amino acid positions in the CH1 domain that restore assembly with mutated CL domains, antibody constant domains PDB ID 1CZ8 were prepared using PyMol. Using human-guided design based on detailed knowledge of the structure and function of the heavy chain CH1 domain and light chain CL domain, substitutions at positions L128, G143, L145, S183, and V185, alone or in combination, of the CH1 domain were tested. Heavy chains bearing a charged amino acid substitution mutation at position S183 were shown to improve antibody expression in the context of oppositely charged CL substitution mutations (see FIGS. 1A and 1B). FIGS. 1A and 1B show protein A recovery from 1 ml 293T cultures (A280 absorbance units (A.U.)). Thus, S183 mutants were selected for further analysis.

Mutant CH1 and mutant CL domains were screened to initially identify mutation pairs that restore antibody expression. As an initial screen, antibody light chains bearing a CL in which F118, V133, or L135 was substituted with a positively charged amino acid (i.e., K or R) were generated and heavy chains bearing a CH1 in which S183 was substituted with a negatively charged amino acid (i.e., E or D) were generated using standard molecular biology techniques and cloned into mammalian expression vectors. Plasmids encoding a heavy chain CH1 domain bearing an S183E or S183D mutation and alight chain CL domain bearing a F118K, F118R, V133K, V133R, V135K, or L135R substitution mutation were co-transfected in equal concentrations using 1 mL transient transfection cultures of HEK293T cells as previously described (see, e.g., Bos et al. (2014) "Development of a semi-automated high throughput transient transfection system." *Journal of Biotechnology* 180, 10-16). This procedure was repeated for every pairwise combination of CH1 and CL mutants.

Figure 2:
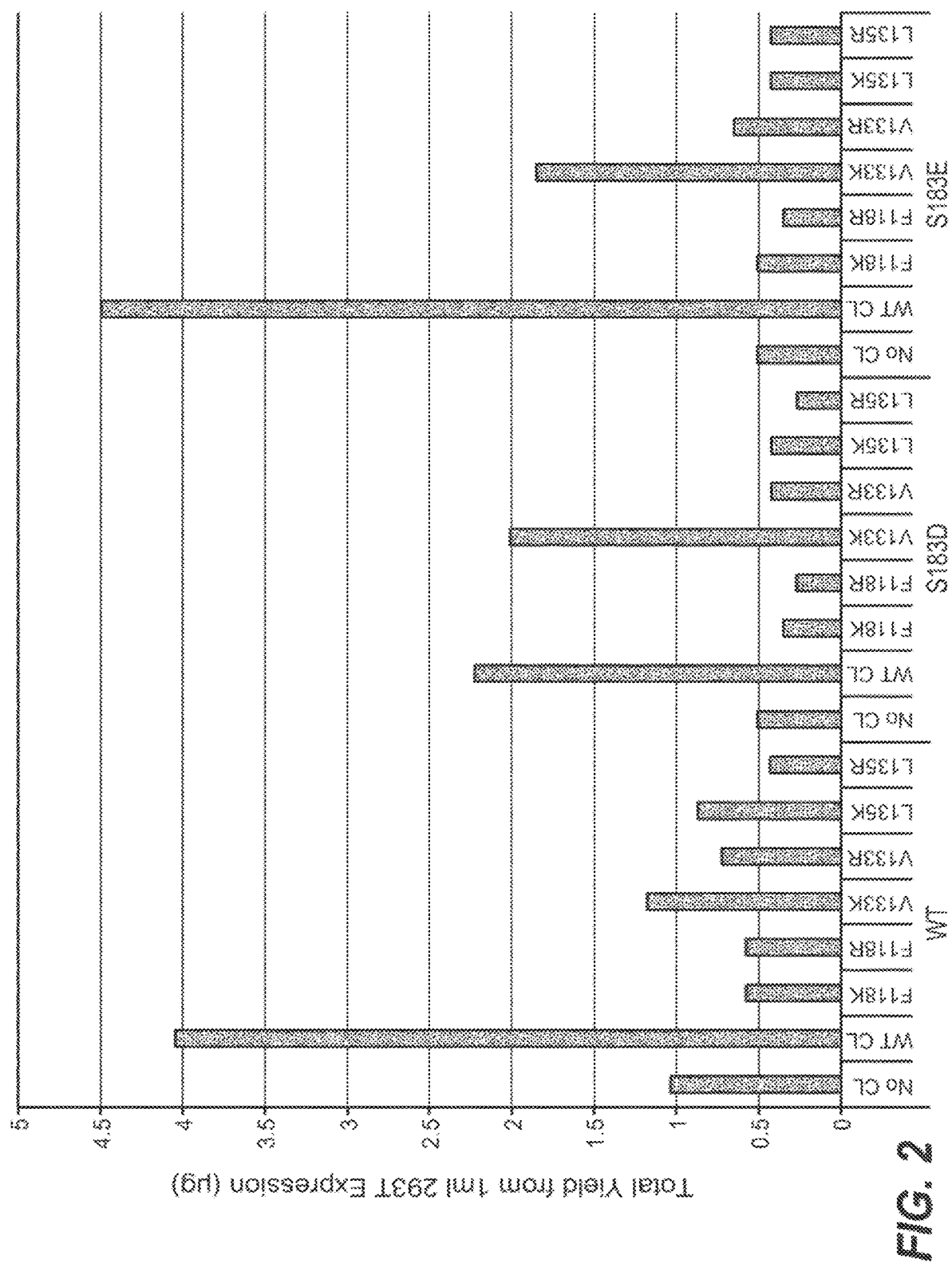
FIG. 2 provides the results of mammalian culture expression assays that were performed to identify amino acid mutations in CH1 that restore antibody expression when co-expressed with CL having a F118, V133, or L135 substitution mutation.

Human IgG1 was purified from mammalian culture supernatants by MabSelectSure (GE Healthcare, USA) according to the manufacturer's protocol, and antibody expression was calculated by OD280 measurement of the purified MabSelectSure eluate. As shown in FIG. 2, antibody expression was improved when the V133K CL mutation was paired with the S183D CH1 mutation or the S183E CH1 mutation as compared to V133K paired with wide type CH1. Total antibody yield (μg) obtained from 150 μL volume MabSelectSure purification eluate is shown on the y-axis of FIG. 2.

Figure 3:
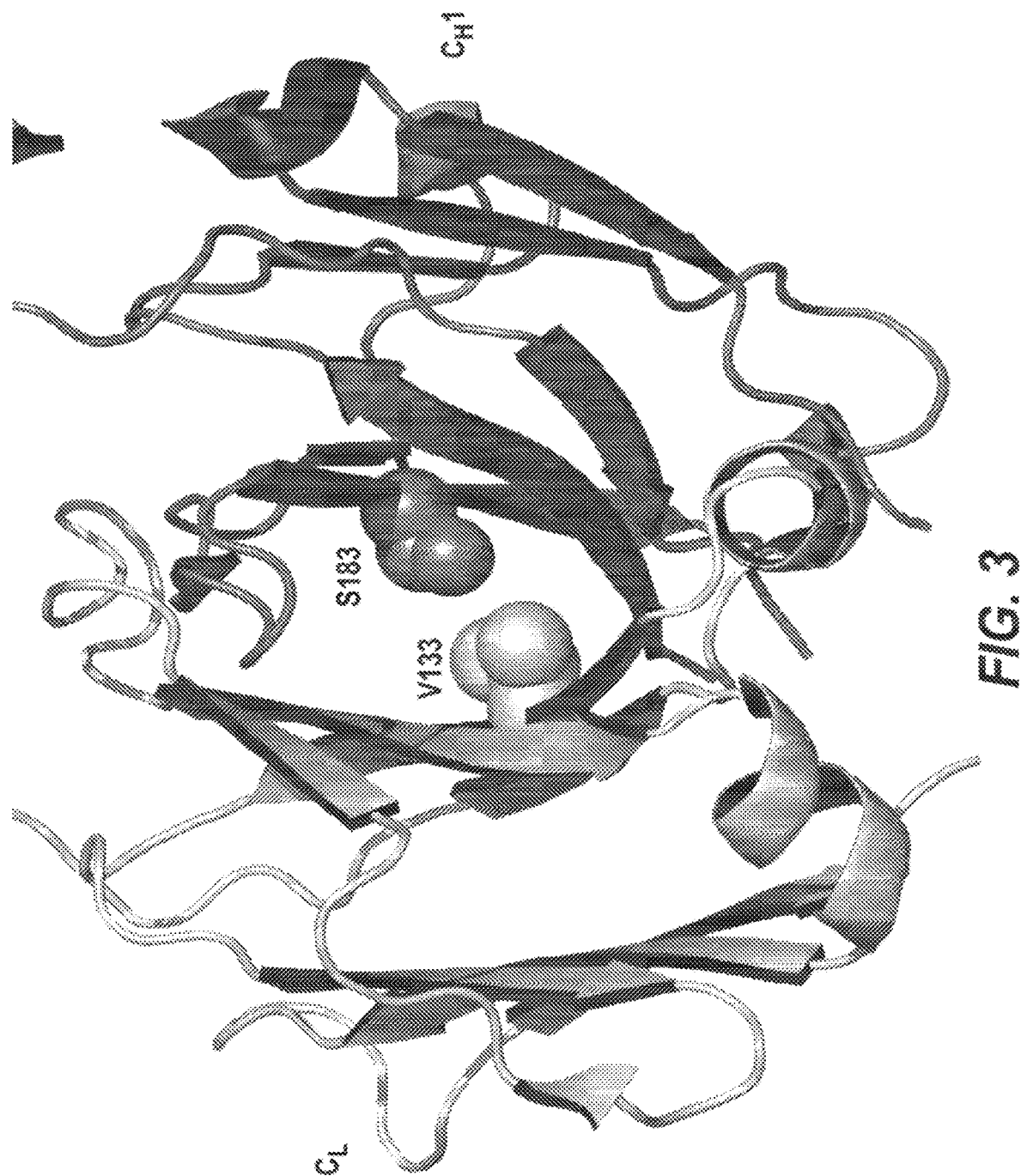
FIG. 3 provides a schematic of the interior of the interface of the light chain constant region (CL) and the heavy chain CH1 domain.

As shown in the X-ray crystal structure provided in FIG. 3, V133 in the light chain constant domain (CL) and S183 in the heavy chain CH1 domain reside at the interior of the interface of the light chain CL and heavy chain CH1 domains of IgG. The structure is similar in IgG4, S183 (EU numbering, equivalent to S188 under the Kabat numbering) of CH1 is conserved across human and mouse germlines, and V133 is present in human and mouse kappa and lambda light chains. Without being limited to any one theory, the substitution of a charged amino acid at V133 and the substitution of an amino acid having an opposite charge at S183 may create new, stabilizing interactions with surrounding amino acid residues (such as S176 and S178 in the CL domain) that are not present in the unmodified CH1/CL interface.

Further experiments were performed to identify additional specific V133X/S183X mutant pairs that showed good levels of antibody expression. V133X/S183X mutant pairs that favor CH1-CL pairing were identified using the antibody expression assay described above. Briefly, antibody heavy chains bearing a CH1 S183X substitution mutation (e.g., S183A, S183T, S183V, S183Y, S183F, S183H, S183N, S183D, S183E, S183R, or S183K) and light chains bearing a V133X substitution mutation (e.g., V133E, V133S, V133L, V133W, V133K, V133R, or V133D) were generated as described above. Plasmids expressing a heavy chain and light chain with each of the above mutations CH1 and CL mutations were co-transfected in equal concentrations using 30 mL transient transfection cultures of HEK293T cells as described above. This procedure was repeated for every combination of V133X/S183X mutant pairs. Total antibody yield (μg) was determined as described above. Expression results for each V133X/S183X mutant pair are provided in FIG. 4. Briefly, FIG. 4 shows the total yield in mg of purified protein from a 30 ml 293T cultures for each V133X/S183X mutant pair. Antibody protein level was calculated from the OD280 measurement of purified MabSelectSure eluates. V133X/S183X mutant pairs such as V133K/S183T, V133K/S183V, V133K/S183Y, and V133K/S183F, which demonstrated good levels of antibody expression, were introduced into one arm of an anti-Her 2/anti-CD3 bispecific antibody. Although the initial result of V133K/S183E expression was not high, V133K/S183E was also tested in the context of the anti-Her 2/anti-CD3 bispecific antibody. The anti-Her 2 (4D5) and anti-CD3 (UCHT1) antibodies were selected based on the following criteria: a) both heavy and light chains are required for antigen binding; b) component antibodies are expressed well and not prone to aggregating; and c) the parent antibodies show no significant preference for cognate over non-cognate heavy/light chain pairing. "4D5" refers to humanized 4D5v8, described in Carter et al. (1992) *Proc. Natl. Acad. Sci. USA* 89, 4285-9. "UCHT1" refers to humanized UCHT1v9, described in Zhu and Carter (1995) *J. Immunol.* 155, 1903-10.

In this experiment, the UCHT1 heavy chain contains a hole mutation in the CH3 domain (T366S, L368A, Y407V) and the 4D5 heavy chain contains a knob mutation in the CH3 domain (T366W). A 4D5/UCHT1 bispecific antibody bearing V133K/S183E mutations in the UCHT1 arm was expressed, purified, and analyzed via quadrupole-time-of-flight (QTOF) mass spectrometry to quantify the relative abundance of each of the antibody species present in the purified sample. The unbiased, expected amount of correct heavy/light chain pairing of wild type sequences+scrambled heavy/light chain pairing (i.e., HC1/LC2 and HC2/LC1) is 50%. As shown below in the first and third rows of Table 14C, correct heavy chain/light chain pairing is improved in the 4D5/UCHT1 antibody variant bearing V133K/S183E in the UCHT1 arm.

4D5/UCHT1 antibodies bearing a V133K/S183T, V133K/S183V, V133K/S183Y, V133K/S183E, or V133K/S183F mutation pair in either the 4D5 arm or the UCHT1 arm were expressed, purified and analyzed via quadrupole-time-of-flight (QTOF) mass spectrometry to quantify the relative abundance of each of the antibody species present in the purified samples.

Prior to expression, purification, and analysis of the 4D5/UCHT1 antibodies, light chain ratio optimization was carried out with 30 ml transient transfection cultures of HEK293T cells using the methods previously described (see, e.g., Bos et al. (2014), supra). Quantities of plasmid DNA encoding the two antibody heavy chains remained constant through all transfections, while the transfected quantity of light chain DNA was varied across a range of LC1 (knob):LC2 (hole) DNA ratios. The products of the transiently transfected cultures were analyzed by Orbitrap mass spectrometry in order to identify conditions with optimally balanced light chain expression, i.e., conditions under which the highest percentage of properly assembled bispecific antibody was produced.

A mathematical formula was developed to distinguish the amount of BsIgG with correctly paired light chains (i.e., a bispecific antibody in which LC-1 is paired with HC-1 and LC-2 is paired with HC-2) from the 2×LC scrambled species (i.e., a bispecific antibody in which LC-2 is paired with HC-1 and LC-1 is paired with HC-2), based on the quantification of the three peaks from high-resolution mass spectrometry. Assuming that the LC pairing of the knob heavy chain ($HC_{knob}$) and hole heavy chain ($HC_{hole}$) are completely independent events. The percentage of the correctly paired BsIgG, % [BsIgG], can be calculated as:

% [BsIgG]=% [Combined BsIgG & 2×LC scrambled]/2+SQRT((% [Combined BsIgG & 2×LC scrambled]/2)$^2$-% [2×$LC_{knob}$]*% [2×$LC_{hole}$])

If ((% [Combined BsIgG & 2×LC scrambled]/2)$^2$-% [2×$LC_{knob}$]*% [2×$LC_{hole}$]) is a negative number, it is forced to be zero; then:

% [BsIgG]=% [Combined BsIgG & 2×scrambled]/2

Therefore, the percentage of the 2×LC scrambled species is calculated as:

% [2×$LC$ scrambled]=% [Combined BsIgG & 2×$LC$ scrambled]-% [BsIgG]

To experimentally confirm this mathematical approach, two samples of purified bispecific antibody were analyzed via mass spectrometry. The combined BsIgG and 2×LC scrambled fractions in Sample 1 were 51.3%, and the combined BsIgG and 2×LC scrambled fractions in Sample 2 were 70.6%. Using the formula above, the numbers of % [BsIgG], % [2×$LC_{knob}$], % [2×$LC_{hole}$] and % [2×LC scrambled] were determined (see Table 10), from which the fractions of each Fab species, % [$Fab_{knob}$], % [$Fab_{hole}$], % [$LC_{knob}$/$HC_{hole}$] and % [$LC_{hole}$/$HC_{knob}$], were also calculated (see Table 11). Both samples were treated with Lysyl endopeptidase before being analyzed by mass spectrometry. The measured fractions of the digested Fab species were then compared to those calculated. The closely matched measured and calculated percentages from both samples verified our mathematical approach for quantifying the correctly paired BsIgG species.

TABLE 10

| | % BsIgG + 2× LC scrambled | % 2× $LC_{knob}$ | % 2× $LC_{hole}$ | % BsIgG | % 2× LC scrambled |
|---|---|---|---|---|---|
| Sample 1 | 51.3 | 27.8 | 20.9 | 25.7 | 25.6 |
| Sample 2 | 70.6 | 6.0 | 23.4 | 68.5 | 2.1 |

TABLE 11

| | % Fab | $Fab_{knob}$ | $Fab_{hole}$ | $LC_{knob}$/$HC_{hole}$ | $LC_{hole}$/$HC_{knob}$ |
|---|---|---|---|---|---|
| Sample 1 | Calculated | 26.8 | 23.3 | 26.7 | 23.2 |
| | Measured | 25.5 | 22.7 | 25.6 | 26.3 |
| | Δ | -1.3 | -0.6 | -1.1 | 3.1 |
| Sample 2 | Calculated | 37.3 | 45.9 | 12.7 | 4.1 |
| | Measured | 38.1 | 47.8 | 11.3 | 2.8 |
| | Δ | 0.8 | 1.9 | -1.4 | -1.3 |

As shown in the exemplary results in Table 12, the % of bispecific assembly was increased as compared to wild type sequence without the V133X/S183X mutations. Percentage of bispecific assembly was comparable when the V133X/S183X mutant pair present in the 4D5 arm as compared to when the V133/S183 mutant pair present in the UCHT1 arm. Such results suggest that proper bispecific antibody assembly is not significantly influenced by the arm into which a V133X/S183X mutant pair is introduced.

TABLE 12

| Optimal LC Ratio (Knob:Hole) | CL/CH1 Mutations | Location (Arm) | Combined BsIgG and LC scrambled | 2x Knob LC | 2x Hole LC | BsIgG | LC Scrambled |
|---|---|---|---|---|---|---|---|
| 1:1 | V133K/S183T | 4D5 | 63.2% | 26.8% | 10.0% | 58.6% | 4.6% |
| 1.5:1 | V133K/S183T | UCHT1 | 64.0% | 16.1% | 19.8% | 58.6% | 5.4% |
| 2:1 | V133K/S183E | 4D5 | 65.1% | 20.1% | 14.8% | 60.2% | 4.9% |
| 1:1 | V133K/S183E | UCHT1 | 51.8% | 29.9% | 18.3% | 37.0% | 14.8% |

The experiment described above was repeated using a different bispecific antibody. Results using a different bispecific antibody also suggest that bispecific antibody assembly is not significantly influenced by the arm into which a V133X/S183X mutant pair is introduced. It was also observed that in cases where the parent antibody already exhibits strong preferential heavy/light chain pairing, further improvement is difficult to achieve or detect.

Figure 5:
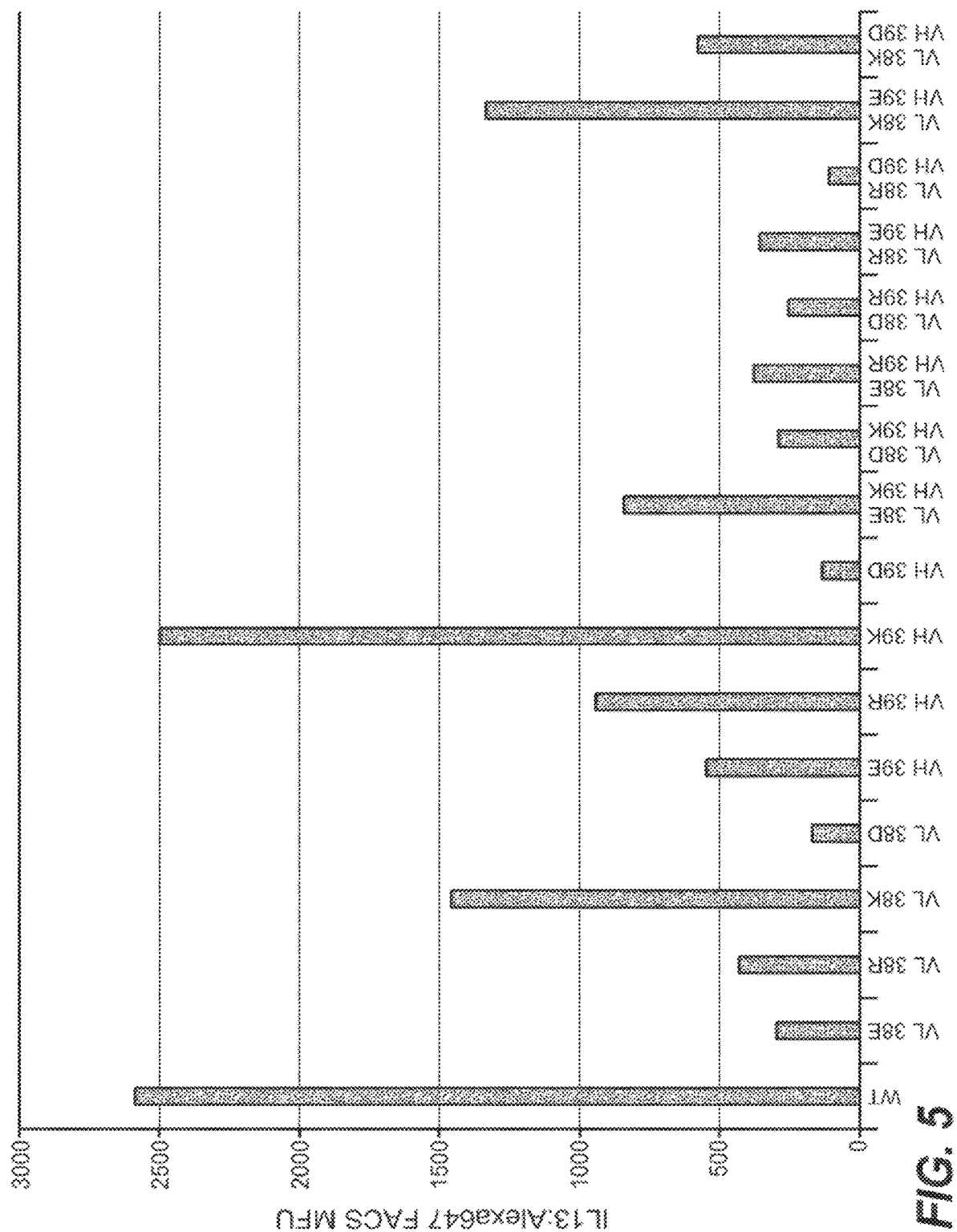
FIG. 5 shows the results of FACS analyses of binding to the antigen IL-13 of various mutant antibodies with amino acid substitutions either in VH Q39 or VL Q38 or both.
Figure 6:
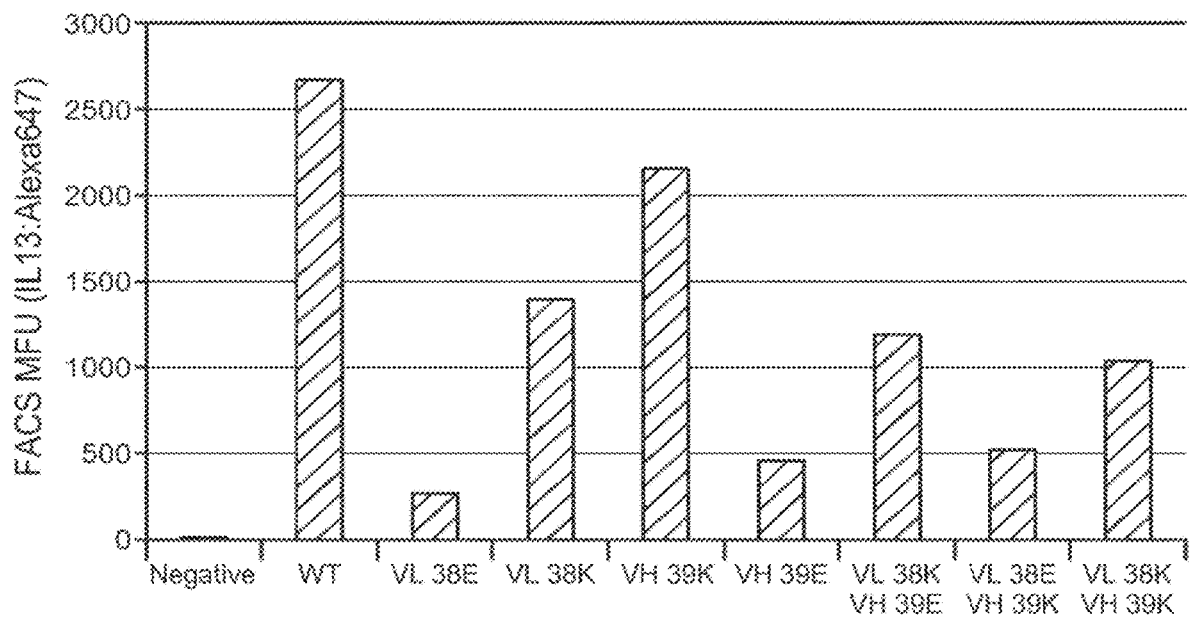
FIG. 6 the results of additional FACS analyses that were performed to identify Q39X-VH/Q38X-VL mutant pairs that favor VH/VL pairing.
Figure 7:
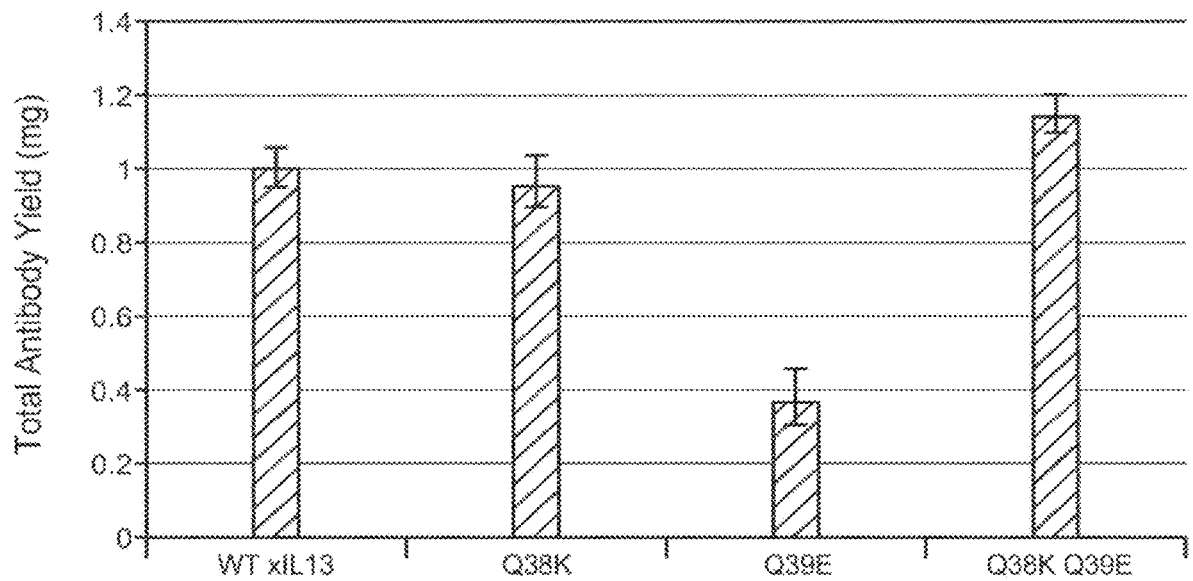
FIG. 7 shows the results of mammalian culture expression assays that were performed to identify Q39X-VH/Q38X-VL mutant pairs that favor VH/VL pairing.

Next, we examined whether additional mutations in the VH and VL non-CDR regions could further improve HC and LC pairing. VL-Q38 and VH-Q39 in the frame work regions that form a hydrogen bond are highly conserved across most germlines. A charged residue was introduced into either the VL-Q38 or the VH-Q39 or into both positions of an IL13 antibody. Q39X mutants, Q38X mutants, or Q39X/Q38X mutant pairs that favor VH/VL pairing were identified by bacterial surface display in the anti-IL13 antibody. Briefly, the mutated antibodies were expressed in a Δlpp derivative of *E. coli* train 33D3 cured of kanamycin resistance (see, e.g., Simmons et al. (2002) "Expression of full-length immunoglobulins in *Escherichia coli*: rapid and efficient production of aglycosylated antibodies." *Journal of Immunological Methods*. 263, 133-147). Individual framework variants were grown as overnight cultures at 30° C., combined equally by volume and used at a 1:100 dilution to inoculate 50 mL CRAP cultures. After 24 hours at 30° C. 1 OD aliquots were harvested and pelleted by centrifugation (4 minutes, 6500 rcf). Cells were resuspended in 100 µL PBS with 2% BSA and 5 mM EDTA and incubated at 4° C. for 30 minutes. After initial incubation, SYTO 41 or 9 nucleic acid stain (Molecular Probes, USA) was added to a final dilution of 1:100, and Alexa$^{488}$ or Alexa$^{647}$ labeled antigen added to a final concentration of 1-2 µM. Incubation was continued at 4° C. in darkness for 1 hour, at which time MgCl$_2$ was added to 10-20 mM final concentration. Unbound proteins were removed by washing 3 times with 1 mL volumes of PBS+20 mM MgCl$_2$. Stained cells were resuspended in SOC medium (New England Biolabs, USA) to a final concentration of 1×10$^7$ cells/ml for analysis using a Becton Dickenson FACS AriaII Flow Cytometer. The FACS gating strategy included cells that were SYTO dye positive. Doublet discrimination gates were used to remove doublets and finally gate were set to determine percentage of single cells binding antigen. As shown in FIG. 5, among the variants with both VL-Q38 and VH-Q39 substitutions, the VL-Q38K/VH-Q39E mutant pair gave the strongest FACS signal, higher than the VL-Q38K/VH-Q39K mutant pair (see FIG. 6). Moreover, antibody was expressed to levels equivalent to or better than wild type when the Q38K VL mutation is paired with the Q39E VH mutation. See FIG. 7. Since the Q38K/Q39K expressed more poorly than the Q38K/WT pair, this led us to introduce EKKE mutations (wherein the four letters refer to the amino acid substitutions at Q39X$_{HC1}$/Q38X$_{LC1}$ knob/Q39X$_{HC2}$/Q38X$_{LC2}$ hole, respectively) to both arms to get the best driving force for correct LC/HC pairing.

Figure 8:
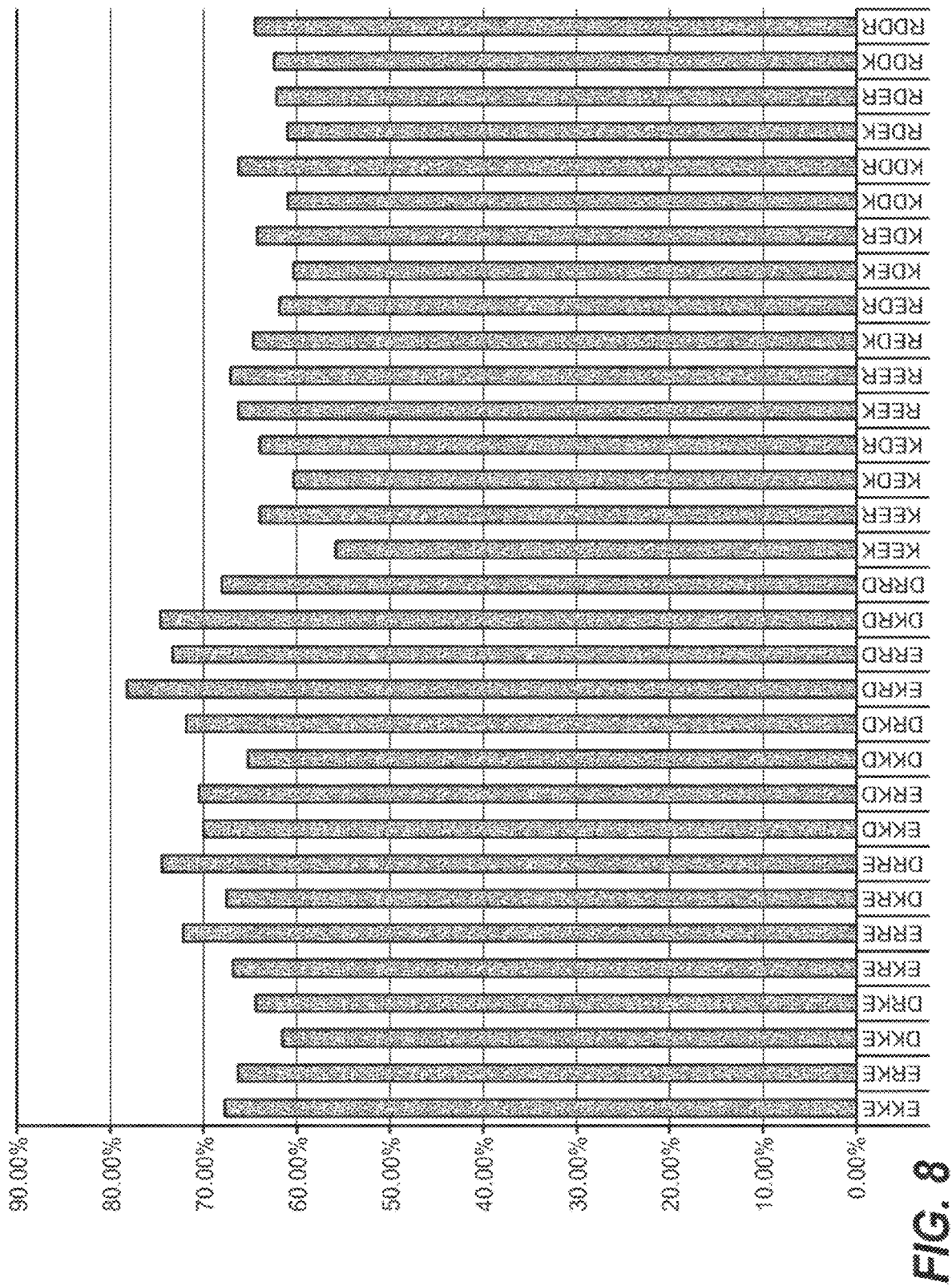
FIG. 8 shows exemplary results for the % presence of bispecific antibody variants with correct heavy chain-light chain pairing, measured by Orbitrap mass spectrometry from mammalian co-expressed antibodies. The mutants tested are shown on the X-axis. The four letters in each set of mutations refers to the amino acid substitutions at $Q39X_{HC1}/Q38X_{LC1}$ knob/$Q39X_{HC2}/Q38X_{LC2}$ hole, respectively.

Next, 4D5/UCHT1 bispecific antibody variants were constructed to contain Q39X/Q38X mutations in both heavy chains and both light chains. The modified bispecific antibodies were expressed, purified and analyzed via high resolution mass spectrometry. High resolution mass spectrometry utilizes the enhanced detection abilities of Orbitrap technology on the EMR Exactive Plus mass spectrometer. For quantitation, antibody product in PBS was buffer exchanged into 0.1% trifluoroacetic acid using Micro spin columns (Spin-6, Bio-Rad) or reversed phase off-line HPLC. Resultant sample fractions were directly infused onto the mass spectrometer. Parameters were optimized in Tune mode to enable baseline resolution of intra-charge state moieties. Mass envelopes were deconvoluted using Protein Deconvolution software (Thermo, score cutoff 50). Intensities of resultant deconvoluted peaks were documented and used to determine % presence of the 'correct' sequence, mispairs, half antibodies and homodimers. Exemplary results in FIG. 8 show the % presence of the 'correct' bispecific antibody variants with proper heavy chain-light chain pairing. The mutants tested are shown on the X-axis. The four letters in each set of mutations refers to the amino acid substitutions at Q39X$_{HC1}$/Q38X$_{LC1}$ knob/Q39X$_{HC2}$/Q38X$_{LC2}$ hole, respectively. The quantified results shown in FIG. 8 are provided in Table 13 below. In these experiments, the 4D5 antibody carried the knob mutation and the UCHT1 antibody carried the hole mutation. The results show that in addition to EKKE, other mutations at Q39/Q38 also improved correct heavy chain/light chain pairing.

TABLE 13

| Mutations | Combined BsIgG and LC scrambled | 2x Knob LC | 2x Hole LC | BsIgG | LC Scrambled |
|---|---|---|---|---|---|
| EKKE | 70.2% | 28.4% | 1.4% | 69.6% | 0.6% |
| ERKE | 66.3% | 28.8% | 4.9% | 64.1% | 2.2% |
| DKKE | 68.0% | 28.9% | 3.1% | 66.7% | 1.3% |
| DRKE | 64.7% | 30.1% | 5.2% | 62.2% | 2.5% |
| EKRE | 74.8% | 22.6% | 2.6% | 74.0% | 0.8% |
| ERRE | 72.2% | 22.3% | 5.5% | 70.5% | 1.7% |
| DKRE | 75.2% | 21.1% | 3.7% | 74.1% | 1.1% |
| DRRE | 74.9% | 20.6% | 4.6% | 73.6% | 1.3% |
| EKKD | 70.2% | 23.9% | 5.9% | 68.1% | 2.1% |
| ERKD | 70.8% | 21.3% | 8.0% | 68.3% | 2.5% |
| DKKD | 65.5% | 26.7% | 7.8% | 62.1% | 3.4% |
| DRKD | 72.2% | 14.2% | 13.5% | 69.4% | 2.8% |
| EKRD | 78.6% | 15.6% | 5.8% | 77.4% | 1.2% |
| ERRD | 73.8% | 18.7% | 7.5% | 71.8% | 2.0% |
| DKRD | 75.0% | 18.4% | 6.7% | 73.3% | 1.7% |
| DRRD | 68.5% | 25.3% | 6.1% | 66.2% | 2.3% |
| KEEK | 56.9% | 39.8% | 3.3% | 54.5% | 2.4% |
| KEER | 64.4% | 31.2% | 4.4% | 62.2% | 2.2% |
| KEDK | 57.8% | 36.4% | 5.7% | 54.0% | 3.8% |
| KEDR | 64.4% | 29.3% | 6.3% | 61.4% | 3.0% |
| REEK | 60.6% | 36.3% | 3.1% | 58.7% | 1.9% |
| REER | 67.2% | 24.1% | 8.6% | 64.0% | 3.2% |
| REDK | 58.6% | 36.8% | 4.5% | 55.6% | 3.0% |
| REDR | 62.4% | 29.8% | 7.8% | 58.4% | 4.0% |
| KDEK | 60.7% | 33.2% | 6.1% | 57.2% | 3.5% |
| KDER | 64.6% | 24.5% | 10.9% | 60.2% | 4.4% |
| KDDK | 61.4% | 30.0% | 8.6% | 56.9% | 4.5% |
| KDDR | 66.5% | 23.9% | 9.6% | 62.8% | 3.7% |
| RDEK | 61.3% | 33.6% | 5.1% | 58.4% | 2.9% |
| RDER | 62.5% | 28.6% | 8.8% | 58.2% | 4.3% |
| RDDK | 62.8% | 30.5% | 6.7% | 59.4% | 3.4% |
| RDDR | 64.8% | 23.2% | 12.0% | 60.2% | 4.6% |

Figure 9A:
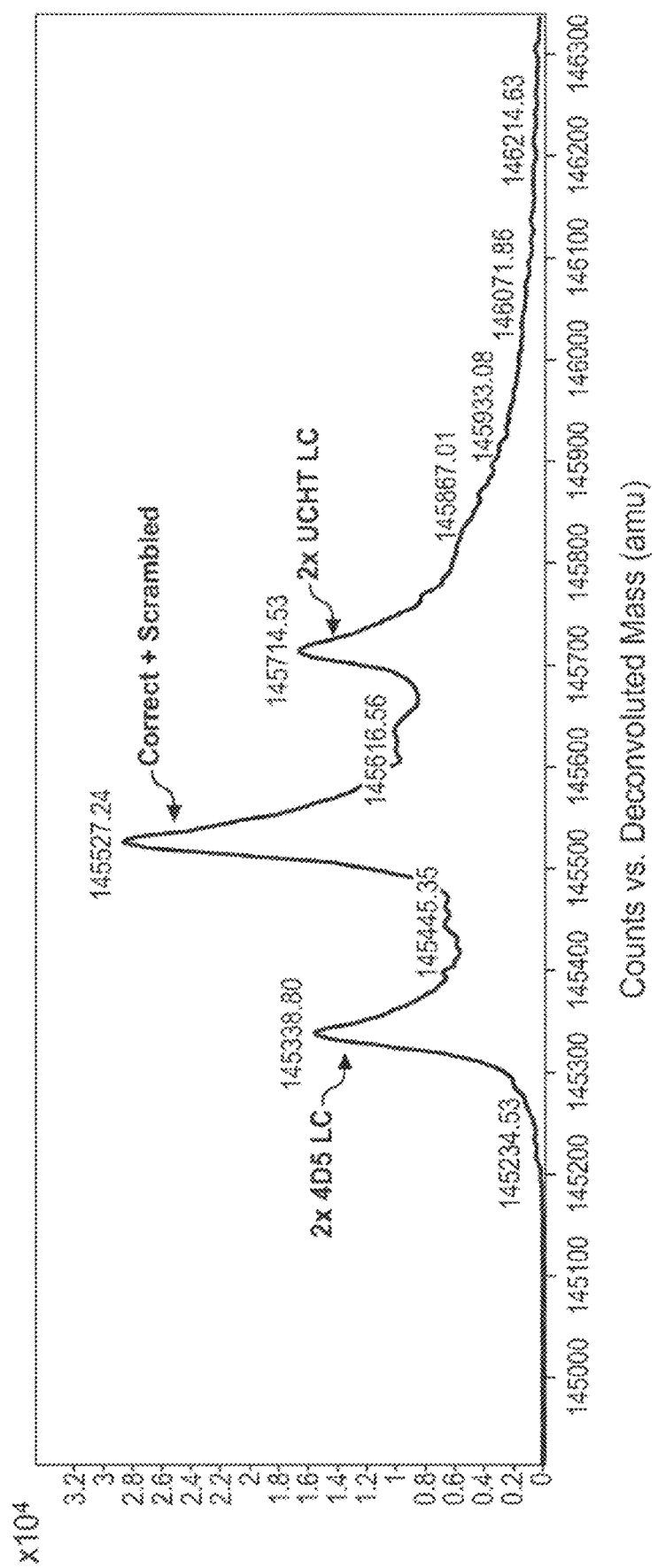
FIG. 9A shows the results of QTOF assays performed to assess heavy chain/light chain pairing in a 4D5/UCHT1 bispecific antibody.
Figure 9B:
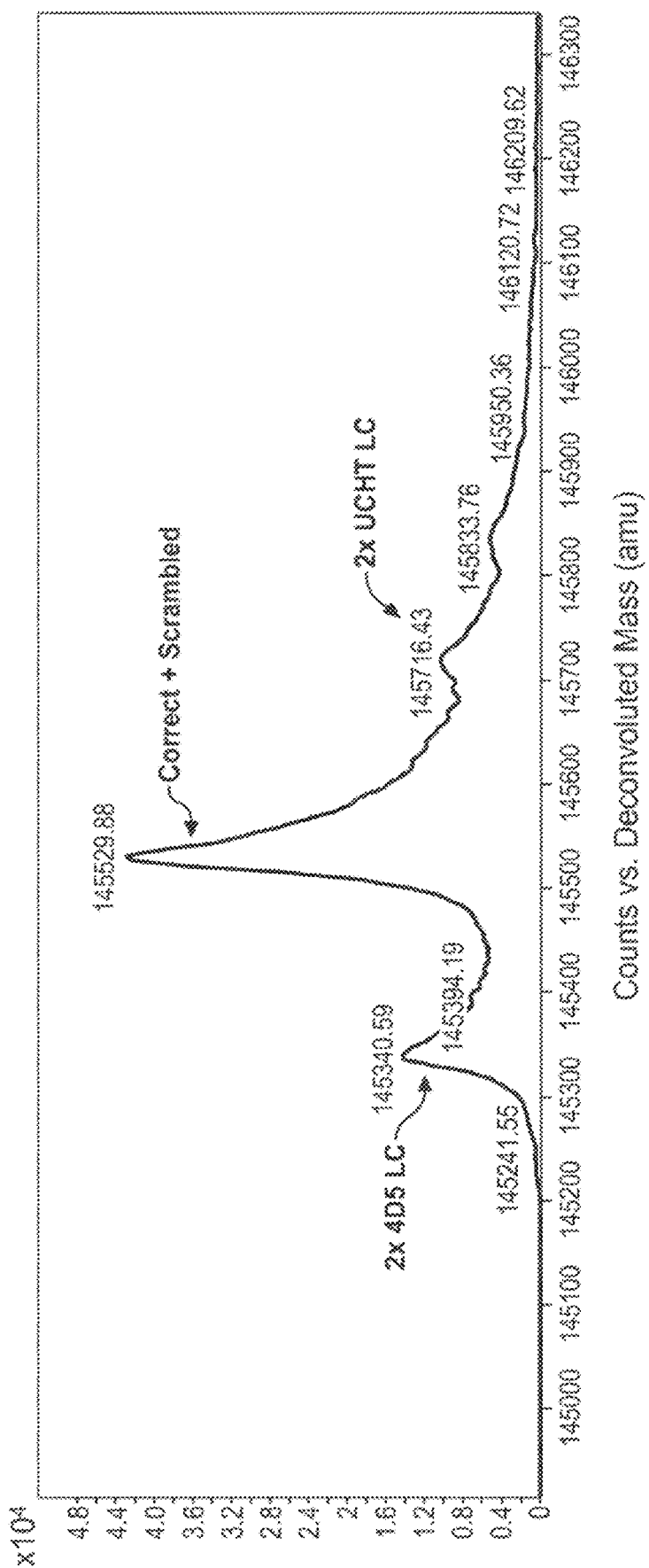
FIG. 9B shows the results of QTOF assays performed to assess heavy chain/light chain pairing in a 4D5/UCHT1 bispecific antibody that was modified so that the 4D5 arm contained a VL having the Q38K mutation and a VH having a Q39E mutation and the UCHT1 arm contained a VL having the Q38E mutation and a VH having a Q39K mutation ("EKKE").

The VL-Q38 VH-Q39 mutations were introduced into the 4D5/UCHT1 bispecific antibody. A 4D5/UCHT1 bispecific antibody was modified so that the 4D5 arm contained a VH having a Q39E mutation and a VL having the Q38K mutation and so that the UCHT1 arm contained a VH having a Q39K mutation and a VL having the Q38E mutation (i.e., "EKKE"). In this experiment, the 4D5 antibody contains a knob mutation in the CH3 domain and the UCHT1 antibody contains a hole mutation in the CH3 domain. In QTOF analyses, shown in FIG. 9, heavy chain-light chain mispairing was significantly reduced in the modified antibody (see FIG. 9B) as compared to the WT bispecific antibody (see FIG. 9A). As shown further below in the exemplary results provided by Table 15, the Q38/Q39 mutations improved the % bispecific IgG produced in a single cell.

Figure 10C:
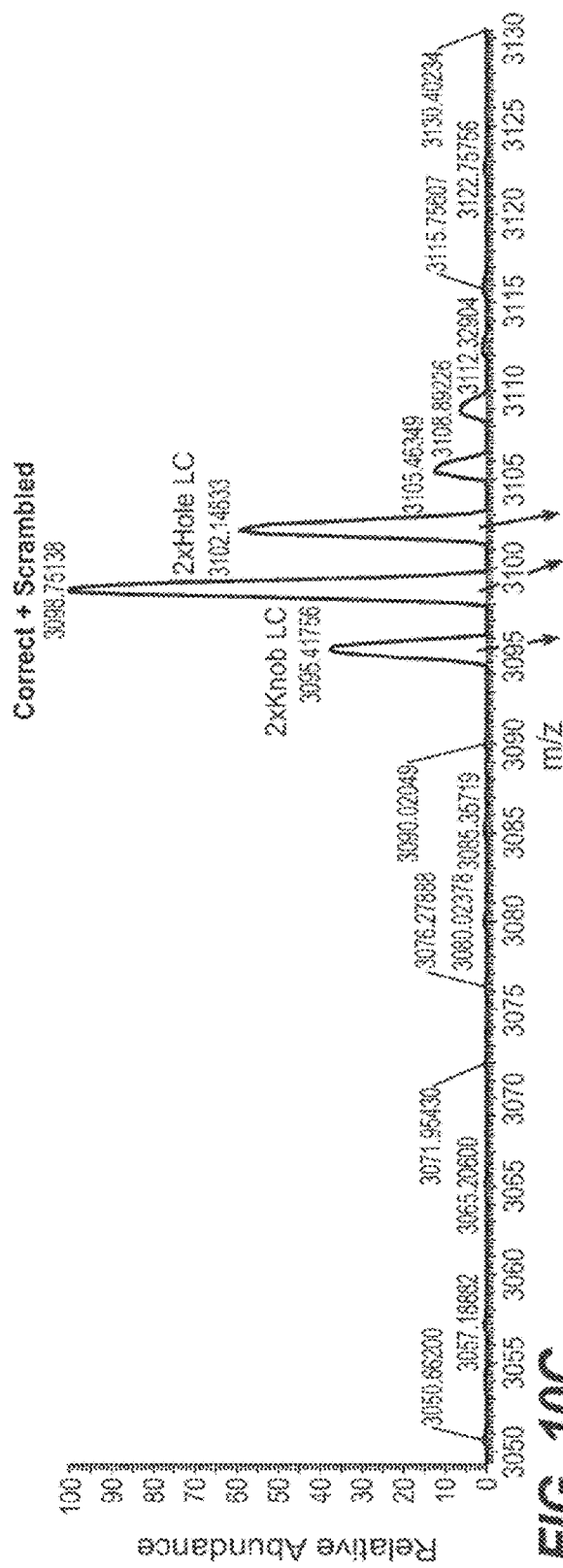
FIG. 10C shows an enlargement of FIG. 10D.
Figure 10D:
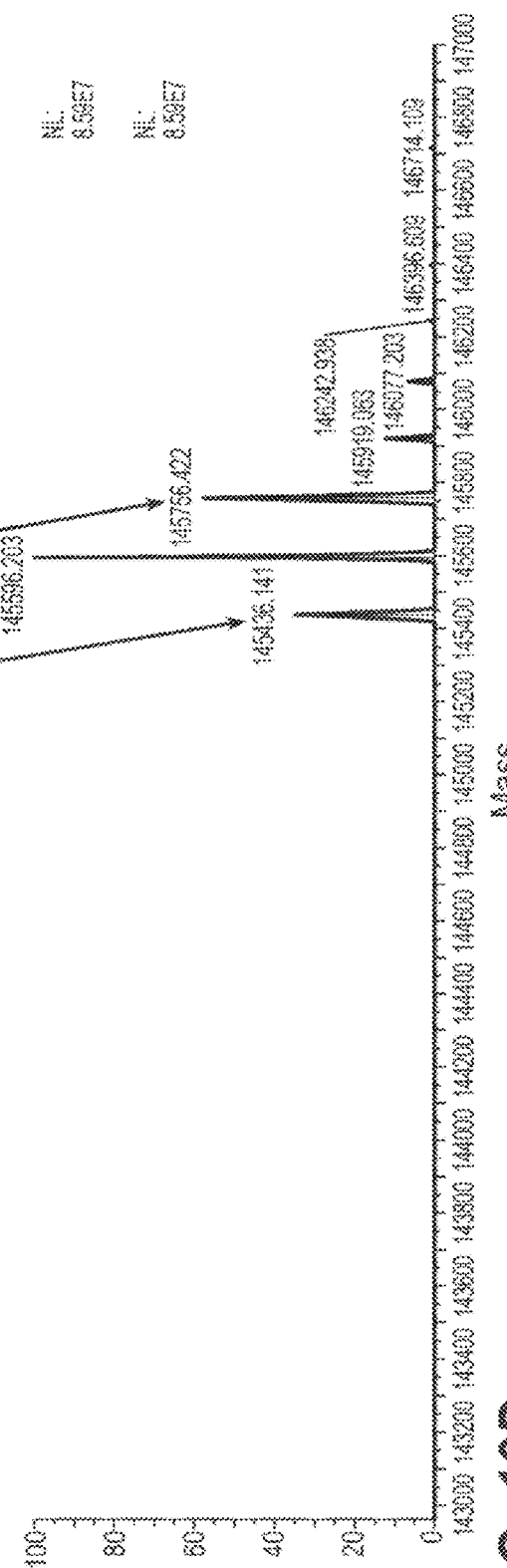
FIG. 10D shows the results of high resolution mass spectrometry performed to assess heavy chain/light chain paring in a bispecific 4D5/UCHT1 antibody in which the UCHT1 arm was modified to contain CL-V133K and CH-1-S183E mutations.
Figure 10E:
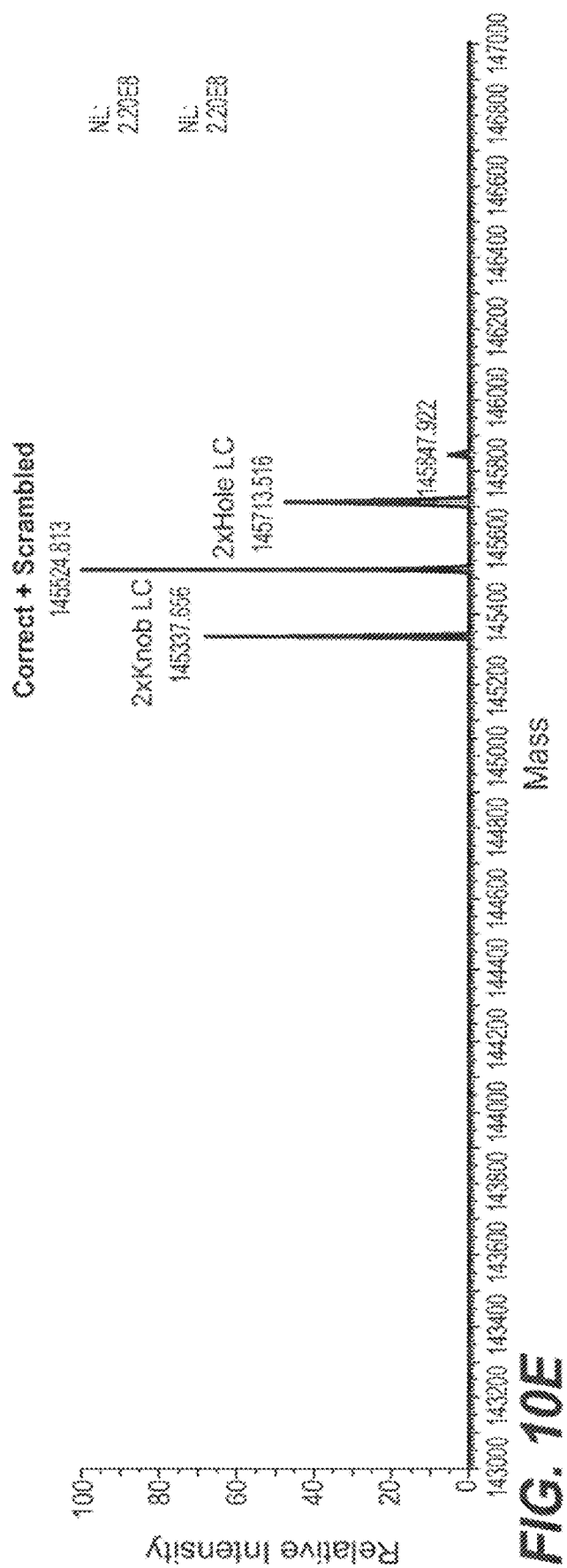
FIG. 10E shows the results of high resolution mass spectrometry performed to assess heavy chain/light chain paring in a WT bispecific 4D5/UCHT1 antibody.

The UCHT1 arm of the bispecific 4D5/UCHT1 antibody, which already contained the VL-Q38E and VH-Q39K mutations, was further modified to include the CL-V133K and CH-1-S183E mutations. The 4D5 arm of the 4D5/UCHT1 antibody was modified to contain the VL-Q38K and VH-Q39E mutations. The modified bispecific antibody was expressed, purified and analyzed via high resolution mass spectrometry. High resolution mass spectrometry utilizes the enhanced detection abilities of Orbitrap technology on the EMR Exactive Plus mass spectrometer. For quantitation, antibody product in PBS was buffer exchanged into 0.1% trifluoroacetic acid using Micro spin columns (Spin-6, Bio-Rad) or reversed phase off-line HPLC. Resultant sample fractions were directly infused onto the mass spectrometer. Parameters were optimized in Tune mode to enable baseline resolution of intra-charge state moieties. Mass envelopes were deconvoluted using Protein Deconvolution software (Thermo, score cutoff 50). Intensities of resultant deconvoluted peaks were documented and used to determine exemplary % presence of the 'correct' sequence, mispairs, half antibodies and homodimers. As shown in FIG. 10A, which shows an enlarged version of FIG. 10B, antibody species containing correctly paired heavy chain/light chain arms were the major population in the sample. (See the fourth row of Table 14C below for quantified results.) The same experiment was performed using a bispecific 4D5/UCHT1 modified to include the CL-V133K and CH-1-S183E mutations in the UCHT1 arm without the EKKE mutations. As shown in FIG. 10C, which shows an enlarged version of FIG. 10D, species containing 2 4D5 light chains or 2 UCHT1 light chains (i.e., mispaired bispecific antibodies) were the major populations in the sample. (See the third row of Table 14C below for quantified results.) FIG. 10E provides high resolution mass spectrometry results for an unmodified WT 4D5/UCHT1 antibody, shows that species containing 2 4D5 light chains or 2 UCHT1 light chains (i.e., mispaired bispecific antibodies) were the major populations in this sample as well. The results show that the V133X/S183X mutation pair on the hole arm of a bispecific antibody reduced heavy/light chain mispairing, and addition of the EKKE mutations further improved bispecific assembly.

Additional bispecific antibodies, including variants having Q39X/Q38X and/or V133X/S183X mutations in both arms, were generated, expressed, purified, and analyzed via high resolution mass spectrometry, as described above, to determine if such bispecific antibodies demonstrated increased preferential heavy chain/light chain pairing. The exemplary results of the high resolution mass spectrometry analyses are provided in Tables 14A and 14B below:

TABLE 14A

| UCHT1 Arm (Hole) | | 4D5 Arm (Knob) | | Combined | | 2x | | |
|---|---|---|---|---|---|---|---|---|
| LC mutation(s) | HC mutation(s) | LC mutation(s) | HC mutation(s) | BsIgG and LC scrambled | 2xKnob LC | Hole LC | BsIgG | LC Scrambled |
| Q38E V133K | Q39K S183E | Q38K V133E | Q39E | 79.4% | 16.6% | 4.0% | 78.6% | 0.8% |
| Q38E V133E | Q39K S183K | Q38K V133K | Q39E S183E | 77.0% | 19.7% | 3.4% | 76.1% | 0.9% |
| Q38E V133K | Q39K S183E | Q38K V133E | Q39E S183K | 82.8% | 16.0% | 1.2% | 82.6% | 0.2% |
| Q38E V133K | Q39K S183F | Q38K | Q39E | 80.1% | 19.9% | 0.0% | 80.1% | 0.0% |
| Q38E V133K | Q39K S183T | Q38K | Q39E | 85.4% | 14.6% | 0.0% | 85.4% | 0.0% |
| Q38E V133K | Q39K S183Y | Q38K | Q39E | 84.9% | 15.1% | 0.0% | 84.9% | 0.0% |
| Q38E V133K | Q39K S183F | Q38K | Q39E S183E | 66.5% | 31.1% | 2.4% | 65.4% | 1.1% |
| Q38E V133K | Q39K S183T | Q38K | Q39E S183E | 75.7% | 24.3% | 0.0% | 75.7% | 0.0% |
| Q38E V133K | Q39K S183Y | Q38K | Q39E S183E | 71.3% | 27.7% | 1.0% | 70.9% | 0.4% |

TABLE 14B

| UCHT1 Arm (Hole) | | 4D5 Arm (Knob) | | Combined | | 2x | | |
|---|---|---|---|---|---|---|---|---|
| LC mutation(s) | HC mutation(s) | LC mutation(s) | HC mutation(s) | BsIgG and LC scrambled | 2xKnob LC | Hole LC | BsIgG | LC Scrambled |
| — | — | — | — | 46.0% | 32.0% | 22.0% | 23.0% | 23.0% |
| Q38E | Q39K | Q38K | Q39E | 77.0% | 19.7% | 3.4% | 76.1% | 0.9% |
| Q38K | Q39E | Q38E | Q39K | 69.0% | 18.5% | 12.5% | 65.5% | 3.5% |
| Q38E V133K | Q39K S183E | Q38K | Q39E | 94.5% | 0.8% | 4.7% | 94.5% | 0.0% |
| Q38K V133K | Q39E S183E | Q38E | Q39K | 70.6% | 12.3% | 17.1% | 67.5% | 3.1% |
| Q38K | Q39E | Q38E V133K | Q39K S183E | 87.0% | 7.0% | 6.0% | 86.5% | 0.5% |

Q39X/Q38X were introduced into the knob and/or hole arms, and/or V133X/S183X mutations were introduced into the hole arm of various bispecific antibodies. The four letter mutations refer to the amino acid substitutions at $Q39X_{HC1}/Q38X_{LC1}$ knob/$Q39X_{HC2}/Q38X_{LC2}$ hole, respectively. Representative results show that the EKKE and V133X/S183X mutation (exemplified in Table 14C using V133K/S183E), alone or in combination, generally improved bispecific assembly in different antibodies. In the examples where the parent antibodies already exhibit strong preferential heavy/light chain pairing, further improvement is difficult to achieve or detect. The V133X/S183X mutations were also introduced into the knob arm of the bispecific antibodies and showed comparable results.

TABLE 14C

| BsIgG Coexpression Pairs | Variants | Combined BsIgG and LC scrambled | 2x Knob LC | 2x Hole LC | BsIgG | LC Scrambled |
|---|---|---|---|---|---|---|
| Anti-HER2/CD3[8,9] | WT | 46.0% | 32.0% | 22.0% | 23.0% | 23.0% |
| | EKKE | 78.6% | 15.9% | 5.5% | 77.5% | 1.1% |
| | V133K/S183E$_{hole}$ | 51.8% | 29.9% | 18.3% | 37.0% | 14.8% |
| | EKKE + V133K/S183E$_{hole}$ | 94.5% | 0.8% | 4.7% | 94.5% | 0.0% |

TABLE 14C-continued

| BsIgG Coexpression Pairs | Variants | Combined BsIgG and LC scrambled | 2x Knob LC | 2x Hole LC | BsIgG | LC Scrambled |
|---|---|---|---|---|---|---|
| Anti-EGFR/cMET[1,2] | WT | 89.8% | 6.0% | 4.30 | 89.5% | 0.3% |
| | EKKE | 89.3% | 4.90 | 5.90 | 89.0% | 0.3% |
| | V133K/S183E$_{hole}$ | 94.0% | 2.2% | 3.90 | 93.9% | 0.1% |
| | EKKE + V133K/S183E$_{hole}$ | 94.3% | 2.8% | 2.9% | 94.2% | 0.1% |
| Anti-VEGFA/VEGFC[3,4] | WT | 62.20% | 7.70% | 30.10% | ND | ND |
| | EKKE | 62.10% | 30.90% | 7.00% | ND | ND |
| | V133K/S183E$_{hole}$ | 72.60% | 9.80% | 17.60% | ND | ND |
| | EKKE + V133K/S183E$_{hole}$ | 81.90% | 15.10% | 3.00% | ND | ND |
| Anti-VEGFA/VEGFC[3,4] (LC1:LC2 ratio optimized) | WT | 62.5% | 16.6% | 20.9% | 56.3% | 6.2% |
| | EKKE | 78.1% | 8.1% | 13.8% | 76.6% | 1.5% |
| | V133K/S183E$_{hole}$ | 68.7% | 18.2% | 13.1% | 65.0% | 3.7% |
| | EKKE + V133K/S183E$_{hole}$ | 92.1% | 4.6% | 3.3% | 91.9% | 0.2% |
| Anti-IL-13/IL-4[5,6,7] | WT | 81.8% | 7.2% | 11.0% | 80.8% | 1.0% |
| | EKKE | 89.6% | 7.7% | 2.6% | 89.4% | 0.2% |
| | V133K/S183E$_{hole}$ | 88.4% | 6.6% | 5.0% | 88.0% | 0.4% |
| | EKKE + V133K/S183E$_{hole}$ | 98.4% | 0.0% | 1.6% | 98.4% | 0.0% |
| Anti-VEGFA/ANG2[10] | WT | 49.0% | 17.0% | 34.0% | 29.2% | 19.8% |
| | EKKE | 100.00%[#] | 0.0% | 0.0% | 100.0% | 0.0% |
| | V133K/S183E$_{hole}$ | 57.9% | 24.5% | 17.6% | 49.1% | 8.8% |
| | EKKE + V133K/S183E$_{hole}$ | 100.00%[#] | 0.0% | 0.0% | 100.0% | 0.0% |

[#]In the Anti-VEGFA/ANG2 sample, the molecular masses of the correctly assembled bispecific Ab, "2x Hole LC" Ab, and "2X Knob" Ab are very similar. To distinguish the "correct" population from the "2x Hole LC" and "2X Knob" populations, Orbitrap resolution was increased, thus decreasing sensitivity slightly. The 100% correct pairing is therefore likely to be closer to >95%.
[1]Schaefer, et al. A two-in-one antibody against HER3 and EGFR has superior inhibitory activity compared with monospecific antibodies. Cancer Cell. 2011; 20: 472-86.
[2]Merchant, et al. Monovalent antibody design and mechanism of action of onartuzumab, a MET antagonist with anti-tumor activity as a therapeutic agent. Proc Natl Acad Sci USA. 2013; 110: E2987-96.
[3]Presta, et al. Humanization of an anti-vascular endothelial growth factor monoclonal antibody for the therapy of solid tumors and other disorders. Cancer Res. 1997; 57: 4593-9.
[4]Gogineni, et al. Inhibition of VEGF-C modulates distal lymphatic remodeling and secondary metastasis. PLoS One. 2013; 8: e68755.
[5]WO 2014/165771
[6]WO 2005/062967
[7]Ultsch M, Bevers J, Nakamura G, Vandlen R, Kelley R F, Wu L C, et al. Structural basis of signaling blockade by anti-IL-13 antibody Lebrikizumab. J Mol Biol. 2013; 425: 1330-9.
[8]Carter P, Presta L, Gorman C M, Ridgway J B, Henner D, Wong W L, et al. Humanization of an anti-p185HER2 antibody for human cancer therapy. Proc Natl Acad Sci USA. 1992; 89: 4285-9.
[9]Zhu Z, Carter P. Identification of heavy chain residues in a humanized anti-CD3 antibody important for efficient antigen binding and T cell activation. J Immunol. 1995; 155: 1903-10.
[10]Liang W C, Wu X, Peale F V, Lee C V, Meng Y G, Gutierrez J, et al. Cross-species vascular endothelial growth factor (VEGF)-blocking antibodies completely inhibit the growth of human tumor xenografts and measure the contribution of stromal VEGF. J Biol Chem. 2006; 281: 951-61.

The anti-HER2/CD3 antibody comprising Q39E$_{HC1}$/Q38K$_{LC1}$ knob/Q39K$_{HC2}$/Q38E$_{LC2}$ hole and V133K/S183E hole mutations was further modified to contain V133E/S183K knob mutations. The antibody expressed, purified, and analyzed via high resolution mass spectrometry, as described above, to determine if such bispecific antibodies demonstrated increased preferential heavy chain/light chain pairing. The exemplary results of the high resolution mass spectrometry analyses are provided in Table 14D below:

TABLE 14D

| BsIgG Coexpression Pairs | Variants | Combined BsIgG and LC scrambled | 2x Knob LC | 2x Hole LC | BsIgG | LC Scrambled |
|---|---|---|---|---|---|---|
| Anti-HER2/CD3[8,9] | WT | 46.0% | 32.0% | 22.0% | 23.0% | 23.0% |
| | EKKE + V133K/S183E$_{hole}$ | 94.5% | 0.8% | 4.7% | 94.5% | 0.0% |
| | EKKE + V133K/S183E$_{hole}$ + V133E/S183K$_{knob}$ | 99.1% | 0.0% | 0.9% | 99.1% | 0.0% |

The exemplary results in Table 14D show that the V133E/S183K knob mutations in combination with the EKKE and V133K/S183E hole mutations improved bispecific assembly to almost 100%.

Figure 23:
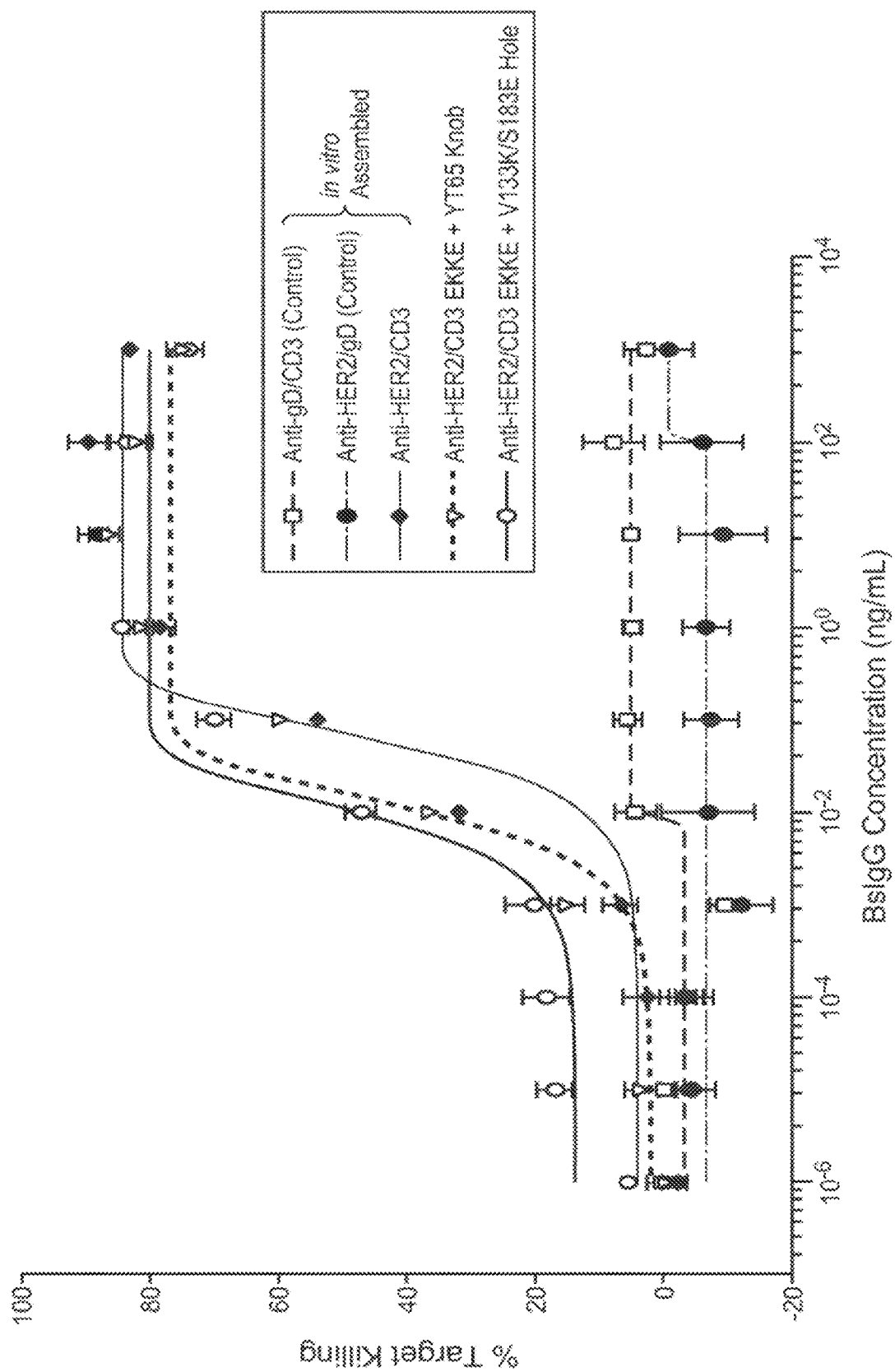
FIG. 23 shows the biological activities of anti-HER2/CD3+EKKE+V133K/S183E$_{hole}$, anti-HER2/CD3+EKKE+YT65$_{knob}$, and unmodified anti-HER2/CD3 in an in vitro T-cell mediated B-cell cytotoxicity assay.

The activity of the anti-HER2/CD3 antibody having the EKKE and V133K/S183E hole mutations was compared to that of an unmodified anti-HER2/CD3 antibody in an in vitro cytotoxicity assay. Briefly, peripheral blood mononuclear cells (PBMC) were separated from the blood of healthy volunteers using lymphocyte separation medium (MP biomedicals, Solon, OH). CD8+ cells were extracted from PBMC using human CD8+ Isolation Kit from Miltenyi (#130-094-156) by negative selection. 1×10$^4$ PBMC cells were plated on 96 well plates and incubated overnight. 5×10$^4$ CD8+ T-cells were added (a) with anti-HER2/CD3 antibody having the EKKE and V133K/S183E hole mutations, (b) without anti-HER2/CD3 antibody having the EKKE and V133K/S183E hole mutations, (c) with unmodified anti-HER2/CD3, and (d) without unmodified anti-HER2/CD3. The mixtures were incubated 48h in 37° C. The T cells were removed by washing twice with PBS. Viability of the PBMCs was measured using CellTiter-Glo® Luminescent Cell Viability Assay (Promega, Madison, WI). As shown in FIG. 23, the activities of the modified and unmodified anti-HER2/CD3 antibodies were comparable.

Differential scanning fluorimetry (DSF) was performed to determine the melting temperatures of (a) a 4D5 Fab modified to contain VL-Q38K and VH-Q39E mutations; (b) an UCHT1Fab modified to contain VL-Q38E, CL-V133K, VH-Q39K, and CH-1 S183E mutations; and (c) an UCHT1 arm modified to contain VL-Q38E, CL-V133K, VH-Q39K, and CH-1 S183T mutations (see, e.g., Niesen et al. (2007) Nat Protoc 2, 2212-2221.) Protein stability was determined in a Biorad CFX96 Real-Time System (Biorad, USA) with a final dilution of 1:500 of the Sypro Orange dye stock (Molecular Probes, USA). Fluorescence of a 25 µL Fab sample in PBS was recorded from 20-100° C. (0.2° C. increments, 10 seconds hold per step). The results shown in Table 15 below demonstrate that the mutations introduced in the variable and/or constant regions described herein do not greatly affect the Tm of the antibodies.

TABLE 15

| LC | HC | LC mutations | | HC Mutations | | Tm [° C.] |
|---|---|---|---|---|---|---|
| 4D5 | 4D5 | | | | | 80° |
| | | Q38E | | Q39K | | 78.6° |
| | | Q38K | | Q39E | | 79.8° |
| | | | V133K | | S183T | 76.8° |
| | | | V133K | | S183E | 79.0° |
| | | Q38K | V133K | Q39E | S183T | 75.4° |
| | | Q38K | V133K | Q39E | S183E | 78.0° |
| | | Q38E | V133K | Q39K | S183E | 77.4° |
| | | Q38E | V133K | Q39K | S183T | 75.2° |
| UCHT1v9 | UCHT1v9 | | | | | 87.8° |
| | | Q38E | | Q39K | | 87.2° |
| | | Q38K | | Q39E | | 87.0° |
| | | | V133K | | S183T | 79.4° |
| | | | V133K | | S183E | 83.2° |

TABLE 15-continued

| LC | HC | LC mutations | | HC Mutations | | Tm [° C.] |
|---|---|---|---|---|---|---|
| | | Q38K | V133K | Q39E | S183T | 78.4° |
| | | Q38K | V133K | Q39E | S183E | 83.4° |
| | | Q38E | V133K | Q39K | S183E | 83.2° |
| | | Q38E | V133K | Q39K | S183T | 78.0° |
| 4D5 | 4D5 | | | | | 80.0° |
| 4D5 | 4D5 | Q38K | | Q39E | | 79.8° |
| UCHT1v9 | 4D5 | | V133K | | | 78.0° |
| UCHT1v9 | UCHT1v9 | | | | | 87.8° |
| UCHT1v9 | UCHT1v9 | Q38E | | Q39K | | 87.2° |
| UCHT1v9 | UCHT1v9 | | V133K | | S183E | 83.2° |
| UCHT1v9 | UCHT1v9 | | V133K | | S183T | 79.4° |
| UCHT1v9 | UCHT1v9 | Q38E | V133K | Q39E | S183E | 82.4° |
| UCHT1v9 | UCHT1v9 | Q38E | V133K | Q39K | S183T | 78.0° |
| 4D5 | 4D5 | Q38K | | Q39E | | 79.8° |
| UCHT1v9 | UCHT1v9 | Q38E | V133K | Q39K | S183E | 82.4° |

Based on the results shown in Table 15, the thermostability of the variants that were tested seems to be predominantly driven by the stability of the HC. Although stability can be an explanation for improved bispecific pairing, the data unexpectedly show that the variants that exhibit the best bispecific pairing do not always correlate with the best thermostabiltiy, e.g., properly paired Fab may show lower or similar thermostabiltiy as compared to mispaired Fab. Without being bound by specific mechanism(s), the mutations can, alternatively or additionally, affect the assembly kinetics of the proper pairs, for example, the proper pair can assemble faster followed by disulfide formation between the heavy and light chains. This is further supported by the observation that chain ratio optimization further improved bispecific formation.

$Q39E_{HC1}/Q38K_{LC1}$ knob/$Q39K_{HC2}/Q38E_{LC2}$ hole and V133K/S183E hole mutations were introduced into bispecific anti-4D5/UCHT1 antibodies of human IgG1 isotype, human IgG2 isotype, human IgG4 isotype, and mouse IgG2a isotype. Antibodies of human IgG2 isotype have not been observed to successfully assemble in vitro. The exemplary results in Table 16 below show that the mutations in the light chain and heavy chain variable domains generally improved bispecific assembly in human bispecific antibodies of different isotypes, as well as in a mouse bispecific antibody.

TABLE 16

| BsIgG Coexpression Pairs | Variants | Combined BsIgG and LC scrambled | 2x Knob LC Mab | 2x Hole LC Mab | BsIgG | LC Scrambled Mab |
|---|---|---|---|---|---|---|
| 4D5/UCHT1 huIgG1 | WT | 47.7% | 20.0% | 32.3% | 23.9% | 23.9% |
| | EKKE | 67.3% | 12.8% | 19.9% | 63.3% | 4.0% |
| | EKKE + V133K/S183E$_{hole}$ | 94.5% | 4.7% | 0.8% | 94.5% | 0.0% |
| 4D5/UCHT1 huIgG2 | WT | 50.0% | 27.5% | 22.5% | 27.5% | 22.5% |
| | EKKE | 83.3% | 14.3% | 2.4% | 82.9% | 0.4% |
| | EKKE + V133K/S183E$_{hole}$ | 94.9% | 2.9% | 2.2% | 94.8% | 0.1% |
| 4D5/UCHT1 huIgG4 | WT[†] | 38.6% | 27.7% | 33.7% | 19.3% | 19.3% |
| | EKKE | 84.3% | 6.4% | 9.4% | 83.6% | 0.7% |
| | EKKE + V133K/S183E$_{hole}$ | 92.6% | 2.2% | 5.2% | 92.5% | 0.1% |
| 4D5/UCHT1 muIgG2a | WT[#] | 44.9% | 25.8% | 29.2% | 22.5% | 22.5% |
| | EKKE[#] | 82.2% | 8.5% | 9.4% | 81.2% | 1.0% |
| | EKKE + V133K/S183E$_{hole}$[#] | 89.7% | 0.0% | 10.3% | 89.7% | 0.0% |

*Results were obtained using optimized LC1:LC2 ratio
[†]Uncharacterized mass difference of −110 Da from expected for all peaks.
[#]Uncharacterized mass difference of +160 Da from expected for all peaks.

The crystal structure of a4D5 Fab modified to contain the VL-Q38K. CL-V133E, VH-Q39E, and CH1-S183K mutations was determined to a resolution of 1.63 Å. The overall structure of the mutant does not show significant difference comparing to the wild type 4D5 Fab, indicating the charge mutations introduced to all of the 4 domains do not perturb structural integrity. See FIG. 11A. However, it was found that, in addition to the salt bridge between the mutated residues VL-Q38K and VH-Q39E, both VL-Q38K and VH-Q39E form extra hydrogen bonds with 2 solvent water molecules. VL-Q38K was also found to interact with VH-Y95 and VL-K39 with hydrogen bonds, respectively. The extensive hydrogen bonding network stabilizes the pairing between the mutated VL and VH. See FIG. 11B. In the constant domains containing the CL-V133E and CH1-S183K mutations, in addition to the salt bridge between the mutated residues CL-V133E and CH1-S183K, both CL-V133E and CH1-S183K form extra hydrogen bonds with 3 solvent water molecules. CL-V133E and CH1-S183K also interact with VL-T178 with hydrogen bonds respectively. The unexpected extensive hydrogen bonding network stabilizes the pairing between the mutated CL and CH1, which facilitates the production of correctly paired BsIgG. See FIG. 11C.

Figure 12B:
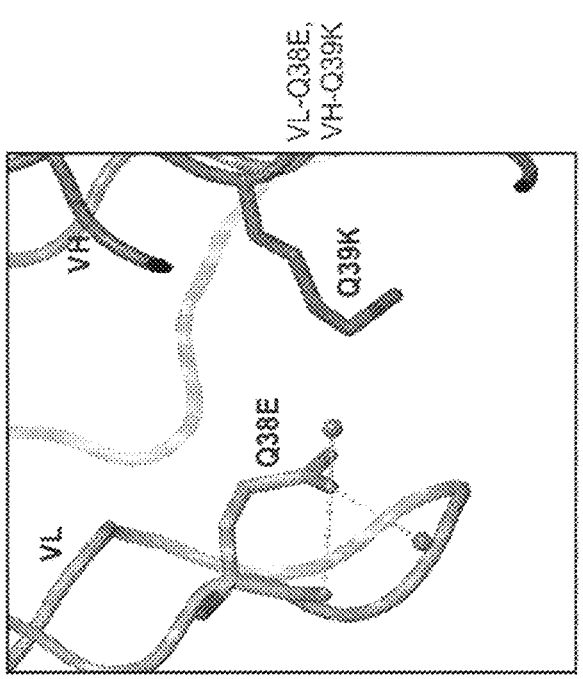
FIG. 12B shows the bonds formed by VL-Q38E and VH-Q39K in the modified 4D5 Fab.
Figure 12C:
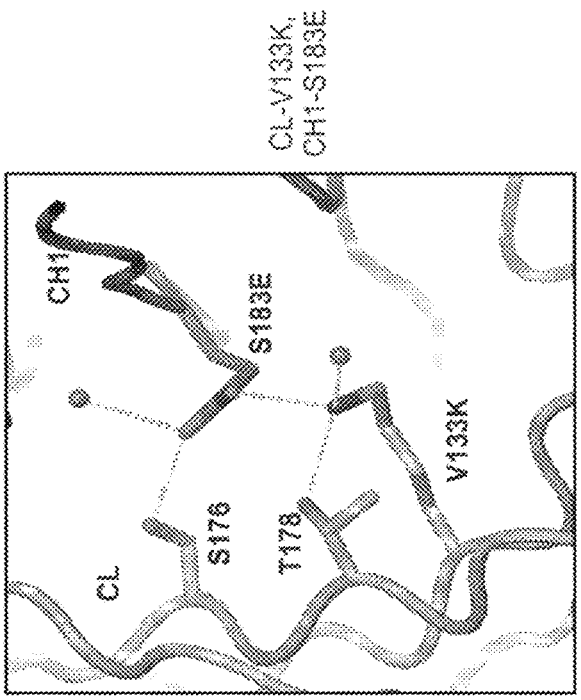
FIG. 12C shows the bonds formed by CL-V133K and CH1-S183E in the modified 4D5 Fab.
Figure 12A:
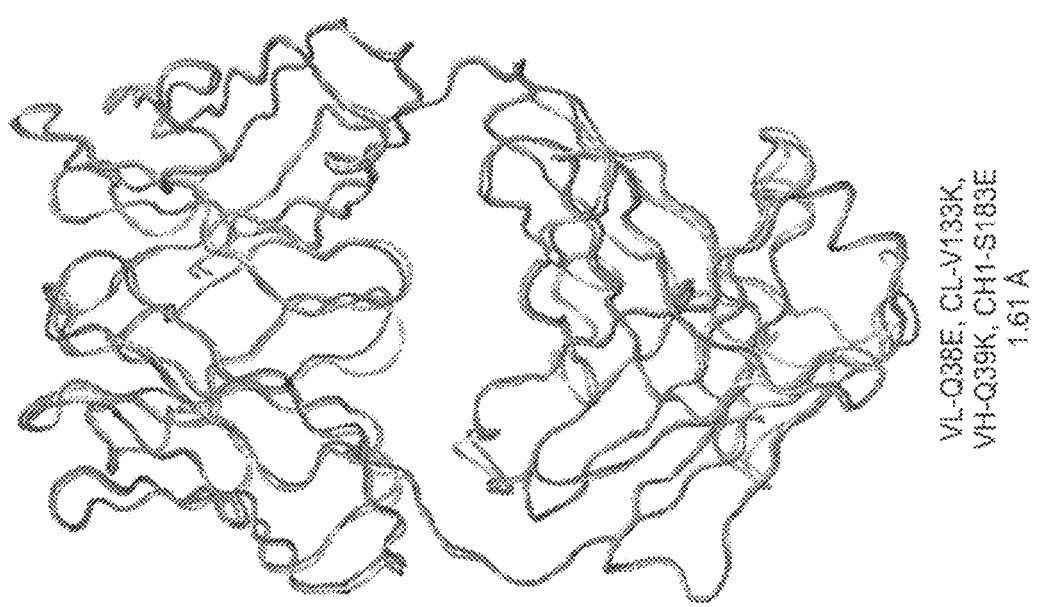
FIG. 12A shows the overlapping crystal structures of the wild type 4D5 Fab and the 4D5 Fab modified to have VL-Q38E. CL-V133K, VH-Q39K, and CH1-S183E mutations.

The crystal structure of a 4D5 Fab modified to contain VL-Q38E. CL-V133K, VH-Q39K, and CH1-S183E mutations was determined to a resolution of 1.61 Å. The overall structure of the mutant does not show significant difference comparing to the wild type 4D5 Fab, indicating the charge mutations introduced to all of the 4 domains do not perturb structural integrity. See FIG. 12A. It was found that VL-Q38E and VH-Q39K do not form hydrogen bonds. VL-Q38E, however, forms hydrogen bonds with 2 solvent water molecules. See FIG. 12B. In the constant domains containing the CL-V133K and CH1-S183E mutations, in addition to the salt bridge between the mutated residues CL-V133K and CH1-S183E, both CL-V133K and CH1-S183E form extra hydrogen bonds with 2 solvent water molecules, respectively. CL-V133K also forms a hydrogen bond with CL-T178, and CH1-S183E forms a hydrogen bond with VL-T76. The unexpected extensive hydrogen bonding network stabilizes the pairing between the mutated CL and CH1, which facilitates the production of correctly paired BsIgG. See FIG. 12C.

In summary, we found that mutation at V133 of CL reduced antibody assembly when paired with a wild type heavy chain. Amino acid substitutions at position S183 of CH1, however, restored assembly of antibody variants when paired with a mutation at position V133 of CL. Thus, the V133X/S183X mutation pairs can direct specific LC and HC pairing when expressed in a single cell. Mutations at positions Q39 of VH and Q38 of VL alone or in combination with CH1/CL mutations further improved LC and HC pairing in the context of a bispecific antibody, thus correspondingly improving correct bispecific formation when the two half antibodies are expressed in a single cell. Optimized light chain ratios, which were determined empirically, further improved bispecific assembly. Mutations at positions Q39 of VH and Q38 of VL alone or in combination with CH1/CL mutations further improved bispecific assembly in all human and mouse antibody isotypes tested. Unexpectedly, the mutations in the variable and constant regions of the heavy or light chain, alone or in combination, do not greatly affect thermostability of the antibodies.

Example 2: Engineering Antibody Heavy Chain/Light Chain Pairs Using Strategy #2

Figure 13A:
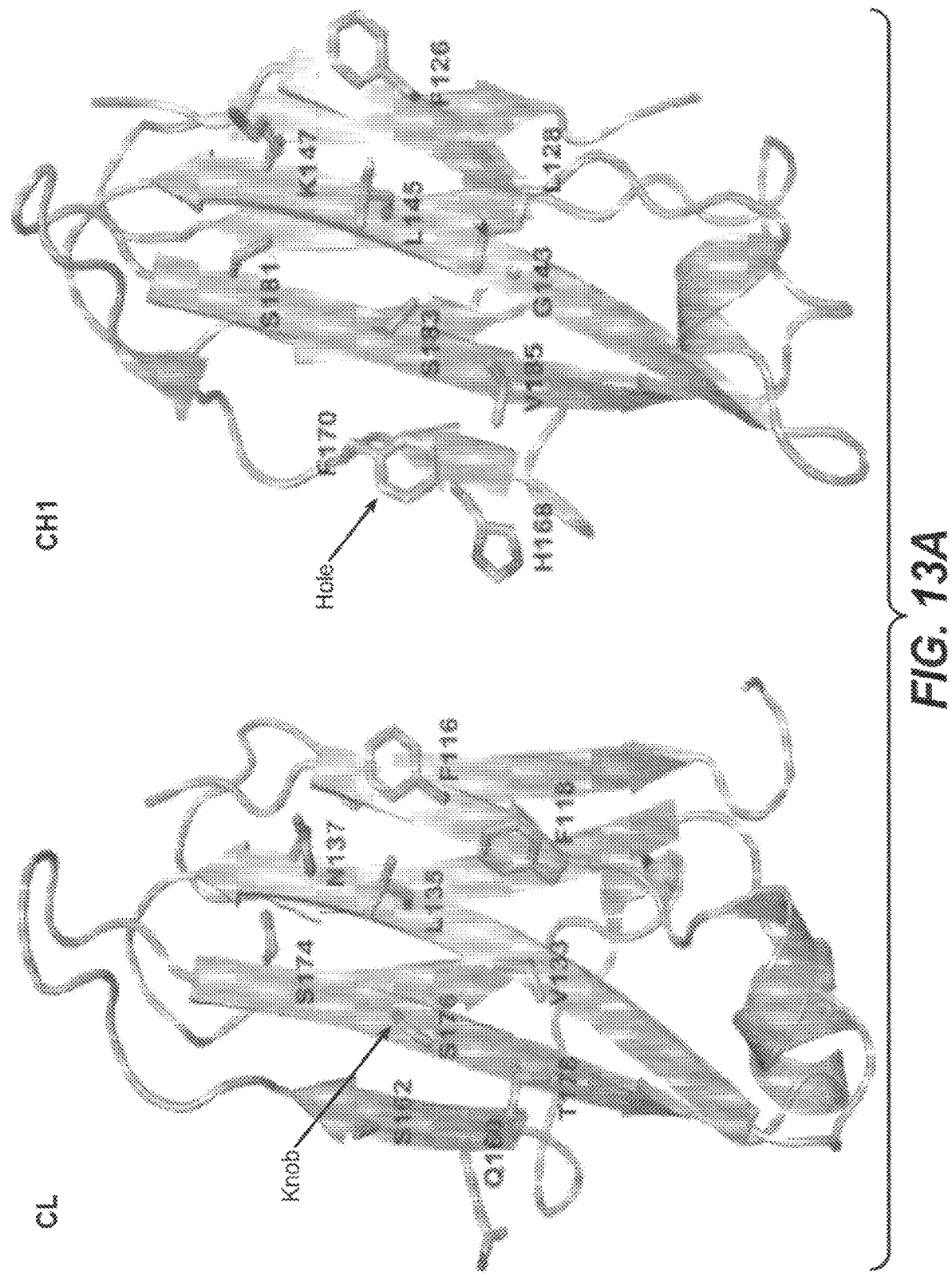
FIG. 13A depicts one design approach (i.e., "Approach A") for generating a mutant CH1/CL pair.

In addition, the CH1-CL interface of the exemplary bispecific antibody 4D5 was computationally redesigned using the molecular modeling program ROSETTA (Leaver-Fay et al. (2011) "ROSETTA3: an object-oriented software suite for the simulation and design of macromolecules." *Methods Enzymol.* 487, 545-74). The ROSETTA program is under active development and is constantly updated. Briefly, the ROSETTA program generates a random sequence from the user-entered repertoire specified for a given design approach. Two design approaches were performed, as described in detail below:

In the first design approach (i.e., Approach A, see FIG. 13A), the S176 amino acid residue of the CL domain was restricted to be any one of F, Y or W; and the F170 amino acid residue of the CH1 domain was restricted to be any one of A, G, I, L, S, T or V. To conserve but optimize the residue identities, the F118 amino acid residue of the CL domain was restricted to be any one of F, Y or W; the F126 amino acid residue of the CH1 domain was restricted to be any one of F, Y or W; and the S183 amino acid residue of CH1 was restricted to be any one of A, G, I, L, S, T or V. The F116, V133, L135, S174 amino acid residues of the CL domain and the L128, G143, L145, S181 amino acid residues of the CH1 domain were restricted to be non-polar amino acids. Other residues, such as S131, S162, T164, T178 of the CL domain and A141, V185 of the CH1 domain, were allowed to be redesigned as any amino acid except cysteine.

Figure 13B:
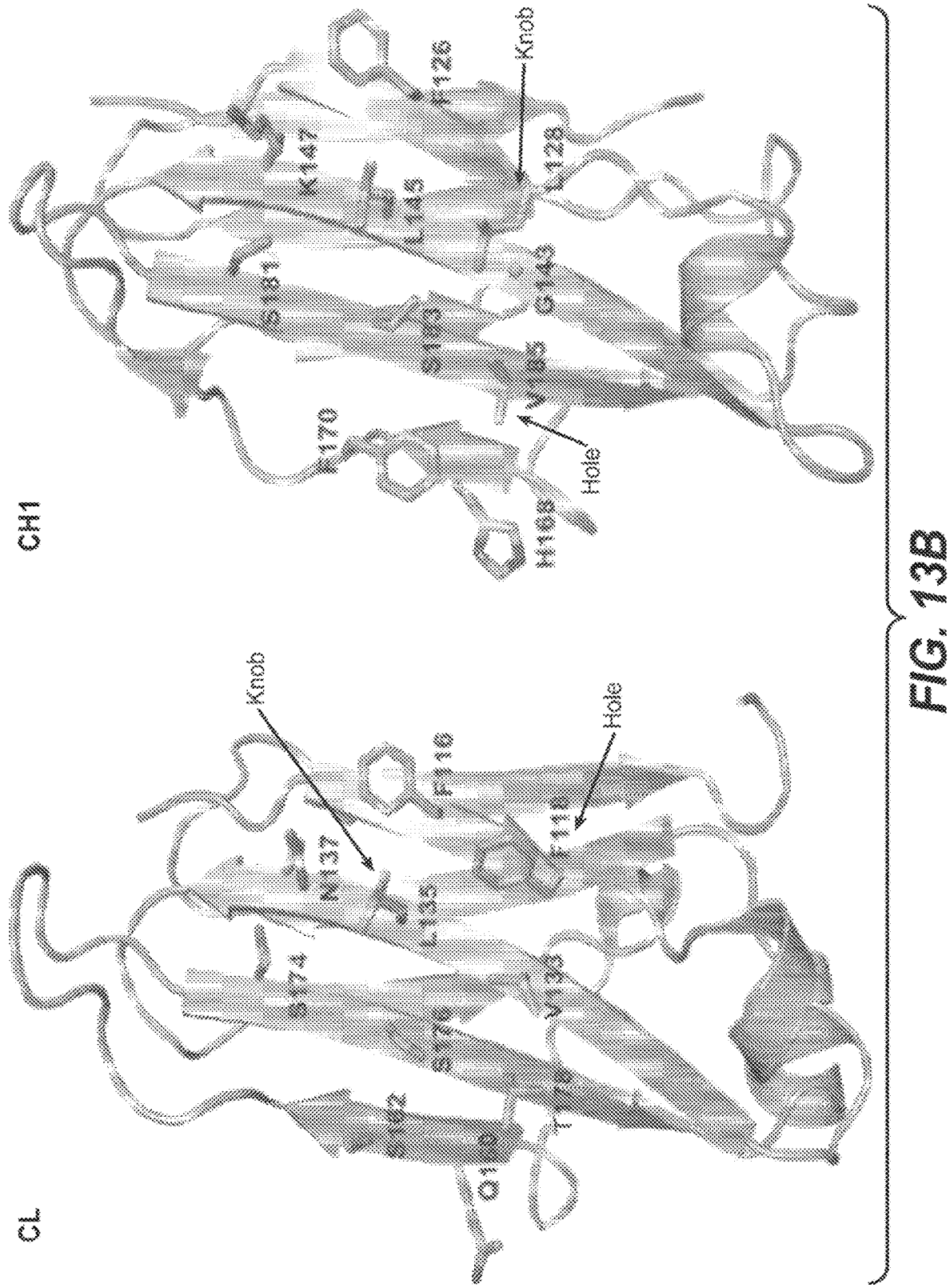
FIG. 13B depicts a second design approach (i.e., "Approach B") for generating a mutant CH1/CL pair for 4D5/UCHT1 bispecific antibody (anti-HER2/anti-CD3).

In the second design approach (i.e., Approach B, see FIG. 13B), the L135 amino acid residue of the CL domain and the L128 amino acid residue of the CH1 domain were restricted to be any one of F, Y or W; and the F118 amino acid residue of the CL domain and the L145 amino acid residue of the CH1 domain were restricted to be any one of A, I, L, S, T or V. The S181 amino acid residue of the CH1 domain was also restricted to be any one of A, I, L, S, T or V. In addition, the F116 amino acid residue of the CL domain was restricted to be an one of A, F, I, L, M, S, T, V or Y; the V133 amino acid residue of the CL domain was restricted to be any one of A, F, I, L, S, T, V, W or Y; and the V185 amino acid residue of the CH1 domain was restricted to be a non-polar amino acid. The S131, S162, T164, S176, and T178 amino acid residues of the CL domain and the A141 and F170 amino acid residues of the CH1 domain were allowed to be redesigned as any amino acid except cysteine.

ROSETTA calculated multiple binding energy scores for modeled structures, including the redesigned CH1 and redesigned CL domains (H'L'), the wild type CH1 and redesigned CL domains (HL), as well as the redesigned CH1 and wild type CL domains (H'L). A contrast score is calculated afterwards as the energy difference between H'L' and the more stable pair between HL' and H'L. Every designed sequence was then subject to defined filters in order to discard sequences with unfavorable binding energy scores and contrast scores.

Score12 and Talaris are two scoring functions adopted by ROSETTA. Both were used to analyze the design approaches described above. For score12, Approach A and Approach B were run with 1,000 CPU cores for 10 weeks. As shown in Table 17 below, Approach A returned with 36,831 total outputs containing 275 unique sequences; Approach B returned with 3,464 total outputs containing 184 unique sequences. For Talaris, both design approaches were run with 1,000 CPU cores for 5 weeks. Approach A returned with 33,286 total outputs containing 110 unique sequences; Approach B returned with 1,253 total outputs containing 47 unique sequences. See Table 17 below. 182 sequences were selected for gene synthesis and evaluation.

TABLE 17

| Design Options | Scoring Functions | Run Time (weeks)* | Total Output | Unique Output |
|---|---|---|---|---|
| Approach A | score12 | 10 | 36,831 | 275 |
| | Talaris | 5 | 33,286 | 110 |
| Approach B | score12 | 10 | 3,464 | 184 |
| | Talaris | 5 | 1,253 | 47 |
| | SUM | | 74,834 | 616 |

*1000 CPU cores

In addition to selecting candidate sequences based on their energy scores, a phylogenetic tree for all 616 unique output sequences was generated. Each branch of the tree was considered to represent a type of CH1/CL pairing solution. Since the computational program might not be accurate enough for predicting the contrast energy (selectivity of the correct pairing over the mispairing), selection of at least one sequence from each phylogenetic branch allowed us to get a good sampling of all the outputs. Indeed, the final candidates, such as YT65 and JS78, as described in more detail below, were picked because their sequences were distinctive from others according to the phylogenetic analyses despite of their relatively weak contrast energies.

Select output sequences of the 4D5 CL/CH1 variants generated using Strategy #2 were synthesized. Light chain variants were cloned as KpnI/HindIII fragments into expression vector pRK5 hu4D5-8 L chain (Carter et al. (1992) "Humanization of an anti-p185HER2 antibody for human cancer therapy. Proc. Natl. Acad. Sci. USA 89, 4285-9), and heavy chain variants were cloned as ApaI/NdeI fragments into the expression vector pRK5 hu4D5-8 H Chain. The Fc region of the heavy chain carried a mutation at the glycosylation site (N297G) for aglycosylated IgG production in mammalian cell and a deletion at the C-terminal Lysine (ΔK447). These two mutations gave rise to uniform IgG mass for easy mass spectrometry based quantification without post purification enzymatic treatment. Single cell production of BsIgG for the Strategy #2 variants with partner antibody, UCHT1.v9, was carried out by co-transfecting 4 plasmids each carrying a light chain or a heavy chain gene of the test pair into HEK239T cell (1 ml culture, 96-well deep well plate). Antibody expression was carried out for 7 days at 37° C. with vigorous shaking. The culture supernatants were collected and incubated with 300 µl (50:50 slurry) Mabselect Sure resin (GE Healthcare) overnight. The resin was then transferred to filter plates and washed with 20 times the resin bed volume. The bound material was eluted with 50 mM phosphoric acid pH 3.0 and neutralized (1:20) with 20×PBS pH 11.0. IgG protein was filter (0.22 µm) sterilized. IgG yields for each Strategy #2 variant tested were comparable to WT.

Figure 14:
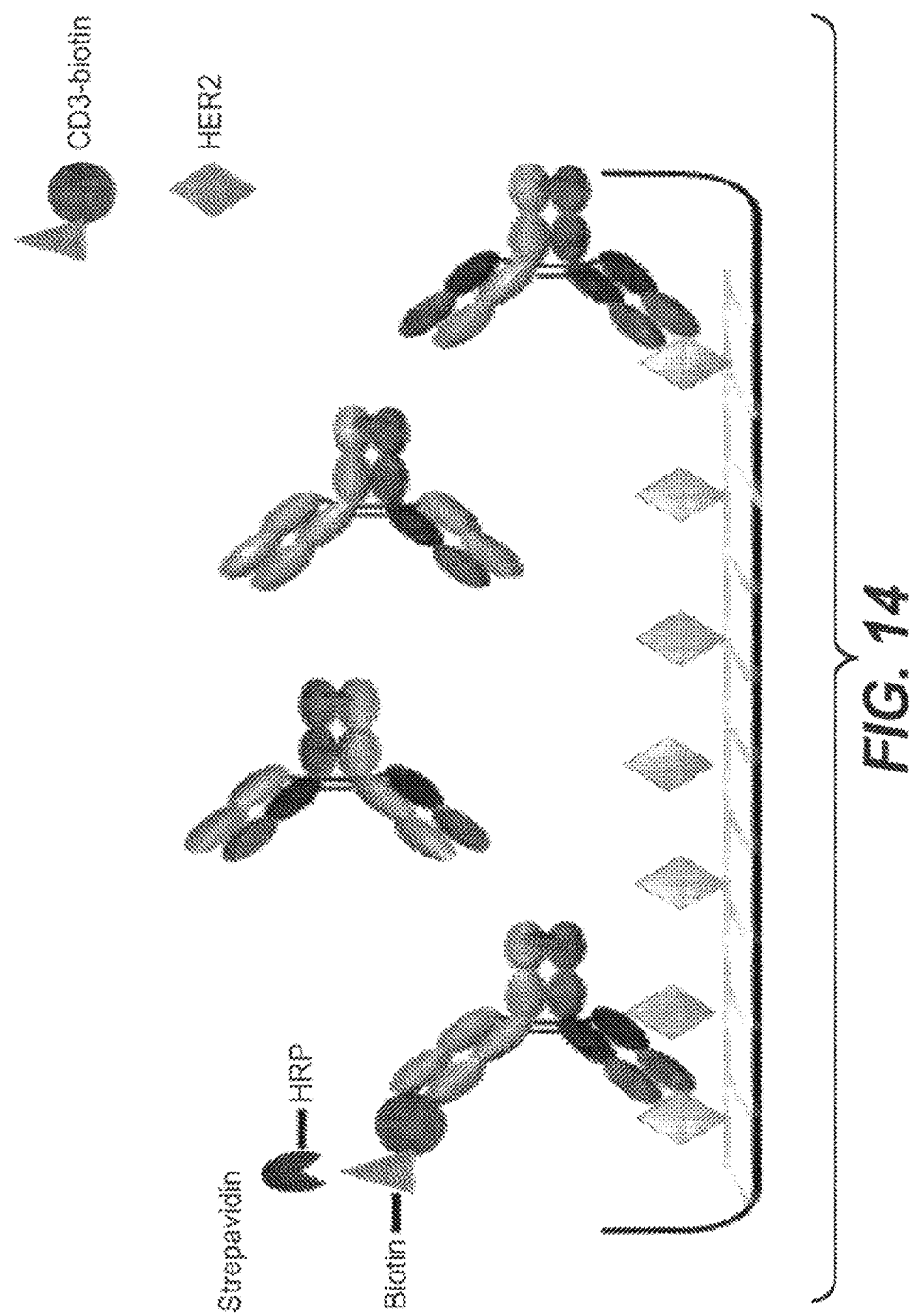
FIG. 14 shows a schematic diagram of the sandwich ELISA experiment used to determine bispecific IgG content from single cell co-expression.

Sandwich ELISA assays, as depicted in FIG. 14, were performed to determine bispecific IgG content from single cell co-expression. First, the bispecific IgG (BsIgG) standard used in Sandwich ELISA as benchmark against Strategy #2 variants was comprised of humanized anti-HER2 (4D5) as the "knob" arm and anti-CD3 (UCHT1.v9) as the "hole" arm (Zhu et al. (1995) "Identification of heavy chain residues in a humanized anti-CD3 antibody important for efficient antigen binding and T cell activation." J. Immunol. 155, 1903-10). The BsIgG standard was generated by expressing each arm in HEK293T cell separately and then annealing them in vitro (Schatz et al. (2013) "Knobs-into-holes antibody production in mammalian cell lines reveals that asymmetric afucosylation is sufficient for full antibody-dependent cellular cytotoxicity." MAbs 5, 872-881). As shown in FIG. 14, binding of the bispecific antibody to both antigens is required to generate sandwich ELISA signal. The ELISA signal strength was then benchmarked against that of the BsIgG standard (assembled in vitro) to determine the BsIgG content in the mixture.

Figure 15:
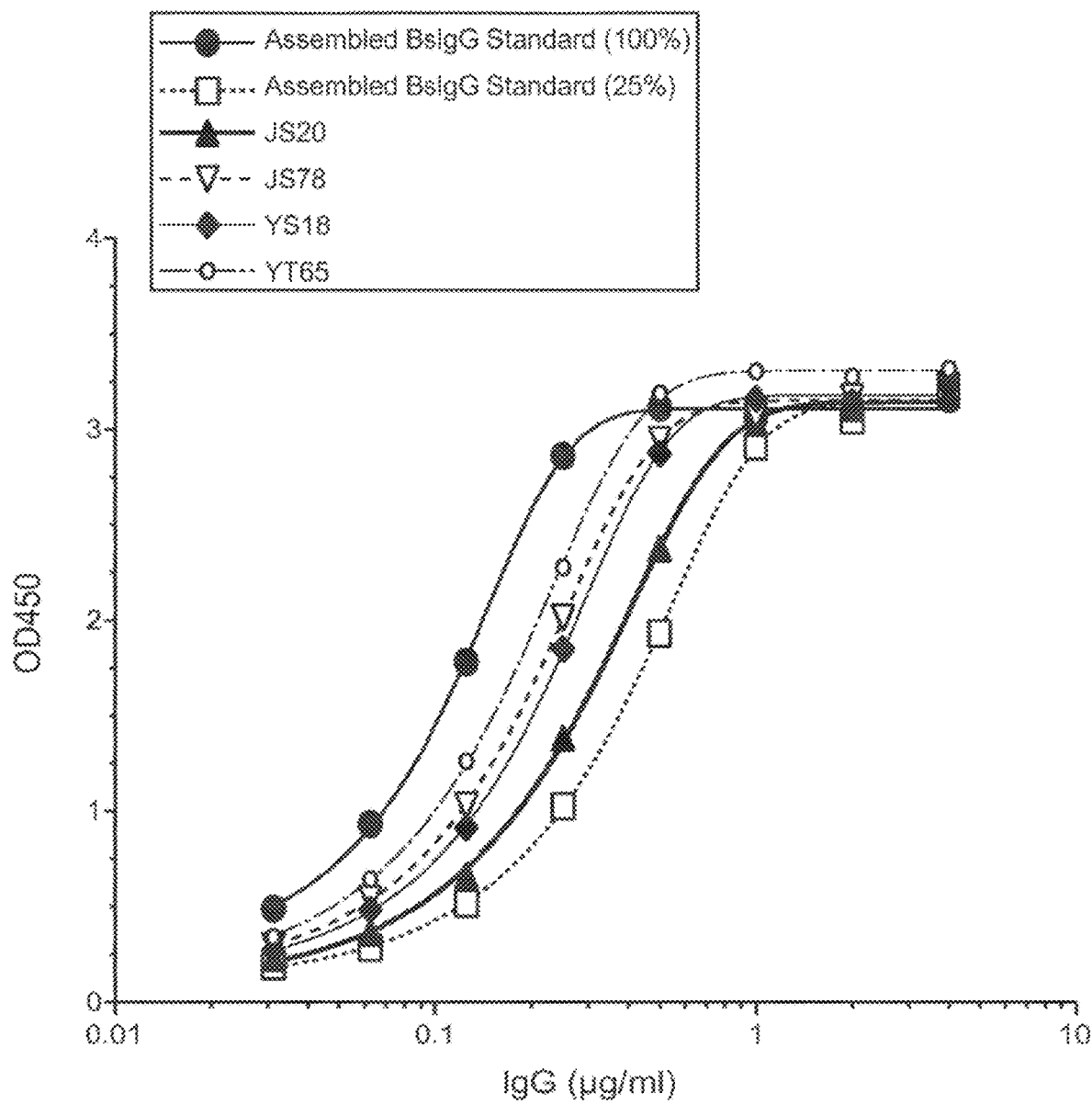
FIG. 15 shows the results of sandwich ELISAs performed on the JS20, JS78, YS18, and YT65 variants.

Briefly, ELISA plate (MaxiSorp, Nunc) was coated with HER2-ECD antigen at 1 µg/ml in PBS and kept at 4° C. overnight. The antigen coated plate was then blocked with 1% BSA in PBST (IX PBS plus 0.05% Tween-20) for 1 hour. Test samples were diluted in the same blocking buffer in a separate 96-well plate and kept at room temperature for 1 hour. The blocked samples were transferred (100 µl/well) to the HER2 coated (blocked) plate and incubated at room temperature for 2 hours. The plate was washed 15 times with PBST. The second antigen, CD3-biotin, was then added to plate at 100 µl/well (0.5 µg/ml CD3-Biotin in blocking buffer) and incubated at room temperature for 2 hours. The plate was washed 15 times with PBST. Streptavidin-HRP (Thermo Fisher, Rockford, IL) was added at 100 µl/well (0.1 µg/ml) and incubated at room temperature for 30 minutes. The plate was washed 15 times with PBST. Horseradish peroxidase substrate, Sureblue Reserve TMB solution (KPL, Gaithersburg, MD), was added at 100 µl/well. Color development was stopped by addition of an equal volume of 1.0 M phosphoric acid ($H_3PO_4$). The plate was then read at $OD_{450}$. As shown in FIG. 15, the variants having JS20, JS78, YS18, and YT65 mutations in the 4D5 arm demonstrated increased preferential heavy chain/light chain pairing exceeding the 25% bispecific assembly standard, which represents the unbiased, expected amount of correct heavy/light chain pairing of wild type sequences not influenced by the sequence modifications.

Light chain DNA ratios and heavy chain DNA ratios were optimized as described above for a 4D5.UCHT1 bispecific antibody. As shown in the exemplary results provided in Table 18 below, optimization of light chain ratio and heavy chain ratios improved bispecific antibody formation for the 4D5. UCHT1 antibody. A DNA ratio of 1:1.4:1:1 for $LC_{KNOB}:LC_{HOLE}:HC_{KNOB}:HC_{HOLE}$ was used in further experiments described below.

TABLE 18

| DNA Ratios* | Percentage 2x $LC_{KNOB}$ | Percentage 2x LC Mispair | Percentage 2x $LC_{HOLE}$ | Percentage 2x Correct BsIgG |
|---|---|---|---|---|
| 2.8:1:1:1 | 74.3 | 24.3 | 1.4 | 18.5 |
| 1.4:1:1:1 | 52.3 | 40.4 | 7.3 | 25.2 |
| 1:1:1.4:1 | 27.1 | 49.4 | 23.5 | 29.8 |
| 1:2.8:1:1 | 9.8 | 41.2 | 49.0 | 28.0 |

*$LC_{KNOB}:LC_{HOLE}:HC_{KNOB}:HC_{HOLE}$

The following variant antibodies were expressed and purified following light chain ratio optimization and heavy chain ratio optimization: 4D5.UCHT1.JS20, 4D5.UCHT1.JS78, 4D5.UCHT1.JT25, 4D5.UCHT1.YS08, 4D5.UCHT1.YS18, and 4D5.UCHT1.YT65 as compared to the 4D5.UCHT1 bispecific, all in the context of EKKE (4D5 knob, Q39E/Q38K; UCHT1 hole. Q39K/Q38E). The JS78, JT25, YS08, YS18, and YT65 mutations were in the 4D5 arm of each variant. Percentage of bispecific antibody produced by each variant was quantified via mass spectrometry and is shown in Table 19 below.

TABLE 19

| Variant | Combined BsIgG and LC scrambled | 2x Knob LC | 2x Hole LC | BsIgG | LC Scrambled | No. of mutations (LC + HC) |
|---|---|---|---|---|---|---|
| 4D5/UCHT1.JS20.EKKE | 85% | 3% | 12% | 84.6% | 0.4% | 13 |
| 4D5/UCHT1.JS78.EKKE | 84% | 1% | 15% | 83.8% | 0.2% | 13 |
| 4D5/UCHT1.JT25.EKKE | 91% | 1% | 8% | 90.9% | 0.1% | 13 |
| 4D5/UCHT1.YS08.EKKE | 77% | 1% | 22% | 76.7% | 0.3% | 12 |
| 4D5/UCHT1.YS18.EKKE | 94% | 4% | 2% | 93.9% | 0.1% | 12 |
| 4D5/UCHT1.YT65.EKKE | 90% | 2% | 8% | 89.8% | 0.2% | 10 |
| 4D5/UCHT1.EKKE | 81% | 17% | 2% | 80.6% | 0.4% | 0 |

Partial sequences of the CH1 and CL domains of 520, JS78, YS18, and YT65 heavy chains are shown in FIG. 16A, and partial sequences of the CH1 and CL domains of S20, JS78, YS18, and YT65 light chains are shown in FIG. 16B.

Figure 17A:
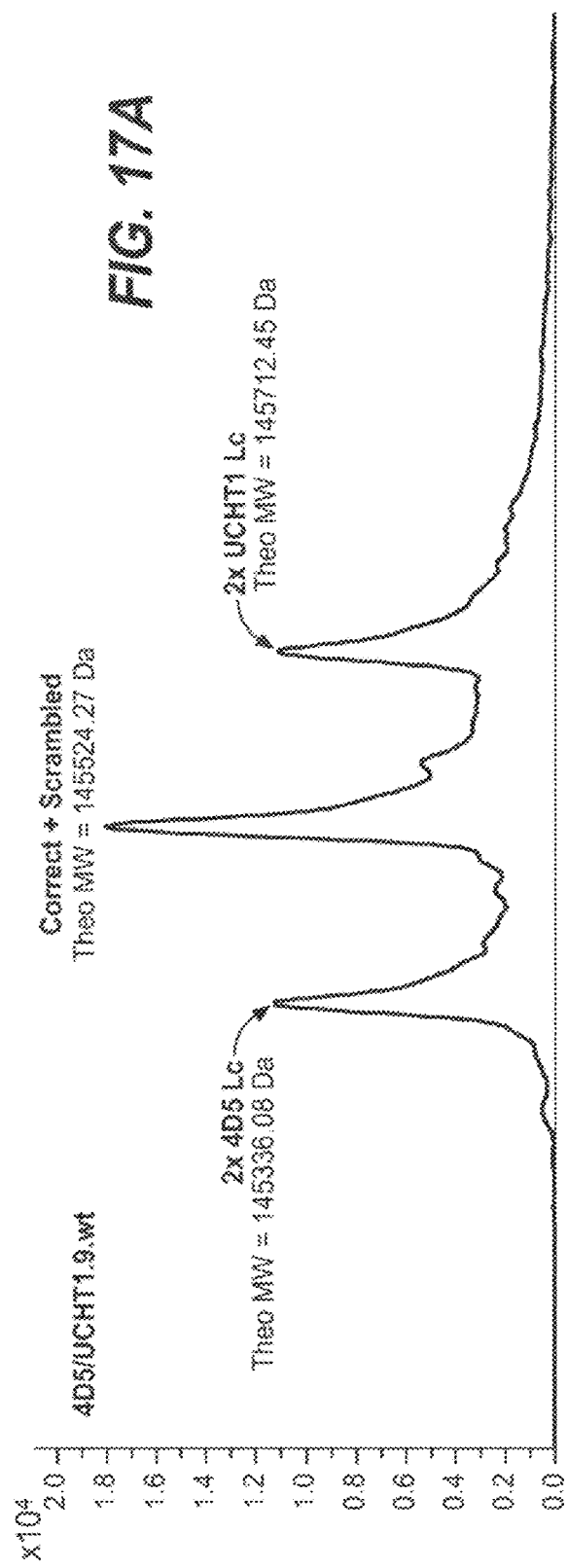
FIG. 17A shows the results of mass spectrometry performed on a wild-type 4D5/UCHT1 coexpressed bispecific antibody.
Figure 17B:
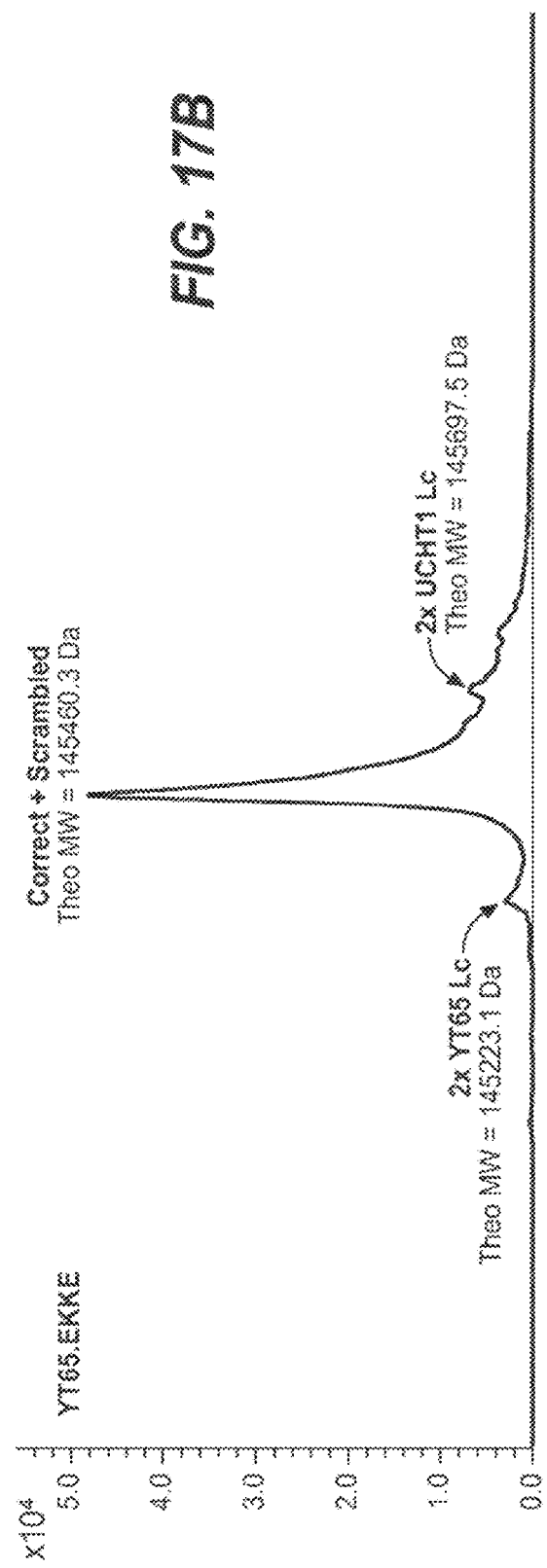
FIG. 17B shows the results of mass spectrometry performed on a 4D5/UCHT1 coexpressed antibody comprising YT65 CH1/CL mutations and VH-Q39E and VL-Q38K mutations on the 4D5 arm, and VL-Q38E and VH-Q39K mutations on the UCHT1 arm.

The results of the sandwich ELISA were confirmed via high resolution mass spectrometry. High resolution mass spectrometry utilizes the enhanced detection abilities of Orbitrap technology on the EMR Exactive Plus mass spectrometer. For quantitation, antibody product in PBS was buffer exchanged into 0.1% trifluoroacetic acid using Micro spin columns (Spin-6. Bio-Rad) or reversed phase off-line HPLC. Resultant sample fractions were directly infused onto the mass spectrometer. Parameters were optimized in Tune mode to enable baseline resolution of intra-charge state moieties. Mass envelopes were deconvoluted using Protein Deconvolution software (Thermo, score cutoff 50). Intensities of resultant deconvoluted peaks were documented and used to determine % presence of the 'correct' sequence, mispairs, half antibodies and homodimers. Seethe exemplary results in FIGS. 17 and 18. FIGS. 17A and 18A show the results of mass spectrometry performed on a wild-type 4D5/UCHT1 bispecific antibody, and FIGS. 17B and 18B show the results of mass spectrometry performed on a 4D5/UCHT1 antibody comprising YT65 CH1/CL mutations and VH-Q39E/VL-Q38K mutations on the 4D5 arm and VH-Q39K/VL-Q38E mutations on the UCHT1 arm ("EKKE"). These exemplary results are quantified in Table 20 below, the VH/VL and CH1/CL mutations, alone or in combination further improved correct heavy chain/light chain pairing in the 4D5/UCHT1v.9 bispecific.

TABLE 20

| Variants | Combined BsIgG and LC scrambled | 2x Knob LC | 2x Hole LC | BsIgG | LC Scrambled |
|---|---|---|---|---|---|
| 4D5/UCHT1.WT | 47.7% | 20.0% | 32.3% | 23.9% | 23.9% |
| 4D5/UCHT1.EKKE | 67.3% | 12.8% | 19.9% | 63.3% | 4.0% |
| 4D5/UCHT1.YT65 | 70.1% | 19.4% | 10.5% | 67.1% | 3.0% |
| 4D5/UCHT1.YT65.EKKE | 90.0% | 1.7% | 8.3% | 89.8% | 0.2% |

As shown in FIGS. 16A and 16B, each of the YT65 heavy chain and light chain sequences contains 5 amino acid substitutions. The YT65 heavy chain and light chain were further modified to restore the wild type amino acid at one or more positions to determine the minimal number of mutations required for driving correct heavy chain/light chain pairing. The amino acid sequences of the "back-mutated" YT65 heavy chain and light chain variants are provided in FIGS. 19A and 193. High resolution mass spectrometry was also performed on the YT65 back-mutated variants to determine if such variants demonstrated increased preferential heavy chain/light chain pairing, as well. As shown in the exemplary results provided in Table 21 below, all back-mutated variants tested demonstrated improved LC and HC pairing in the context of a bispecific antibody, thus correspondingly improving correct bispecific formation when the two half antibodies are expressed in a single cell.

TABLE 21

| Variant | Combined BsIgG and LC scrambled | 2x Knob LC | 2x Hole LC | BsIgG | LC Scrambled | Total Number of mutations (HC + LC) |
|---|---|---|---|---|---|---|
| 4D5/UCHT1.YT65.EKKE | 87% | 6% | 7% | 86.5% | 0.5% | 10 (parental) |
| 4D5/UCHT1.YT65.Hc12.Lc3 | 73% | 23% | 4% | 71.7% | 1.3% | 6 |
| 4D5/UCHT1.YT65.Hc13.Lc3 | 73% | 21% | 6% | 71.2% | 1.8% | 5 |
| 4D5/UCHT1.YT65.Hc12.Lc4 | 65% | 29% | 6% | 62.2% | 2.8% | 6 |
| 4D5/UCHT1.YT65.Hc13.Lc4 | 66% | 28% | 6% | 63.3% | 2.7% | 5 |
| 4D5/UCHT1.YT65.Hc12.Lc6 | 66% | 31% | 3% | 64.6% | 1.4% | 5 |
| 4D5/UCHT1.YT65.Hc13.Lc6 | 66% | 31% | 3% | 64.6% | 1.4% | 4 |
| 4D5/UCHT1.YT65.Hc12.Lc7 | 68% | 26% | 7% | 65.2% | 2.8% | 4 |
| 4D5/UCHT1.YT65.Hc13.Lc7 | 67% | 26% | 8% | 63.7% | 3.3% | 3 |
| 4D5/UCHT1.YT65.Hc10.LC.EKKE | 87% | 9% | 4% | 86.6% | 0.4% | 8 |
| 4D5/UCHT1.YT65.Hc12.LC.EKKE | 86% | 9% | 5% | 85.5% | 0.5% | 7 |
| 4D5/UCHT1.YT65.Hc13.LC.EKKE | 81% | 10% | 9% | 79.9% | 1.1% | 6 |

Figure 20A:
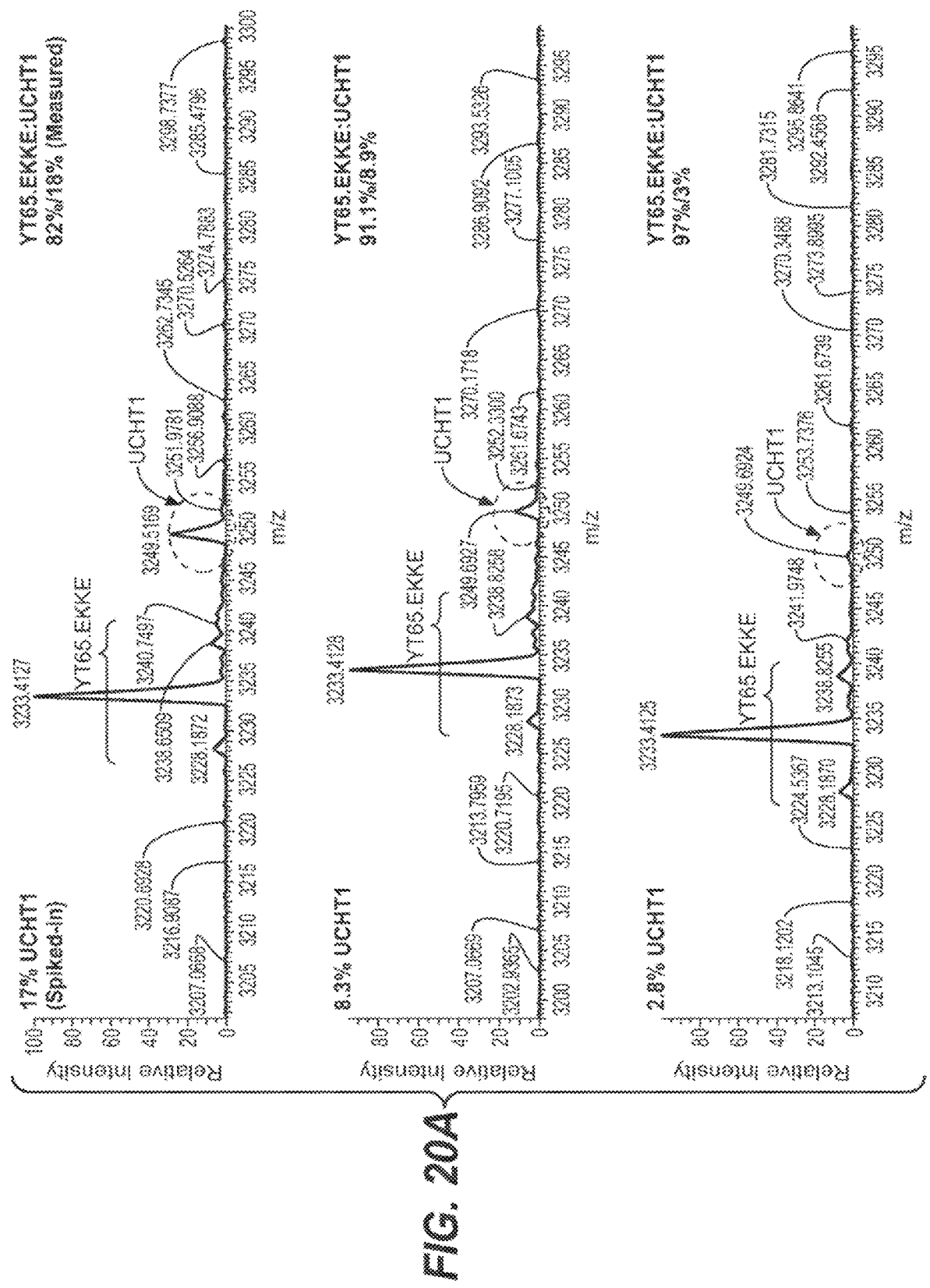
FIG. 20A shows the results of pH neutral native mass spectrometry performed on a 4D5/UCHT1 antibody comprising YT65 CH1/CL mutations and VH-Q39E and VL-Q38K mutations on the 4D5 arm, and VH-Q39K and VL-Q38E mutations on the UCHT1 arm.

Qualitative examination of the modified bispecific sample complexity under neutral pH conditions was performed by native mass spectrometry. Native MS provides information on antibody multimers and other forms of aggregates (i.e. half antibody-monomer interactions). Samples were buffer exchanged into 10 mM ammonium acetate using SEC HPLC or spin columns and ionized into the EMR MS through direct infusion. Analysis was performed using Protein Deconvolution software with a score cutoff of 10. As shown in FIG. 20A, the 4D5/UCHT1 antibody comprising YT65 CH1/CL mutations and VL-Q38K and VH-Q39E mutations on the 4D5 arm and VL-Q38E and VH-Q39K mutations on the UCHT1 arm demonstrated increased correct heavy chain/light chain pairing. UCHT1 antibody was spiked into the sample to determine the sensitivity and limit of detection for the assay and to aid in the quantification of the bispecific antibody, 2×LC knob antibody, and 2×LC hole antibody species. FIG. 20A shows that the limit of quantification for the 2×LC knob antibody and 2×LC hole antibody species is below 2.8%.

Figure 20B:
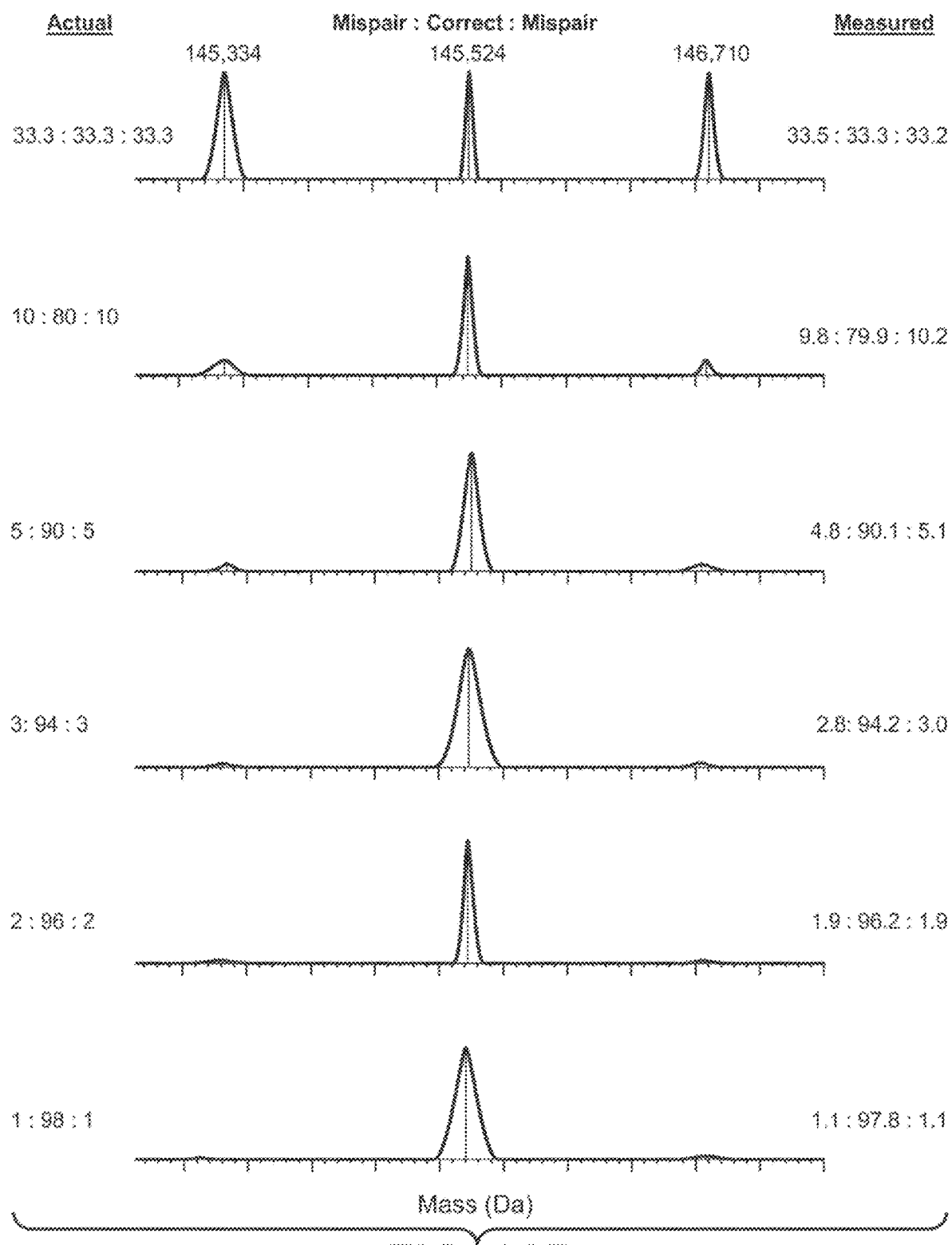
FIG. 20B shows the results of experiments that were performed to confirm the detection sensitivity of the analysis used to obtain the data in FIG. 20A.

FIG. 20B confirms the detection sensitivity of the analysis used to obtain the data in FIG. 20A. In FIG. 20B, a sample containing 100% correctly paired HER2/UCHT1 (i.e., HER2 LC/HER2 HC/UCHT1 HC/UCHT1 LC, middle peak) was spiked with both a mispaired HER2/UCHT1 comprising two HER2 LCs (i.e., HER2 LC/HER2 HC/UCHT1 HC/HER2 LC, left peak) and a mispaired HER2/UCHT1 comprising two UCHT1 LCs (i.e., UCHT1 LC/HER2 HC/UCHT1 HC/UCHT1 LC, right peak) at decreasing ratios, as shown at the left of FIG. 20B. The measured ratios, shown at the right of FIG. 20B, indicate that there is very little difference between the actual ratios and measured ratios of each of the species in the sample.

Example 3: Comparison of Antibody Variants with Wild Type Antibodies in Tm and $K_D$ Differential scanning calorimetry (DSC) was performed to determine the melting temperatures of 4D5 Fabs that were modified to contain (a) Q39E in VH and Q38K in VL; (b) S183K in the CH1 and V133E in the CL; (c) Q39E in VH, Q38K in VL, S183K in the CH1, and V133E in the CL; (d) Q39K in VH and Q38E in VL (e) S183E in the CH1 and V133K in the CL; (f) Q39K in VH, Q38E in VL, S183E in the CH1, and V133K in the CL; (g) YT65 mutations in the CH1 and CL; or (h) Q39E in VH and Q38K in VL and YT65 mutations in the CH1 and CL (see Ionescu et al. (2008) *J Pharm Sci* 97, 1414-1426). DSC was performed on 4D5 containing no mutations in parallel. The exemplary results shown in Table 22-1 below demonstrate that the mutations introduced in the variable and/or constant regions described herein do not greatly affect the Tm of the antibodies.

TABLE 22-1

| | Mutations | | | | |
|---|---|---|---|---|---|
| | VH | VL | CH1 | CL | Tm (° C.) |
| WT | | | | | 81.9° C. |
| $EK_{variable}$ | Q39E | Q38K | | | 81.5° C. |
| $KE_{constant}$ | | | S183K | V133E | 78.5° C. |
| $EK_{variable}/KE_{constant}$ | Q39E | Q38K | S183K | V133E | 77.9° C. |

TABLE 22-1-continued

| | Mutations | | | | |
|---|---|---|---|---|---|
| | VH | VL | CH1 | CL | Tm (° C.) |
| $KE_{variable}$ | Q39K | Q38E | | | 79.9° C. |
| $EK_{constant}$ | | | S183E | V133K | 80.2° C. |
| $KE_{variable}/EK_{constant}$ | Q39K | Q38E | S183E | V133K | 78.2° C. |
| YT65 | | | YT65 | Y165 | 82.0° C. |
| YT65/$EK_{variable}$ | Q39E | Q38K | Y165 | YT65 | 81.4° C. |

Surface plasmon resonance (SPR) analyses were performed to calculate the binding affinities of the 4D5 variants described above for HER2. The results shown in Table 22-2 below demonstrate that the mutations introduced in the variable and/or constant regions described herein do not greatly affect the $K_D$ of the antibodies.

TABLE 22-2

| | Mutations | | | | $K_D$ |
|---|---|---|---|---|---|
| | VH | VL | CH1 | CL | (nM) |
| WT | | | | | 0.63 |
| $EK_{variable}$ | Q39E | Q38K | | | 0.67 |
| $KE_{constant}$ | | | S183K | V133E | 0.78 |
| $EK_{variable}/KE_{constant}$ | Q39E | Q38K | S183K | V133E | 0.75 |
| $KE_{variable}$ | Q39K | Q38E | | | 0.44 |
| $EK_{constant}$ | | | S183E | V133K | 0.59 |
| $KE_{variable}/EK_{constant}$ | Q39K | Q38E | S183E | V133K | 0.46 |
| YT65 | | | YT65 | YT65 | 0.42 |
| YT65/$EK_{variable}$ | Q39E | Q38K | YT65 | YT65 | 0.72 |

Example 4: Application of VH/VL and CH1/CL Mutations to Other Bispecific Pairs

Figure 21:
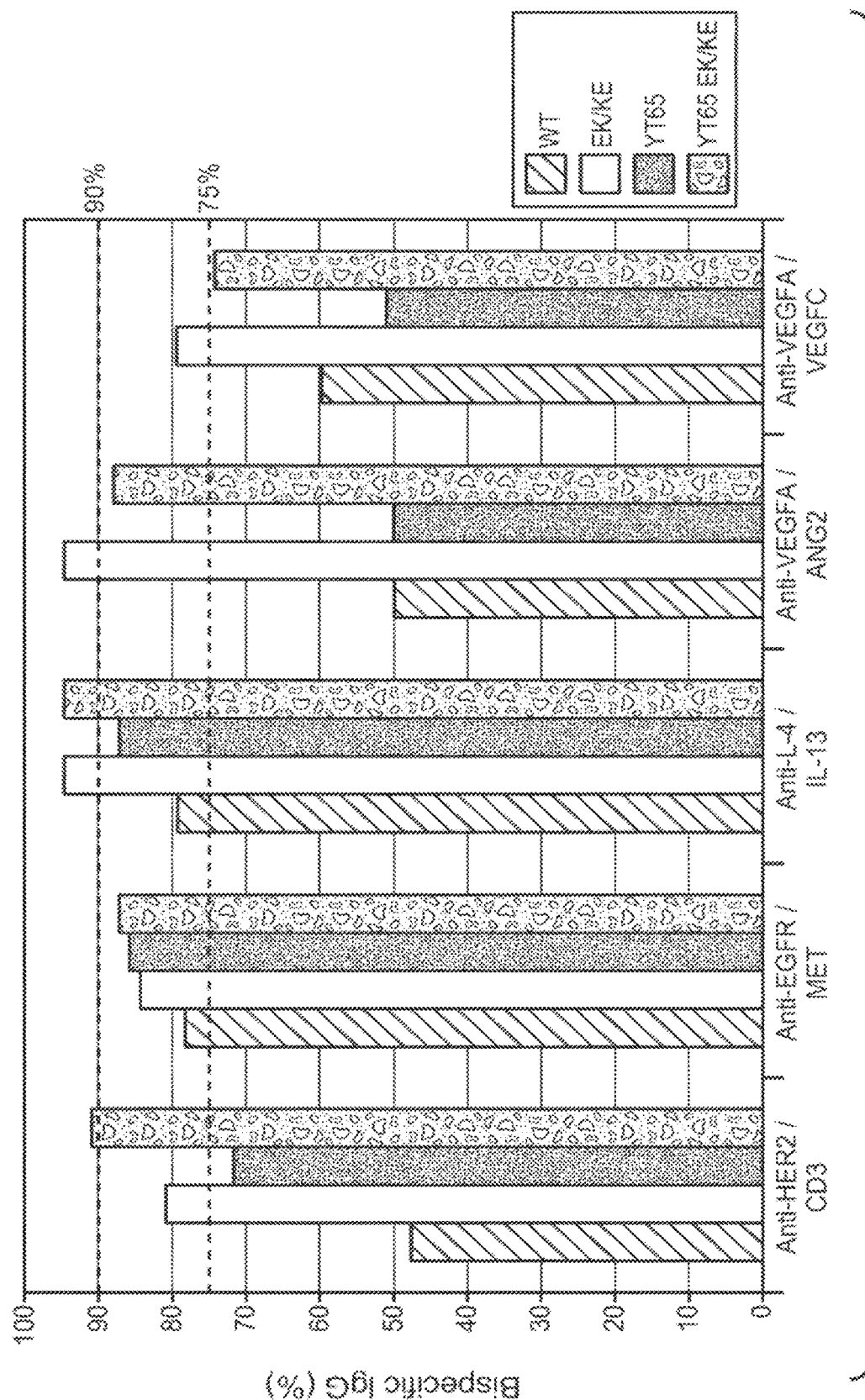
FIG. 21 shows the quantitative results of high resolution mass spectrometry experiments performed to assess the effects of YT65, EKKE, and both YT65 and EKKE on heavy chain/light chain pairing in anti-IL4/IL13, anti-EGFR/MET, anti-VEGFA/ANG2 anti-VEGFA/VEGFC, and anti-HER2/CD3 (i.e., 4D5/UCHT1) bispecific antibodies.

Next, the effects of YT65, EKKE, or YT65 and EKKE mutations on heavy chain/light chain paring in bispecific antibodies other than 4D5/UCHT1 were analyzed. Briefly, YT65 CH1/CL mutations, EKKE VH/VL mutation, or both YT65 and EKKE mutations were introduced into each of the following bispecific antibodies: anti-IL4/IL13, anti-EGFR/MET, anti-VEGFA/ANG2, and anti-VEGFA/VEGFC. The YT65 CH/CL mutations were introduced into the knob arm of each bispecific antibody. Unmodified and modified bispecific antibodies were analyzed via high-resolution mass spectroscopy as described above. As shown in the exemplary results provided in Table 23 and FIG. 21, the EKKE and YT.65 mutations, alone or in combination, generally improved bispecific assembly in different antibodies. In the examples where the parent antibodies already exhibit strong preferential heavy/light chain pairing, further improvement is difficult to achieve or detect.

TABLE 23

| BsIgG Coexpression Pairs | Variants | Combined BsIgG and LC scrambled | 2x Knob LC | 2x Hole LC | BsIgG | LC Scrambled |
|---|---|---|---|---|---|---|
| Anti-IL4/IL13 | WT | 79%‡ | 17% | 4% | 78.1%‡ | 0.9% |
|  | EKKE | 95% | 4% | 1% | 95.0% | 0.0% |
|  | YT65$_{knob}$ | 87% | 7% | 6% | 86.5% | 0.5% |
|  | YT65 EKKE | 95% | 2% | 3% | 94.9% | 0.1% |
| Anti-EGFR/MET | WT | 79% | 9% | 13% | 77.5%‡ | 1.5% |
|  | EKKE | 84% | 13% | 3% | 83.5% | 0.5% |
|  | YT65$_{knob}$ | 86% | 10% | 4% | 85.5% | 0.5% |
|  | YT65.EKKE | 87% | 11% | 2% | 86.7% | 0.3% |
| Anti-VEGFA/ANG2 | WT | 50% | 21% | 29% | 29.0%‡ | 21.0% |
|  | EKKE | 95% | 1% | 4% | 95.0% | 0.0% |
|  | YT65$_{knob}$ | 50% | 29% | 21% | 29.0% | 21.0% |
|  | YT65.EKKE | 87% | 7% | 6% | 86.5% | 0.5% |
| Anti-VEGFA/VEGFC | WT | 59% | 4% | 36% | 56.4%‡ | 2.6% |
|  | EKKE | 79% | 3% | 18% | 78.3% | 0.7% |
|  | YT65$_{knob}$ | 52% | 13% | 36% | 40.4% | 11.6% |
|  | YT65.EKKE | 75% | 1% | 24% | 74.7% | 0.3% |
| Anti-HER2/CD3 | WT | 48% | 20% | 32% | 24.0%‡ | 24.0% |
|  | EKKE | 81% | 17% | 2% | 80.6% | 0.4% |
|  | YT65$_{knob}$ | 70% | 19% | 10% | 67.2% | 2.8% |
|  | YT65.EKKE | 90% | 2% | 8% | 89.8% | 0.2% |

‡Unmodified bispecific antibody shows correct HC/LC pairing

The activity of the anti-HER2/CD3 antibody having the EKKE and YT65 knob mutations was compared to that of an unmodified anti-HER2/CD3 antibody in an in vitro cytotoxicity assay, as described above. As shown in FIG. 23, the activities of the modified and unmodified anti-HER2/CD3 antibodies were comparable.

The effects of YT65 and EKKE mutations on heavy chain/light chain paring in bispecific 4D5/UCHT1 antibodies of different isotypes were analyzed. Q39E$_{HC1}$/Q38K$_{LC1}$ knob/Q39K$_{HC2}$/Q38E$_{LC2}$ hole and YT65 knob mutations were introduced into bispecific anti-4D5/UCHT1 antibodies of human IgG1 isotype, human IgG2 isotype, human IgG4 isotype and murine IgG2a isotype. Antibodies of human IgG2 isotype have not been observed to successfully assemble in vitro. The exemplary results in Table 24 below show that the mutations in the light chain and heavy chain variable domains significantly improved bispecific assembly in human bispecific antibodies of different isotypes.

TABLE 24

| BsIgG Coexpression Pairs | Variants | Combined BsIgG and LC scrambled | 2x Knob LC | 2x Hole LC | BsIgG | LC Scrambled |
|---|---|---|---|---|---|---|
| 4D5/UCHT1 huIgG1 | WT | 47.7% | 20.0% | 32.3% | 23.9% | 23.9% |
|  | YT65.EKKE | 90.0% | 1.7% | 8.3% | 89.8% | 0.2% |
| 4D5/UCHT1 huIgG2 | WT | 50.0% | 27.5% | 22.5% | 27.5% | 22.5% |
|  | YT65.EKKE | 87.3% | 1.6% | 11.1% | 87.1% | 0.2% |
| 4D5/UCHT1 huIgG4 | WT | 38.6% | 27.7% | 33.7% | 19.3% | 19.3% |
|  | YT65.EKKE | 88.4% | 9.6% | 2.0% | 88.2% | 0.2% |
| 4D5/UCHT1 muIgG2a | WT | 44.9% | 25.8% | 29.2% | 22.5% | 22.5% |
|  | YT65.EKKE | 94.5% | 2.5% | 3.0% | 94.4% | 0.1% |

Next, a stable cell line expressing a bispecific 4D5/UCHT1 antibody having Q39E$_{HC1}$/Q38K$_{LC1}$ knob/Q39K$_{HC2}$/Q38E$_{LC2}$ hole and YT65 knob mutations was constructed. CHO cells were transfected via electroporation, and transformant were selected in the presence of MSX (methionine sulfoximine). Isolates were picked several weeks later and were screened for antibody titer and percentage of correctly assembled bispecific antibody. Top clones were evaluated employing a 14-day fed-batch culture process. Bispecific antibody was harvested, purified, and analyzed via high-resolution mass spectroscopy as described above. As shown in the exemplary results provided in Table 25 below, over 97% of the bispecific antibody expressed from the cell line was correctly assembled. A transiently transfected cell line expressing the 4D5/UCHT1 antibody having Q39E$_{HC1}$/Q38K$_{LC1}$ knob/Q39K$_{HC2}$/Q38E$_{LC2}$ hole and YT65 knob mutations was found to express 90% correctly assembled bispecific antibody. Such results show that the percentage of correctly assembled bispecific antibody expressed by the stable cell line is comparable to that expressed by the transiently transfected cells. Stable cell lines expressing 4D5/UCHT1 bispecific antibody having Q39E$_{HC1}$/Q38K$_{LC1}$ knob/Q39K$_{HC2}$/Q38E$_{LC2}$ hole and V133E/S183K knob/V133K/S183E hole mutations or anti-IL 13/IL4 Q39E$_{HC1}$/Q38K$_{LC1}$ knob/Q39K$_{HC2}$/Q38E$_{LC2}$ V133K/S183E hole mutations were constructed. Exemplary results show that over 98% or 91% of the bispecific antibody expressed from the cell line was correctly assembled (Table 25).

TABLE 25

| Stable Cell Line | BsIgG | 2x Knob LC | 2x Hole LC | LC Scrambled |
|---|---|---|---|---|
| 4D5/UCHT1.YT65.EKKE | 97.5% | 2.5% | 0.0% | 0.0% |
| 4D5/UCHT1.EKKE + V133K/S183E$_{hole}$ + V133E/S183K$_{knob}$ | 98.3% | 0.0% | 1.7% | 0.0% |

TABLE 25-continued

| Stable Cell Line | BsIgG | 2x Knob LC | 2x Hole LC | LC Scrambled |
|---|---|---|---|---|
| aIL13/aIL4.EKKE + V133K/S183E$_{hole}$ | 91.3% | 1.3% | 7.3% | 0.1% |

Next, the effects of the combination of YT65, EKKE, and V133K/S183E mutations on heavy chain/light chain paring in 4D5/UCHT1 were analyzed. Briefly, a 4D5/UCHT1 bispecific antibody comprising EKKE mutations, YT65 mutations on the knob arm (i.e., the 4D5 arm), and V133K/S183E mutations on the hole arm (i.e., the UCHT1 arm) was constructed, produced, purified, and analyzed via high-resolution mass spectroscopy as described above. Bispecific assembly of 4D5/UCHT1.YT65$_{KNOB}$.V133K/S183E$_{HOLE}$.EKKE was compared to bispecific assembly of 4D5/UCHT1, V133K/S183E$_{HOLE}$.EKKE. The exemplary results in Table 26 below show that the introduction of YT65 mutations into the knob arm of a 4D5/UCHT1 bispecific antibody having V133K/S183E$_{HOLE}$ and EKKE mutations improved correct heavy chain/light chain pairing from approximately 95% to 100%.

TABLE 26

| 4D5 (KNOB) MUTATIONS | UCHT1 (HOLE) MUTATIONS | BsIgG | 2x knob LC | 2x Hole LC | LC Scrambled |
|---|---|---|---|---|---|
| Q39E/Q38K | Q39K/Q38E V133K/S183E | 94.75 | 4.7% | 0.0% | 0.0% |
| Q39E/Q38K YT65 | Q39K/Q38E V133K/S183E | 100% | 0.0% | 0.0% | 0.0% |

Further experiments were performed to assess the transferability of the mutations tested in Table 26 to other bispecific antibodies. The exemplary results in Table 27 below show that the introduction of V133K/S183E mutations into the hole arm of five different bispecific antibodies having EKKE and YT65$_{KNOB}$ mutations improved correct heavy chain/light chain pairing from approximately 79-95% to 95-100%.

TABLE 27

| | BsIgG (%) | | | | |
|---|---|---|---|---|---|
| VARIANTS | Anti-HER2/CD3 (4D5/UCHT1) | Anti-IL4/IL13 | Anti-EGFR/cMET | Anti-VEGFA/ANG2 | Anti-VEGFA/VEGFC |
| WT | 25 | 71 | 73 | 30 | 35 |
| EKKE + YT65$_{KNOB}$ | 84 | 84 | 95 | 79 | 80 |
| EKKE + YT65$_{KNOB}$ + V133K/S183E$_{HOLE}$ | 100 | 96 | 100 | 95 | 98 |

Additional experiments were performed to assess the transferability of the mutations tested in Tables 26 and 27 to anti-HER2/CD3 (4D5/UCHT1) bispecific antibodies of other human IgG subclasses. The exemplary results in Table 28 below show that the introduction of V133K/S183E mutations into the hole arm of three different human IgG subtypes having EKKE and YT65$_{KNOB}$ mutations improved correct heavy chain/light chain pairing from approximately 77-85% to 98-100%.

TABLE 28

| Anti-HER2/CD3 | BsIgG (%) | | |
|---|---|---|---|
| | Human IgG1 | Human IgG2 | Human IgG4 |
| WT | 25 | 27 | 22 |
| EKKE + YT65$_{KNOB}$ | 85 | 77 | 80 |
| EKKE + YT65$_{KNOB}$ + V133K/S183E$_{HOLE}$ | 100 | 100 | 98 |

The crystal structure of 4D5 Fab containing VL-Q38K, VH-Q39E, and the YT65 mutations was determined to a resolution of 1.72 Å. The overall structure of the mutant does not show significant difference compared to the wild type 4D5 Fab, indicating the mutations introduced to the CH1/CL interface do not perturb structural integrity. See FIG. 22A. The CL-S176F mutation and the CH1-F170S mutation showed good conformational complementarity, resulting in a well packed CL/CH1 interface. This is consistent with the observed high thermostability of the 4D5 Fab containing the YT65 mutations described in Table 22-1.

According to the structure, the CL-S176F mutation disfavors the pairing of the mutant LC with the wild type HC because the mutated residue CL-S176F and wild type CH1-F170 are not conformationally compatible. The CH1-F170S mutation disfavors the pairing of the mutant HC with the wild type LC because such pairing would generate a vacancy at the hydrophobic core which is energetically unstable. See FIG. 22B. Therefore, the selective pairing between CL-S176F and CH1-F170S contributes to an increased yield of correctly paired BsIgG production.

Table 29 below provides the results of experiments that were performed to assess the transferability of different combinations of EK$_{KNOB}$, EK$_{HOLE}$, KE$_{KNOB}$, KE$_{HOLE}$, EKKE, KEEK, S183E/V133K$_{KNOB}$, S183/V133K$_{HOLE}$, S183K/V133E$_{KNOB}$, S183K/V133E$_{HOLE}$, YT65$_{KNOB}$, AND YT65$_{HOLE}$ to anti-HER2/CD3 IgG1, anti-IL4/IL13 IgG1, anti-EGFR/MET IgG1, anti-VEGFA/ANG2 IgG1, anti-VEGFA/VEGFC IgG1, anti-HER2/CD3 IgG2, anti-HER2/CD3 IgG4, and anti-HER2/CD3 mIgG2a. The exemplary results in Table 29 below show that the mutations improved correct heavy chain/light chain pairing.

TABLE 29

| | Knob HC 1 | | LC 1 | | Hole HC 2 | | LC 2 | | Deconvoluted |
|---|---|---|---|---|---|---|---|---|---|
| | VH1 | CH1 | VL1 | CL1 | VH2 | CH1 | VL2 | CL | Assembly % |
| Anti-HER2/CD3 IgG1 | Q39E | | Q38K | | Q39K | | Q38E | | 24.6% |
| | | | | | | | | | 55.7% |
| | | | | | | S183E | | V133K | 44.2% |

TABLE 29-continued

| | Knob HC 1 | | LC 1 | | Hole HC 2 | | LC 2 | | Deconvoluted Assembly % |
|---|---|---|---|---|---|---|---|---|---|
| | VH1 | CH1 | VL1 | CL1 | VH2 | CH1 | VL2 | CL | |
| | | S183K | | V133E | | | | | 24.9% |
| | | YT65H | | YT65L | | | | | 59.5% |
| | | S183K | | V133E | | S183E | | V133K | 46.4% |
| | | YT65H | | YT65L | | S183E | | V133K | 87.0% |
| | Q39E | | Q38K | | Q39K | S183E | Q38E | V133K | 81.2% |
| | Q39E | S183K | Q38K | V133E | Q39K | | Q38E | | 63.0% |
| | Q39E | YT65H | Q38K | YT65L | Q39K | | Q38E | | 84.4% |
| | Q39E | S183K | Q38K | V133E | Q39K | S183E | Q38E | V133K | 91.7% |
| | Q39E | YT65H | Q38K | YT65L | Q39K | S183E | Q38E | V133K | 100.0% |
| | Q39E | | Q38K | | | | | | 37.5% |
| | Q39E | | Q38K | | | S183E | | V133K | 65.6% |
| | Q39E | S183K | Q38K | V133E | | | | | 38.3% |
| | Q39E | YT65H | Q38K | YT65L | | | | | 73.7% |
| | Q39E | S183K | Q38K | V133E | | S183E | | V133K | 66.2% |
| | Q39E | YT65H | Q38K | YT65L | | S183E | | V133K | 85.3% |
| | | | | | Q39K | | Q38E | | 53.1% |
| | | | | | Q39K | S183E | Q38E | V133K | 78.6% |
| | | S183K | | V133E | Q39K | | Q38E | | 55.3% |
| | | YT65H | | YT65L | Q39K | | Q38E | | 75.5% |
| | | S183K | | V133E | Q39K | S183E | Q38E | V133K | 89.8% |
| | | YT65H | | YT65L | Q39K | S183E | Q38E | V133K | 98.2% |
| | Q39K | S183E | Q38E | V133K | Q39E | S183K | Q38K | V133E | 73.0% |
| Anti-IL13/1L4 IgG1 | | | | | | | | | 70.8% |
| | Q39E | | Q38K | | Q39K | | Q38E | | 76.3% |
| | | | | | | S183E | | V133K | 81.6% |
| | | S183K | | V133E | | | | | 73.7% |
| | | YT65H | | YT65L | | | | | 68.3% |
| | | S183K | | V133E | | S183E | | V133K | 86.2% |
| | | YT65H | | YT65L | | S183E | | V133K | 93.7% |
| | Q39E | | Q38K | | Q39K | S183E | Q38E | V133K | 91.9% |
| | Q39E | S183K | Q38K | V133E | Q39K | | Q38E | | 81.5% |
| | Q39E | YT65H | Q38K | YT65L | Q39K | | Q38E | | 84.2% |
| | Q39E | S183K | Q38K | V133E | Q39K | S183E | Q38E | V133K | 100.0% |
| | Q39E | YT65H | Q38K | YT65L | Q39K | S183E | Q38E | V133K | 95.6% |
| Anti-EGFFt/cMET IgG1 | | | | | | | | | 73.4% |
| | Q39E | | Q38K | | Q39K | | Q38E | | 83.2% |
| | | | | | | S183E | | V133K | 81.7% |
| | | S183K | | V133E | | | | | 84.6% |
| | | YT65H | | YT65L | | | | | 84.4% |
| | | S183K | | V133E | | S183E | | V133K | 93.1% |
| | | YT65H | | YT65L | | S183E | | V133K | 96.5% |
| | Q39E | | Q38K | | Q39K | S183E | Q38E | V133K | 87.4% |
| | Q39E | S183K | Q38K | V133E | Q39K | | Q38E | | 88.3% |
| | Q39E | YT65H | Q38K | YT65L | Q39K | | Q38E | | 95.3% |
| | Q39E | S183K | Q38K | V133E | Q39K | S183E | Q38E | V133K | 100.0% |
| | Q39E | YT65H | Q38K | YT65L | Q39K | S183E | Q38E | V133K | 100.0% |
| Anti-VEGFA/ANG2 IgG1 | | | | | | | | | 24.00% |
| | Q39E | | Q38K | | Q39K | | Q38E | | 78.39% |
| | | | | | | S183E | | V133K | 69.3% |
| | | S183K | | V133E | | | | | 50.3% |
| | | YT65H | | YT65L | | | | | 52.7% |
| | | S183K | | V133E | | S183E | | V133K | 44.8% |
| | | YT65H | | YT65L | | S183E | | V133K | 79.9% |
| | Q39E | | Q38K | | Q39K | S183E | Q38E | V133K | 100.0% |
| | Q39E | S183K | Q38K | V133E | Q39K | | Q38E | | 84.8% |
| | Q39E | YT65H | Q38K | YT65L | Q39K | | Q38E | | 78.9% |
| | Q39E | S183K | Q38K | V133E | Q39K | S183E | Q38E | V133K | 98.9% |
| | Q39E | YT65H | Q38K | YT65L | Q39K | S183E | Q38E | V133K | 94.9% |
| Anti-VEGFA/VEGFC IgG1 | | | | | | | | | 34.5% |
| | Q39E | | Q38K | | Q39K | | Q38E | | 58.2% |
| | | | | | | S183E | | V133K | 46.7% |
| | | S183K | | V133E | | | | | 58.8% |
| | | YT65H | | YT65L | | | | | 38.7% |
| | | S183K | | V133E | | S183E | | V133K | 74.4% |
| | | YT65H | | YT65L | | S183E | | V133K | 100.0% |
| | Q39E | | Q38K | | Q39K | S183E | Q38E | V133K | 73.2% |
| | Q39E | S183K | Q38K | V133E | Q39K | | Q38E | | 86.2% |
| | Q39E | YT65H | Q38K | YT65L | Q39K | | Q38E | | 74.0% |
| | Q39E | S183K | Q38K | V133E | Q39K | S183E | Q38E | V133K | 100.0% |
| | Q39E | YT65H | Q38K | YT65L | Q39K | S183E | Q38E | V133K | 100.0% |
| Anti-HER2/CD3 IgG2 | | | | | | | | | 24.4% |
| | Q39E | | Q38K | | Q39K | | Q38E | | 74.2% |
| | | | | | | S183E | | V133K | 48.1% |
| | | S183K | | V133E | | | | | 40.7% |
| | | YT65H | | YT65L | | | | | 29.3% |

TABLE 29-continued

| | Knob HC 1 | | LC 1 | | Hole HC 2 | | LC 2 | | Deconvoluted |
|---|---|---|---|---|---|---|---|---|---|
| | VH1 | CH1 | VL1 | CL1 | VH2 | CH1 | VL2 | CL | Assembly % |
| | | S183K | | V133E | | S183E | | V133K | 59.1% |
| | | YT65H | | YT65L | | S183E | | V133K | 85.5% |
| | Q39E | | Q38K | | Q39K | S183E | Q38E | V133K | 83.7% |
| | Q39E | S183K | Q38K | V133E | Q39K | | Q38E | | 76.0% |
| | Q39E | YT65H | Q38K | YT65L | Q39K | | Q38E | | 76.6% |
| | Q39E | S183K | Q38K | V133E | Q39K | S183E | Q38E | V133K | 97.8% |
| | Q39E | YT65H | Q38K | YT65L | Q39K | S183E | Q38E | V133K | 99.0% |
| Anti- | | | | | | | | | 22.2% |
| HER2/CD3 | Q39E | | Q38K | | Q39K | | Q38E | | 72.0% |
| IgG4 | | | | | | S183E | | V133K | 49.5% |
| | | S183K | | V133E | | | | | 18.5% |
| | | YT65H | | YT65L | | | | | 18.1% |
| | | S183K | | V133E | | S183E | | V133K | 47.6% |
| | | YT65H | | YT65L | | S183E | | V133K | 75.7% |
| | Q39E | | Q38K | | Q39K | S183E | Q38E | V133K | 84.9% |
| | Q39E | S183K | Q38K | V133E | Q39K | | Q38E | | 73.4% |
| | Q39E | YT65H | Q38K | YT65L | Q39K | | Q38E | | 79.5% |
| | Q39E | S183K | Q38K | V133E | Q39K | S183E | Q38E | V133K | 90.6% |
| | Q39E | YT65H | Q38K | YT65L | Q39K | S183E | Q38E | V133K | 97.6% |
| xHER2/xCD3 | Q39E | S183K | Q38K | V133E | Q39K | S183E | Q38E | V133K | 98.5% |
| mIgG2a | Q39E | YT65H | Q38K | YT65L | Q39K | S183E | Q38E | V133K | 91.2% |

Example 5: Pharmacokinetics Studies of Single Cell-Produced Bispecific Antibodies Additional studies were designed to evaluate and compare the pharmacokinetics (PK) properties (such as non-specific clearance) of single cell-produced anti-HER2/CD3 knob-in-hole (KIH) bispecific antibodies comprising EKKE, YT65, and/or V133X/S183X (CL/CH1) mutations with (a) an in vitro-assembled anti-HER2/CD3 knob-in-hole (KIH) bispecific antibodies without the mutations in VH/VL and CH1/CL and (b) trastuzumab (i.e., bivalent monospecific anti-HER2) in C.B-17 SCID mice.

C.B-17 SCID mice (Charles River Laboratories, Hollister, CA) were organized into five groups (n=9). The mice in the first group were each given a single 5 mg/kg intravenous (IV) dose of in vitro-assembled anti-HER2/CD3 Knob-in-Hole bispecific antibody. The mice in the second group were each given a single 5 mg/kg intravenous (IV) dose of in vitro-assembled anti-gD/CD3 Knob-in-Hole bispecific antibody. The mice in the third group were each given a single 5 mg/kg intravenous (IV) dose of single cell-produced anti-HER2/CD3 Knob-in-Hole bispecific antibody with EKKE+YT65$_{KNOB}$ mutations. The mice in the fourth group were each given a single 5 mg/kg intravenous (IV) dose of single cell-produced anti-HER2/CD3 Knob-in-Hole bispecific antibody with EKKE+V133E/S183K$_{KNOB}$+V133K/S183E$_{HOLE}$ mutations. The mice in the fifth group were each given a single 5 mg/kg intravenous (IV) dose of rastuzumab (i.e., an anti-HER2 monospecific bivalent antibody). The animals were from 6 to 8 weeks old and weighed approximately 16.6-21.4 g at the initiation of the study. Blood samples were collected via the femoral vein at various time points for up to 28 days. Total antibody concentrations in serum were determined by ELISAs and used for PK evaluations. PK parameters were estimated using a two-compartmental model with IV bolus input model (Model 8) (Phoenix™ WinNonlin®, Version 6.4; Pharsight Corporation; Mountain View, CA). Nominal sample collection time and nominal dose concentrations were used in the data analysis. All PK analysis was based on the naïve pool of individual animal data.

The concentration of (i) anti-HER2/CD3 Knob-in-Hole bispecific antibody, (ii) anti-HER2/CD3 Knob-in-Hole bispecific antibody with EKKE+YT65$_{KNOB}$ mutations and (iii) anti-HER2/CD3 Knob-in-Hole bispecific antibody with EKKE+V133E/S183K$_{KNOB}$+V133K/S183E$_{HOLE}$ mutation in serum was analyzed using a specific ELISA (coated with HER2 extracellular domain and detected with a biotinylated CD3, as exemplified in FIG. 14) with lower limit of quantitation of 0.08 μg/mL. The concentrations of (iv) anti-gD/CD3 Knob-in-Hole bispecific antibody and (v) trastuzumab in serum were determined using a generic ELISA. The assay used a sheep anti-human IgG as the capture reagent and a goat anti-human IgG conjugated to horseradish peroxidase as the detection reagent with lower limit of quantitation of 0.03 μg/mL.

Figure 24:
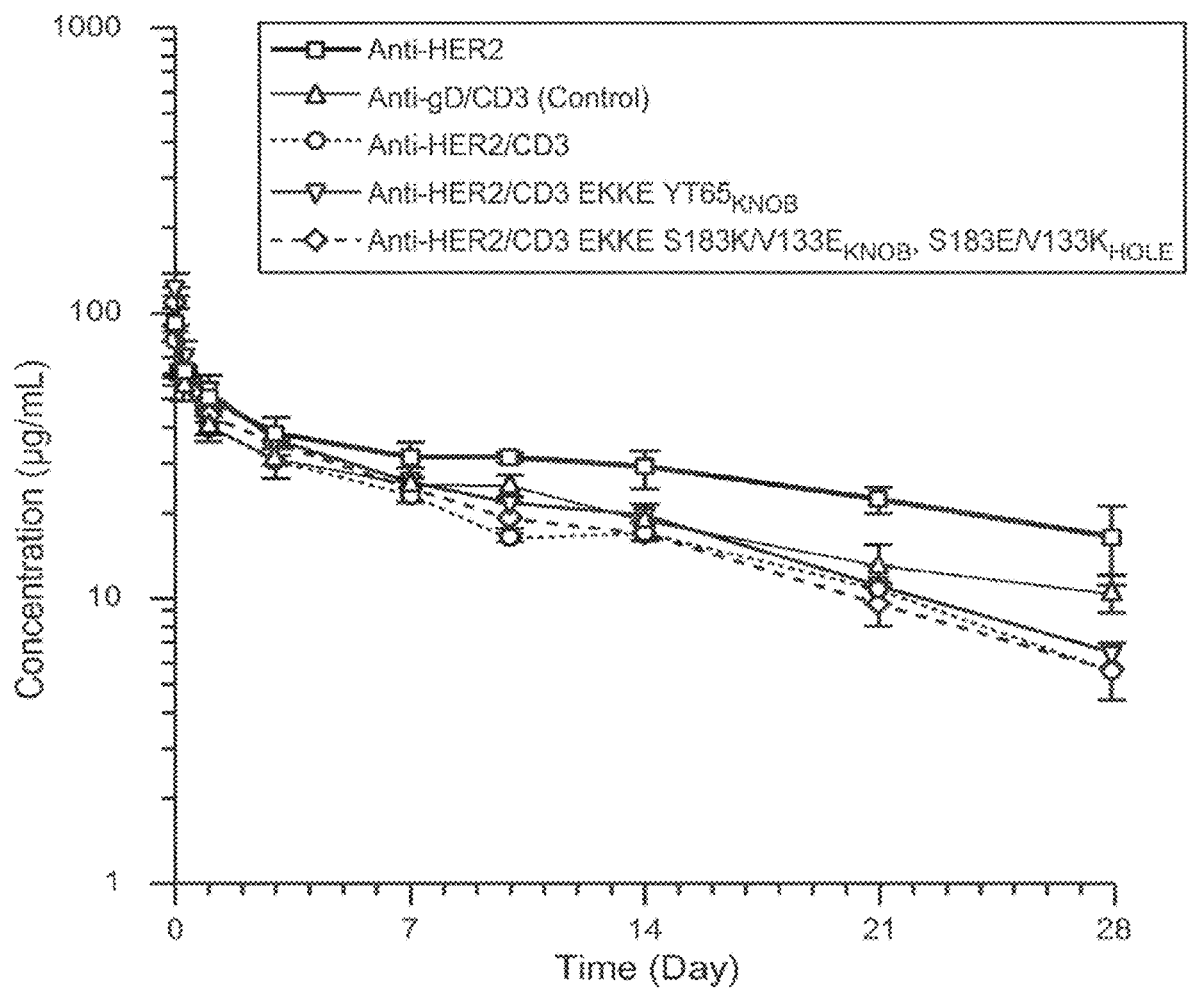
FIG. 24 shows the mean serum levels of (i) anti-HER2, (ii) anti-gD/CD3, (iii) anti-HER2/CD3, (iv) anti-HER2/CD3+EKKE+YT65$_{knob}$, and (iv) anti-HER2/CD3+EKKE+V133E/S183K$_{knob}$+V133K/S183E$_{hole}$ at various time points following 5 mg/kg intravenous administration of the antibody in C.B-17 SCID mice.

All antibodies showed biphasic disposition typical of an IgG antibody with initial faster distribution followed by slower elimination (FIG. 24). Pharmacokinetics of single cell-produced anti-HER2/CD3 Knob-in-Hole bispecific antibody with EKKE+YT65$_{KNOB}$ mutations and anti-HER2/CD3 Knob-in-Hole bispecific antibody with EKKE+V133E/S183K$_{KNOB}$+V133K/S183E$_{HOLE}$ mutations were similar to the conventional in vitro-assembled anti-HER2/CD3 Knob-in-Hole bispecific antibody (see Table 30 below). The drug clearance (CL) of single cell-produced anti-HER2/CD3 Knob-in-Hole bispecific antibody with EKKE+YT65$_{KNOB}$ mutations and anti-HER2/CD3 Knob-in-Hole bispecific antibody with EKKE+V133E/S183K$_{KNOB}$+V133K/S183E$_{HOLE}$ mutations ranged from 7.14 to 8.08 mL/day/kg and the t$_{1/2, β}$ ranged from 9.34 to 9.38 days. In vitro-assembled anti-HER2/CD3 Knob-in-Hole bispecific antibody has a CL of 8.23 mL/day/kg and t$_{1/2, β}$ of 11.4 days. In vitro-assembled anti-gD/CD3 Knob-in-Hole bispecific antibody appeared to have a slightly slower CL and longer terminal half-life compared to in vitro-assembled anti-HER2/CD3 Knob-in-Hole bispecific antibody. In this experiment, the anti-HER2/CD3 Knob-in-Hole bispecific antibody, anti-HER2/CD3 Knob-in-Hole bispecific antibody with EKKE+YT65$_{KNOB}$, and anti-HER2/CD3 Knob-in-Hole bispecific antibody with EKKE+V133E/S183K$_{KNOB}$+V133K/S183E$_{HOLE}$ had approximately two-fold faster clearance and 2-fold shorter half-life compared to trastuzumab.

TABLE 30

Pharmacokinetic Parameter Estimates of anti-HER2/CD3, anti-gD/CD3, and Herceptin after 5 mg/kg IV Administration in C.B-17 SCID mice

| | $C_{max}$ (μg/mL) | AUC (day*μg/mL) | CL (mL/day/kg) | $t_{1/2, \beta}$ (day) | $V_1$ (mL/kg) | $V_{ss}$ (mL/kg) |
|---|---|---|---|---|---|---|
| anti-HER2/CD3 + KIH, in vitro assembled | 83.5 | 608 | 8.23 | 11.4 | 59.8 | 131 |
| anti-gD/CD3 + KIH, in vitro assembled | 98.9 | 804 | 6.22 | 14.3 | 50.5 | 126 |
| anti-HER2/CD3 + KIH + EKKE + YT65$_{KNOB}$ | 110 | 619 | 8.08 | 9.34 | 45.4 | 107 |
| anti-HER2/CD3 + KIH + EKKE + V133E/S183K$_{KNOB}$ + V133K/S183E$_{HOLE}$ | 129 | 700 | 7.14 | 9.39 | 38.9 | 94.5 |
| Herceptin (anti-HER2) | 92.2 | 1320 | 3.80 | 20.6 | 54.2 | 111 |

AUC = area under the serum concentration versus time curve;
CL = clearance;
$C_{max}$ = maximum concentration;
IV = intravenous;
PK = pharmacokinetic;
$t_{1/2,\beta}$ = beta-phase half-life;
$V_1$ = volume of distribution of the central compartment;
$V_{ss}$ = volume of distribution at steady state.

The preceding Examples are offered for illustrative purposes only, and are not intended to limit the scope of the present invention in any way. Various modifications of the invention in addition to those shown and described herein will become apparent to those skilled in the art from the foregoing description and fall within the scope of the appended claims.

SEQUENCE LISTING

```
<160> NUMBER OF SEQ ID NOS: 131

<210> SEQ ID NO 1
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1
```

Gly Gln Gly Thr Lys Val Glu Ile Lys Arg Thr Val Ala Ala Pro Ser
1               5                   10                  15

Val Phe Ile Phe Pro Pro Ser Asp Glu Gln Leu Lys Ser Gly Thr Ala
            20                  25                  30

Ser Val Glu Cys Leu Leu Asn Asn Phe Tyr Pro Arg Glu Ala Lys Val
        35                  40                  45

Gln Trp Lys Val Asp Asn Ala Leu Gln Ser Gly Asn Ser Gln Glu Ser
    50                  55                  60

Val Thr Glu Gln Asp Ser Lys Asp Ser Thr Tyr Ser Leu Ser Ser Thr
65                  70                  75                  80

Leu Thr Leu Ser Lys Ala Asp Tyr Glu Lys His Lys Val Tyr Ala Cys
                85                  90                  95

Glu Val Thr His Gln Gly Leu Ser Ser Pro Val Thr Lys Ser Phe Asn
            100                 105                 110

Arg Gly Glu Cys

-continued

115

<210> SEQ ID NO 2
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Gly Gln Gly Thr Lys Val Glu Ile Lys Arg Thr Val Ala Ala Pro Ser
1               5                   10                  15

Val Phe Ile Phe Pro Pro Ser Asp Glu Gln Leu Lys Ser Gly Thr Ala
            20                  25                  30

Ser Val Ser Cys Leu Leu Asn Asn Phe Tyr Pro Arg Glu Ala Lys Val
        35                  40                  45

Gln Trp Lys Val Asp Asn Ala Leu Gln Ser Gly Asn Ser Gln Glu Ser
    50                  55                  60

Val Thr Glu Gln Asp Ser Lys Asp Ser Thr Tyr Ser Leu Ser Ser Thr
65                  70                  75                  80

Leu Thr Leu Ser Lys Ala Asp Tyr Glu Lys His Lys Val Tyr Ala Cys
                85                  90                  95

Glu Val Thr His Gln Gly Leu Ser Ser Pro Val Thr Lys Ser Phe Asn
            100                 105                 110

Arg Gly Glu Cys
        115

<210> SEQ ID NO 3
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gly Gln Gly Thr Lys Val Glu Ile Lys Arg Thr Val Ala Ala Pro Ser
1               5                   10                  15

Val Phe Ile Phe Pro Pro Ser Asp Glu Gln Leu Lys Ser Gly Thr Ala
            20                  25                  30

Ser Val Leu Cys Leu Leu Asn Asn Phe Tyr Pro Arg Glu Ala Lys Val
        35                  40                  45

Gln Trp Lys Val Asp Asn Ala Leu Gln Ser Gly Asn Ser Gln Glu Ser
    50                  55                  60

Val Thr Glu Gln Asp Ser Lys Asp Ser Thr Tyr Ser Leu Ser Ser Thr
65                  70                  75                  80

Leu Thr Leu Ser Lys Ala Asp Tyr Glu Lys His Lys Val Tyr Ala Cys
                85                  90                  95

Glu Val Thr His Gln Gly Leu Ser Ser Pro Val Thr Lys Ser Phe Asn
            100                 105                 110

Arg Gly Glu Cys
        115

<210> SEQ ID NO 4
<211> LENGTH: 116
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 4

Gly Gln Gly Thr Lys Val Glu Ile Lys Arg Thr Val Ala Ala Pro Ser
1               5                   10                  15

Val Phe Ile Phe Pro Pro Ser Asp Glu Gln Leu Lys Ser Gly Thr Ala
            20                  25                  30

Ser Val Trp Cys Leu Leu Asn Asn Phe Tyr Pro Arg Glu Ala Lys Val
        35                  40                  45

Gln Trp Lys Val Asp Asn Ala Leu Gln Ser Gly Asn Ser Gln Glu Ser
    50                  55                  60

Val Thr Glu Gln Asp Ser Lys Asp Ser Thr Tyr Ser Leu Ser Ser Thr
65                  70                  75                  80

Leu Thr Leu Ser Lys Ala Asp Tyr Glu Lys His Lys Val Tyr Ala Cys
                85                  90                  95

Glu Val Thr His Gln Gly Leu Ser Ser Pro Val Thr Lys Ser Phe Asn
            100                 105                 110

Arg Gly Glu Cys
        115

<210> SEQ ID NO 5
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Gly Gln Gly Thr Lys Val Glu Ile Lys Arg Thr Val Ala Ala Pro Ser
1               5                   10                  15

Val Phe Ile Phe Pro Pro Ser Asp Glu Gln Leu Lys Ser Gly Thr Ala
            20                  25                  30

Ser Val Lys Cys Leu Leu Asn Asn Phe Tyr Pro Arg Glu Ala Lys Val
        35                  40                  45

Gln Trp Lys Val Asp Asn Ala Leu Gln Ser Gly Asn Ser Gln Glu Ser
    50                  55                  60

Val Thr Glu Gln Asp Ser Lys Asp Ser Thr Tyr Ser Leu Ser Ser Thr
65                  70                  75                  80

Leu Thr Leu Ser Lys Ala Asp Tyr Glu Lys His Lys Val Tyr Ala Cys
                85                  90                  95

Glu Val Thr His Gln Gly Leu Ser Ser Pro Val Thr Lys Ser Phe Asn
            100                 105                 110

Arg Gly Glu Cys
        115

<210> SEQ ID NO 6
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6
```

```
Gly Gln Gly Thr Lys Val Glu Ile Lys Arg Thr Val Ala Ala Pro Ser
1               5                   10                  15

Val Phe Ile Phe Pro Pro Ser Asp Glu Gln Leu Lys Ser Gly Thr Ala
            20                  25                  30

Ser Val Arg Cys Leu Leu Asn Asn Phe Tyr Pro Arg Glu Ala Lys Val
        35                  40                  45

Gln Trp Lys Val Asp Asn Ala Leu Gln Ser Gly Asn Ser Gln Glu Ser
    50                  55                  60

Val Thr Glu Gln Asp Ser Lys Asp Ser Thr Tyr Ser Leu Ser Ser Thr
65                  70                  75                  80

Leu Thr Leu Ser Lys Ala Asp Tyr Glu Lys His Lys Val Tyr Ala Cys
                85                  90                  95

Glu Val Thr His Gln Gly Leu Ser Ser Pro Val Thr Lys Ser Phe Asn
                100                 105                 110

Arg Gly Glu Cys
        115
```

<210> SEQ ID NO 7
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Gly Gln Gly Thr Lys Val Glu Ile Lys Arg Thr Val Ala Ala Pro Ser
1               5                   10                  15

Val Phe Ile Phe Pro Pro Ser Asp Glu Gln Leu Lys Ser Gly Thr Ala
            20                  25                  30

Ser Val Asp Cys Leu Leu Asn Asn Phe Tyr Pro Arg Glu Ala Lys Val
        35                  40                  45

Gln Trp Lys Val Asp Asn Ala Leu Gln Ser Gly Asn Ser Gln Glu Ser
    50                  55                  60

Val Thr Glu Gln Asp Ser Lys Asp Ser Thr Tyr Ser Leu Ser Ser Thr
65                  70                  75                  80

Leu Thr Leu Ser Lys Ala Asp Tyr Glu Lys His Lys Val Tyr Ala Cys
                85                  90                  95

Glu Val Thr His Gln Gly Leu Ser Ser Pro Val Thr Lys Ser Phe Asn
                100                 105                 110

Arg Gly Glu Cys
        115
```

<210> SEQ ID NO 8
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

```
Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
```

35                  40                  45

His Thr Phe Pro Ala Val Leu Gln Ser Ser Gly Leu Tyr Ser Leu Ala
    50                  55                  60

Ser Val Val Thr Val Pro Ser Ser Ser Leu Gly Thr Gln Thr Tyr Ile
65                  70                  75                  80

Cys Asn

<210> SEQ ID NO 9
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
                20                  25                  30

Glu Pro Val Thr Val Ser Trp Asn Ser Gly Ala Leu Thr Ser Gly Val
            35                  40                  45

His Thr Phe Pro Ala Val Leu Gln Ser Ser Gly Leu Tyr Ser Leu Thr
    50                  55                  60

Ser Val Val Thr Val Pro Ser Ser Ser Leu Gly Thr Gln Thr Tyr Ile
65                  70                  75                  80

Cys Asn

<210> SEQ ID NO 10
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
                20                  25                  30

Glu Pro Val Thr Val Ser Trp Asn Ser Gly Ala Leu Thr Ser Gly Val
            35                  40                  45

His Thr Phe Pro Ala Val Leu Gln Ser Ser Gly Leu Tyr Ser Leu Val
    50                  55                  60

Ser Val Val Thr Val Pro Ser Ser Ser Leu Gly Thr Gln Thr Tyr Ile
65                  70                  75                  80

Cys Asn

<210> SEQ ID NO 11
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
            35                  40                  45

His Thr Phe Pro Ala Val Leu Gln Ser Ser Gly Leu Tyr Ser Leu Tyr
    50                  55                  60

Ser Val Val Thr Val Pro Ser Ser Leu Gly Thr Gln Thr Tyr Ile
65                  70                  75                  80

Cys Asn

<210> SEQ ID NO 12
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
            35                  40                  45

His Thr Phe Pro Ala Val Leu Gln Ser Ser Gly Leu Tyr Ser Leu Phe
    50                  55                  60

Ser Val Val Thr Val Pro Ser Ser Leu Gly Thr Gln Thr Tyr Ile
65                  70                  75                  80

Cys Asn

<210> SEQ ID NO 13
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
            35                  40                  45

His Thr Phe Pro Ala Val Leu Gln Ser Ser Gly Leu Tyr Ser Leu His
    50                  55                  60

Ser Val Val Thr Val Pro Ser Ser Leu Gly Thr Gln Thr Tyr Ile
65                  70                  75                  80

Cys Asn

<210> SEQ ID NO 14
<211> LENGTH: 82

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Phe Pro Ala Val Leu Gln Ser Ser Gly Leu Tyr Ser Leu Asn
    50                  55                  60

Ser Val Val Thr Val Pro Ser Ser Ser Leu Gly Thr Gln Thr Tyr Ile
65                  70                  75                  80

Cys Asn

<210> SEQ ID NO 15
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Phe Pro Ala Val Leu Gln Ser Ser Gly Leu Tyr Ser Leu Glu
    50                  55                  60

Ser Val Val Thr Val Pro Ser Ser Ser Leu Gly Thr Gln Thr Tyr Ile
65                  70                  75                  80

Cys Asn

<210> SEQ ID NO 16
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Phe Pro Ala Val Leu Gln Ser Ser Gly Leu Tyr Ser Leu Asp
    50                  55                  60
```

-continued

Ser Val Val Thr Val Pro Ser Ser Leu Gly Thr Gln Thr Tyr Ile
65                  70                  75                  80

Cys Asn

<210> SEQ ID NO 17
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Gly Gln Gly Thr Lys Val Glu Ile Lys Arg Thr Val Ala Ala Pro Ser
1               5                   10                  15

Val Ala Ile Phe Pro Pro Ser Asp Glu Gln Leu Lys Ser Gly Thr Ala
                20                  25                  30

Ser Val Ile Cys Val Leu Asn Asn Phe Tyr Pro Arg Glu Ala Lys Val
            35                  40                  45

Gln Trp Lys Val Asp Asn Ala Leu Gln Ser Gly Asn Ser Gln Glu Met
    50                  55                  60

Val Thr Glu Gln Asp Ser Lys Asp Ser Thr Tyr Ala Leu Phe Ser Val
65                  70                  75                  80

Leu Thr Leu Ser Lys Ala Asp Tyr Glu Lys His Lys Val Tyr Ala Cys
                85                  90                  95

Glu Val Thr His Gln Gly Leu Ser Ser Pro Val Thr Lys Ser Phe Asn
                100                 105                 110

Arg Gly Glu Cys
        115

<210> SEQ ID NO 18
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Gly Gln Gly Thr Lys Val Glu Ile Lys Arg Thr Val Ala Ala Pro Ser
1               5                   10                  15

Val Ala Ile Phe Pro Pro Ser Asp Glu Gln Leu Lys Ser Gly Thr Ala
                20                  25                  30

Asp Val Val Cys Val Leu Asn Asn Phe Tyr Pro Arg Glu Ala Lys Val
            35                  40                  45

Gln Trp Lys Val Asp Asn Ala Leu Gln Ser Gly Asn Ser Gln Glu Ala
    50                  55                  60

Val Thr Glu Gln Asp Ser Lys Asp Ser Thr Tyr Ala Leu Phe Ser Ile
65                  70                  75                  80

Leu Thr Leu Ser Lys Ala Asp Tyr Glu Lys His Lys Val Tyr Ala Cys
                85                  90                  95

Glu Val Thr His Gln Gly Leu Ser Ser Pro Val Thr Lys Ser Phe Asn
                100                 105                 110

Arg Gly Glu Cys
        115

<210> SEQ ID NO 19

<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

Gly Gln Gly Thr Lys Val Glu Ile Lys Arg Thr Val Ala Ala Pro Ser
1               5                   10                  15

Val Ala Ile Phe Pro Pro Ser Asp Glu Gln Leu Lys Ser Gly Thr Ala
            20                  25                  30

Ser Val Val Cys Val Leu Asn Asn Phe Tyr Pro Arg Glu Ala Lys Val
        35                  40                  45

Gln Trp Lys Val Asp Asn Ala Leu Gln Ser Gly Asn Ser Gln Glu Ser
    50                  55                  60

Val Thr Glu Gln Asp Ser Lys Asp Ser Thr Tyr Ala Leu Phe Ser Val
65                  70                  75                  80

Leu Thr Leu Ser Lys Ala Asp Tyr Glu Lys His Lys Val Tyr Ala Cys
                85                  90                  95

Glu Val Thr His Gln Gly Leu Ser Ser Pro Val Thr Lys Ser Phe Asn
            100                 105                 110

Arg Gly Glu Cys
        115

<210> SEQ ID NO 20
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

Gly Gln Gly Thr Lys Val Glu Ile Lys Arg Thr Val Ala Ala Pro Ser
1               5                   10                  15

Val Phe Ile Phe Pro Pro Ser Asp Glu Gln Leu Lys Ser Gly Thr Ala
            20                  25                  30

Ser Val Val Cys Val Leu Asn Asn Phe Tyr Pro Arg Glu Ala Lys Val
        35                  40                  45

Gln Trp Lys Val Asp Asn Ala Leu Gln Ser Gly Asn Ser Gln Glu Ser
    50                  55                  60

Val Thr Glu Gln Asp Ser Lys Asp Ser Thr Tyr Ala Leu Phe Ser Val
65                  70                  75                  80

Leu Thr Leu Ser Lys Ala Asp Tyr Glu Lys His Lys Val Tyr Ala Cys
                85                  90                  95

Glu Val Thr His Gln Gly Leu Ser Ser Pro Val Thr Lys Ser Phe Asn
            100                 105                 110

Arg Gly Glu Cys
        115

<210> SEQ ID NO 21
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 21

Gly Gln Gly Thr Lys Val Glu Ile Lys Arg Thr Val Ala Ala Pro Ser
1               5                   10                  15

Val Ala Ile Phe Pro Pro Ser Asp Glu Gln Leu Lys Ser Gly Thr Ala
            20                  25                  30

Ser Val Val Cys Leu Leu Asn Asn Phe Tyr Pro Arg Glu Ala Lys Val
        35                  40                  45

Gln Trp Lys Val Asp Asn Ala Leu Gln Ser Gly Asn Ser Gln Glu Ser
    50                  55                  60

Val Thr Glu Gln Asp Ser Lys Asp Ser Thr Tyr Ala Leu Phe Ser Val
65                  70                  75                  80

Leu Thr Leu Ser Lys Ala Asp Tyr Glu Lys His Lys Val Tyr Ala Cys
                85                  90                  95

Glu Val Thr His Gln Gly Leu Ser Ser Pro Val Thr Lys Ser Phe Asn
                100                 105                 110

Arg Gly Glu Cys
        115

<210> SEQ ID NO 22
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Gly Gln Gly Thr Lys Val Glu Ile Lys Arg Thr Val Ala Ala Pro Ser
1               5                   10                  15

Val Ala Ile Phe Pro Pro Ser Asp Glu Gln Leu Lys Ser Gly Thr Ala
            20                  25                  30

Ser Val Val Cys Val Leu Asn Asn Phe Tyr Pro Arg Glu Ala Lys Val
        35                  40                  45

Gln Trp Lys Val Asp Asn Ala Leu Gln Ser Gly Asn Ser Gln Glu Ser
    50                  55                  60

Val Thr Glu Gln Asp Ser Lys Asp Ser Thr Tyr Ser Leu Phe Ser Val
65                  70                  75                  80

Leu Thr Leu Ser Lys Ala Asp Tyr Glu Lys His Lys Val Tyr Ala Cys
                85                  90                  95

Glu Val Thr His Gln Gly Leu Ser Ser Pro Val Thr Lys Ser Phe Asn
                100                 105                 110

Arg Gly Glu Cys
        115

<210> SEQ ID NO 23
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Gly Gln Gly Thr Lys Val Glu Ile Lys Arg Thr Val Ala Ala Pro Ser
1               5                   10                  15

Val Ala Ile Phe Pro Pro Ser Asp Glu Gln Leu Lys Ser Gly Thr Ala

```
            20                  25                  30

Ser Val Val Cys Val Leu Asn Asn Phe Tyr Pro Arg Glu Ala Lys Val
        35                  40                  45

Gln Trp Lys Val Asp Asn Ala Leu Gln Ser Gly Asn Ser Gln Glu Ser
    50                  55                  60

Val Thr Glu Gln Asp Ser Lys Asp Ser Thr Tyr Ala Leu Phe Ser Thr
65                  70                  75                  80

Leu Thr Leu Ser Lys Ala Asp Tyr Glu Lys His Lys Val Tyr Ala Cys
            85                  90                  95

Glu Val Thr His Gln Gly Leu Ser Ser Pro Val Thr Lys Ser Phe Asn
                100                 105                 110

Arg Gly Glu Cys
        115

<210> SEQ ID NO 24
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Gly Gln Gly Thr Lys Val Glu Ile Lys Arg Thr Val Ala Ala Pro Ser
1               5                   10                  15

Val Ala Ile Phe Pro Pro Ser Asp Glu Gln Leu Lys Ser Gly Thr Ala
            20                  25                  30

Ser Val Val Cys Leu Leu Asn Asn Phe Tyr Pro Arg Glu Ala Lys Val
        35                  40                  45

Gln Trp Lys Val Asp Asn Ala Leu Gln Ser Gly Asn Ser Gln Glu Ser
    50                  55                  60

Val Thr Glu Gln Asp Ser Lys Asp Ser Thr Tyr Ser Leu Phe Ser Val
65                  70                  75                  80

Leu Thr Leu Ser Lys Ala Asp Tyr Glu Lys His Lys Val Tyr Ala Cys
            85                  90                  95

Glu Val Thr His Gln Gly Leu Ser Ser Pro Val Thr Lys Ser Phe Asn
                100                 105                 110

Arg Gly Glu Cys
        115

<210> SEQ ID NO 25
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gly Gln Gly Thr Lys Val Glu Ile Lys Arg Thr Val Ala Ala Pro Ser
1               5                   10                  15

Val Ala Ile Phe Pro Pro Ser Asp Glu Gln Leu Lys Ser Gly Thr Ala
            20                  25                  30

Ser Val Val Cys Val Leu Asn Asn Phe Tyr Pro Arg Glu Ala Lys Val
        35                  40                  45

Gln Trp Lys Val Asp Asn Ala Leu Gln Ser Gly Asn Ser Gln Glu Ser
    50                  55                  60
```

Val Thr Glu Gln Asp Ser Lys Asp Ser Thr Tyr Ser Leu Phe Ser Thr
65                  70                  75                  80

Leu Thr Leu Ser Lys Ala Asp Tyr Glu Lys His Lys Val Tyr Ala Cys
                85                  90                  95

Glu Val Thr His Gln Gly Leu Ser Ser Pro Val Thr Lys Ser Phe Asn
            100                 105                 110

Arg Gly Glu Cys
        115

<210> SEQ ID NO 26
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Gly Gln Gly Thr Lys Val Glu Ile Lys Arg Thr Val Ala Ala Pro Ser
1               5                   10                  15

Val Ala Ile Phe Pro Pro Ser Asp Glu Gln Leu Lys Ser Gly Thr Ala
            20                  25                  30

Ser Val Val Cys Leu Leu Asn Asn Phe Tyr Pro Arg Glu Ala Lys Val
            35                  40                  45

Gln Trp Lys Val Asp Asn Ala Leu Gln Ser Gly Asn Ser Gln Glu Ser
        50                  55                  60

Val Thr Glu Gln Asp Ser Lys Asp Ser Thr Tyr Ser Leu Phe Ser Thr
65                  70                  75                  80

Leu Thr Leu Ser Lys Ala Asp Tyr Glu Lys His Lys Val Tyr Ala Cys
                85                  90                  95

Glu Val Thr His Gln Gly Leu Ser Ser Pro Val Thr Lys Ser Phe Asn
            100                 105                 110

Arg Gly Glu Cys
        115

<210> SEQ ID NO 27
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gly Gln Gly Thr Lys Val Glu Ile Lys Arg Thr Val Ala Ala Pro Ser
1               5                   10                  15

Val Ala Ile Phe Pro Pro Ser Asp Glu Gln Leu Lys Ser Gly Thr Ala
            20                  25                  30

Ser Val Val Cys Val Leu Asn Asn Phe Tyr Pro Arg Glu Ala Lys Val
            35                  40                  45

Gln Trp Lys Val Asp Asn Ala Leu Gln Ser Gly Asn Ser Gln Glu Met
        50                  55                  60

Val Thr Glu Gln Asp Ser Lys Asp Ser Thr Tyr Ala Leu Phe Ser Val
65                  70                  75                  80

Leu Thr Leu Ser Lys Ala Asp Tyr Glu Lys His Lys Val Tyr Ala Cys
                85                  90                  95

Glu Val Thr His Gln Gly Leu Ser Ser Pro Val Thr Lys Ser Phe Asn
            100                 105                 110

Arg Gly Glu Cys
        115

<210> SEQ ID NO 28
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Thr Lys Gly Pro Ser Val Phe Pro Leu Ala Pro Ser Ser Lys Ser Thr
1               5                   10                  15

Ser Gly Gly Thr Ala Ile Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Ser Pro Ala Val Leu Gln Ser Ser Gly Leu Tyr Met Leu Val
    50                  55                  60

Ser Ala Val Thr Val Pro Ser Ser Ser Leu Gly Thr Gln Thr Tyr Ile
65                  70                  75                  80

Cys Asn

<210> SEQ ID NO 29
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Thr Lys Gly Pro Ser Val Phe Pro Leu Ala Pro Ser Ser Lys Ser Thr
1               5                   10                  15

Ser Gly Gly Thr Ala Ile Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Ser Pro Ala Val Leu Gln Ser Ser Gly Leu Tyr Met Leu Ala
    50                  55                  60

Ser Ala Val Thr Val Pro Ser Ser Ser Leu Gly Thr Gln Thr Tyr Ile
65                  70                  75                  80

Cys Asn

<210> SEQ ID NO 30
<211> LENGTH: 107
<212> TYPE: PRT
<213> ORGANISM: Homo sapiens

<400> SEQUENCE: 30

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln

```
                35                  40                  45
Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 31
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

```
Thr Lys Gly Pro Ser Val Phe Pro Leu Ala Pro Ser Ser Lys Ser Thr
1               5                  10                  15

Ser Gly Gly Thr Ala Ala Leu Gly Cys Leu Val Lys Asp Tyr Phe Pro
                20                  25                  30

Glu Pro Val Thr Val Ser Trp Asn Ser Gly Ala Leu Thr Ser Gly Val
            35                  40                  45

His Thr Ser Pro Ala Val Leu Gln Ser Ser Gly Leu Tyr Met Leu Ala
        50                  55                  60

Ser Ala Val Thr Val Pro Ser Ser Ser Leu Gly Thr Gln Thr Tyr Ile
65                  70                  75                  80

Cys Asn
```

<210> SEQ ID NO 32
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

```
Thr Lys Gly Pro Ser Val Phe Pro Leu Ala Pro Ser Ser Lys Ser Thr
1               5                  10                  15

Ser Gly Gly Thr Ala Ile Leu Gly Cys Leu Val Lys Asp Tyr Phe Pro
                20                  25                  30

Glu Pro Val Thr Val Ser Trp Asn Ser Gly Ala Leu Thr Ser Gly Val
            35                  40                  45

His Thr Ser Pro Ala Val Leu Gln Ser Ser Gly Leu Tyr Ser Leu Ala
        50                  55                  60

Ser Ala Val Thr Val Pro Ser Ser Ser Leu Gly Thr Gln Thr Tyr Ile
65                  70                  75                  80

Cys Asn
```

<210> SEQ ID NO 33
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 33

Thr Lys Gly Pro Ser Val Phe Pro Leu Ala Pro Ser Ser Lys Ser Thr
1               5                   10                  15

Ser Gly Gly Thr Ala Ile Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Ser Pro Ala Val Leu Gln Ser Ser Gly Leu Tyr Met Leu Ser
    50                  55                  60

Ser Ala Val Thr Val Pro Ser Ser Ser Leu Gly Thr Gln Thr Tyr Ile
65                  70                  75                  80

Cys Asn

<210> SEQ ID NO 34
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 34

Thr Lys Gly Pro Ser Val Phe Pro Leu Ala Pro Ser Ser Lys Ser Thr
1               5                   10                  15

Ser Gly Gly Thr Ala Ile Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Ser Pro Ala Val Leu Gln Ser Ser Gly Leu Tyr Met Leu Ala
    50                  55                  60

Ser Val Val Thr Val Pro Ser Ser Ser Leu Gly Thr Gln Thr Tyr Ile
65                  70                  75                  80

Cys Asn

<210> SEQ ID NO 35
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 35

Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Ser Pro Ala Val Leu Gln Ser Ser Gly Leu Tyr Ser Leu Ala
    50                  55                  60

Ser Ala Val Thr Val Pro Ser Ser Ser Leu Gly Thr Gln Thr Tyr Ile
65                  70                  75                  80

Cys Asn

<210> SEQ ID NO 36
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Ser Pro Ala Val Leu Gln Ser Ser Gly Leu Tyr Met Leu Ser
    50                  55                  60

Ser Ala Val Thr Val Pro Ser Ser Ser Leu Gly Thr Gln Thr Tyr Ile
65                  70                  75                  80

Cys Asn

<210> SEQ ID NO 37
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Ser Pro Ala Val Leu Gln Ser Ser Gly Leu Tyr Met Leu Ala
    50                  55                  60

Ser Val Val Thr Val Pro Ser Ser Ser Leu Gly Thr Gln Thr Tyr Ile
65                  70                  75                  80

Cys Asn

<210> SEQ ID NO 38
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Thr Lys Gly Pro Ser Val Phe Pro Leu Ala Pro Ser Ser Lys Ser Thr
1               5                   10                  15

Ser Gly Gly Thr Ala Ile Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Ser Pro Ala Val Leu Gln Ser Ser Gly Leu Tyr Ser Leu Ser
        50                  55                  60

Ser Ala Val Thr Val Pro Ser Ser Leu Gly Thr Gln Thr Tyr Ile
 65                  70                  75                  80

Cys Asn

<210> SEQ ID NO 39
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Thr Lys Gly Pro Ser Val Phe Pro Leu Ala Pro Ser Ser Lys Ser Thr
 1               5                  10                  15

Ser Gly Gly Thr Ala Ile Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Ser Pro Ala Val Leu Gln Ser Ser Gly Leu Tyr Ser Leu Ala
        50                  55                  60

Ser Val Val Thr Val Pro Ser Ser Ser Leu Gly Thr Gln Thr Tyr Ile
 65                  70                  75                  80

Cys Asn

<210> SEQ ID NO 40
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Thr Lys Gly Pro Ser Val Phe Pro Leu Ala Pro Ser Ser Lys Ser Thr
 1               5                  10                  15

Ser Gly Gly Thr Ala Ile Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Ser Pro Ala Val Leu Gln Ser Ser Gly Leu Tyr Met Leu Ser
        50                  55                  60

Ser Val Val Thr Val Pro Ser Ser Ser Leu Gly Thr Gln Thr Tyr Ile
 65                  70                  75                  80

Cys Asn

<210> SEQ ID NO 41
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Ser Pro Ala Val Leu Gln Ser Ser Gly Leu Tyr Ser Leu Ser
    50                  55                  60

Ser Ala Val Thr Val Pro Ser Ser Leu Gly Thr Gln Thr Tyr Ile
65                  70                  75                  80

Cys Asn

<210> SEQ ID NO 42
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Thr Lys Gly Pro Ser Val Phe Pro Leu Ala Pro Ser Ser Lys Ser Thr
1               5                   10                  15

Ser Gly Gly Thr Ala Ile Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Ser Pro Ala Val Leu Gln Ser Ser Gly Leu Tyr Ser Leu Ser
    50                  55                  60

Ser Val Val Thr Val Pro Ser Ser Leu Gly Thr Gln Thr Tyr Ile
65                  70                  75                  80

Cys Asn

<210> SEQ ID NO 43
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Ser Pro Ala Val Leu Gln Ser Ser Gly Leu Tyr Ser Leu Ser
    50                  55                  60

Ser Val Val Thr Val Pro Ser Ser Leu Gly Thr Gln Thr Tyr Ile
65                  70                  75                  80

Cys Asn

<210> SEQ ID NO 44
<211> LENGTH: 82
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Thr Lys Gly Pro Ser Val Phe Pro Leu Ala Pro Ser Ser Lys Ser Thr
1               5                   10                  15

Ser Gly Gly Thr Ala Ile Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Ala Pro Ala Val Leu Gln Ser Ser Gly Leu Tyr Met Leu Val
    50                  55                  60

Ser Ala Val Thr Val Pro Ser Ser Leu Gly Thr Gln Thr Tyr Ile
65                  70                  75                  80

Cys Asn

<210> SEQ ID NO 45
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Gly Gln Gly Thr Lys Val Glu Ile Lys Arg Thr Val Ala Ala Pro Ser
1               5                   10                  15

Val Phe Ile Val Pro Pro Ser Asp Glu Gln Leu Lys Ser Gly Thr Ala
            20                  25                  30

Thr Val Ala Cys Tyr Leu Asn Asn Phe Tyr Pro Arg Glu Ala Lys Val
        35                  40                  45

Gln Trp Lys Val Asp Asn Ala Leu Gln Ser Gly Asn Ser Gln Glu Ala
    50                  55                  60

Val Ser Glu Gln Asp Ser Lys Asp Ser Thr Tyr Ser Leu Met Ser Leu
65                  70                  75                  80

Leu Thr Leu Ser Lys Ala Asp Tyr Glu Lys His Lys Val Tyr Ala Cys
                85                  90                  95

Glu Val Thr His Gln Gly Leu Ser Ser Pro Val Thr Lys Ser Phe Asn
            100                 105                 110

Arg Gly Glu Cys
        115

<210> SEQ ID NO 46
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Gly Gln Gly Thr Lys Val Glu Ile Lys Arg Thr Val Ala Ala Pro Ser
1               5                   10                  15

Val Phe Ile Val Pro Pro Ser Asp Glu Gln Leu Lys Ser Gly Thr Ala
            20                  25                  30

Thr Val Ala Cys Phe Leu Asn Asn Phe Tyr Pro Arg Glu Ala Lys Val
            35                  40                  45

Gln Trp Lys Val Asp Asn Ala Leu Gln Ser Gly Asn Ser Gln Glu Ala
 50                  55                  60

Val Thr Glu Gln Asp Ser Lys Asp Ser Thr Tyr Ser Leu Ala Ser Leu
65                  70                  75                  80

Leu Thr Leu Ser Lys Ala Asp Tyr Glu Lys His Lys Val Tyr Ala Cys
                85                  90                  95

Glu Val Thr His Gln Gly Leu Ser Ser Pro Val Thr Lys Ser Phe Asn
            100                 105                 110

Arg Gly Glu Cys
        115

<210> SEQ ID NO 47
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Gly Gln Gly Thr Lys Val Glu Ile Lys Arg Thr Val Ala Ala Pro Ser
1               5                   10                  15

Val Phe Ile Val Pro Pro Ser Asp Glu Gln Leu Lys Ser Gly Thr Ala
            20                  25                  30

Thr Val Ala Cys Phe Leu Asn Asn Phe Tyr Pro Arg Glu Ala Lys Val
            35                  40                  45

Gln Trp Lys Val Asp Asn Ala Leu Gln Ser Gly Asn Ser Gln Glu Ala
 50                  55                  60

Val Ser Glu Gln Asp Ser Lys Asp Ser Thr Tyr Ser Leu Thr Ser Leu
65                  70                  75                  80

Leu Thr Leu Ser Lys Ala Asp Tyr Glu Lys His Lys Val Tyr Ala Cys
                85                  90                  95

Glu Val Thr His Gln Gly Leu Ser Ser Pro Val Thr Lys Ser Phe Asn
            100                 105                 110

Arg Gly Glu Cys
        115

<210> SEQ ID NO 48
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Gly Gln Gly Thr Lys Val Glu Ile Lys Arg Thr Val Ala Ala Pro Ser
1               5                   10                  15

Val Phe Ile Val Pro Pro Ser Asp Glu Gln Leu Lys Ser Gly Thr Ala
            20                  25                  30

Thr Val Ala Cys Phe Leu Asn Asn Phe Tyr Pro Arg Glu Ala Lys Val
            35                  40                  45

Gln Trp Lys Val Asp Asn Ala Leu Gln Ser Gly Asn Ser Gln Glu Met
 50                  55                  60

Val Ser Glu Gln Asp Ser Lys Asp Ser Thr Tyr Ser Leu Met Ser Leu

```
                65                  70                  75                  80
Leu Thr Leu Ser Lys Ala Asp Tyr Glu Lys His Lys Val Tyr Ala Cys
                    85                  90                  95

Glu Val Thr His Gln Gly Leu Ser Ser Pro Val Thr Lys Ser Phe Asn
                100                 105                 110

Arg Gly Glu Cys
        115

<210> SEQ ID NO 49
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Thr Lys Gly Pro Ser Val Phe Pro Phe Ala Pro Ser Ser Lys Ser Thr
1               5                   10                  15

Ser Gly Gly Thr Ala Met Leu Gly Cys Leu Val Lys Asp Tyr Phe Pro
                20                  25                  30

Glu Pro Val Thr Val Ser Trp Asn Ser Gly Ala Leu Thr Ser Gly Val
                35                  40                  45

His Thr Met Pro Ala Val Leu Gln Ser Ser Gly Leu Tyr Ile Leu Ala
        50                  55                  60

Ser Val Val Thr Val Pro Ser Ser Ser Leu Gly Thr Gln Thr Tyr Ile
65                  70                  75                  80

Cys Asn

<210> SEQ ID NO 50
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Thr Lys Gly Pro Ser Val Phe Pro Phe Ala Pro Ser Ser Lys Ser Thr
1               5                   10                  15

Ser Gly Gly Thr Ala Met Leu Gly Cys Leu Val Lys Asp Tyr Phe Pro
                20                  25                  30

Glu Pro Val Thr Val Ser Trp Asn Ser Gly Ala Leu Thr Ser Gly Val
                35                  40                  45

His Thr Tyr Pro Ala Val Leu Gln Ser Ser Gly Leu Tyr Ile Leu Ala
        50                  55                  60

Ser Ala Val Thr Val Pro Ser Ser Ser Leu Gly Thr Gln Thr Tyr Ile
65                  70                  75                  80

Cys Asn

<210> SEQ ID NO 51
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

-continued

<400> SEQUENCE: 51

Thr Lys Gly Pro Ser Val Phe Pro Phe Ala Pro Ser Ser Lys Ser Thr
1               5                   10                  15

Ser Gly Gly Thr Ala Thr Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Met Pro Ala Val Leu Gln Ser Ser Gly Leu Tyr Thr Leu Ala
    50                  55                  60

Ser Leu Val Thr Val Pro Ser Ser Ser Leu Gly Thr Gln Thr Tyr Ile
65                  70                  75                  80

Cys Asn

<210> SEQ ID NO 52
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Thr Lys Gly Pro Ser Val Phe Pro Phe Ala Pro Ser Ser Lys Ser Thr
1               5                   10                  15

Ser Gly Gly Thr Ala Met Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Met Pro Ala Val Leu Gln Ser Ser Gly Leu Tyr Thr Leu Ala
    50                  55                  60

Ser Val Val Thr Val Pro Ser Ser Ser Leu Gly Thr Gln Thr Tyr Ile
65                  70                  75                  80

Cys Asn

<210> SEQ ID NO 53
<211> LENGTH: 98
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 54
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 54

Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 55
<211> LENGTH: 450
<212> TYPE: PRT
<213> ORGANISM: Homo sapiens

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys

-continued

```
            195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Trp Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 56
<211> LENGTH: 214
<212> TYPE: PRT
<213> ORGANISM: Homo sapiens

<400> SEQUENCE: 56

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys Arg Thr Val Ala Ala
            100                 105                 110
```

-continued

```
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 57
<211> LENGTH: 330
<212> TYPE: PRT
<213> ORGANISM: Homo sapiens

<400> SEQUENCE: 57

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 58
<211> LENGTH: 327
<212> TYPE: PRT
<213> ORGANISM: Homo sapiens

<400> SEQUENCE: 58

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
```

```
                305                 310                 315                 320
Leu Ser Leu Ser Leu Gly Lys
                325

<210> SEQ ID NO 59
<211> LENGTH: 107
<212> TYPE: PRT
<213> ORGANISM: Homo sapiens

<400> SEQUENCE: 59

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 60
<211> LENGTH: 330
<212> TYPE: PRT
<213> ORGANISM: Mus sp.

<400> SEQUENCE: 60

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
```

```
                 195                 200                 205
Lys Asp Leu Pro Ala Pro Ile Glu Arg Thr Ile Ser Lys Pro Lys Gly
210                 215                 220

Ser Val Arg Ala Pro Gln Val Tyr Val Leu Pro Pro Glu Glu Glu
225                 230                 235                 240

Met Thr Lys Lys Gln Val Thr Leu Thr Cys Met Val Thr Asp Phe Met
                    245                 250                 255

Pro Glu Asp Ile Tyr Val Glu Trp Thr Asn Asn Gly Lys Thr Glu Leu
                260                 265                 270

Asn Tyr Lys Asn Thr Glu Pro Val Leu Asp Ser Asp Gly Ser Tyr Phe
            275                 280                 285

Met Tyr Ser Lys Leu Arg Val Glu Lys Lys Asn Trp Val Glu Arg Asn
        290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 61
<211> LENGTH: 107
<212> TYPE: PRT
<213> ORGANISM: Mus sp.

<400> SEQUENCE: 61

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 62
<211> LENGTH: 106
<212> TYPE: PRT
<213> ORGANISM: Mus sp.

<400> SEQUENCE: 62

Gly Gln Pro Lys Ser Ser Pro Ser Val Thr Leu Phe Pro Pro Ser Ser
1               5                   10                  15

Glu Glu Leu Glu Thr Asn Lys Ala Thr Leu Val Cys Thr Ile Thr Asp
            20                  25                  30

Phe Tyr Pro Gly Val Val Thr Val Asp Trp Lys Val Asp Gly Thr Pro
        35                  40                  45

Val Thr Gln Gly Met Glu Thr Thr Gln Pro Ser Lys Gln Ser Asn Asn
    50                  55                  60

Lys Tyr Met Ala Ser Ser Tyr Leu Thr Leu Thr Ala Arg Ala Trp Glu
65                  70                  75                  80

Arg His Ser Ser Tyr Ser Cys Gln Val Thr His Glu Gly His Thr Val
```

Glu Lys Ser Leu Ser Arg Ala Asp Cys Ser
        100             105

<210> SEQ ID NO 63
<211> LENGTH: 105
<212> TYPE: PRT
<213> ORGANISM: Mus sp.

<400> SEQUENCE: 63

Gly Gln Pro Lys Ser Thr Pro Thr Leu Thr Val Phe Pro Pro Ser Ser
1               5                   10                  15

Glu Glu Leu Lys Glu Asn Lys Ala Thr Leu Val Cys Leu Ile Ser Asn
            20                  25                  30

Phe Ser Pro Ser Gly Val Thr Val Ala Trp Lys Ala Asn Gly Thr Pro
        35                  40                  45

Ile Thr Gln Gly Val Asp Thr Ser Asn Pro Thr Lys Glu Gly Asn Lys
    50                  55                  60

Phe Met Ala Ser Ser Phe Leu His Leu Thr Ser Asp Gln Trp Arg Ser
65                  70                  75                  80

His Asn Ser Phe Thr Cys Gln Val Thr His Glu Gly Asp Thr Val Glu
                85                  90                  95

Lys Ser Leu Ser Pro Ala Glu Cys Leu
            100             105

<210> SEQ ID NO 64
<211> LENGTH: 105
<212> TYPE: PRT
<213> ORGANISM: Mus sp.

<400> SEQUENCE: 64

Gly Gln Pro Lys Ser Thr Pro Thr Leu Thr Met Phe Pro Pro Ser Pro
1               5                   10                  15

Glu Glu Leu Gln Glu Asn Lys Ala Thr Leu Val Cys Leu Ile Ser Asn
            20                  25                  30

Phe Ser Pro Ser Gly Val Thr Val Ala Trp Lys Ala Asn Gly Thr Pro
        35                  40                  45

Ile Thr Gln Gly Val Asp Thr Ser Asn Pro Thr Lys Glu Asp Asn Lys
    50                  55                  60

Tyr Met Ala Ser Ser Phe Leu His Leu Thr Ser Asp Gln Trp Arg Ser
65                  70                  75                  80

His Asn Ser Phe Thr Cys Gln Val Thr His Glu Gly Asp Thr Val Glu
                85                  90                  95

Lys Ser Leu Ser Pro Ala Glu Cys Leu
            100             105

<210> SEQ ID NO 65
<211> LENGTH: 330
<212> TYPE: PRT
<213> ORGANISM: Homo sapiens

<400> SEQUENCE: 65

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

```
Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 66
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 66

His His His His His His
1               5

<210> SEQ ID NO 67
<211> LENGTH: 82
<212> TYPE: PRT
<213> ORGANISM: Homo sapiens

<400> SEQUENCE: 67

Thr Lys Gly Pro Ser Val Phe Pro Leu Ala Pro Ser Ser Lys Ser Thr
```

```
                1               5                  10                  15
            Ser Gly Gly Thr Ala Ala Leu Gly Cys Leu Val Lys Asp Tyr Phe Pro
                            20                  25                  30
            Glu Pro Val Thr Val Ser Trp Asn Ser Gly Ala Leu Thr Ser Gly Val
                            35                  40                  45
            His Thr Phe Pro Ala Val Leu Gln Ser Ser Gly Leu Tyr Ser Leu Ser
                            50                  55                  60
            Ser Val Val Thr Val Pro Ser Ser Ser Leu Gly Thr Gln Thr Tyr Ile
            65                  70                  75                  80
            Cys Asn

<210> SEQ ID NO 68
<211> LENGTH: 81
<212> TYPE: PRT
<213> ORGANISM: Homo sapiens

<400> SEQUENCE: 68

Gly Gln Gly Thr Lys Val Glu Ile Lys Arg Thr Val Ala Ala Pro Ser
            1               5                  10                  15
            Val Phe Ile Phe Pro Pro Ser Asp Glu Gln Leu Lys Ser Gly Thr Ala
                            20                  25                  30
            Ser Val Val Cys Leu Leu Asn Asn Phe Tyr Pro Arg Glu Ala Lys Val
                            35                  40                  45
            Gln Trp Lys Val Asp Asn Ala Leu Gln Ser Gly Asn Ser Gln Glu Ser
                            50                  55                  60
            Val Thr Glu Gln Asp Ser Lys Asp Ser Thr Tyr Ser Leu Ser Ser Thr
            65                  70                  75                  80
            Leu

<210> SEQ ID NO 69
<211> LENGTH: 81
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Gly Gln Gly Thr Lys Val Glu Ile Lys Arg Thr Val Ala Ala Pro Ser
            1               5                  10                  15
            Val Phe Ile Val Pro Pro Ser Asp Glu Gln Leu Lys Ser Gly Thr Ala
                            20                  25                  30
            Thr Val Ala Cys Tyr Leu Asn Asn Phe Tyr Pro Arg Glu Ala Lys Val
                            35                  40                  45
            Gln Trp Lys Val Asp Asn Ala Leu Gln Ser Gly Asn Ser Gln Glu Ala
                            50                  55                  60
            Val Ser Glu Gln Asp Ser Lys Asp Ser Thr Tyr Ser Leu Met Ser Leu
            65                  70                  75                  80
            Leu

<210> SEQ ID NO 70
<211> LENGTH: 81
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 70

Gly Gln Gly Thr Lys Val Glu Ile Lys Arg Thr Val Ala Ala Pro Ser
1               5                   10                  15

Val Phe Ile Val Pro Pro Ser Asp Glu Gln Leu Lys Ser Gly Thr Ala
            20                  25                  30

Thr Val Ala Cys Phe Leu Asn Asn Phe Tyr Pro Arg Glu Ala Lys Val
        35                  40                  45

Gln Trp Lys Val Asp Asn Ala Leu Gln Ser Gly Asn Ser Gln Glu Ala
    50                  55                  60

Val Thr Glu Gln Asp Ser Lys Asp Ser Thr Tyr Ser Leu Ala Ser Leu
65                  70                  75                  80

Leu

<210> SEQ ID NO 71
<211> LENGTH: 81
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Gly Gln Gly Thr Lys Val Glu Ile Lys Arg Thr Val Ala Ala Pro Ser
1               5                   10                  15

Val Phe Ile Val Pro Pro Ser Asp Glu Gln Leu Lys Ser Gly Thr Ala
            20                  25                  30

Thr Val Ala Cys Phe Leu Asn Asn Phe Tyr Pro Arg Glu Ala Lys Val
        35                  40                  45

Gln Trp Lys Val Asp Asn Ala Leu Gln Ser Gly Asn Ser Gln Glu Ala
    50                  55                  60

Val Ser Glu Gln Asp Ser Lys Asp Ser Thr Tyr Ser Leu Thr Ser Leu
65                  70                  75                  80

Leu

<210> SEQ ID NO 72
<211> LENGTH: 81
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Gly Gln Gly Thr Lys Val Glu Ile Lys Arg Thr Val Ala Ala Pro Ser
1               5                   10                  15

Val Phe Ile Val Pro Pro Ser Asp Glu Gln Leu Lys Ser Gly Thr Ala
            20                  25                  30

Thr Val Ala Cys Phe Leu Asn Asn Phe Tyr Pro Arg Glu Ala Lys Val
        35                  40                  45

Gln Trp Lys Val Asp Asn Ala Leu Gln Ser Gly Asn Ser Gln Glu Met
    50                  55                  60

Val Ser Glu Gln Asp Ser Lys Asp Ser Thr Tyr Ser Leu Met Ser Leu
65                  70                  75                  80

Leu

```
<210> SEQ ID NO 73
<211> LENGTH: 81
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Gly Gln Gly Thr Lys Val Glu Ile Lys Arg Thr Val Ala Ala Pro Ser
1               5                   10                  15

Val Ala Ile Phe Pro Pro Ser Asp Glu Gln Leu Lys Ser Gly Thr Ala
            20                  25                  30

Ser Val Ile Cys Val Leu Asn Asn Phe Tyr Pro Arg Glu Ala Lys Val
        35                  40                  45

Gln Trp Lys Val Asp Asn Ala Leu Gln Ser Gly Asn Ser Gln Glu Met
    50                  55                  60

Val Thr Glu Gln Asp Ser Lys Asp Ser Thr Tyr Ala Leu Phe Ser Val
65                  70                  75                  80

Leu

<210> SEQ ID NO 74
<211> LENGTH: 81
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Gly Gln Gly Thr Lys Val Glu Ile Lys Arg Thr Val Ala Ala Pro Ser
1               5                   10                  15

Val Ala Ile Phe Pro Pro Ser Asp Glu Gln Leu Lys Ser Gly Thr Ala
            20                  25                  30

Asp Val Val Cys Val Leu Asn Asn Phe Tyr Pro Arg Glu Ala Lys Val
        35                  40                  45

Gln Trp Lys Val Asp Asn Ala Leu Gln Ser Gly Asn Ser Gln Glu Ala
    50                  55                  60

Val Thr Glu Gln Asp Ser Lys Asp Ser Thr Tyr Ala Leu Phe Ser Ile
65                  70                  75                  80

Leu

<210> SEQ ID NO 75
<211> LENGTH: 81
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Gly Gln Gly Thr Lys Val Glu Ile Lys Arg Thr Val Ala Ala Pro Ser
1               5                   10                  15

Val Ala Ile Phe Pro Pro Ser Asp Glu Gln Leu Lys Ser Gly Thr Ala
            20                  25                  30

Ser Val Val Cys Val Leu Asn Asn Phe Tyr Pro Arg Glu Ala Lys Val
        35                  40                  45

Gln Trp Lys Val Asp Asn Ala Leu Gln Ser Gly Asn Ser Gln Glu Ser
```

```
                50                  55                  60
Val Thr Glu Gln Asp Ser Lys Asp Ser Thr Tyr Ala Leu Phe Ser Val
 65                  70                  75                  80

Leu

<210> SEQ ID NO 76
<211> LENGTH: 81
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Gly Gln Gly Thr Lys Val Glu Ile Lys Arg Thr Val Ala Ala Pro Ser
 1               5                  10                  15

Val Ala Ile Phe Pro Pro Ser Asp Glu Gln Leu Lys Ser Gly Thr Ala
                20                  25                  30

Ser Val Val Cys Val Leu Asn Asn Phe Tyr Pro Arg Glu Ala Lys Val
             35                  40                  45

Gln Trp Lys Val Asp Asn Ala Leu Gln Ser Gly Asn Ser Gln Glu Met
 50                  55                  60

Val Thr Glu Gln Asp Ser Lys Asp Ser Thr Tyr Ala Leu Phe Ser Val
 65                  70                  75                  80

Leu

<210> SEQ ID NO 77
<211> LENGTH: 62
<212> TYPE: PRT
<213> ORGANISM: Homo sapiens

<400> SEQUENCE: 77

Ser Ser Lys Ser Thr Ser Gly Gly Thr Ala Ala Leu Gly Cys Leu Val
 1               5                  10                  15

Lys Asp Tyr Phe Pro Glu Pro Val Thr Val Ser Trp Asn Ser Gly Ala
                20                  25                  30

Leu Thr Ser Gly Val His Thr Phe Pro Ala Val Leu Gln Ser Ser Gly
             35                  40                  45

Leu Tyr Ser Leu Ser Ser Val Val Thr Val Pro Ser Ser Ser
 50                  55                  60

<210> SEQ ID NO 78
<211> LENGTH: 62
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Ser Ser Lys Ser Thr Ser Gly Gly Thr Ala Ile Leu Gly Cys Leu Val
 1               5                  10                  15

Lys Asp Tyr Phe Pro Glu Pro Val Thr Val Ser Trp Asn Ser Gly Ala
                20                  25                  30

Leu Thr Ser Gly Val His Thr Ser Pro Ala Val Leu Gln Ser Ser Gly
             35                  40                  45

Leu Tyr Met Leu Ala Ser Ala Val Thr Val Pro Ser Ser Ser
 50                  55                  60
```

<210> SEQ ID NO 79
<211> LENGTH: 62
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Ser Ser Lys Ser Thr Ser Gly Gly Thr Ala Ala Leu Gly Cys Leu Val
1               5                   10                  15

Lys Asp Tyr Phe Pro Glu Pro Val Thr Val Ser Trp Asn Ser Gly Ala
            20                  25                  30

Leu Thr Ser Gly Val His Thr Ser Pro Ala Val Leu Gln Ser Ser Gly
        35                  40                  45

Leu Tyr Met Leu Ala Ser Ala Val Thr Val Pro Ser Ser Ser
    50                  55                  60

<210> SEQ ID NO 80
<211> LENGTH: 62
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Ser Ser Lys Ser Thr Ser Gly Gly Thr Ala Ile Leu Gly Cys Leu Val
1               5                   10                  15

Lys Asp Tyr Phe Pro Glu Pro Val Thr Val Ser Trp Asn Ser Gly Ala
            20                  25                  30

Leu Thr Ser Gly Val His Thr Ser Pro Ala Val Leu Gln Ser Ser Gly
        35                  40                  45

Leu Tyr Ser Leu Ala Ser Ala Val Thr Val Pro Ser Ser Ser
    50                  55                  60

<210> SEQ ID NO 81
<211> LENGTH: 62
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Ser Ser Lys Ser Thr Ser Gly Gly Thr Ala Ile Leu Gly Cys Leu Val
1               5                   10                  15

Lys Asp Tyr Phe Pro Glu Pro Val Thr Val Ser Trp Asn Ser Gly Ala
            20                  25                  30

Leu Thr Ser Gly Val His Thr Ser Pro Ala Val Leu Gln Ser Ser Gly
        35                  40                  45

Leu Tyr Met Leu Ser Ser Ala Val Thr Val Pro Ser Ser Ser
    50                  55                  60

<210> SEQ ID NO 82
<211> LENGTH: 62
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 82

Ser Ser Lys Ser Thr Ser Gly Gly Thr Ala Ile Leu Gly Cys Leu Val
1               5                   10                  15

Lys Asp Tyr Phe Pro Glu Pro Val Thr Val Ser Trp Asn Ser Gly Ala
                20                  25                  30

Leu Thr Ser Gly Val His Thr Ser Pro Ala Val Leu Gln Ser Ser Gly
            35                  40                  45

Leu Tyr Met Leu Ala Ser Val Val Thr Val Pro Ser Ser Ser
    50                  55                  60

<210> SEQ ID NO 83
<211> LENGTH: 62
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Ser Ser Lys Ser Thr Ser Gly Gly Thr Ala Ala Leu Gly Cys Leu Val
1               5                   10                  15

Lys Asp Tyr Phe Pro Glu Pro Val Thr Val Ser Trp Asn Ser Gly Ala
                20                  25                  30

Leu Thr Ser Gly Val His Thr Ser Pro Ala Val Leu Gln Ser Ser Gly
            35                  40                  45

Leu Tyr Ser Leu Ala Ser Ala Val Thr Val Pro Ser Ser Ser
    50                  55                  60

<210> SEQ ID NO 84
<211> LENGTH: 62
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Ser Ser Lys Ser Thr Ser Gly Gly Thr Ala Ala Leu Gly Cys Leu Val
1               5                   10                  15

Lys Asp Tyr Phe Pro Glu Pro Val Thr Val Ser Trp Asn Ser Gly Ala
                20                  25                  30

Leu Thr Ser Gly Val His Thr Ser Pro Ala Val Leu Gln Ser Ser Gly
            35                  40                  45

Leu Tyr Met Leu Ser Ser Ala Val Thr Val Pro Ser Ser Ser
    50                  55                  60

<210> SEQ ID NO 85
<211> LENGTH: 62
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Ser Ser Lys Ser Thr Ser Gly Gly Thr Ala Ala Leu Gly Cys Leu Val
```

```
                1               5                  10                 15
Lys Asp Tyr Phe Pro Glu Pro Val Thr Val Ser Trp Asn Ser Gly Ala
                20                 25                 30

Leu Thr Ser Gly Val His Thr Ser Pro Ala Val Leu Gln Ser Ser Gly
            35                 40                 45

Leu Tyr Met Leu Ala Ser Val Val Thr Val Pro Ser Ser
        50                 55                 60
```

<210> SEQ ID NO 86
<211> LENGTH: 62
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

```
Ser Ser Lys Ser Thr Ser Gly Gly Thr Ala Ile Leu Gly Cys Leu Val
1               5                  10                 15

Lys Asp Tyr Phe Pro Glu Pro Val Thr Val Ser Trp Asn Ser Gly Ala
                20                 25                 30

Leu Thr Ser Gly Val His Thr Ser Pro Ala Val Leu Gln Ser Ser Gly
            35                 40                 45

Leu Tyr Ser Leu Ser Ser Ala Val Thr Val Pro Ser Ser
        50                 55                 60
```

<210> SEQ ID NO 87
<211> LENGTH: 62
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

```
Ser Ser Lys Ser Thr Ser Gly Gly Thr Ala Ile Leu Gly Cys Leu Val
1               5                  10                 15

Lys Asp Tyr Phe Pro Glu Pro Val Thr Val Ser Trp Asn Ser Gly Ala
                20                 25                 30

Leu Thr Ser Gly Val His Thr Ser Pro Ala Val Leu Gln Ser Ser Gly
            35                 40                 45

Leu Tyr Ser Leu Ala Ser Val Val Thr Val Pro Ser Ser
        50                 55                 60
```

<210> SEQ ID NO 88
<211> LENGTH: 62
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

```
Ser Ser Lys Ser Thr Ser Gly Gly Thr Ala Ile Leu Gly Cys Leu Val
1               5                  10                 15

Lys Asp Tyr Phe Pro Glu Pro Val Thr Val Ser Trp Asn Ser Gly Ala
                20                 25                 30

Leu Thr Ser Gly Val His Thr Ser Pro Ala Val Leu Gln Ser Ser Gly
            35                 40                 45
```

```
Leu Tyr Met Leu Ser Ser Val Val Thr Val Pro Ser Ser
        50                  55                  60
```

<210> SEQ ID NO 89
<211> LENGTH: 62
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

```
Ser Ser Lys Ser Thr Ser Gly Gly Thr Ala Ala Leu Gly Cys Leu Val
1               5                   10                  15

Lys Asp Tyr Phe Pro Glu Pro Val Thr Val Ser Trp Asn Ser Gly Ala
            20                  25                  30

Leu Thr Ser Gly Val His Thr Ser Pro Ala Val Leu Gln Ser Ser Gly
        35                  40                  45

Leu Tyr Ser Leu Ser Ser Ala Val Thr Val Pro Ser Ser
        50                  55                  60
```

<210> SEQ ID NO 90
<211> LENGTH: 62
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

```
Ser Ser Lys Ser Thr Ser Gly Gly Thr Ala Ile Leu Gly Cys Leu Val
1               5                   10                  15

Lys Asp Tyr Phe Pro Glu Pro Val Thr Val Ser Trp Asn Ser Gly Ala
            20                  25                  30

Leu Thr Ser Gly Val His Thr Ser Pro Ala Val Leu Gln Ser Ser Gly
        35                  40                  45

Leu Tyr Ser Leu Ser Ser Val Val Thr Val Pro Ser Ser
        50                  55                  60
```

<210> SEQ ID NO 91
<211> LENGTH: 62
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 91

```
Ser Ser Lys Ser Thr Ser Gly Gly Thr Ala Ala Leu Gly Cys Leu Val
1               5                   10                  15

Lys Asp Tyr Phe Pro Glu Pro Val Thr Val Ser Trp Asn Ser Gly Ala
            20                  25                  30

Leu Thr Ser Gly Val His Thr Ser Pro Ala Val Leu Gln Ser Ser Gly
        35                  40                  45

Leu Tyr Ser Leu Ser Ser Val Val Thr Val Pro Ser Ser
        50                  55                  60
```

<210> SEQ ID NO 92
<211> LENGTH: 68

```
<212> TYPE: PRT
<213> ORGANISM: Homo sapiens

<400> SEQUENCE: 92

Pro Ser Val Phe Ile Phe Pro Pro Ser Asp Glu Gln Leu Lys Ser Gly
1               5                   10                  15

Thr Ala Ser Val Val Cys Leu Leu Asn Asn Phe Tyr Pro Arg Glu Ala
            20                  25                  30

Lys Val Gln Trp Lys Val Asp Asn Ala Leu Gln Ser Gly Asn Ser Gln
        35                  40                  45

Glu Ser Val Thr Glu Gln Asp Ser Lys Asp Ser Thr Tyr Ser Leu Ser
    50                  55                  60

Ser Thr Leu Thr
65

<210> SEQ ID NO 93
<211> LENGTH: 68
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Pro Ser Val Ala Ile Phe Pro Pro Ser Asp Glu Gln Leu Lys Ser Gly
1               5                   10                  15

Thr Ala Ser Val Val Cys Val Leu Asn Asn Phe Tyr Pro Arg Glu Ala
            20                  25                  30

Lys Val Gln Trp Lys Val Asp Asn Ala Leu Gln Ser Gly Asn Ser Gln
        35                  40                  45

Glu Ser Val Thr Glu Gln Asp Ser Lys Asp Ser Thr Tyr Ala Leu Phe
    50                  55                  60

Ser Val Leu Thr
65

<210> SEQ ID NO 94
<211> LENGTH: 68
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Pro Ser Val Phe Ile Phe Pro Pro Ser Asp Glu Gln Leu Lys Ser Gly
1               5                   10                  15

Thr Ala Ser Val Val Cys Val Leu Asn Asn Phe Tyr Pro Arg Glu Ala
            20                  25                  30

Lys Val Gln Trp Lys Val Asp Asn Ala Leu Gln Ser Gly Asn Ser Gln
        35                  40                  45

Glu Ser Val Thr Glu Gln Asp Ser Lys Asp Ser Thr Tyr Ala Leu Phe
    50                  55                  60

Ser Val Leu Thr
65

<210> SEQ ID NO 95
<211> LENGTH: 68
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 95

Pro Ser Val Ala Ile Phe Pro Pro Ser Asp Glu Gln Leu Lys Ser Gly
1               5                   10                  15

Thr Ala Ser Val Val Cys Leu Leu Asn Asn Phe Tyr Pro Arg Glu Ala
            20                  25                  30

Lys Val Gln Trp Lys Val Asp Asn Ala Leu Gln Ser Gly Asn Ser Gln
        35                  40                  45

Glu Ser Val Thr Glu Gln Asp Ser Lys Asp Ser Thr Tyr Ala Leu Phe
    50                  55                  60

Ser Val Leu Thr
65

<210> SEQ ID NO 96
<211> LENGTH: 68
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Pro Ser Val Ala Ile Phe Pro Pro Ser Asp Glu Gln Leu Lys Ser Gly
1               5                   10                  15

Thr Ala Ser Val Val Cys Val Leu Asn Asn Phe Tyr Pro Arg Glu Ala
            20                  25                  30

Lys Val Gln Trp Lys Val Asp Asn Ala Leu Gln Ser Gly Asn Ser Gln
        35                  40                  45

Glu Ser Val Thr Glu Gln Asp Ser Lys Asp Ser Thr Tyr Ser Leu Phe
    50                  55                  60

Ser Val Leu Thr
65

<210> SEQ ID NO 97
<211> LENGTH: 68
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

Pro Ser Val Ala Ile Phe Pro Pro Ser Asp Glu Gln Leu Lys Ser Gly
1               5                   10                  15

Thr Ala Ser Val Val Cys Val Leu Asn Asn Phe Tyr Pro Arg Glu Ala
            20                  25                  30

Lys Val Gln Trp Lys Val Asp Asn Ala Leu Gln Ser Gly Asn Ser Gln
        35                  40                  45

Glu Ser Val Thr Glu Gln Asp Ser Lys Asp Ser Thr Tyr Ala Leu Phe
    50                  55                  60

Ser Thr Leu Thr
65

<210> SEQ ID NO 98
<211> LENGTH: 68
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Pro Ser Val Ala Ile Phe Pro Pro Ser Asp Glu Gln Leu Lys Ser Gly
1               5                   10                  15

Thr Ala Ser Val Val Cys Leu Leu Asn Asn Phe Tyr Pro Arg Glu Ala
            20                  25                  30

Lys Val Gln Trp Lys Val Asp Asn Ala Leu Gln Ser Gly Asn Ser Gln
        35                  40                  45

Glu Ser Val Thr Glu Gln Asp Ser Lys Asp Ser Thr Tyr Ser Leu Phe
    50                  55                  60

Ser Val Leu Thr
65

<210> SEQ ID NO 99
<211> LENGTH: 68
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Pro Ser Val Ala Ile Phe Pro Pro Ser Asp Glu Gln Leu Lys Ser Gly
1               5                   10                  15

Thr Ala Ser Val Val Cys Val Leu Asn Asn Phe Tyr Pro Arg Glu Ala
            20                  25                  30

Lys Val Gln Trp Lys Val Asp Asn Ala Leu Gln Ser Gly Asn Ser Gln
        35                  40                  45

Glu Ser Val Thr Glu Gln Asp Ser Lys Asp Ser Thr Tyr Ser Leu Phe
    50                  55                  60

Ser Thr Leu Thr
65

<210> SEQ ID NO 100
<211> LENGTH: 68
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

Pro Ser Val Ala Ile Phe Pro Pro Ser Asp Glu Gln Leu Lys Ser Gly
1               5                   10                  15

Thr Ala Ser Val Val Cys Leu Leu Asn Asn Phe Tyr Pro Arg Glu Ala
            20                  25                  30

Lys Val Gln Trp Lys Val Asp Asn Ala Leu Gln Ser Gly Asn Ser Gln
        35                  40                  45

Glu Ser Val Thr Glu Gln Asp Ser Lys Asp Ser Thr Tyr Ser Leu Phe
    50                  55                  60

Ser Thr Leu Thr
65
```

-continued

```
<210> SEQ ID NO 101
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
                20                  25                  30

Glu Pro Val Thr Val Ser Trp Asn Ser Gly Ala Leu Thr Ser Gly Val
            35                  40                  45

His Thr Phe Pro Ala Val Leu Gln Ser Ser Gly Leu Tyr Ser Leu Arg
    50                  55                  60

Ser Val Val Thr Val Pro Ser Ser Ser Leu Gly Thr Gln Thr Tyr Ile
65                  70                  75                  80

Cys Asn

<210> SEQ ID NO 102
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
                20                  25                  30

Glu Pro Val Thr Val Ser Trp Asn Ser Gly Ala Leu Thr Ser Gly Val
            35                  40                  45

His Thr Phe Pro Ala Val Leu Gln Ser Ser Gly Leu Tyr Ser Leu Lys
    50                  55                  60

Ser Val Val Thr Val Pro Ser Ser Ser Leu Gly Thr Gln Thr Tyr Ile
65                  70                  75                  80

Cys Asn

<210> SEQ ID NO 103
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Thr Lys Gly Pro Ser Val Phe Pro Leu Ala Pro Cys Ser Arg Ser Thr
1               5                   10                  15

Ser Glu Ser Thr Ala Ile Leu Gly Cys Leu Val Lys Asp Tyr Phe Pro
                20                  25                  30

Glu Pro Val Thr Val Ser Trp Asn Ser Gly Ala Leu Thr Ser Gly Val
            35                  40                  45

His Thr Ser Pro Ala Val Leu Gln Ser Ser Gly Leu Tyr Met Leu Ala
```

```
                    50                  55                  60
Ser Ala Val Thr Val Pro Ser Ser Asn Phe Gly Thr Gln Thr Tyr Thr
 65                  70                  75                  80

Cys Asn

<210> SEQ ID NO 104
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 104

Thr Lys Gly Pro Ser Val Phe Pro Leu Ala Pro Cys Ser Arg Ser Thr
  1               5                  10                  15

Ser Gly Gly Thr Ala Ile Leu Gly Cys Leu Val Lys Asp Tyr Phe Pro
                 20                  25                  30

Glu Pro Val Thr Val Ser Trp Asn Ser Gly Ala Leu Thr Ser Gly Val
             35                  40                  45

His Thr Ser Pro Ala Val Leu Gln Ser Ser Gly Leu Tyr Met Leu Ala
         50                  55                  60

Ser Ala Val Thr Val Pro Ser Ser Ser Leu Gly Thr Gln Thr Tyr Thr
 65                  70                  75                  80

Cys Asn

<210> SEQ ID NO 105
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 105

Thr Lys Gly Pro Ser Val Phe Pro Leu Ala Pro Cys Ser Arg Ser Thr
  1               5                  10                  15

Ser Glu Ser Thr Ala Ile Leu Gly Cys Leu Val Lys Asp Tyr Phe Pro
                 20                  25                  30

Glu Pro Val Thr Val Ser Trp Asn Ser Gly Ala Leu Thr Ser Gly Val
             35                  40                  45

His Thr Ser Pro Ala Val Leu Gln Ser Ser Gly Leu Tyr Met Leu Ala
         50                  55                  60

Ser Ala Val Thr Val Pro Ser Ser Ser Leu Gly Thr Lys Thr Tyr Thr
 65                  70                  75                  80

Cys Asn

<210> SEQ ID NO 106
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Thr Lys Gly Pro Ser Val Phe Pro Phe Ala Pro Cys Ser Arg Ser Thr
  1               5                  10                  15
```

```
Ser Glu Ser Thr Ala Met Leu Gly Cys Leu Val Lys Asp Tyr Phe Pro
            20                  25                  30

Glu Pro Val Thr Val Ser Trp Asn Ser Gly Ala Leu Thr Ser Gly Val
            35                  40                  45

His Thr Tyr Pro Ala Val Leu Gln Ser Ser Gly Leu Tyr Ile Leu Ala
            50                  55                  60

Ser Ala Val Thr Val Pro Ser Ser Asn Phe Gly Thr Gln Thr Tyr Thr
65                      70                  75                  80

Cys Asn

<210> SEQ ID NO 107
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Thr Lys Gly Pro Ser Val Phe Pro Phe Ala Pro Cys Ser Arg Ser Thr
1               5                   10                  15

Ser Gly Gly Thr Ala Met Leu Gly Cys Leu Val Lys Asp Tyr Phe Pro
            20                  25                  30

Glu Pro Val Thr Val Ser Trp Asn Ser Gly Ala Leu Thr Ser Gly Val
            35                  40                  45

His Thr Tyr Pro Ala Val Leu Gln Ser Ser Gly Leu Tyr Ile Leu Ala
            50                  55                  60

Ser Ala Val Thr Val Pro Ser Ser Ser Leu Gly Thr Gln Thr Tyr Thr
65                      70                  75                  80

Cys Asn

<210> SEQ ID NO 108
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108

Thr Lys Gly Pro Ser Val Phe Pro Phe Ala Pro Cys Ser Arg Ser Thr
1               5                   10                  15

Ser Glu Ser Thr Ala Met Leu Gly Cys Leu Val Lys Asp Tyr Phe Pro
            20                  25                  30

Glu Pro Val Thr Val Ser Trp Asn Ser Gly Ala Leu Thr Ser Gly Val
            35                  40                  45

His Thr Phe Pro Ala Val Leu Gln Ser Ser Gly Leu Tyr Ile Leu Ala
            50                  55                  60

Ser Ala Val Thr Val Pro Ser Ser Ser Leu Gly Thr Lys Thr Tyr Thr
65                      70                  75                  80

Cys Asn

<210> SEQ ID NO 109
<211> LENGTH: 82
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic polypeptide"

<400> SEQUENCE: 109

Thr Lys Gly Pro Ser Val Phe Pro Leu Ala Pro Ser Ser Lys Ser Thr
1               5                   10                  15

Ser Gly Gly Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Phe Pro Ala Val Leu Gln Ser Ser Gly Leu Tyr Ser Leu Ser
    50                  55                  60

Ser Val Val Thr Val Pro Ser Ser Ser Leu Gly Thr Gln Thr Tyr Ile
65                  70                  75                  80

Cys Asn

<210> SEQ ID NO 110
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110

Thr Lys Gly Pro Ser Val Phe Pro Leu Ala Pro Cys Ser Arg Ser Thr
1               5                   10                  15

Ser Glu Ser Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Phe Pro Ala Val Leu Gln Ser Ser Gly Leu Tyr Ser Leu Ser
    50                  55                  60

Ser Val Val Thr Val Pro Ser Ser Asn Phe Gly Thr Gln Thr Tyr Thr
65                  70                  75                  80

Cys Asn

<210> SEQ ID NO 111
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Thr Lys Gly Pro Ser Val Phe Pro Leu Ala Pro Cys Ser Arg Ser Thr
1               5                   10                  15

Ser Gly Gly Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Phe Pro Ala Val Leu Gln Ser Ser Gly Leu Tyr Ser Leu Ser
    50                  55                  60

Ser Val Val Thr Val Pro Ser Ser Ser Leu Gly Thr Gln Thr Tyr Thr
65                  70                  75                  80

Cys Asn

<210> SEQ ID NO 112
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 112

Thr Lys Gly Pro Ser Val Phe Pro Leu Ala Pro Cys Ser Arg Ser Thr
1               5                   10                  15

Ser Glu Ser Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

His Thr Phe Pro Ala Val Leu Gln Ser Ser Gly Leu Tyr Ser Leu Ser
    50                  55                  60

Ser Val Val Thr Val Pro Ser Ser Ser Leu Gly Thr Lys Thr Tyr Thr
65                  70                  75                  80

Cys Asn

<210> SEQ ID NO 113
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 113

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 114
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 114

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Glu Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 115
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Ser Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 116
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Leu Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Lys Ser Tyr Ser Cys Gln Val Thr His Glu Gly Ser Thr Val

```
                    85                  90                  95

Glu Lys Thr Val Ala Pro Thr Glu Cys Ser
                100                 105

<210> SEQ ID NO 117
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Trp Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
 50                 55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
                100                 105

<210> SEQ ID NO 118
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 118

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Lys Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
 50                 55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
                100                 105

<210> SEQ ID NO 119
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 119

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Arg Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 120
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Asp Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 121
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

Thr Lys Gly Pro Ser Val Phe Pro Leu Ala Pro Cys Ser Arg Ser Thr
1               5                   10                  15

Ser Glu Ser Thr Ala Ala Leu Gly Cys Leu Val Lys Asp Tyr Phe Pro
            20                  25                  30

Glu Pro Val Thr Val Ser Trp Asn Ser Gly Ala Leu Thr Ser Gly Val
        35                  40                  45

```
His Thr Phe Pro Ala Val Leu Gln Ser Ser Gly Leu Tyr Ser Leu Glu
    50                  55                  60

Ser Val Val Thr Val Pro Ser Ser Asn Phe Gly Thr Gln Thr Tyr Thr
65                  70                  75                  80

Cys Asn
```

<210> SEQ ID NO 122
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

```
Thr Lys Gly Pro Ser Val Phe Pro Leu Ala Pro Cys Ser Arg Ser Thr
1               5                   10                  15

Ser Gly Gly Thr Ala Ala Leu Gly Cys Leu Val Lys Asp Tyr Phe Pro
                20                  25                  30

Glu Pro Val Thr Val Ser Trp Asn Ser Gly Ala Leu Thr Ser Gly Val
            35                  40                  45

His Thr Phe Pro Ala Val Leu Gln Ser Ser Gly Leu Tyr Ser Leu Glu
    50                  55                  60

Ser Val Val Thr Val Pro Ser Ser Leu Gly Thr Gln Thr Tyr Thr
65                  70                  75                  80

Cys Asn
```

<210> SEQ ID NO 123
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

```
Thr Lys Gly Pro Ser Val Phe Pro Leu Ala Pro Cys Ser Arg Ser Thr
1               5                   10                  15

Ser Glu Ser Thr Ala Ala Leu Gly Cys Leu Val Lys Asp Tyr Phe Pro
                20                  25                  30

Glu Pro Val Thr Val Ser Trp Asn Ser Gly Ala Leu Thr Ser Gly Val
            35                  40                  45

His Thr Phe Pro Ala Val Leu Gln Ser Ser Gly Leu Tyr Ser Leu Glu
    50                  55                  60

Ser Val Val Thr Val Pro Ser Ser Leu Gly Thr Lys Thr Tyr Thr
65                  70                  75                  80

Cys Asn
```

<210> SEQ ID NO 124
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124

```
Thr Lys Gly Pro Ser Val Phe Pro Leu Ala Pro Cys Ser Arg Ser Thr
```

```
                1               5                  10                 15
            Ser Glu Ser Thr Ala Ala Leu Gly Cys Leu Val Lys Asp Tyr Phe Pro
                            20              25                  30

Glu Pro Val Thr Val Ser Trp Asn Ser Gly Ala Leu Thr Ser Gly Val
                        35              40                  45

His Thr Phe Pro Ala Val Leu Gln Ser Ser Gly Leu Tyr Ser Leu Lys
                    50                  55                  60

Ser Val Val Thr Val Pro Ser Ser Asn Phe Gly Thr Gln Thr Tyr Thr
             65                  70                  75                  80

Cys Asn
```

<210> SEQ ID NO 125
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 125

```
            Thr Lys Gly Pro Ser Val Phe Pro Leu Ala Pro Cys Ser Arg Ser Thr
             1               5                  10                  15

Ser Gly Gly Thr Ala Ala Leu Gly Cys Leu Val Lys Asp Tyr Phe Pro
                            20              25                  30

Glu Pro Val Thr Val Ser Trp Asn Ser Gly Ala Leu Thr Ser Gly Val
                        35              40                  45

His Thr Phe Pro Ala Val Leu Gln Ser Ser Gly Leu Tyr Ser Leu Lys
                    50                  55                  60

Ser Val Val Thr Val Pro Ser Ser Ser Leu Gly Thr Gln Thr Tyr Thr
             65                  70                  75                  80

Cys Asn
```

<210> SEQ ID NO 126
<211> LENGTH: 82
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 126

```
            Thr Lys Gly Pro Ser Val Phe Pro Leu Ala Pro Cys Ser Arg Ser Thr
             1               5                  10                  15

Ser Glu Ser Thr Ala Ala Leu Gly Cys Leu Val Lys Asp Tyr Phe Pro
                            20              25                  30

Glu Pro Val Thr Val Ser Trp Asn Ser Gly Ala Leu Thr Ser Gly Val
                        35              40                  45

His Thr Phe Pro Ala Val Leu Gln Ser Ser Gly Leu Tyr Ser Leu Lys
                    50                  55                  60

Ser Val Val Thr Val Pro Ser Ser Ser Leu Gly Thr Lys Thr Tyr Thr
             65                  70                  75                  80

Cys Asn
```

<210> SEQ ID NO 127
<211> LENGTH: 106
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 127

Gly Gln Pro Lys Ala Ala Pro Ser Val Ala Leu Phe Pro Pro Ser Ser
1               5                   10                  15

Glu Glu Leu Gln Ala Asn Lys Ala Thr Leu Val Cys Val Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
50                  55                  60

Lys Tyr Ala Ala Phe Ser Val Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 128
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Gly Gln Pro Lys Ala Ala Pro Ser Val Thr Leu Val Pro Pro Ser Ser
1               5                   10                  15

Glu Glu Leu Gln Ala Asn Lys Ala Thr Leu Ala Cys Phe Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Ala Thr Pro Ser Lys Gln Ser Asn Asn
50                  55                  60

Lys Tyr Ala Ala Ala Ser Leu Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 129
<211> LENGTH: 15
<212> TYPE: PRT
<213> ORGANISM: Homo sapiens

<400> SEQUENCE: 129

Glu Pro Lys Ser Cys Asp Lys Thr His Thr Cys Pro Pro Cys Pro
1               5                   10                  15

<210> SEQ ID NO 130
<211> LENGTH: 110
<212> TYPE: PRT
<213> ORGANISM: Homo sapiens

<400> SEQUENCE: 130
```

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
                100                 105                 110

<210> SEQ ID NO 131
<211> LENGTH: 107
<212> TYPE: PRT
<213> ORGANISM: Homo sapiens

<400> SEQUENCE: 131

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
                100                 105
```

What is claimed is:

1. One or more nucleic acids encoding a multispecific antigen binding protein comprising: a) a first heavy chain/light chain pair binding to a first antigen which comprises a first heavy chain polypeptide (H1) and a first light chain polypeptide (L1), and b) a second heavy chain/light chain pair binding to a second antigen which comprises a second heavy chain polypeptide (H2) and a second light chain polypeptide (L2), wherein each H1 and H2 comprises a heavy chain variable domain (VH) and a heavy chain constant domain (CH1), and each L1 and L2 comprises a light chain variable domain (VL) and a light chain constant domain (CL);

wherein:

(i) an amino acid at S183 according to EU numbering in the CH1 domain of H1 is replaced with a positively charged residue, an amino acid at Q39 according to Kabat numbering in the VH domain of H1 is replaced with a negatively charged residue, an amino acid at V133 according to EU numbering in the CL domain of L1 is replaced with a negatively charged residue, and an amino acid at Q38 according to Kabat numbering in the VL domain of L1 is replaced with a positively charged residue; and an amino acid at Q39 according to Kabat numbering in the VH domain of H2 is replaced with a positively charged residue, and an amino acid at Q38 according to Kabat numbering in the VL domain of L2 is replaced with a negatively charged residue;

or (ii) an amino acid at S183 according to EU numbering in the CH1 domain of H1 is replaced with a negatively charged residue, an amino acid at Q39 according to Kabat numbering in the VH domain of H1 is replaced with a positively charged residue, an amino acid at V133 according to EU numbering in the CL domain of L1 is replaced with a positively charged residue, and an amino acid at Q38 according to Kabat numbering in the VL domain of L1 is replaced with a negatively charged residue; and an amino acid at Q39 according to Kabat numbering in the VH domain of H2 is replaced with a negatively charged residue, and an amino acid at Q38 according to Kabat numbering in the VL domain of L2 is replaced with a positively charged residue; and wherein the positively charged residue is selected from the group consisting of R and K, and wherein the negatively charged residue is selected from the group consisting of D and E.

2. The one or more nucleic acids of claim 1, wherein the CH1 domain of H1 consists of the amino acid substitution at S183 according to EU numbering, and wherein the CL domain of L1 consists of the amino acid substitution at V133 according to EU numbering.

3. The one or more nucleic acids of claim 1, wherein the amino acid at S183 according to EU numbering in the CH1 domain of H1 is replaced with a positively charged residue, the amino acid at Q39 according to Kabat numbering in the VH domain of H1 is replaced with a negatively charged residue, the amino acid at V133 according to EU numbering in the CL domain of L1 is replaced with a negatively charged residue, and the amino acid at Q38 according to Kabat numbering in the VL domain of L1 is replaced with a positively charged residue; the amino acid at Q39 according to Kabat numbering in the VH domain of H2 is replaced with a positively charged residue, and the amino acid at Q38 according to Kabat numbering in the VL domain of L2 is replaced with a negatively charged residue; and wherein an amino acid at S183 according to EU numbering in the CH1 domain of H2 is replaced with a negatively charged residue, and an amino acid at V133 according to EU numbering in the CL domain of L2 is replaced with a positively charged residue.

4. The one or more nucleic acids of claim 3, wherein the CH1 domain of H2 consists of the amino acid substitution at S183 according to EU numbering, and wherein the CL domain of L2 consists of the amino acid substitution at V133 according to EU numbering.

5. The one or more nucleic acids of claim 1, wherein the amino acid at S183 according to EU numbering in the CH1 domain of H1 is replaced with a negatively charged residue, the amino acid at Q39 according to Kabat numbering in the VH domain of H1 is replaced with a positively charged residue, the amino acid at V133 according to EU numbering in the CL domain of L1 is replaced with a positively charged residue, and the amino acid at Q38 according to Kabat numbering in the VL domain of L1 is replaced with a negatively charged residue; the amino acid at Q39 according to Kabat numbering in the VH domain of H2 is replaced with a negatively charged residue and the amino acid at Q38 according to abat numbering in the VL domain of L2 is replaced with a positively charged residue; and wherein an amino acid at S183 according to EU numbering in the CH1 domain of H2 is replaced with a positively charged residue, and an amino acid at V133 according to EU numbering in the CL domain of L2 is replaced with a negatively charged residue.

6. The one or more nucleic acids of claim 1, wherein (a) the CH1 domain of H2 comprises A141I, F170S, S181M, S183V, and V185A mutations, and the CL domain of L2 comprises F116A, V133I, L135V, S162M, S174A, S176F, and T178V mutations;

(b) the CH1 domain of H2 comprises A141I, F170S, S181M, S183A, and V185A mutations, and the CL domain of L2 comprises F116A, S131D, L135V, S162A, S174A, S176F, and T178I mutations;

(c) the CH1 domain of H2 comprises A141I, F170S, S181M, S183A, and V185A mutations, and the CL domain of L2 comprises F116A, L135V, S174A, S176F, and T178V mutations;

(d) the CH1 domain of H2 comprises A141I, F170A, S181M, S183V, and V185A mutations, and the CL domain of L2 comprises F116A, L135V, S162M, S174A, S176F, and T178V mutations;

(e) the CH1 domain of H2 comprises L128F, A141M, F170M, S181I, and S183A mutations, and the CL domain of L2 comprises F118V, S13IT, V133A, L135Y, S162A, T164S, S176M, and T178L mutations;

(f) the CH1 domain of H2 comprises L128F, A141M, F170Y, S181I, S183A, and V185A mutations, and the CL domain of L2 comprises F118V, S131T, V133A, L135F, S162A, S176A, and T178L mutations;

(g) the CH1 domain of H2 comprises L128F, A141T, F170M, S181T, S183A, and V185L mutations, and the CL domain of L2 comprises F118V, S13IT, V133A, L135F, S162A, T164S, S176T, and T178L mutations; or (h) the CH1 domain of H2 comprises L128F, A141M, F170M, S181T, and S183A mutations, and the CL domain of L2 comprises F118V, S131T, V133A, L135F, S162M, T164S, S176M, and T178L mutations; and wherein the amino acid positions are according to EU numbering.

7. The one or more nucleic acids of claim 1, wherein the amino acid at S183 according to EU numbering in the CH1 domain of H1 is replaced with a negatively charged residue, the amino acid at Q39 according to Kabat numbering in the VH domain of H1 is replaced with a positively charged residue, the amino acid at V133 according to EU numbering in the CL domain of L1 is replaced with a positively charged residue, the amino acid at Q38 according to Kabat numbering in the VL domain of L1 is replaced with a negatively charged residue, the amino acid at Q39 according to Kabat numbering in the VH domain of H2 is replaced with a negatively charged residue, and the amino acid at Q38 according to Kabat numbering in the VL domain of L2 is replaced with a positively charged residue; and wherein the VH domain of H1 comprises a Q39K mutation, the CH1 domain of H1 comprises an S183E mutation, the VL domain of L1 comprises a Q38E mutation, the CL domain of L1 comprises a V133K mutation, the VH domain of H2 comprises a Q39E mutation, and the VL domain of L2 comprises a Q38K mutation.

8. The one or more nucleic acids of claim 7, wherein the CH1 domain of H2 comprises an S183K mutation, and the CL domain of L2 comprises a V133E mutation, and wherein the amino acid positions are according to EU numbering.

9. The one or more nucleic acids of claim 7, wherein the CH1 domain of H2 comprises A141I, F170S, S181M, S183A, and V185A mutations, and the CL domain of L2 comprises F116A, L135V, S174A, S176F, and T178V mutations, and wherein the amino acid positions are according to EU numbering.

10. The one or more nucleic acids of claim 1, wherein the amino acid at S183 according to EU numbering in the CH1 domain of H1 is replaced with a positively charged residue, the amino acid at Q39 according to Kabat numbering in the VH domain of H1 is replaced with a negatively charged residue, the amino acid at V133 according to EU numbering in the CL domain of L1 is replaced with a negatively charged residue, the amino acid at Q38 according to Kabat numbering in the VL domain of L1 is replaced with a positively charged residue, the amino acid at Q39 according to Kabat numbering in the VH domain of H2 is replaced with a positively charged residue, and the amino acid at Q38 according to Kabat numbering in the VL domain of L2 is replaced with a negatively charged residue; and wherein the VH domain of H1 comprises a Q39E mutation, the CH1 domain of H1 comprises an S183K mutation, the VL domain of L1 comprises a Q38K mutation, the CL domain of L1 comprises a V133E mutation, the VH domain of H2 comprises a Q39K mutation, and the VL domain of L2 comprises a Q38E mutation.

11. The one or more nucleic acids of claim 10, wherein the CH1 domain of H2 comprises an S183E mutation, and the CL domain of L2 comprises a V133K mutation, and wherein the amino acid positions are according to EU numbering.

12. The one or more nucleic acids of claim 10, wherein the CH1 domain of H2 comprises A141I, F170S, S181M, S183A, and V185A mutations, and the CL domain of L2 comprises F116A, L135V, S174A, S176F, and T178V mutations, and wherein the amino acid positions are according to EU numbering.

13. The one or more nucleic acids of claim 1, wherein each of H1 and/or H2 comprises an Fc region, and wherein the Fc region is a human IgG1 Fc region, human IgG2 Fc region, or human IgG4 Fc region.

14. The one or more nucleic acids of claim 1,
wherein each of H1 and H2 comprises an Fc region that comprises a CH2 domain and a CH3 domain,
wherein the CH3 domain of H1 is altered, so that within the CH3/CH3 interface, one or more amino acid residues are replaced with one or more amino acid residues having a larger side chain volume, thereby generating a knob on the surface of the CH3 domain of H1 that interacts with the CH3 domain of H2, and wherein the CH3 domain of H2 is altered, so that within the CH3/CH3 interface, one or more amino acid residues are replaced with amino acid residues having a smaller side chain volume, thereby generating a hole on the surface of the CH3 domain of H2 that interacts with the CH3 domain of H1; or
wherein the CH3 domain of H2 is altered, so that within the CH3/CH3 interface, one or more amino acid residues are replaced with one or more amino acid residues having a larger side chain volume, thereby generating a knob on the surface of the CH3 domain of H2 that interacts with the CH3 domain of H1, and wherein the CH3 domain of H1 is altered, so that within the CH3/CH3 interface, one or more amino acid residues are replaced with amino acid residues having a smaller side chain volume, thereby generating a hole on the surface of the CH3 domain of H1 that interacts with the CH3 domain of H2.

15. The one or more nucleic acids of claim 14, wherein the knob mutation comprises T366W according to EU numbering, and wherein the hole mutation comprises at least one, at least two, or all three of T366S, L368A, and Y407V according to EU numbering.

16. A vector comprising the one or more nucleic acids of claim 1.

17. A host cell comprising the one or more nucleic acids of claim 1.

18. The host cell of claim 17, wherein the host cell is a prokaryotic host cell, and *E. coli* cell, a eukaryotic host cell, a yeast cell, a mammalian cell, or a CHO cell.

19. A method of producing a multispecific antigen binding protein, comprising: culturing the host cell of claim 17 under appropriate conditions to cause expression of the multispecific antigen binding protein.

20. The method of claim 19, further comprising recovering the multispecific antigen binding protein.

21. The one or more nucleic acids of claim 5, wherein the CH1 domain of H2 consists of the amino acid substitution at S183 according to EU numbering, and wherein the CL domain of L2 consists of the amino acid substitution at V133 according to EU numbering.

* * * * *